United States Patent
Caligiuri et al.

(10) Patent No.: US 8,455,646 B2
(45) Date of Patent: Jun. 4, 2013

(54) ALKALOID AMINOESTER DERIVATIVES AND MEDICINAL COMPOSITION THEREOF

(75) Inventors: Antonio Caligiuri, Parma (IT); Mauro Riccaboni, Parma (IT); Gabriele Amari, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 614 days.

(21) Appl. No.: 12/644,322

(22) Filed: Dec. 22, 2009

(65) Prior Publication Data

US 2010/0173880 A1 Jul. 8, 2010

(30) Foreign Application Priority Data

Dec. 23, 2008 (EP) .................................... 08172818

(51) Int. Cl.
- *C07D 453/02* (2006.01)
- *C07D 207/00* (2006.01)
- *C07D 223/08* (2006.01)

(52) U.S. Cl.
USPC ............................ 546/137; 548/566; 540/604

(58) Field of Classification Search
USPC ............................ 546/137; 548/566; 540/604
See application file for complete search history.

(56) References Cited

U.S. PATENT DOCUMENTS

| | | | |
|---|---|---|---|
| 2,824,106 A | | 2/1958 | Zeile et al. |
| 2,856,407 A | * | 10/1958 | Biel .............................. 544/130 |
| 5,583,142 A | * | 12/1996 | Bartolini et al. ............. 514/304 |

FOREIGN PATENT DOCUMENTS

| | | |
|---|---|---|
| EP | 0 424 021 A1 | 4/1991 |
| JP | 9521820 * | 8/1995 |
| WO | WO 98/11063 | 3/1998 |
| WO | WO 99/20612 | 4/1999 |
| WO | WO 02/051841 A1 | 7/2002 |
| WO | WO 2006/048225 A1 | 5/2006 |
| WO | WO 2008/012290 A2 | 1/2008 |
| WO | WO 2008/053158 A1 | 5/2008 |
| WO | WO 2008/059245 A1 | 5/2008 |
| WO | 2008/075006 * | 6/2008 |
| WO | WO 2008/075005 A1 | 6/2008 |
| WO | WO 2008/075006 A1 | 6/2008 |

OTHER PUBLICATIONS

U.S. Appl. No. 13/303,413, filed Nov. 23, 2011, Amari, et al.
R. G. Glushkov, et al., "Synthesis and Pharmacological Activity of the Tropine Ester of Phenylglyoxylic Acid and its Derivatives. New Method for Preparing Homatropine", Chemical Abstract Service, Khimiko-Farmatsevticheskii Zhurnal, 11 (7), 30-5, Database Accession No. 1978:15869, 1 page (Abstract only).
Takeuchi Yoshio, et al., "Amino Acids and Peptides. II. One-Step Synthesis of Atropine and Other Related Alkaloids from dl-phenylalanine 3.alpha.-tropanyl ester", Chemical Abstract Service, Chemical & Pharmaceutical Bulletin, 19 (12), 2603-8. Database Accession No. 1972:46353, 1 page (Abstract only).
Fulvio Gualtieri, et al., "Presynaptic Cholinergic Modulators as Potent Cognition Enhancers and Analgesic Drugs. 2. 2-Phenoxy-, 2-(Phenylthio)-, and 2-(Phenylamino)alkanoic Acid Esters", Journal of Medicinal Chemistry, 37 (11), XP002527089, 1994, pp. 1712-1719.
U.S. Appl. No. 13/165,936, filed Jun. 22, 2011, Amari, et al.
U.S. Appl. No. 13/165,948, filed Jun. 22, 2011, Amari, et al.
U.S. Appl. No. 13/165,930, filed Jun. 22, 2011, Amari, et al.
U.S. Appl. No. 13/219,109, filed Aug. 26, 2011, Amari, et al.
U.S. Appl. No. 13/232,415, filed Sep. 14, 2011, Amari, et al.

* cited by examiner

*Primary Examiner* — Nizal Chandrakumar
(74) *Attorney, Agent, or Firm* — Oblon, Spivak, McClelland, Maier & Neustadt, L.L.P.

(57) ABSTRACT

Alkaloid aminoester compounds which act as muscarinic receptor antagonists are useful for the prevention and/or treatment of a broncho-obstructive or inflammatory diseases.

19 Claims, No Drawings

ALKALOID AMINOESTER DERIVATIVES AND MEDICINAL COMPOSITION THEREOF

CROSS REFERENCES TO RELATED APPLICATIONS

This application claims priority to European Patent Application No. 08172818.0, filed on Dec. 23, 2008, which is incorporated herein by reference in its entirety.

BACKGROUND OF THE INVENTION

1. Field of the Invention

The present invention relates to alkaloid aminoester derivatives, which act as muscarinic receptor antagonists. The present invention also relates to processes for preparing such a compound and compositions which contain such a compound. The present invention further relates to methods of treating and/or preventing various conditions and/or diseases by administering such a compound.

2. Discussion of the Background

Quaternary ammonium salts, which act as muscarinic (M) receptor antagonist drugs, are currently used in therapy to induce bronchodilation for the treatment of respiratory diseases. Examples of well known M receptor antagonists are represented by ipratropium bromide and tiotropium bromide.

Several chemical classes acting as selective M3 receptor antagonist drugs have been developed for the treatment of inflammatory or obstructive airway diseases such as asthma and chronic obstructive pulmonary disease (COPD).

Quinuclidine carbamate derivatives and their use as M3 antagonists are disclosed in WO 02/051841, WO 03/053966 and WO 2008/012290.

Said M and M3 receptor antagonists are currently administered through inhalation in order to deliver the drug directly at the site of action and hence limiting the systemic exposure. However, even though the systemic exposure may be reduced through the inhalatory route, the compounds of the prior art may still exhibit undesired side effects due to systemic absorption. It is hence highly desirable to provide M3 receptor antagonists which are able to act locally, while having high potency and long duration of action. Said drugs, once adsorbed, are degraded to inactive compounds which are deprived of any systemic side effects typical of muscarinic antagonists.

U.S. Pat. No. 2,824,106 discloses quaternary alkyl derivatives of the tropeine series with increased spasmolytic activity and in particular N-phenyl amino acetyl derivatives.

J. Med. Chem., 1994, 37, 1712-1719 refers to presynaptic cholinergic modulators as potent cognition enhancers and analgesic drugs and in particular to N-phenyl amino acetyl derivatives.

U.S. Pat. No. 2,856,407 discloses aminoacid esters of hydroxypiperidines; among them are N-methyl-3-piperidyl-2'-N'-dimethylaminoacetate and N-methyl-4-piperidyl-2'-N'-dimethylaminoacetate.

WO 99/20612 describes compounds that inhibit the farnesylation of mutant ras gene products and in particular 4-(methylsulfanyl) butanoate derivatives.

WO 2008/053158 refers to inhibitors of p38 MAP kinase activity, useful in the treatment of inflammatory and autoimmune disease and in particular to methylpiperidin-4-yl L-leucinate derivatives.

Khimiko-Farmatsevticheskii Zhurnal, (1977), 11(7), 30-5 refers to tropine ester of phenylglyoxylic acid and in particular to phenylalanine ester derivatives.

Chemical & Pharmaceutical Bulletin, (1971), 19(12), 2603-8 describes the one-step synthesis of atropine and other related alkaloids from dl-phenylalanine 3α-tropanyl ester and in particular to phenylalanine ester derivatives.

However, there remains a need for M3 receptor antagonists which are able to act locally, while having high potency and long duration of action.

SUMMARY OF THE INVENTION

Accordingly, it is one object of the present invention to provide novel M receptor antagonists.

It is another object of the present invention to provide novel M3 receptor antagonists.

It is another object of the present invention to provide novel methods for preparing such a compound.

It is another object of the present invention to provide novel compositions which contain such a compound.

It is another object of the present invention to provide novel methods for treating and/or preventing various conditions and/or diseases by administering such a compound.

These and other objects, which will become apparent during the following detailed description, have been achieved by the inventors' discovery of alkaloid aminoester derivatives of formula (I):

wherein:

R1 may be selected from the group consisting of H, $(C_1-C_{10})$-alkyl, aryl, $(C_3-C_8)$-cycloalkyl, arylalkyl, and heteroaryl, optionally substituted by one or more substituents selected from the group consisting of halogen atoms, OH, oxo (=O), SH, $NO_2$, CN, $CON(R5)_2$, COOH, NHCOR5, COR5, $CO_2R5$, $CF_3$, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, and $(C_1-C_{10})$-alkoxyl;

R2 may be selected from the group consisting of $(C_1-C_{10})$-alkyl, aryl, $(C_3-C_8)$-cycloalkyl, arylalkyl, and heteroaryl, optionally substituted by one or more substituents selected from the group consisting of halogen atoms, OH, oxo (=O), SH, $NO_2$, CN, $CON(R5)_2$, COOH, NHCOR5, COR5, $CO_2R5$, $CF_3$, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, and $(C_1-C_{10})$-alkoxyl;

R3 is selected from the group consisting of H, $(C_1-C_{10})$-alkyl, aryl, $(C_3-C_8)$-cycloalkyl, heteroaryl, arylalkyl, and heteroarylalkyl, optionally substituted by one or more substituents selected from the group consisting of halogen atoms, OH, oxo (=O), SH, $NO_2$, CN, $CON(R5)_2$, COOH, $CO_2R5$, $CF_3$, $(C_1-C_{10})$-alkoxycarbonyl, $(C_1-C_{10})$-alkylsulfinyl, $(C_1-C_{10})$-alkylsulfonyl, $(C_1-C_{10})$-alkyl, and $(C_1-C_{10})$-alkoxyl;

R6 represents a group of formula (i) or (ii) or (iii) or (iv)

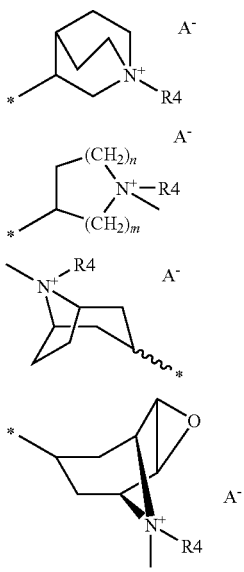

wherein
* indicates the position at which R6 is bonded to formula (I)
m=1, 2, or 3;
n=1, 2, or 3;
A⁻ is a physiologically acceptable anion;
R4 is a group of formula (Y):

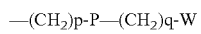

wherein
p is 0 or an integer from 1 to 4;
q is 0 or an integer from 1 to 4;
P is absent or is selected from the group consisting of O, S, SO, SO$_2$, CO, NR5 CH=CH, N(R5)SO$_2$, N(R5)COO, N(R5)C(O), SO$_2$N(R5), CO(O)N(R5), and C(O)N(R5);
W is selected from the group consisting of H, (C$_1$-C$_6$)-alkyl, (C$_3$-C$_8$)-cycloalkyl, aryl, and heteroaryl, optionally substituted by one or more substituents selected from the group consisting of halogen atoms, OH, oxo (=O), SH, NO$_2$, CN, CON(R5)$_2$, COOH, NH$_2$, NHCOR5, CO$_2$R5, (C$_1$-C$_{10}$)-alkoxycarbonyl, (C$_1$-C$_{10}$)-alkylsulfanyl, (C$_1$-C$_{10}$)-alkylsulfinyl, (C$_1$-C$_{10}$)-alkylsulfonyl, (C$_1$-C$_{10}$-alkyl, and (C$_1$-C$_{10}$)-alkoxyl;
R5 is selected from the group consisting of H, (C$_1$-C$_{10}$)alkyl, (C$_1$-C$_6$)alkylhalo, (C$_2$-C$_6$)alkynyl, (C$_2$-C$_6$)alkenyl, (C$_3$-C$_7$)cycloalkyl, (C$_3$-C$_7$)cycloalkyl-(C$_1$-C$_6$)alkyl, heteroaryl, (C$_1$-C$_6$)alkyl-heteroaryl, and aryl optionally substituted by one or more substituents selected from the group consisting of halogen atoms, OH, oxo (=O), SH, NO$_2$, CN, CONH$_2$, COOH, (C$_1$-C$_{10}$)-alkoxycarbonyl, (C$_1$-C$_{10}$)-alkylsulfanyl, (C$_1$-C$_{10}$)-alkylsulfinyl, (C$_1$-C$_{10}$)-alkylsulfonyl, (C$_1$-C$_{10}$)-alkyl, and (C$_1$-C$_{10}$)-alkoxyl;
and pharmaceutically acceptable salts thereof,
with the proviso that when R1 is H, R2 is phenyl, R3 is H, then R6 is not a group of formula (iii).

The present invention is also directed to compounds of general formula (VI):

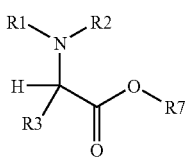

wherein:
R1, R2, and R3 are as described above;
R7 represents a group of formula (vi) or (vii) or (viii) or (ix)

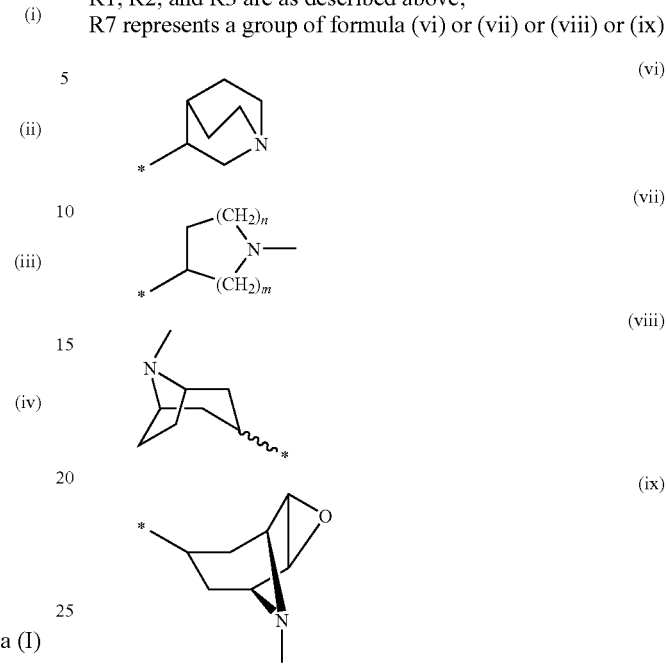

wherein
* indicates the position at which R7 is bonded to formula (VI)
m and n are as described above;
and pharmaceutically acceptable salts thereof,
with the provisos that:
when R1 is H or CH$_3$, R2 is phenyl, R3 is H or CH$_3$, then R6 is not a group of formula (viii) and
the compounds of general formula (VI) are not N-methyl-3-piperidyl-2'-N'dimethylaminoacetate and N-methyl-4-piperidyl-2'-N'-dimethylaminoacetate.

The present invention is also directed to processes for the preparation of a compound of formula (I) as reported in Scheme 1, which comprise the alkylation of a compound of general formula (VI)

with an alkylating agent of general formula (XI):

in which A is a suitable leaving group selected from the group consisting of halide and sulfonate, and R6 has the above reported meanings.

The present invention is also directed to processes for the preparation of a compound of formula (I) as reported in Scheme 1, which comprise the alkylation of an amine compound of general formula (II):

with a compound of general formula (III),

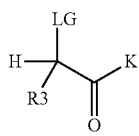
(III)

in which LG is a suitable leaving group and K may be either a hydroxyl group or a suitably protected hydroxyl group, to yield a compound of formula (IV):

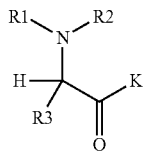
(IV)

which is condensed with a compound of formula (V)

(V)

to obtain compound (VI), and converting the compound to a further compound of formula (I).

The present invention is also directed to processes for the preparation of a compound of formula (I) as reported in Scheme 1, which comprise coupling an amine of general formula (II):

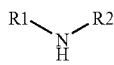
(II)

with a ketone of formula (VII),

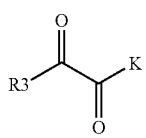
(VII)

to yield a compound of formula (IV),

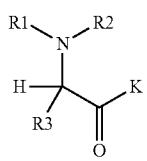
(IV)

which is condensed with a compound of formula (V)

(V)

to obtain compound (VI)

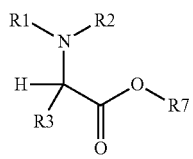
(VI)

and converting the compound to a further compound of formula (I).

The present invention is also directed to processes for the preparation of a compound of formula (I) as reported in scheme 1, which comprise reacting compound

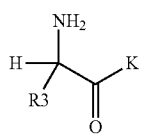
(IX)

with an alkylating agent of general formula (VIII),

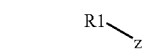
(VIII)

in which z is a carbonyl group or a suitable leaving group such as a a halide, to yield a compound of formula (IV) in which R2 is hydrogen,

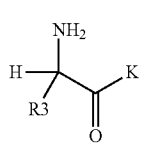
(IV)

which is condensed with a compound of formula (V)

(V)

to obtain compound (VI)

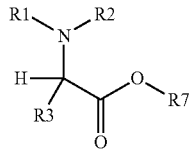
(VI)

and converting the compound to a further compound of formula (I).

The present invention is also directed to processes for the preparation of a compound of formula (I) as reported in Scheme 1, which comprise coupling a compound of general formula (III)

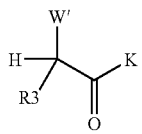
(III)

to compound of general formula (V)

(V)

to yield compound (X),

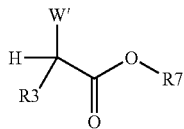
(X)

which is reacted with an amine of formula (II),

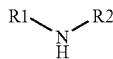
(II)

to obtain compound (VI)

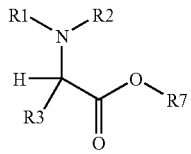
(VI)

and converting the compound to a further compound of formula (I).

The present invention also provides pharmaceutical compositions which contain a compound of general formula (I) alone or in combination with or in admixture with one or more pharmaceutically acceptable carriers and/or excipients.

The present invention also provides pharmaceutical compositions which contain a compound of general formula (VI) alone or in combination with or in admixture with one or more pharmaceutically acceptable carriers and/or excipients.

The present invention also provides compounds of general formula (I) for use as a medicament.

The present invention also provides compounds of general formula (VI) for use as a medicament.

In a further aspect the present invention provides the use of compounds of general formula (I) for the manufacture of a medicament for the prevention and/or treatment of bronchoobstructive or inflammatory diseases, preferably asthma or chronic bronchitis or chronic obstructive pulmonary disease (COPD).

In a further aspect the present invention provides the use of compounds of general formula (VI) for the manufacture of a medicament for the prevention and/or treatment of bronchoobstructive or inflammatory diseases, preferably asthma or chronic bronchitis or chronic obstructive pulmonary disease (COPD).

In a further aspect the present invention provides the use of the compounds of general formula (XIX)

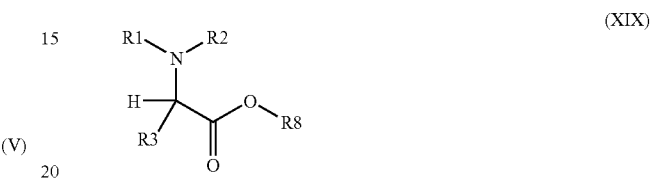
(XIX)

wherein:
R1 and R2 may be independently selected from the group consisting of H, $(C_1-C_{10})$-alkyl, aryl, $(C_3-C_8)$-cycloalkyl, arylalkyl, and heteroaryl optionally substituted by one or more substituents selected from the group consisting of halogen atoms, OH, oxo (=O), SH, $NO_2$, CN, $CON(R5)_2$, COOH, NHCOR5, COR5, $CO_2R5$, $CF_3$, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, and $(C_1-C_{10})$-alkoxyl;

R3 is selected from the group consisting of H, $(C_1-C_{10})$-alkyl, aryl, $(C_3-C_8)$-cycloalkyl, heteroaryl, arylalkyl, and heteroarylalkyl optionally substituted by one or more substituents selected from the group consisting of halogen atoms, OH, oxo (=O), SH, $NO_2$, CN, $CON(R5)_2$, COOH, $CO_2R5$, $CF_3$, $(C_1-C_{10})$-alkoxycarbonyl, $(C_1-C_{10})$-alkylsulfinyl, $(C_1-C_{10})$-alkylsulfonyl, $(C_1-C_{10}$-alkyl, and $(C_1-C_{10})$-alkoxyl;

R8 represents a group of formula (i) or (ii) or (iii) or (iv) or (vi) or (vii) or (viii) or (ix)

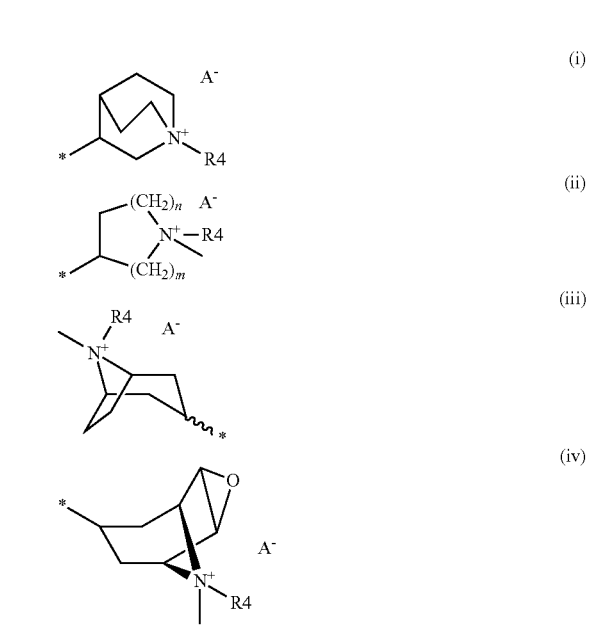

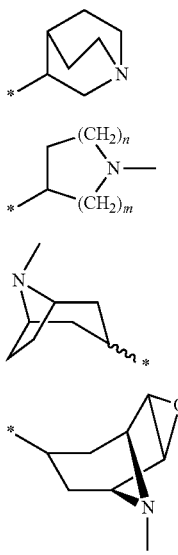

wherein
* indicates the position at which R8 is bonded to formula (XIX)
m=1, 2, or 3;
n=1, 2 or 3;
$A^-$ is a physiologically acceptable anion;
R4 is a group of formula (Y)

wherein
p is 0 or an integer from 1 to 4;
q is 0 or an integer from 1 to 4;
P is absent or is selected from the group consisting of O, S, SO, $SO_2$, CO, NR5 CH=CH, N(R5)$SO_2$, N(R5)COO, N(R5)C(O), $SO_2$N(R5), CO(O)N(R5), and C(O)N(R5);
W is selected from the group consisting of H, ($C_1$-$C_6$)-alkyl, ($C_3$-$C_8$)-cycloalkyl, aryl, and heteroaryl, optionally substituted by one or more substituents selected from the group consisting of halogen atoms, OH, oxo (=O), SH, $NO_2$, CN, CON(R5)$_2$, COOH, $NH_2$, NHCOR5, $CO_2$R5, ($C_1$-$C_{10}$)-alkoxycarbonyl, ($C_1$-$C_{10}$)-alkylsulfanyl, ($C_1$-$C_{10}$-alkylsulfinyl, ($C_1$-$C_{10}$)-alkylsulfonyl, ($C_1$-$C_{10}$)-alkyl, and ($C_1$-$C_{10}$)-alkoxyl;
R5 is selected from the group consisting of H, ($C_1$-$C_{10}$)alkyl, ($C_1$-$C_6$)alkylhalo, ($C_2$-$C_6$)alkynyl, ($C_2$-$C_6$)alkenyl, ($C_3$-$C_7$)cycloalkyl, ($C_3$-$C_7$)cycloalkyl-($C_1$-$C_6$)alkyl, heteroaryl, ($C_1$-$C_6$)alkyl-heteroaryl, and aryl optionally substituted by one or more substituents selected from the group consisting of halogen atoms, OH, oxo (=O), SH, $NO_2$, CN, $CONH_2$, COOH, ($C_1$-$C_{10}$)-alkoxycarbonyl, ($C_1$-$C_{10}$)-alkylsulfanyl, ($C_1$-$C_{10}$)-alkylsulfinyl, ($C_1$-$C_{10}$)-alkylsulfonyl, ($C_1$-$C_{10}$)-alkyl, and ($C_1$-$C_{10}$)-alkoxyl for the preparation of a medicament for the prevention and/or treatment of broncho-obstructive or inflammatory diseases, preferably asthma or chronic bronchitis or chronic obstructive pulmonary disease (COPD).

Moreover, the present invention provides methods for the prevention, amelioration, and/or treatment of a broncho-obstructive or inflammatory disease, preferably asthma or chronic bronchitis or chronic obstructive pulmonary disease (COPD), which comprise administering to a subject in need thereof a therapeutically effective amount of a compound of general formula (I).

Moreover, the present invention provides methods for the prevention, amelioration, and/or treatment of a broncho-obstructive or inflammatory disease, preferably asthma or chronic bronchitis or chronic obstructive pulmonary disease (COPD), which comprise administering to a subject in need thereof a therapeutically effective amount of a compound of general formula (VI).

Moreover the present invention provides methods for the prevention, amelioration, and/or treatment of a broncho-obstructive or inflammatory disease, preferably selected from the group consisting of asthma or chronic bronchitis or chronic obstructive pulmonary disease (COPD), which comprise administering to a subject in need thereof a therapeutically effective amount of compound (XIX).

The present invention also provides pharmaceutical preparations suitable for administration by inhalation. Inhalable preparations include inhalable powders, propellant-containing metering aerosols or propellant-free inhalable formulations.

The present invention is also directed to devices which may be a single- or multi-dose dry powder inhaler, a metered dose inhaler or a soft mist nebulizer and which contain a compound of general formula (I).

The present invention is also directed to devices which may be a single- or multi-dose dry powder inhaler, a metered dose inhaler or a soft mist nebulizer and which contain a compound of general formula (VI).

The present invention is also directed to kits which contain a pharmaceutical composition which contains a compound of general formula (I) alone or in combination with or in admixture with one or more pharmaceutically acceptable carriers and/or excipients and a device which may be a single- or multi-dose dry powder inhaler, a metered dose inhaler and a soft mist nebulizer comprising a compounds of general formula (I).

The present invention is also directed to kits which contain a pharmaceutical compositions which contains a compound of general formula (VI) alone or in combination with or in admixture with one or more pharmaceutically acceptable carriers and/or excipients and a device which may be a single- or multi-dose dry powder inhaler, a metered dose inhaler and a soft mist nebulizer comprising a compound of general formula (VI).

The present invention provides alkaloid aminoester derivatives with desirable therapeutic characteristics. The compounds of general formula (I) behave as soft-drugs, since they are able to produce a persistent bronchodilating effect in the lung but are consistently and rapidly transformed into inactive metabolites after passing into human plasma. This behavior gives great advantages in terms of safety.

DETAILED DESCRIPTION OF THE PREFERRED EMBODIMENTS

The term "halogen atoms" as used herein includes fluorine, chlorine, bromine, and iodine.

As used herein, the expression "($C_1$-$C_{10}$) alkyl", refers to straight or branched chain alkyl groups wherein the number of constituent carbon atoms is in the range 1 to 10. Examples of said groups are methyl, ethyl, n-propyl, isopropyl, t-butyl, pentyl, hexyl, heptyl, octanyl, nonenyl and decenyl.

Optionally, as formerly reported, in alkyl one or more hydrogen atoms can be replaced by halogen atoms. The derived expressions "($C_1$-$C_{10}$)-alkoxycarbonyl", ($C_1$-$C_{10}$)-alkylsulfanyl", "($C_1$-$C_{10}$)-alkylsulfinyl", "($C_1$-$C_{10}$)-alkylsulfonyl" and "($C_1$-$C_{10}$)-alkoxyl" are to be construed in an analogous manner.

The derived expressions "$(C_2-C_{10})$ alkenyl" and "$(C_2-C_{10})$ alkynyl", are to be construed in an analogous manner, as referring to groups at least comprising one double or triple bond.

As used herein, the expression "aryl" refers to mono, bi- or tricyclic ring systems which have 5 to 20 ring atoms, preferably from 5 to 15 and wherein at least one ring is aromatic. In said rings one or more hydrogen atoms may be replaced by one or more halogen atoms.

As used herein, the expression "heteroaryl" refers to mono, bi- or tricyclic ring systems which have 5 to 20 ring atoms, preferably from 5 to 15, in which at least one ring is aromatic and in which at least one ring atom is a heteroatom or heteroaromatic group (e.g. N, NH, S or O). In said rings one or more hydrogen atoms may be replaced by one or more halogen atoms.

As used herein, the expression "arylalkyl" refers to a "$(C_1-C_4)$ alkyl" optionally substituted by aryl as above defined. Examples of suitable arylalkyl groups include benzyl and diphenylmethyl.

As used herein, the expression "heteroarylalkyl" refers to a "$(C_1-C_4)$ alkyl" optionally substituted by a heteroaryl group as above defined. Examples of suitable heteroarylalkyl groups include thiophenylmethyl. Examples of suitable monocyclic systems include thiophene, cyclopentadiene, benzene, pyrrole, pyrazole, imidazole, isoxazole, oxazole, isothiazole, thiazole, pyridine, imidazolidine, piperidine and furan radicals. Examples of suitable bicyclic systems include naphthalene, biphenyl, purine, pteridine, benzotriazole, quinoline, isoquinoline, indole, isoindole and benzothiophene radicals. Examples of suitable tricyclic systems include fluorene radicals.

The invention is directed to alkaloid aminoester derivatives of formula (I) and (VI) which act as muscarinic receptor antagonists, and to the salts thereof, said derivatives preferably acting on the M3 receptors.

Advantageously, physiologically acceptable anions $A^-$ include those selected from the group consisting of chloride, bromide, iodide, trifluoroacetate, formate, sulfate, phosphate, methanesulfonate, nitrate, maleate, acetate, citrate, fumarate, tartrate, oxalate, succinate, benzoate, and p-toluenesulfonate, preferably chloride, bromide and iodide.

A preferred group of compounds of general formula (I) is that wherein R1 is hydrogen, R2 is arylalkyl or $(C_1-C_{10})$-alkyl or aryl or $(C_3-C_8)$-cycloalkyl or heteroaryl and R3 is $(C_1-C_{10})$-alkyl or aryl or $(C_3-C_8)$-cycloalkyl or arylalkyl or heteroaryl, preferably substituted with one or more halogen atoms and wherein R6 is as defined above.

A preferred group of compounds of general formula (VI) is that wherein R1 is H, R2 is arylalkyl or $(C_1-C_{10}$-alkyl or aryl or $(C_3-C_8)$-cycloalkyl or heteroaryl and R3 is $(C_1-C_{10})$-alkyl or aryl or $(C_3-C_8)$-cycloalkyl or heteroaryl, preferably substituted with one or more halogen atoms and wherein R7 is a group of formula (vi)

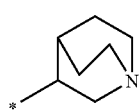

(vi)

according to the general formula (XII):

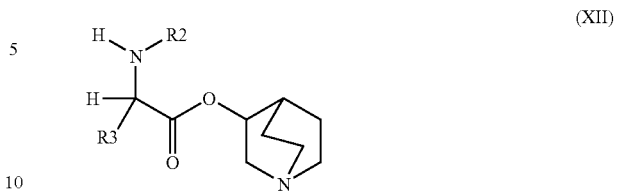

(XII)

A preferred group of compounds of general formula (I) is that wherein R1 is H, R2 is arylalkyl or $(C_1-C_{10})$-alkyl or aryl or $(C_3-C_8)$-cycloalkyl or heteroaryl and R3 is $(C_1-C_{10})$-alkyl or aryl or $(C_3-C_8)$-cycloalkyl or arylalkyl or heteroaryl, preferably substituted with one or more halogen atoms and wherein R6 is a group of formula (i)

(i)

according to the general formula (XIII):

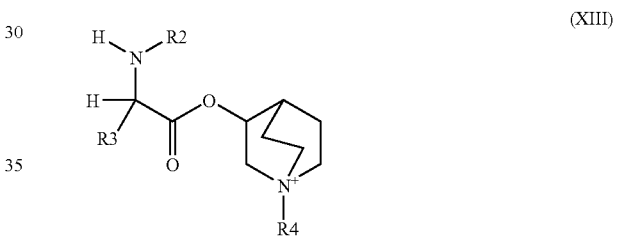

(XIII)

A preferred group of compounds of general formula (XII) is that wherein R2 and R3 are phenyl.

A preferred group of compounds of general formula (XIII) is that wherein R2 and R3 are phenyl.

A preferred group of compounds of general formula (XIII) is represented by the compounds wherein R4 is a group of formula (Y)

(Y)

wherein p is 1, P is CO, q is 0 and W is aryl or heteroaryl.

A preferred group of compounds of general formula (XIII) is represented by the compounds wherein R4 is a group of formula (Y), wherein p is 1, P is CO, q is 0 and W is an optionally phenyl.

A preferred group of compounds of general formula (XIII) is represented by the compounds wherein R4 is a group of formula (Y), wherein p is 1, P is CO, q is 0 and W is thienyl or thiazolyl.

A preferred group of compounds of general formula (XIII) is represented by the compounds wherein R4 is a group of formula (Y), wherein p is 2, P is O, q is 0 and W is phenyl.

A preferred group of compounds of general formula (XIII) is represented by the compounds wherein R4 is a group of formula (Y), wherein p is 3, P is O, q is 0 and W is phenyl.

A preferred group of compounds of general formula (VI) is that wherein R1 is H, R2 is arylalkyl or $(C_1-C_{10})$-alkyl or aryl or $(C_3-C_8)$-cycloalkyl or heteroaryl and R3 is $(C_1-C_{10})$-alkyl or aryl or $(C_3-C_8)$-cycloalkyl or arylalkyl or heteroaryl, preferably substituted with one or more halogen atoms and wherein R7 is a group of formula (vii)

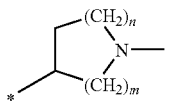
(vii)

wherein m=2 and n=1, according to the general formula (XIV):

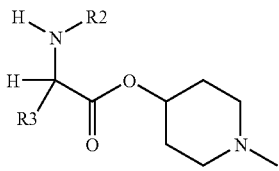
(XIV)

A preferred group of compounds of general formula (XIV) is that wherein R2 and R3 are phenyl, preferably substituted with one or more halogen atoms.

A preferred group of compounds of general formula (VI) is that wherein R1 is H, R2 is arylalkyl or $(C_1-C_{10})$-alkyl or aryl or $(C_3-C_8)$-cycloalkyl or heteroaryl and R3 is $(C_1-C_{10})$-alkyl or aryl or $(C_3-C_8)$-cycloalkyl or arylalkyl or heteroaryl, preferably substituted with one or more halogen atoms and wherein R7 is a group of formula (vii), wherein m=1 and n=1, according to the general formula (XV):

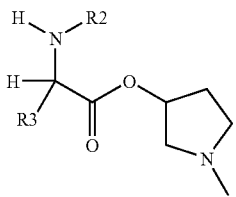
(XV)

A preferred group of compounds of general formula (XV) is that wherein R2 and R3 are phenyl, preferably substituted with one or more halogen atoms.

A preferred group of compounds of general formula (VI) is that wherein R1 is H, R2 is arylalkyl or $(C_1-C_{10})$-alkyl or aryl or $(C_3-C_8)$-cycloalkyl or heteroaryl and R3 is $(C_1-C_{10})$-alkyl or aryl or $(C_3-C_8)$-cycloalkyl or arylalkyl or arylalkyl or heteroaryl, preferably substituted with one or more halogen atoms and wherein R7 is a group of formula (vii), wherein m=1 and n=2, according to the general formula (XVI):

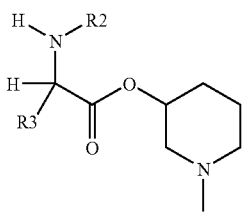
(XVI)

A preferred group of compounds of general formula (XVI) is that wherein R2 and R3 are phenyl, preferably substituted with one or more halogen atoms.

A preferred group of compounds of general formula (VI) is that wherein R1 is H, R2 is arylalkyl or $(C_1-C_{10})$-alkyl or aryl or $(C_3-C_8)$-cycloalkyl or heteroaryl and R3 is $(C_1-C_{10})$-alkyl or aryl or $(C_3-C_8)$-cycloalkyl or arylalkyl or arylalkyl or heteroaryl, preferably substituted with one or more halogen atoms and wherein R7 is a group of formula (viii)

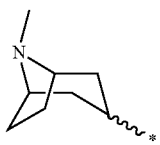
(viii)

according to the general formula (XVII):

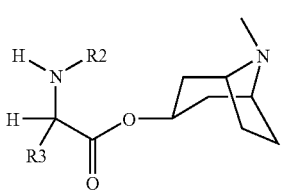
(XVII)

A preferred group of compounds of general formula (XVII) is that wherein R2 and R3 are phenyl, preferably substituted with one or more halogen atoms.

A preferred group of compounds of general formula (VI) is that wherein R1 is H, R2 is arylalkyl or $(C_1-C_{10})$-alkyl or aryl or $(C_3-C_8)$-cycloalkyl or heteroaryl and R3 is $(C_1-C_{10})$-alkyl or aryl or $(C_3-C_8)$-cycloalkyl or arylalkyl or arylalkyl or heteroaryl, preferably substituted with one or more halogen atoms and wherein R7 is a group of formula (ix)

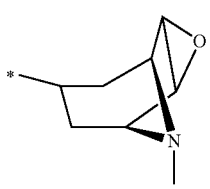
(ix)

according to the general formula (XVIII):

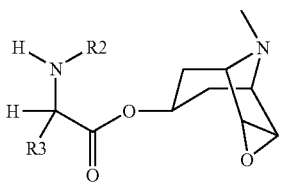
(XVIII)

A preferred group of compounds of general formula (XVIII) is that wherein R2 and R3 are phenyl.

A preferred group of compounds are the corresponding quaternary ammonium salts of compounds of general formula (XII), (XIV), (XV), (XVII), and (XVIII).

It will be apparent to those skilled in the art that the compounds of general formula (I) and (VI) may contain asymmetric centers. Therefore the invention also includes the optical stereoisomers and mixtures thereof.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The active compounds of general formula (VI) and in particular compounds of general formula (XII), (XIII), (XV), and (XVI) wherein R3 is different from H, show at least two chiral centers, which are respectively represented by the alkaloid carbon atom bearing the aminoester group and the carbon atom bearing H, R3 and NHR2. Compounds of general formula (XII), (XIII), (XV), and (XVI) wherein R3 is different from H can be obtained in S—R, R—R, R—S, S—S configuration or as a mixture of diastereoisomers (R—R and S—R configuration or R—S and S—S configuration).

According to a preferred embodiment, compounds of general formula (XII), (XIII), (XV), and (XVI) wherein R3 is different from H, show a (R,R) configuration.

The active compounds of formula (I) and (VI) show at least one chiral center, which is represented by the alkaloid carbon atom bearing the aminoester group.

According to a further embodiment, compound (I) is in the form of (S)-enantiomer when R6 is a group of formula (i).

According to a preferred embodiment, compound (I) is in the form of (R)-enantiomer when R6 is a group of formula (i).

According to specific embodiments, the present invention provides the compounds reported below:

| Compound | Chemical name |
|---|---|
| C2 | (R)-quinuclidin-3-yl 2-phenyl-2-(phenylamino)acetate |
| C3 | (R)-quinuclidin-3-yl 2-(4-fluorophenyl)-2-(4-fluorophenylamino)acetate |
| C4 | (R)-quinuclidin-3-yl 2-(methyl(phenyl)amino)-2-phenylacetate |
| C12 | (R)-quinuclidin-3-yl 2-(3-fluorophenyl)-2-(3-fluorophenylamino)acetate |
| C13 | (R)-1-methylpiperidin-4-yl-2-phenyl-2-(phenylamino)acetate |
| C14 | (R)-1-methylpyrrolidin-4-yl-2-phenyl-2-(phenylamino)acetate |
| C15 | (S)-1-methylpyrrolidin-4-yl-2-phenyl-2-(phenylamino)acetate |
| C16 | (R)-1-methylpiperidin-3-yl 2-phenyl-2-(phenylamino)acetate |
| C17 | 8-methyl-8-azabicyclo[3.2.1]octan-3-yl 2-phenyl-2-(phenylamino)acetate |
| C18 | Phenyl-phenylamino-acetic acid 9-methyl-3-oxa-9-aza-tricyclo[3.3.1.0*2,4*]non-7-yl ester |
| C20 | (R)-quinuclidin-3-yl) 2-amino-3-phenylpropanoate di-trifluoroacetate |
| C22 | 3-phenyl-2-phenylamino-propionic acid (R)-(1-aza-bicyclo[2.2.2]oct-3-yl) ester |
| C24 | (R)-quinuclidin-3-yl 2-(benzylamino)-2-phenylacetate |
| C25 | (R)-quinuclidin-3-yl 2-amino-2-phenylacetate di-hydrochloride |
| C26 | (R)-quinuclidin-3-yl 2-(cyclopentylamino)-2-phenylacetate di-trifluoroacetate |
| C27 | (R)-quinuclidin-3-yl 2-(cyclohexylamino)-2-phenylacetate |
| C29 | ((4-chloro-phenylamino)-phenyl-acetic acid (R)-(1-aza-bicyclo[2.2.2]oct-3-yl) ester |
| C30 | 4-({[(R)-(1-aza-bicyclo[2.2.2]oct-3-yl)oxycarbonyl]-phenyl-methyl}-amino)-benzoic acid methyl ester |
| C31 | 3-({[(R)-(1-aza-bicyclo[2.2.2]oct-3-yl)oxycarbonyl]-phenyl-methyl}-amino)-thiophene-2-carboxylic acid methyl ester |
| C32 | (4-fluoro-phenylamino)-phenyl-acetic acid (R)-(1-aza-bicyclo[2.2.2]oct-3-yl) ester |
| C33 | (4-fluoro-phenyl)-phenylamino-acetic acid (R)-(1-aza-bicyclo[2.2.2]oct-3-yl) ester |
| C35 | 2-({[(R)-(1-aza-bicyclo[2.2.2]oct-3-yl)oxycarbonyl]-phenyl-methyl}-amino)-benzoic acid methyl ester |
| C37 | (2-methoxy-phenylamino)-phenyl-acetic acid (R)-(1-aza-bicyclo[2.2.2]oct-3-yl) ester |
| C39 | phenyl-o-methyl phenylamino-acetic acid (R)-(1-aza-bicyclo[2.2.2]oct-3-yl) ester |
| C41 | phenyl-(3-trifluoromethoxy-phenylamino)-acetic acid (R)-(1-aza-bicyclo[2.2.2]oct-3-yl) ester |
| C43 | (3-ethyl-phenylamino)-phenyl-acetic acid (R)-(1-aza-bicyclo[2.2.2]oct-3-yl) ester |
| C46 | (3-acetylamino-phenylamino)-phenyl-acetic acid (R)-(1-aza-bicyclo[2.2.2]oct-3-yl) ester |
| C47 | (3-methylcarbamoyl-phenylamino)-phenyl-acetic acid (R)-(1-aza-bicyclo[2.2.2]oct-3-yl) ester |
| C52 | (3-methylsulfanyl-phenylamino)-phenyl-acetic acid (R)-(1-aza-bicyclo[2.2.2]oct-3-yl) ester |
| C53 | (3-acetyl-phenylamino)-phenyl-acetic acid (R)-(1-aza-bicyclo[2.2.2]oct-3-yl) ester |
| C55 | (2,5-dimethoxy-phenylamino)-phenyl-acetic acid (R)-(1-aza-bicyclo[2.2.2]oct-3-yl) ester |
| C58 | (2,5-difluoro-phenylamino)-phenyl-acetic acid (R)-(1-aza-bicyclo[2.2.2]oct-3-yl) ester |
| C59 | (2,6-dimethyl-phenylamino)-phenyl-acetic acid (R)-(1-aza-bicyclo[2.2.2]oct-3-yl) ester |
| C61 | (2-ethyl-phenylamino)-phenyl-acetic acid (R)-(1-aza-bicyclo[2.2.2]oct-3-yl) ester |
| C64 | (2-acetyl-phenylamino)-phenyl-acetic acid (R)-(1-aza-bicyclo[2.2.2]oct-3-yl) ester |

-continued

| Compound | Chemical name |
|---|---|
| C65 | (3,5-difluoro-phenylamino)-phenyl-acetic acid (R)-(1-aza-bicyclo[2.2.2]oct-3-yl) ester |
| C67 | 3-({[(R)-(1-aza-bicyclo[2.2.2]oct-3-yl)oxycarbonyl]-phenyl-methyl}-amino)-benzoic acid ethyl ester |
| C69 | (3-methoxy-phenylamino)-phenyl-acetic acid (R)-(1-aza-bicyclo[2.2.2]oct-3-yl) ester |
| C72 | [(4-fluoro-phenyl)-methyl-amino]-phenyl-acetic acid (R)-(1-aza-bicyclo[2.2.2]oct-3-yl) ester |
| C75 | (methyl-phenyl-amino)-phenyl-acetic acid (R)-(1-aza-bicyclo[2.2.2]oct-3-yl) ester |
| C77 | (4-methyl-benzylamino)-phenyl-acetic acid (R)-(1-aza-bicyclo[2.2.2]oct-3-yl) ester |
| C78 | (4-fluoro-benzylamino)-phenyl-acetic acid (R)-(1-aza-bicyclo[2.2.2]oct-3-yl) ester |
| C79 | (4-methoxy-benzylamino)-phenyl-acetic acid (R)-(1-aza-bicyclo[2.2.2]oct-3-yl) ester |
| C80 | benzylamino-phenyl-acetic acid (R)-(1-aza-bicyclo[2.2.2]oct-3-yl) ester |
| C82 | (4-fluoro-benzylamino)-phenyl-acetic acid (R)-(1-aza-bicyclo[2.2.2]oct-3-yl) ester |
| C84 | (4-fluoro-phenyl)-(3-fluoro-phenylamino)-acetic acid (R)-(1-aza-bicyclo[2.2.2]oct-3-yl) ester |
| C85 | (4-fluoro-phenyl)-(2-fluoro-phenylamino)-acetic acid (R)-(1-aza-bicyclo[2.2.2]oct-3-yl) ester |
| C90 | (R)-quinuclidin-3-yl 2-(phenylamino)-2-(thiophen-2-yl)acetate hydrochloride |
| C93 | (4-methoxy-phenyl)-phenylamino-acetic acid (R)-(1-aza-bicyclo[2.2.2]oct-3-yl) ester |
| C95 | 4-{[(R)-(1-aza-bicyclo[2.2.2]oct-3-yl)oxycarbonyl]-phenylamino-methyl}-benzoic acid methyl ester |
| C99 | (3-fluoro-phenyl)-phenylamino-acetic acid (R)-(1-aza-bicyclo[2.2.2]oct-3-yl) ester |
| C100 | (4-fluoro-phenyl)-phenylamino-acetic acid (R)-(1-aza-bicyclo[2.2.2]oct-3-yl) ester |
| C105 | phenylamino-(4-trifluoromethyl-phenyl)-acetic acid (R)-(1-aza-bicyclo[2.2.2]oct-3-yl) ester |
| C106 | (S)-quinuclidin-3-yl 2-phenyl-2-(phenylamino)-acetate |
| C107 | phenyl-phenylamino-acetic acid 1-methyl-azepan-4-yl ester |
| C108 | (R)-1-(2-phenoxyethyl)-3-(2-phenyl-2-(phenylamino)acetoxy)-1-azonia-bicyclo[2.2.2]octane trifluoroacetate |
| C109 | (R)-1-(2-oxo-2-(thiophen-2-yl)ethyl)-3-(2-phenyl-2-(phenylamino)acetoxy)-1-azonia-bicyclo[2.2.2]octane trifluoroacetate |
| C110 | (R)-1-(3-phenoxypropyl)-3-(2-phenyl-2-(phenylamino)acetoxy)-1-azonia-bicyclo[2.2.2]octane trifluoroacetate |
| C111 | (R)-1-methyl-3-(2-phenyl-2-(phenylamino)acetoxy)-1-azonia-bicyclo[2.2.2]octane trifluoroacetate |
| C112 | (R)-1-(2-phenoxyethyl)-3-(2-phenyl-2-(phenylamino)acetoxy)-1-azonia-bicyclo[2.2.2]octane trifluoroacetate |
| C113 | (R)-1-(2-oxo-2-phenylethyl)-3-(2-phenyl-2-(phenylamino)acetoxy)-1-azonia-bicyclo[2.2.2]octane trifluoroacetate |
| C114 | (3R)-1-oxo-2-(thiophen-3-yl)ethyl)-3-(2-phenyl-2-(phenylamino)-acetoxy)-1-azonia-bicyclo[2.2.2]octane trifluoroacetate |
| C115 | (3R)-1-(2-(4-fluorophenyl)-2-oxoethyl)-3-(2-phenyl-2-(phenylamino)-acetoxy)-1-azonia-bicyclo[2.2.2]octane trifluoroacetate |
| C116 | (R)-1-phenethyl-3-(2-phenyl-2-(phenylamino)acetoxy)-1-azonia-bicyclo[2.2.2]octane trifluoroacetate |
| C117 | (R)-1-(2-(benzo[b]thiophen-2-yl)-2-oxoethyl)-3-(2-phenyl-2-(phenylamino)acetoxy)-1-azonia-bicyclo[2.2.2]octane trifluoroacetate |
| C118 | (3R)-3-(2-(4-fluorophenyl)-2-(4-fluorophenylamino)acetoxy)-1-(2-oxo-2-(thiophen-2-yl)ethyl)-1-azonia-bicyclo[2.2.2]octane trifluoroacetate |
| C119 | (3R)-3-(2-(4-fluorophenyl)-2-(4-fluorophenylamino)acetoxy)-1-(2-oxo-2-phenylethyl)-1-azonia-bicyclo[2.2.2]octane trifluoroacetate |
| C120 | (3R)-3-(2-(4-fluorophenyl)-2-(4-fluorophenylamino)acetoxy)-1-methyl-1-azonia-bicyclo[2.2.2]octane trifluoroacetate |
| C121 | (3R)-3-(2-(3-fluorophenyl)-2-(3-fluorophenylamino)acetoxy)-1-(2-oxo-2-phenylethyl)-1-azonia-bicyclo[2.2.2]octane trifluoroacetate |
| C122 | (3R)-3-(2-(methyl(phenyl)amino)-2-phenylacetoxy)-1-(2-oxo-2-(thiophen-2-yl)ethyl)-1-azonia-bicyclo[2.2.2]octane trifluoroacetate |
| C123 | (3R)-3-(2-(methyl(phenyl)amino)-2-phenylacetoxy)-1-(2-oxo-2-phenylethyl)-1-azonia-bicyclo[2.2.2]octane trifluoroacetate |
| C124 | (R)-1-(2-phenoxyethyl)-3-(3-phenyl-2-(phenylamino)propanoyloxy)-1-azonia-bicyclo[2.2.2]octane trifluoroacetate |
| C125 | (R)-1-(2-oxo-2-(thiophen-2-yl)ethyl)-3-((S)-3-phenyl-2-(phenylamino)propanoyloxy)-1-azonia-bicyclo[2.2.2]octane trifluoroacetate |
| C126 | (R)-1-methyl-3-(3-phenyl-2-(phenylamino)propanoyloxy)-1-azonia-bicyclo[2.2.2]octane trifluoroacetate |
| C127 | (R)-1-(2-oxo-2-phenylethyl)-3-((S)-3-phenyl-2-(phenylamino)propanoyloxy)-1-azonia-bicyclo[2.2.2]octane trifluoroacetate |

-continued

| Compound | Chemical name |
|---|---|
| C128 | (3R)-3-(2-(benzylamino)-2-phenylacetoxy)-1-(2-oxo-2-phenylethyl)-1-azonia-bicyclo[2.2.2]octane trifluoroacetate |
| C129 | (R)-1-(2-oxo-2-pyridin-4-yl-ethyl)-3-(2-phenyl-2-phenylamino-acetoxy)-1-azonia-bicyclo[2.2.2]octane trifluoroacetate |
| C130 | (R)-1-[2-(3-chloro-thiophen-2-yl)-2-oxo-ethyl]-3-(2-phenyl-2-phenylamino-acetoxy)-1-azonia-bicyclo[2.2.2]octane trifluoroacetate |
| C131 | (R)-1-[2-(5-methyl-thiophen-2-yl)-2-oxo-ethyl]-3-(2-phenyl-2-phenylamino-acetoxy)-1-azonia-bicyclo[2.2.2]octane trifluoroacetate |
| C132 | (R)-1-[2-(1-methyl-1H-pyrrol-2-yl)-2-oxo-ethyl]-3-(2-phenyl-2-phenylamino-acetoxy)-1-azonia-bicyclo[2.2.2]octane trifluoroacetate |
| C133 | (R)-1-[2-(2,4-dimethyl-oxazol-5-yl)-2-oxo-ethyl]-3-(2-phenyl-2-phenylamino-acetoxy)-1-azonia-bicyclo[2.2.2]octane trifluoroacetate |
| C134 | (R)-3-(2-phenyl-2-phenylamino-acetoxy)-1-(3-phenylsulfanyl-propyl)-1-azonia-bicyclo[2.2.2]octane formate |
| C135 | (R)-3-[2-(3-ethyl-phenylamino)-2-phenyl-acetoxy]-1-(2-oxo-2-phenyl-ethyl)-1-azonia-bicyclo[2.2.2]octane formate |
| C136 | (R)-3-[2-(4-methoxycarbonyl-phenylamino)-2-phenyl-acetoxy]-1-(2-oxo-2-phenyl-ethyl)-1-azonia-bicyclo[2.2.2]octane trifluoroacetate |
| C137 | (3R)-3-(2-phenyl-2-(phenylamino)acetoxy)-1-(2-(phenylthio)ethyl)-1-azonia-bicyclo[2.2.2]octane trifluoroacetate |
| C138 | (3R)-1-(cyclohexylmethyl)-3-(2-phenyl-2-(phenylamino)acetoxy)-1-azonia-bicyclo[2.2.2]octane trifluoroacetate |
| C139 | (3R)-1-(4-methylpent-3-enyl)-3-(2-phenyl-2-(phenylamino)acetoxy)-1-azonia-bicyclo[2.2.2]octane trifluoroacetate |
| C140 | (3R)-1-(2-(3,4-dichlorophenyl)-2-oxoethyl)-3-(2-phenyl-2-(phenylamino)acetoxy)-1-azonia-bicyclo[2.2.2]octane trifluoroacetate |
| C141 | (R)-1-(2-oxo-2-phenylethyl)-3-(2-phenyl-2-(phenylamino)acetoxy)-1-azonia-bicyclo[2.2.2]octane trifluoroacetate |
| C142 | 3-(3-(3-fluorophenyl)-3-(3-fluorophenylamino)-2-oxopropyl)-1-(2-oxo-2-(thiophen-2-yl)ethyl)-1-azonia-bicyclo[2.2.2]octane chloride |
| C143 | (R)-1-(2-amino-2-oxoethyl)-3-(2-phenyl-2-(phenylamino)acetoxy)-1-azonia-bicyclo[2.2.2]octane bromide |
| C144 | (R)-1-(2-oxo-2-(phenylamino)ethyl)-3-(2-phenyl-2-(phenylamino)-acetoxy)-1-azonia-bicyclo[2.2.2]octane bromide |
| C145 | (3R)-1-(2-oxo-2-phenylethyl)-3-(2-phenyl-2-(phenylamino)acetoxy)-1-azonia-bicyclo[2.2.2]octane bromide |
| C146 | (3R)-3-(2-(benzylamino)-2-phenylacetoxy)-1-(2-oxo-2-(thiophen-2-yl)ethyl)-1-azonia-bicyclo[2.2.2]octane chloride |
| C147 | (R)-1-(2-oxo-2-phenyl-ethyl)-3-((R)-2-phenyl-2-phenylamino-acetoxy)-1-azonia-bicyclo[2.2.2]octane bromide |
| C149 | (R)-3-((S)-2-amino-phenylpropanoyloxy)-1-(2-phenoxyethyl)-1-azonia-bicyclo[2.2.2]octane trifluoroacetate |
| C150 | (R)-3-((S)-2-amino-3-phenylpropanoyloxy)-1-(2-oxo-2-(thiophen-2-yl)ethyl)-1-azonia-bicyclo[2.2.2]octane trifluoroacetate |
| C151 | (R)-3-((S)-2-amino-3-phenylpropanoyloxy)-1-(3-phenoxypropyl)-1-azonia-bicyclo[2.2.2]octane trifluoroacetate |
| C152 | (R)-3-((S)-2-amino-3-phenylpropanoyloxy)-1-(2-oxo-2-phenylethyl)-1-azonia-bicyclo[2.2.2]octane trifluoroacetate |
| C153 | (R)-1-(2-oxo-2-phenylethyl)-3-((R)-3-phenyl-2-(phenylamino)-propanoyloxy)-1-azoniabicyclo[2.2.2]octane bromide |
| C154 | (R)-1-(2-oxo-2-(thiophen-2-yl)ethyl)-3-((R)-3-phenyl-2-(phenylamino)-propanoyloxy)-1-azonia-bicyclo[2.2.2]octane chloride |
| C155 | (R)-1-[2-(4-methoxy-phenyl)-2-oxo-ethyl]-3-(2-phenyl-2-phenylamino-acetoxy)-1-azonia-bicyclo[2.2.2]octane trifluoroacetate |
| C156 | (R)-1-(4-oxo-4-phenyl-butyl)-3-(2-phenyl-2-phenylamino-acetoxy)-1-azonia-bicyclo[2.2.2]octane trifluoroacetate |
| C157 | (R)-1-(4-oxo-4-phenyl-butyl)-3-(2-phenyl-2-phenylamino-acetoxy)-1-azonia-bicyclo[2.2.2]octane trifluoroacetate |
| C158 | (R)-1-benzyl-3-(2-phenyl-2-phenylamino-acetoxy)-1-azonia-bicyclo[2.2.2]octane trifluoroacetate |
| C159 | (R)-1-benzyl-3-(2-phenyl-2-phenylamino-acetoxy)-1-azonia-bicyclo[2.2.2]octane trifluoroacetate |
| C160 | (R)-1-benzyl-3-(2-phenyl-2-phenylamino-acetoxy)-1-azonia-bicyclo[2.2.2]octane trifluoroacetate |
| C161 | (R)-1-[2-(4-methoxy-phenyl)-2-oxo-ethyl]-3-(2-phenyl-2-phenylamino-acetoxy)-1-azonia-bicyclo[2.2.2]octane trifluoroacetate |
| C162 | (R)-1-[2-(4-methylsulfonyl-phenyl)-2-oxo-ethyl]-3-(2-phenyl-2-phenylamino-acetoxy)-1-azonia-bicyclo[2.2.2]octane trifluoroacetate |
| C163 | (R)-1-[2-(3-hydroxy-phenyl)-2-oxo-ethyl]-3-(2-phenyl-2-phenylamino-acetoxy)-1-azonia-bicyclo[2.2.2]octane trifluoroacetate |
| C164 | (R)-1-dimethylcarbamoylmethyl-3-(2-phenyl-2-phenylamino-acetoxy)-1-azonia-bicyclo[2.2.2]octane trifluoroacetate |
| C165 | (R)-1-(2-oxo-propyl)-3-(2-phenyl-2-phenylamino-acetoxy)-1-azonia-bicyclo[2.2.2]octane trifluoroacetate |
| C166 | (R)-3-[2-(2-methoxycarbonyl-thiophen-3-yl)-2-phenylamino-acetoxy]-1-(2-oxo-2-phenyl-ethyl)-1-azonia-bicyclo[2.2.2]octane trifluoroacetate |
| C167 | (R)-3-[2-(2-methoxycarbonyl-thiophen-3-yl)-2-phenylamino-acetoxy]-1-(2-oxo-2-thiophen-2-yl-ethyl)-1-azonia-bicyclo[2.2.2]octane trifluoroacetate |

-continued

| Compound | Chemical name |
|---|---|
| C168 | (R)-3-[2-(4-methoxy-phenyl)-2-phenylamino-acetoxy]-1-(2-oxo-2-phenyl-ethyl)-1-azonia-bicyclo[2.2.2]octane formate |
| C169 | (R)-3-[2-(4-chloro-phenylamino)-2-phenyl-acetoxy]-1-(2-oxo-2-phenyl-ethyl)-1-azonia-bicyclo[2.2.2]octane trifluoroacetate |
| C170 | (R)-1-(2-oxo-2-phenyl-ethyl)-3-[2-phenylamino-2-(4-trifluoromethyl-phenyl)-acetoxy]-1-azonia-bicyclo[2.2.2]octane trifluoroacetate |
| C171 | (R)-1-methyl-1-(2-oxo-2-phenyl-ethyl)-3-(2-phenyl-2-phenylamino-acetoxy)-pyrrolidinium trifluoroacetate |
| C172 | 1,1-dimethyl-4-(2-phenyl-2-phenylamino-acetoxy)-piperidinium trifluoroacetate |
| C173 | (R)-1-[2-(5-methyl-thiophen-3-yl)-2-oxo-ethyl]-3-(2-phenyl-2-phenylamino-acetoxy)-1-azonia-bicyclo[2.2.2]octane trifluoroacetate |
| C174 | (R)-1-[2-(2,4-difluoro-phenyl)-2-oxo-ethyl]-3-(2-phenyl-2-phenylamino-acetoxy)-1-azonia-bicyclo[2.2.2]octane bromide |
| C175 | (R)-1-[2-(3,4-difluoro-phenyl)-2-oxo-ethyl]-3-(2-phenyl-2-phenylamino-acetoxy)-1-azonia-bicyclo[2.2.2]octane bromide |
| C176 | (R)-1-[2-(2-fluoro-phenyl)-2-oxo-ethyl]-3-(2-phenyl-2-phenylamino-acetoxy)-1-azonia-bicyclo[2.2.2]octane bromide |
| C177 | (R)-1-[2-(3-fluoro-phenyl)-2-oxo-ethyl]-3-(2-phenyl-2-phenylamino-acetoxy)-1-azonia-bicyclo[2.2.2]octane bromide |
| C178 | (R)-1-[2-(2,4-dibromo-phenyl)-2-oxo-ethyl]-3-(2-phenyl-2-phenylamino-acetoxy)-1-azonia-bicyclo[2.2.2]octane chloride |
| C179 | (R)-1-[2-(4-nitro-phenyl)-2-oxo-ethyl]-3-(2-phenyl-2-phenylamino-acetoxy)-1-azonia-bicyclo[2.2.2]octane bromide |
| C180 | (R)-1-[2-(4-hydroxy-phenyl)-2-oxo-ethyl]-3-(2-phenyl-2-phenylamino-acetoxy)-1-azonia-bicyclo[2.2.2]octane bromide |
| C181 | (R)-1-[2-oxo-2-(2-oxo-2,3-dihydro-1H-indol-5-yl)-ethyl]-3-(2-phenyl-2-phenylamino-acetoxy)-1-azonia-bicyclo[2.2.2]octane bromide |
| C182 | (R)-1-(2-benzo[1,3]dioxol-5-yl-2-oxo-ethyl)-3-(2-phenyl-2-phenylamino-acetoxy)-1-azonia-bicyclo[2.2.2]octane bromide |
| C183 | (R)-1-(2-oxo-2-thiazol-2-yl-ethyl)-3-(2-phenyl-2-phenylamino-acetoxy)-1-azonia-bicyclo[2.2.2]octane bromide |
| C184 | (R)-1-[2-(3-ethoxycarbonyl-isoxazol-5-yl)-2-oxo-ethyl]-3-(2-phenyl-2-phenylamino-acetoxy)-1-azonia-bicyclo[2.2.2]octane bromide |
| C185 | (R)-1-[2-(4-methyl-thiophen-2-yl)-2-oxo-ethyl]-3-(2-phenyl-2-phenylamino-acetoxy)-1-azonia-bicyclo[2.2.2]octane bromide |
| C186 | (R)-1-(2-benzo[b]thiophen-5-yl-2-oxo-ethyl)-3-(2-phenyl-2-phenylamino-acetoxy)-1-azonia-bicyclo[2.2.2]octane bromide |
| C187 | (R)-3-(2-phenyl-2-phenylamino-acetoxy)-1-phenylsulfanylmethyl-1-azonia-bicyclo[2.2.2]octane chloride |
| C188 | (R)-1-(2-oxo-2-piperidin-1-yl-ethyl)-3-(2-phenyl-2-phenylamino-acetoxy)-1-azonia-bicyclo[2.2.2]octane chloride |
| C189 | (R)-3-(2-phenyl-2-phenylamino-acetoxy)-1-(thiazol-2-ylcarbamoylmethyl)-1-azonia-bicyclo[2.2.2]octane chloride |
| C190 | (R)-1-(isoxazol-3-ylcarbamoylmethyl)-3-(2-phenyl-2-phenylamino-acetoxy)-1-azonia-bicyclo[2.2.2]octane chloride |
| C191 | (R)-1-(2-oxo-2-phenyl-ethyl)-3-(2-phenyl-2-p-methylphenylamino-acetoxy)-1-azonia-bicyclo[2.2.2]octane bromide |
| C192 | (R)-3-[2-(4-fluoro-phenylamino)-2-phenyl-acetoxy]-1-(2-oxo-2-phenyl-ethyl)-1-azonia-bicyclo[2.2.2]octane bromide |
| C193 | (R)-3-[2-(4-fluoro-phenylamino)-2-phenyl-acetoxy]-1-(2-oxo-2-thiophen-2-yl-ethyl)-1-azonia-bicyclo[2.2.2]octane chloride |
| C194 | (R)-3-[2-(2-methoxycarbonyl-phenylamino)-2-phenyl-acetoxy]-1-(2-oxo-2-phenyl-ethyl)-1-azonia-bicyclo[2.2.2]octane bromide |
| C195 | (R)-3-[2-(2-methoxy-phenylamino)-2-phenyl-acetoxy]-1-(2-oxo-2-phenyl-ethyl)-1-azonia-bicyclo[2.2.2]octane bromide |
| C196 | (R)-1-(2-oxo-2-phenyl-ethyl)-3-[2-phenyl-2-(3-trifluoromethoxy-phenylamino)-acetoxy]-1-azonia-bicyclo[2.2.2]octane bromide |
| C197 | (R)-1-(2-oxo-2-phenyl-ethyl)-3-(2-phenyl-2-(phenylamino-acetoxy)-1-azonia-bicyclo[2.2.2]octane bromide |
| C198 | (R)-3-[2-(3-acetylamino-phenylamino)-2-phenyl-acetoxy]-1-(2-oxo-2-phenyl-ethyl)-1-azonia-bicyclo[2.2.2]octane bromide |
| C199 | (R)-3-[2-(3-methylcarbamoyl-phenylamino)-2-phenyl-acetoxy]-1-(2-oxo-2-phenyl-ethyl)-1-azonia-bicyclo[2.2.2]octane bromide |
| C200 | (R)-3-[2-(3-methylsulfanyl-phenylamino)-2-phenyl-acetoxy]-1-(2-oxo-2-phenyl-ethyl)-1-azonia-bicyclo[2.2.2]octane bromide |
| C201 | (R)-3-[2-(4-fluoro-phenyl)-2-(3-fluoro-phenylamino)-acetoxy]-1-(2-oxo-2-phenyl-ethyl)-1-azonia-bicyclo[2.2.2]octane bromide |
| C202 | (R)-3-[2-(4-fluoro-phenyl)-2-(3-fluoro-phenylamino)-acetoxy]-1-(2-oxo-2-thiophen-2-yl-ethyl)-1-azonia-bicyclo[2.2.2]octane chloride |
| C203 | (R)-3-[2-(4-fluoro-phenyl)-2-(2-fluoro-phenylamino)-acetoxy]-1-(2-oxo-2-phenyl-ethyl)-1-azonia-bicyclo[2.2.2]octane bromide |
| C204 | (R)-3-[2-(4-fluoro-phenyl)-2-(2-fluoro-phenylamino)-acetoxy]-1-(2-oxo-2-thiophen-2-yl-ethyl)-1-azonia-bicyclo[2.2.2]octane chloride |
| C205 | (R)-3-[2-(4-methoxycarbonyl-phenyl)-2-phenylamino-acetoxy]-1-(2-oxo-2-phenyl-ethyl)-1-azonia-bicyclo[2.2.2]octane bromide |
| C206 | (R)-3-(2-cyclohexylamino-2-phenyl-acetoxy)-1-(2-oxo-2-phenyl-ethyl)-1-azonia-bicyclo[2.2.2]octane bromide |

-continued

| Compound | Chemical name |
|---|---|
| C207 | (R)-3-(2-cyclohexylamino-2-phenyl-acetoxy)-1-(2-oxo-2-thiophen-2-yl-ethyl)-1-azonia-bicyclo[2.2.2]octane chloride |
| C208 | (R)-1-(2-oxo-2-phenyl-ethyl)-3-(2-phenylamino-2-thiophen-2-yl-acetoxy)-1-azonia-bicyclo[2.2.2]octane bromide |
| C209 | (R)-3-[2-(3-fluoro-4-methyl-phenylamino)-2-phenyl-acetoxy]-1-(2-oxo-2-phenyl-ethyl)-1-azonia-bicyclo[2.2.2]octane bromide |
| C210 | (R)-3-[2-(2,5-dimethoxy-phenylamino)-2-phenyl-acetoxy]-1-(2-oxo-2-phenyl-ethyl)-1-azonia-bicyclo[2.2.2]octane bromide |
| C211 | (R)-3-[2-(2,5-difluoro-phenylamino)-2-phenyl-acetoxy]-1-(2-oxo-2-phenyl-ethyl)-1-azonia-bicyclo[2.2.2]octane bromide |
| C212 | (R)-3-[2-(2,6-dimethyl-phenylamino)-2-phenyl-acetoxy]-1-(2-oxo-2-phenyl-ethyl)-1-azonia-bicyclo[2.2.2]octane bromide |
| C213 | (R)-3-[2-(2-ethyl-phenylamino)-2-phenyl-acetoxy]-1-(2-oxo-2-phenyl-ethyl)-1-azonia-bicyclo[2.2.2]octane bromide |
| C214 | (R)-3-[2-(2-acetyl-phenylamino)-2-phenyl-acetoxy]-1-(2-oxo-2-phenyl-ethyl)-1-azonia-bicyclo[2.2.2]octane bromide |
| C215 | (R)-3-[2-(3-ethoxycarbonyl-phenylamino)-2-phenyl-acetoxy]-1-(2-oxo-2-phenyl-ethyl)-1-azonia-bicyclo[2.2.2]octane bromide |
| C216 | (R)-3-[2-(3,5-difluoro-phenylamino)-2-phenyl-acetoxy]-1-(2-oxo-2-phenyl-ethyl)-1-azonia-bicyclo[2.2.2]octane bromide |
| C217 | (R)-3-[2-(3-methoxy-phenylamino)-2-phenyl-acetoxy]-1-(2-oxo-2-phenyl-ethyl)-1-azonia-bicyclo[2.2.2]octane bromide |
| C218 | (R)-3-[2-(3-fluoro-phenyl)-2-phenylamino-acetoxy]-1-(2-oxo-2-phenyl-ethyl)-1-azonia-bicyclo[2.2.2]octane bromide |
| C219 | (R)-3-[2-(4-fluoro-phenyl)-2-phenylamino-acetoxy]-1-(2-oxo-2-phenyl-ethyl)-1-azonia-bicyclo[2.2.2]octane bromide |
| C220 | (R)-1-cyanomethyl-3-(2-phenyl-2-phenylamino-acetoxy)-1-azonia-bicyclo[2.2.2]octane bromide |
| C221 | (R)-1-tert-butoxycarbonylmethyl-3-(2-phenyl-2-phenylamino-acetoxy)-1-azonia-bicyclo[2.2.2]octane bromide |
| C222 | (S)-1-(2-oxo-2-phenyl-ethyl)-3-(2-phenyl-2-phenylamino-acetoxy)-1-azonia-bicyclo[2.2.2]octane chloride |
| C223 | (R)-3-[2-(3-acetyl-phenylamino)-2-phenyl-acetoxy]-1-(2-oxo-2-phenyl-ethyl)-1-azonia-bicyclo[2.2.2]octane formate |
| C224 | (R)-1-[2-(4-acetylamino-phenyl)-2-oxo-ethyl]-3-(2-phenyl-2-phenylamino-acetoxy)-1-azonia-bicyclo[2.2.2]octane bromide |
| C225 | (R)-1-[2-(4-methoxycarbonyl-phenyl)-2-oxo-ethyl]-3-(2-phenyl-2-phenylamino-acetoxy)-1-azonia-bicyclo[2.2.2]octane bromide |
| C226 | (R)-3-(2-phenyl-2-phenylamino-acetoxy)-1-pyridin-2-ylmethyl-1-azonia-bicyclo[2.2.2]octane trifluoroacetate trifluoroacetate anion |
| C227 | (R)-1-(2-oxo-2-pyridin-2-yl-ethyl)-3-(2-phenyl-2-phenylamino-acetoxy)-1-azonia-bicyclo[2.2.2]octane formate formate anion |
| C229 | (R)-1-(2-(2-methylthiazol-4-yl)-2-oxoethyl)-3-((R)-2-phenyl-2-(phenylamino)acetoxy)-1-azoniabicyclo[2.2.2]octane bromide |
| C233 | (R)-1-(6-amino-pyridin-2-ylmethyl)-3-(2-phenyl-2-phenylamino-acetoxy)-1-azonia-bicyclo[2.2.2]octane trifluoroacetate trifluoroacetate anion |
| C234 | (R)-3-{2-[(4-fluoro-phenyl)-methyl-amino]-2-phenyl-acetoxy}-1-(2-oxo-2-thiophen-2-yl-ethyl)-1-azonia-bicyclo[2.2.2]octane chloride |
| C235 | (R)-3-[2-(methyl-phenyl-amino)-2-phenyl-acetoxy]-1-(2-oxo-2-thiazol-2-yl-ethyl)-1-azonia-bicyclo[2.2.2]octane bromide |
| C236 | (R)-3-[2-(methyl-phenyl-amino)-2-phenyl-acetoxy]-1-(2-oxo-2-thiophen-3-yl-ethyl)-1-azonia-bicyclo[2.2.2]octane |
| C237 | (R)-3-(2-benzylamino-2-phenyl-acetoxy)-1-[2-(3-ethoxycarbonyl-isoxazol-5-yl)-2-oxo-ethyl]-1-azonia-bicyclo[2.2.2]octane bromide |
| C238 | (R)-3-(2-benzylamino-2-phenyl-acetoxy)-1-(2-oxo-2-thiazol-2-yl-ethyl)-1-azonia-bicyclo[2.2.2]octane trifluoroacetate trifluoroacetate anion |
| C239 | (R)-3-(2-benzylamino-2-phenyl-acetoxy)-1-(2-oxo-2-thiophen-3-yl-ethyl)-1-azonia-bicyclo[2.2.2]octane bromide |
| C240 | (R)-3-[2-(4-methyl-benzylamino)-2-phenyl-acetoxy]-1-(2-oxo-2-thiophen-2-yl-ethyl)-1-azonia-bicyclo[2.2.2]octane formate formate anion |
| C241 | (R)-3-[2-(4-methoxy-benzylamino)-2-phenyl-acetoxy]-1-(2-oxo-2-thiophen-2-yl-ethyl)-1-azonia-bicyclo[2.2.2]octane formate formate anion |
| C242 | (R)-3-[2-(4-fluoro-benzylamino)-2-phenyl-acetoxy]-1-(2-oxo-2-thiophen-2-yl-ethyl)-1-azonia-bicyclo[2.2.2]octane chloride |
| C243 | (R)-3-[2-(4-fluoro-benzylamino)-2-phenyl-acetoxy]-1-(2-oxo-2-phenyl-ethyl)-1-azonia-bicyclo[2.2.2]octane bromide |
| C245 | 4-methyl-phenyl-amino-phenyl-acetic acid (R)-(1-aza-bicyclo[2.2.2]oct-3-yl) ester |
| C246 | (R)-1-(2-oxo-2-phenyl-ethyl)-3-(2-phenyl-4-methyl-phenyl-amino-acetoxy)-1-azonia-bicyclo[2.2.2]octane bromide |
| C248 | (2-fluoro-phenylamino)-phenyl-acetic acid (R)-(1-aza-bicyclo[2.2.2]oct-3-yl) ester |
| C249 | (R)-3-[2-(2-fluoro-phenylamino)-2-phenyl-acetoxy]-1-(2-oxo-2-phenyl-ethyl)-1-azonia-bicyclo[2.2.2]octane trifluoroacetate |
| C250 | (R)-3-[2-(3-fluoro-phenylamino)-2-phenyl-acetoxy]-1-(2-oxo-2-phenyl-ethyl)-1-azonia-bicyclo[2.2.2]octane trifluoroacetate |
| C251 | (R)-3-[2-(3-fluoro-phenylamino)-2-phenyl-acetoxy]-1-(2-oxo-2-thiophen-2-yl-ethyl)-1-azonia-bicyclo[2.2.2]octane trifluoroacetate |

-continued

| Compound | Chemical name |
| --- | --- |
| C254 | (R)-(4-fluoro-phenylamino)-phenyl-acetic acid (R)-(1-aza-bicyclo[2.2.2]oct-3-yl) ester |
| C255 | (R)-3-[(R)-2-(4-fluoro-phenylamino)-2-phenyl-acetoxyl-1-(2-oxo-2-thiophen-2-yl-ethyl)-1-azonia-bicyclo[2.2.2]octane chloride |
| C257 | (4-chloro-phenyl)-phenylamino-acetic acid (R)-(1-aza-bicyclo[2.2.2]oct-3-yl) ester |
| C258 | (R)-3-[2-(4-chloro-phenyl)-2-phenylamino-acetoxy]-1-(2-oxo-2-phenyl-ethyl)-1-azonia-bicyclo[2.2.2]octane trifluoroacetate |
| C262 | (2-fluoro-phenyl)-phenylamino-acetic acid (R)-(1-aza-bicyclo[2.2.2]oct-3-yl) ester |
| C263 | (R)-3-[2-(2-fluoro-phenyl)-2-phenylamino-acetoxy]-1-(2-oxo-2-phenyl-ethyl)-1-azonia-bicyclo[2.2.2]octane trifluoroacetate |
| C269 | (5-methyl-thiophen-2-yl)-phenylamino-acetic acid (R)-(1-aza-bicyclo[2.2.2]oct-3-yl) ester |
| C270 | (R)-3-[2-(5-methyl-thiophen-2-yl)-2-phenylamino-acetoxy]-1-(2-oxo-2-phenyl-ethyl)-1-azonia-bicyclo[2.2.2]octane trifluoroacetate |
| C271 | (R)-1-[2-(4-amino-phenyl)-2-oxo-ethyl]-3-((R)-2-phenyl-2-phenylamino-acetoxy)-1-azonia-bicyclo[2.2.2]octane formate |
| C272 | (R)-1-(2-hydroxy-2-phenyl-ethyl)-3-((R)-2-phenyl-2-phenylamino-acetoxy)-1-azonia-bicyclo[2.2.2]octane trifluoroacetate |

The compounds of general formula (I) and (VI) may be prepared according to methods known or evident to a person skilled in the art. Some of the processes which may be used are described below and reported in Scheme 1.

compounds of general formula (III), in which LG is a suitable leaving group (e.g. an halide such as bromine) and K may be either a hydroxyl group or a suitably protected hydroxyl group (e.g. K=OAlkyl such as OMe). The reaction may be

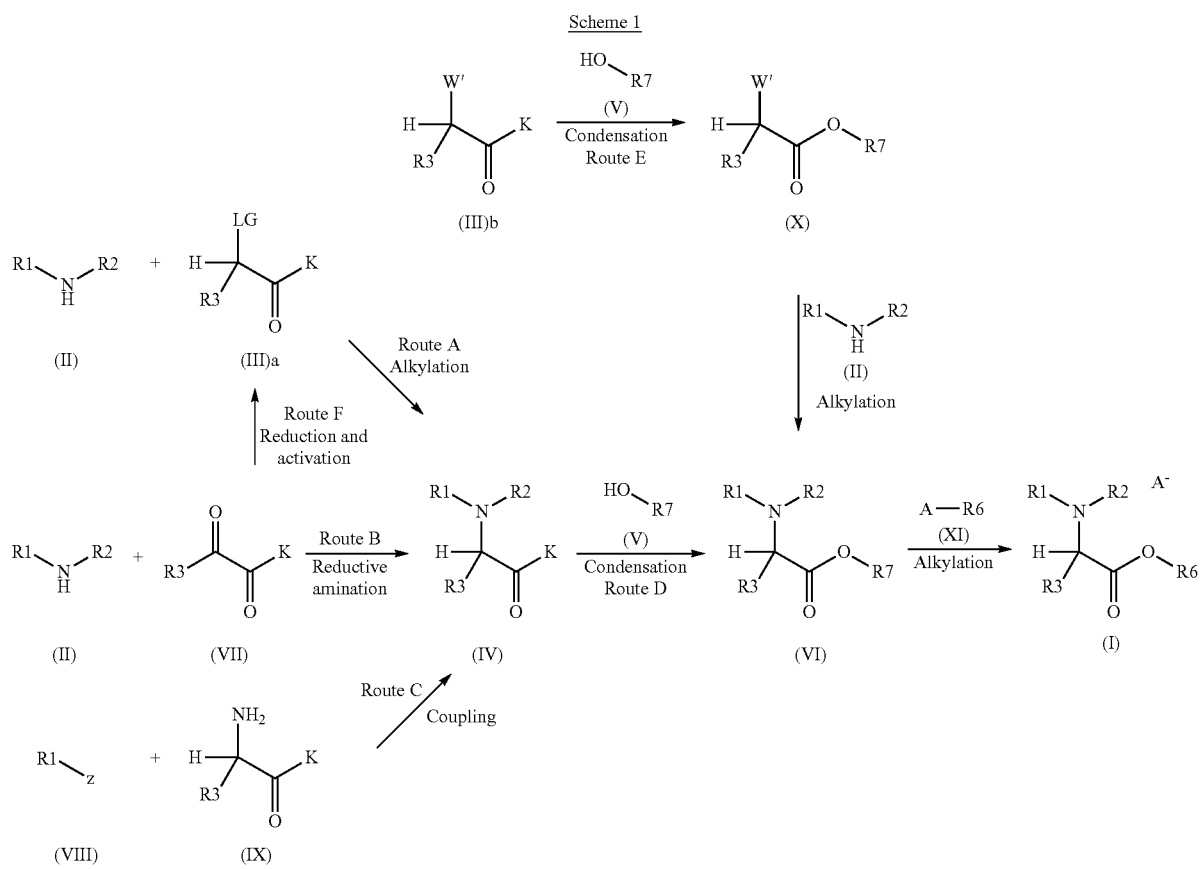

Procedure for the Preparation of Compounds of Formula (I)

Compounds of general formula (IV) may be prepared according to three different routes: A, B and C.

Route A. Alkylation of amine compounds of general formula (II), wherein R1 and R2 are as described above, with promoted by a base selected from the group consisting of triethylamine, pyridine and 4-dimethylaminopyridine, either neat or in a suitable solvent (e.g. acetonitrile). This reaction is usually performed in a temperature range from 0° C. to 130° C. over a period of 1 hour up to 74 hours. The reaction may be conducted under conventional heating (using an oil bath) or under microwave heating. The reaction may be carried out in an open vessel or in a sealed tube.

Reagents of general formula (III) are commercially available or may be conveniently prepared according to standard procedures extensively reported in literature. For instance compounds of general formula (III) in which LG is a halogen such as a bromine, may be prepared by halogenation of the opportunely substituted phenyl acetic ester (for example following the procedure reported by Epstein, J. W., in *J. Med. Chem.*, 1981, 24/5, 481). Alternatively, compounds of general formula (III) may be prepared starting from the appropriately substituted mandelic derivative, using procedures readily apparent to those skilled in the art (a survey of the suitable reactions is given by Larock, L. C., *Comprehensive Organic Transformation*, Second edition (1999), John Wiley & Son Inc, pg 689-700).

Route B. The coupling of amine of general formula (II) and ketones of general formula (VII) may be carried out using a reductive amination reaction, following one of the different procedures reported in literature (e.g.: Suwa T., *Synthesis*, 2000, 6, 789 or Fache, F. *Tetrahedron*, 1996, 52/29, 9777 or Quiang, K., *Adv. Synth. Catal.*, 2007, 349, 1657).

Alternatively, compounds of general formula (VII) can be most conveniently converted into compounds of general formula (III) (Route F) using conditions well known to those skilled in the art. In a typical procedure, ketones (VII) are treated with a reducing agent such as sodium borohydride and the like, in a suitable solvent (e.g. ethanol and methanol) to smoothly provide the corresponding alcohol intermediate. The subsequent conversion of the alcohol moiety in a leaving group (LG) affords compounds of general formula (III). This activation can be effected according to one of the standard procedures broadly reported in the literature (a survey of the suitable reactions is given by Carey, F. A. and Sundeberg, R. J., *Advanced Organic Chemistry*, Third Edition (1990), Plenum Press, New York and London, pg 121). For instance, the alcohol intermediate could be treated with methanesulphonyl chloride (LG=Ms) in presence of a base such as triethylamine, pyridine, 4-dimethylaminopyridine and the like, either neat or in aprotic solvent (e.g. dichloromethane). This reaction is usually performed in a temperature range from 0° C. to 130° C. over a period of 1 hour up to 74 hours.

Route C. Compound (IX) may be reacted with an alkylating agent of general formula (VIII), in which z is a suitable leaving group such as a carbonyl group or an halide (i.e. bromine, iodine, chlorine) or sulfonate ester (i.e. tosylate, triflates, mesylate), according to procedures readily available to those skilled in the art (e.g. Huang, *Tetrahedron*, 1997, 53/37, 12391).

In case z=O, compounds (IX) are reacted with aldehydes or ketones of general formula (VIII) to achieve the corresponding imines that are reduced to compound (IV) by treatment with a suitable reducing agent, following one of the procedures reported in literature (a survey of the suitable reactions is given by Carey, F. A. and Sundeberg, R. J., *Advanced Organic Chemistry*, Third Edition (1990), Plenum Press, New York and London, chapter 5, 219 or Ando, A., Tetrahedron, 1989, 45/16, 4969).

In case R1 is an aryl or heteroaryl and z is a halogen (typically a iodine or bromine), the coupling between compounds of general formula (VIII) and (IX) may be promoted by a suitable catalyst. In a typical procedure the catalyst is a copper catalyst (e.g. copper iodide), and the reaction is performed in the presence of a suitable base selected from the group consisting of potassium and cesium carbonate or amines such as triethylamine, in solvents selected from the group consisting of dimethyl sulfoxide (DMSO) and DMF, at a temperature ranging from ambient to 110° C., over a period ranging from one to 48 hours. The reaction may be carried out under conventional heating (using an oil bath) or under microwave irradiation. The reaction may be conducted either in an open vessel or in a sealed tube (Ma, D., *Tetrahedron Asymmetry*, 1996, 7/11, 3075 or Kurokawa, M., *Heterocycles*, 2007, 71/4, 847).

In case R1 is an aryl or heteroaryl and z is a halogen (typically fluorine or chlorine), compound of general formula (VIII) and (IX) may react under the typical conditions of the aromatic nucleophilic substitution to afford compound (IV). Compounds of general formula (VI) may then be prepared according to two different routes.

Route D. Compounds of formula (VI) may be prepared by coupling alcohols of formula (V) with compounds of formula (IV).

The method for the preparation of compounds of formula (VI) from alcohols (V) and compounds (IV) is chosen on the basis of the reactivity of the alcohol (V), the commercial availability of reagents such as (IV) and the compatibility with the groups present in both the starting materials.

The coupling between (IV) and (V) may be conducted in several ways, in which K may be either a hydroxyl group or a halide such as chlorine (a survey of the suitable reactions is given by Carey, F. A. and Sundeberg, R. J., *Advanced Organic Chemistry*, Third Edition (1990), Plenum Press, New York and London, pg 145 and Montalbetti, C., *Tetrahedron*, 2005, 61, 10827).

In particular, in the case K is a protected hydroxyl group, the protecting group has to be removed before performing the coupling with (V). For instance, if K=OMe, hydrolysis of ester moiety may be performed treating the compound (IV; K=OMe) with a suitable aqueous base selected from the group consisting of sodium, lithium and potassium hydroxide in the opportune solvents (e.g. tetrahydrofuran, dioxane etc). The reaction proceeds at room temperature (RT), over a period of 1 hour up to 36 hours.

Alternative one. In a typical procedure compounds (VI) may be prepared by condensation between (V) and acid (IV) (K=OH) under standard amidation and peptide coupling conditions. For instance, treatment of the acid (IV) (K=OH) with one or more equivalents of a commercially available condensing agent such as a carbodiimide (e.g. 1-(3-dimethylamino)propyl)-3-ethylcarbodiimide hydrochloride (EDC) and the like) for example in the presence of N-hydroxybenzotriazole (HOBt) followed by reaction of the activated intermediate with alcohol (V), results in the formation of compounds (VI). An organic base such as triethylamine may be also present in the reaction mixture. The activated intermediate may be either isolated, or pre-formed or generated in situ. Suitable solvents for the coupling include, but are not limited to, halocarbon solvents (e.g. dichloromethane), tetrahydrofuran, dioxane and acetonitrile. The reaction proceeds at temperature range from 0° C. up to 170° C., for a time in the range of about 1 hour up to 72 hours. The reaction may be carried out under conventional heating (using an oil bath) or under microwave irradiation. The reaction may be conducted either in an open vessel or in a sealed tube.

Alternative two. In the case where K is halogen such as chlorine, the alcohol (V) is reacted with the suitable acyl halide (IV), using methods that are readily apparent to those skilled in the art. The reaction may be promoted by a base such as triethylamine, pyridine and 4-dimethylaminopyridine, in a suitable solvent (e.g. dichloromethane). This reaction is performed in a temperature range from 0° C. to 130° C. over a period of 1 hour up to 74 hours. The reaction may be conducted under conventional heating (using an oil bath) or under microwave heating. The reaction may be carried out in an open vessel or in a sealed tube.

In some embodiments of the present invention, the needed acyl halide (IV) may be readily prepared from the corresponding acid (IV) (K=OH). This activation may be effected according to one of the standard procedures reported in the literature. For instance, treatment of acid (IV) (K=OH) with one or more equivalents of oxalyl chloride in the presence of a catalytic amount of dimethylformamide (DMF) in a halocarbon solvent, such as dichloromethane, at temperature ranging form 0° C. to 35° C., affords the required acyl chloride (IV) (K=Cl).

Alternative three. Alternatively, acylation of alcohol (V) to give compounds of general formula (VI) may be accomplished using procedures which convert in situ the acid (IV) (K=OH) into the corresponding acyl halides. For example, alcohols (V) are reacted with acids (IV) (K=OH) in presence of triphenylphosphine and a halocarbon solvent such as carbon tetrachloride or dichloromethane, at about RT, in a maximum period of time of 16 hours (Lee, J. B., *J. Am. Chem. Soc.*, 1966, 88, 3440).

Alternative four. In another process for the preparation of the compounds of the present invention, acid (IV) (K=OH) may be activated with other commercially available activating agents such as bromotripyrrolidinophosphonium hexafluorophosphate (PyBrOP) or carbonylimidazole, in the suitable aprotic solvent (e.g. dichloromethane, tetrahydrofuran), at about RT. Subsequent reaction of the activated intermediate with alcohol (V) provides the desired compound of formula (VI). The reaction may also require the use of an organic base such as diisopropylethylamine and usually proceeds at about RT.

Alternative five. In another process for the preparation of the compounds of the present invention, compounds (VI) can be efficiently prepared by the condensation between acids (IV) (K=OH) and alcohol (V) under typical Mitsunobu conditions (Kumara Swamy, K. C., *Chem. Rev.*, 2009, 109, 2551-2651). For example, acids (IV) and alcohol (V) are reacted in presence of a phosphine (e.g. triphenylphosphine) and an azadicarboxylate ester (e.g. diethyl azodicarboxylate or diisopropyl azodicarboxylate) in an aprotic solvent such as tetrahydrofuran. The reaction typically proceeds at temperature range from 0° C. up to 100° C., for a time in the range of about 30 minutes up to 72 hours.

Alternatively compounds of formula (VI) may be prepared according to route E. W' may be LG or hydroxy. Compounds of general formula (III) may be coupled to compound of general formula (V) to yield compound (X), applying one of the procedures readily apparent to those skilled in the art. For instance, the conditions used to perform the coupling may be selected among those described to produce the coupling between compound (IV) and (V) in Scheme 1.

In case W' is a halide, the resulting intermediate (X) may then be used as the alkylating agent of amines of general formula (II) to furnish the desired intermediate (VI). This reaction may be performed under the typical conditions extensively reported in literature, such as those described to obtain compound (IV) by coupling (II) and (III) (Scheme 1).

In case W' in compound (III) is hydroxy, it must be converted into a opportune leaving group selected from the group consisting of halide (i.e. bromine, iodine, chlorine) and sulfonate ester (i.e. tosylate, triflates, mesylate), according to procedures available to those skilled in the art (a general overview is given by Carey, F. A. and Sundeberg, R. J., *Advanced Organic Chemistry*, Third Edition (1990), Plenum Press, New York and London, chapter 3, 121), before performing the coupling with amines (II). In case W' is a suitably protected hydroxyl group, it must be deprotected and activated as above before performing the coupling with amines (II).

Compound of general formula (VI), in which R3 and R7 are defined hereinbefore, can be achieved either as single diastereoisomer or as a mixture of diasteroisomers. For instance, in the case R7 is a group of formula (vi), the alcohol can feature either a R or a S configuration. If R-enantiomer is used, compound VI can be obtained in S—R configuration, in R—R configuration or as a mixture of diasteroisomers (R—R and S—R configuration).

The mixture of diastereoisomers may be converted to compounds of formula (I) of Scheme 1 or can be most conveniently resolved to give the two single diasteroisomers, which in turn may be converted to compounds of formula (I) of Scheme 1. This separation can be accomplished using procedures well known to those skilled in the art. These procedures include, but are not limited to, chromatography purification, preparative HPLC purification and crystallization. For example, the two diastereoisomers can be separated by flash chromatography on silica gel eluting with suitable solvents or mixture of solvents such as DCM and Methanol and the like. In another process of the present invention separation of distereoisomers may be obtained using a column filled with a chiral stationary phase, for example Chiralpack AY or Chiralcel OD or Chiralcel OZ, and eluting, for example, with acetonitrile and/or with mixtures of acetonitrile and an alcohol. Alternatively the separatation of diastereoisomers may be most conveniently achieved by crystallization from an opportune solvent (e.g. ethyl ether), as a free base or after the formation of a suitable salt (e.g. (+)-tartaric acid)).

The alkylation of compounds of general formula (VI)

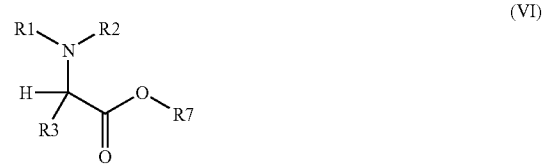

by alkylating agents of general formula (XI)

in which A is a suitable leaving group selected from the group consisting of halide (i.e. bromine, iodine, chlorine) and sulfonate ester (i.e. tosylate, triflates, mesylate) provides compounds of general formula (I).

This kind of reaction is largely described in literature under several different conditions, for instance, the reaction may be performed neat or in a suitable solvent selected from the group consisting of acetonitrile, DMF, DMSO and tetrahydrofuran. The reaction typically proceeds at temperature range from 0° C. up to 170° C., for a time in the range of few minutes up to 72 hours. The reaction may be carried out under conventional heating (using an oil bath) or under microwave irradiation. The reaction may be conducted either in an open vessel or in a sealed tube.

Compounds of general formula (I) in Scheme 1 can be either considered as final products or can be further reacted to prepare other compounds of general formula (I). Thus, a moiety of R1, R2, R3 or R6 group in general formula (I) could undergo reactions of oxidation, reduction or cleavage (e.g to remove a needed protecting group) to afford other final compounds of general formula (I).

The present invention also provides pharmaceutical compositions of compounds of general formula (I) and (VI) in admixture with one or more pharmaceutically acceptable carriers, for example those described in Remington's Pharmaceutical Sciences Handbook, XVII Ed., Mack Pub., N.Y., U.S.A, which is incorporated herein by reference in its entirety.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers or by soft-mist nebulizers.

The compounds of the invention may be administered as the sole active agent or in combination with other pharmaceutical active ingredients including those currently used in the treatment of respiratory disorders, e.g. beta2-agonists, corticosteroids and anticholinergic or antimuscarinic agents.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage comprised between 0.001 and 1000 mg/day, preferably between 0.1 and 500 mg/day.

When the compounds of formula (I) are administered by inhalation route, they are preferably given at a dosage comprised between 0.001 and 500 mg/day, preferably between 0.1 and 200 mg/day.

The compounds of formula (I) may be administered for the prevention and/or treatment of any disease wherein M3 antagonists are active. Said disease include: diseases involving inflammation such as asthma and COPD, acute rhinitis; diseases involving the gastrointestinal tract such as peptic ulcer; diseases involving the cardiovascular system such as acute myocardial infarction; diseases involving the genitourinary tract such as renal colic; anticholinesterase and mushroom poisoning; uses in anesthesia; uses in ophthalmology.

They also include neurological and psychiatric disorders such as Parkinsonism and motion sickness.

Preferably, the compounds of formula (I) may be administered for the prevention and/or treatment of respiratory diseases such as from mild to acute severe conditions of asthma and COPD.

Other respiratory diseases include bronchitis, bronchiolitis, bronchiectasis, acute nasoparyngitis, acute and chronic sinusitis, maxillary sinusitis, pharyngitis, tonsillitis, laryngitis, tracheitis, epiglottitis, croup, chronic disease of tonsils and adenoids, hypertrophy of tonsils and adenoids, peritonsillar abscess, rhinitis, abscess or ulcer and nose, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, and mediastinitis.

Other features of the invention will become apparent in the course of the following descriptions of exemplary embodiments which are given for illustration of the invention and are not intended to be limiting thereof.

EXAMPLES

In the following examples,
I=intermediates; and
C=compounds.

In the entries of NMR data in the following tables, the symbols have the following meanings:
s=singlet
d=doublet
t=triplet
q=quartet
dd=doublet of doublets
m=multiplet
br=broad

Example 1

Preparation of (R)-quinuclidin-3-yl 2-phenyl-2-(phenylamino)-acetate (Diasteroisomers 1 and 2 of C2)

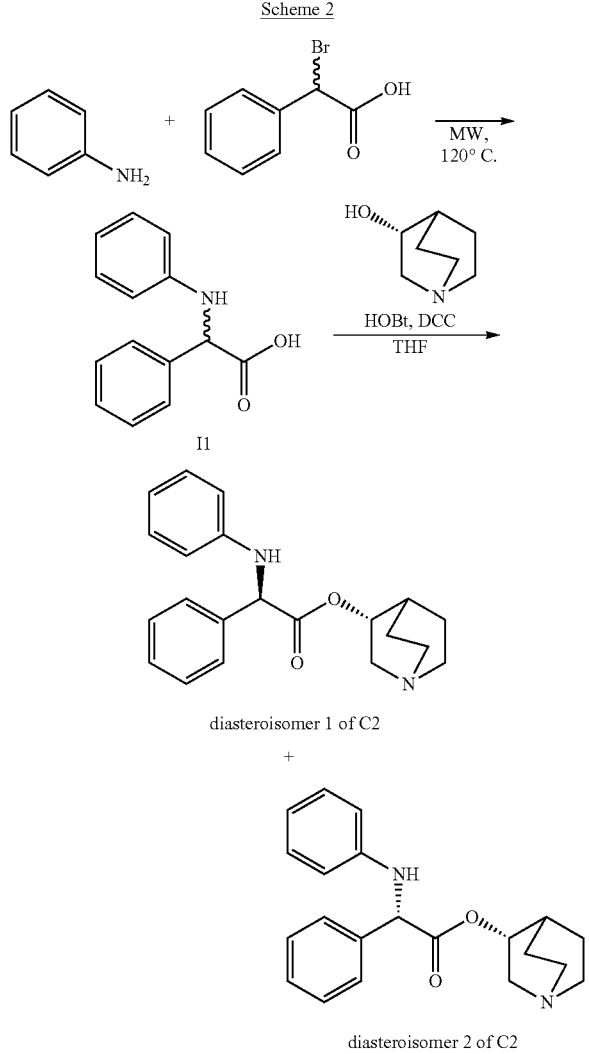

Preparation of 2-phenyl-2-(phenylamino)acetic acid (I1)

α-Bromophenylacetic acid (5.01 g, 23.2 mmol.) is dissolved in aniline (25 mL, 274 mmol) and the mixture reacted in a closed vessel under MW irradiation at 120° C. for 5 minutes (LC-MS monitoring: complete conversion). Dichloromethane (DCM) (100 mL) is added to the reaction mixture and the resulting solid is filtered; 2M $Na_2CO_3$ (50 mL) is added to the solution, and the aqueous layer is washed with DCM (3×100 mL). The aqueous layer is acidified with 12N HCl (36 mL), and the title compound is recovered as racemic mixture by filtration (5.1 g, 97% yield, white solid).

Preparation of (R)-quinuclidin-3-yl 2-phenyl-2-(phenylamino)-acetate (Diasteroisomers 1 and 2 of C2)

To a solution of 2-phenyl-2-(phenylamino)acetic acid (I1) (1.90 g, 8.41 mmol) in dioxane, is added a 4M solution of HCl in dioxane (5 mL) and the reaction is allowed to stir at RT for 1 hour; the solvent is evaporated under reduced pressure to obtain a white solid which is dissolved in dry THF (40 mL). DCC (2.12 g, 10.0 mmol), HOBt (1.33 g, 10.0 mmol) and 3(R)-quinuclidinol (3.10 g, 25.1 mmol) are added to the resulting solution and the mixture stirred for 96 hours at RT under nitrogen flowstream (LC-MS monitoring: complete conversion). The solvent is evaporated, 1N HCl (50 mL) is added to the resulting crude and the aqueous layer is washed with EtOAc (2×100 mL); a saturated solution of $NaHCO_3$ is added to the aqueous layer (pH=7-8) and the desired compound is extracted with DCM. The resulting crude is purified by flash chromatography (DCM/MeOH=95/5, 0.1% $NH_3$ (aq.)) recovering diastereoisomer 1 of C2 as a white solid (0.8 g; 28% yield, single diastereoisomer), and subsequently diastereoisomer 2 of C2 as a white solid (0.4 g, 14% yield, single diastereoisomer).

Diastereoisomer 1 of C2 (80 mg) is furthermore purified by preparative LC-MS in order to obtain 55.3 mg of a pale yellow oil (TFA salt).

Diastereoisomer 2 of C2 (65 mg) is furthermore purified by preparative LC-MS in order to obtain 28.3 mg of a pale yellow oil (TFA salt).

Diastereoisomer 1 of C2:

$^1$H NMR (300 MHz, DMSO-$d_6$) ppm: 9.38 (br. s., 1H), 7.50-7.72 (m, 2H), 7.26-7.50 (m, 3H), 6.98-7.25 (m, 2H), 6.68-6.83 (m, 2H), 6.52-6.68 (m, 1H), 5.34 (s, 1H), 4.92-5.18 (m, 1H), 3.57-3.67 (m, 1H), 3.05-3.33 (m, 3H), 2.57-2.81 (m, 2H), 2.08-2.30 (m, 1H), 1.63-1.94 (m, 4H);

LC-MS (ESI POS): 337.3 (MH+);

$[\alpha]_D$=−32.0° (c=0.5, MeOH).

Diastereoisomer 2 of C2:

$^1$H NMR (300 MHz, DMSO-$d_6$) ppm: 9.49 (br. s., 1H), 7.48-7.64 (m, 2H), 7.25-7.48 (m, 3H), 7.00-7.15 (m, 2H), 6.66-6.78 (m, 2H), 6.52-6.65 (m, 1H), 5.30 (s, 1H), 4.94-5.16 (m, 1H), 3.54-3.76 (m, 1H), 3.03-3.28 (m, 5H), 2.03 (br. s., 1H), 1.65-1.93 (m, 2H), 1.33-1.65 (m, 2H);

LC-MS (ESI POS): 337.3 (MH+);

$[\alpha]_D$=2.4° (c=0.5, MeOH).

The compounds listed in Table 1 are obtained by LC-MS purification as previously described for C2, starting from the suitable commercially available 2-bromo-phenylacetic acid derivatives and anilines.

TABLE 1

| Compound | Structure | Yield and appearance | Analytical |
|---|---|---|---|
| Diastereoisomer 1 of C3 | Single diastereoisomer (TFA salt) | 10% overall yield Pale yellow oil | LC-MS (ESI POS): 373.2 (MH+) $^1$H NMR (300 MHz, DMSO-$d_6$) ppm: 9.50 (br. s., 1 H), 7.47-7.72 (m, 2 H), 7.13-7.38 (m, 2 H), 6.83-7.04 (m, 2 H), 6.60-6.82 (m, 2 H), 5.36 (s, 1 H), 4.92-5.14 (m, 1 H), 3.61 (ddd, 1 H), 3.05-3.29 (m, 3 H), 2.61-2.85 (m, 2 H), 2.16-2.34 (m, 1 H), 1.75-2.03 (m, 3 H), 1.53-1.75 (m, 1 H) |
| Diastereoisomer 2 of C3 | Single diastereoisomer (TFA salt) | 8% overall yield Pale yellow oil | LC-MS (ESI POS): 373.2 (MH+) $^1$H NMR (300 MHz, DMSO-d6) ppm: 9.58 (br. s., 1 H), 7.51-7.67 (m, 2 H), 7.15-7.32 (m, 2 H), 6.83-7.02 (m, 2 H), 6.58-6.81 (m, 2 H), 5.32 (s, 1 H), 4.92-5.13 (m, 1 H), 3.52-3.78 (m, 1 H), 3.04-3.29 (m, 5 H), 1.97-2.10 (m, 1 H), 1.66-1.97 (m, 2 H), 1.42-1.64 (m, 2 H) |
| C4 | Mixture of diastereoisomers (TFA salt) | 13% overall yield Pale yellow oil | LC-MS (ESI POS): 351.3 (MH+) $^1$H NMR (300 MHz, DMSO-d6) ppm: 9.57 (br. s., 1 H), 7.31-7.57 (m, 5 H), 7.14-7.31 (m, 2 H), 6.85-7.02 (m, 2 H), 6.67-6.85 (m, 1 H), 5.92 (s, 1 H), 5.00-5.27 (m, 1 H), 3.59-3.76 (m, 1 H), 2.79-3.29 (m, 5 H), 2.75 (s, 3 H), 2.08-2.24 (m, 1 H), 1.73-2.00 (m, 2 H), 1.45-1.73 (m, 2 H) |

Example 2

Alternative Preparation of (R)-quinuclidin-3-yl 2-phenyl-2-(phenylamino)-acetate (Diastereoisomers 1 and 2 of C2)

To a solution of 2-phenyl-2-(phenylamino)acetic acid (I1) (3.40 g, 14.9 mmol) in THF (600 mL), is added DCC (4.02 g, 19.4 mmol), HOBt (3.06 g, 19.44 mmol) and 3(R)-quinuclidinol (3.80 g, 29.9 mmol). The resulting mixture is stirred for 16 hours at RT (LC-MS monitoring: complete conversion). The solvent is evaporated, the residue is taken up with EtOAc and the insoluble is eliminated by filtration. The clear solution is washed with 1M $K_2CO_3$ and then with brine, is dried over $Na_2SO_4$, filtered and evaporated to dryness. The resulting crude is purified by flash chromatography (DCM/MeOH=95/5, 0.1% $NH_3$ (aq.)) recovering first diastereoisomer 1 of C2 as a white solid (1.13 g, 22.5% yield, single diastereoisomer), and subsequently diastereoisomer 2 of C2 as a white solid (0.69 g, 13.7% yield, single diastereoisomer).

Diastereoisomer 1 of C2:
$^1$H NMR (300 MHz, DMSO-$d_6$) ppm: 7.48-7.59 (m, 2H), 7.26-7.46 (m, 3H), 7.02-7.14 (m, 2H), 6.67-6.79 (m, 2H), 6.51-6.64 (m, 1H), 6.27 (d, 1H), 5.26 (d, 1H) m 4.61-4.78 (m, 1H), 2.96 (ddd, 1H), 2.55-2.67 (m, 3H), 2.16-2.37 (m, 1H), 2.06 (d, 1H), 1.79-1.94 (m, 1H), 1.59-1.76 (m, 1H), 1.35-1.59 (m, 2H), 1.20-1.34 (m, 1H);
LC-MS (ESI POS): 337.04 (MH+);
$[\alpha]_D$=−44.6 (c=0.25 MeOH).

Diastereoisomer 2 of C2:
$^1$H NMR (300 MHz, DMSO-$d_6$) ppm: 7.48-7.60 (m, 2H), 7.24-7.43 (m, 3H), 6.97-7.14 (m, 2H), 6.66-6.78 (m, 2H), 6.51-6.66 (m, 1H), 6.26 (d, 1H), 5.24 (d, 1H), 4.62-4.81 (m, 1H), 3.08 (ddd, 1H), 2.54-2.70 (m, 5H), 1.64-1.79 (m, 1H), 1.32-1.64 (m, 2H), 1.16-1.32 (m, 1H), 0.93-1.16 (m, 1H);
LC-MS (ESI POS): 337.04 (MH+);
$[\alpha]_D$=+27.6 (c=0.25 MeOH)

Example 3

Alternative Preparation of (R)-phenyl-phenylamino-acetic acid (R)-(1-aza-bicyclo[2.2.2]oct-3-yl) ester (Diasteroisomers 1 of C2)

Preparation of (R)-2-phenyl-2-(phenylamino)acetic acid (I7)

12N HCl (85 mL) is added to a solution of (R)-methyl 2-phenyl-2-(phenylamino)acetate (I6) (20.3 g, 84.0 mmol), Scheme 3

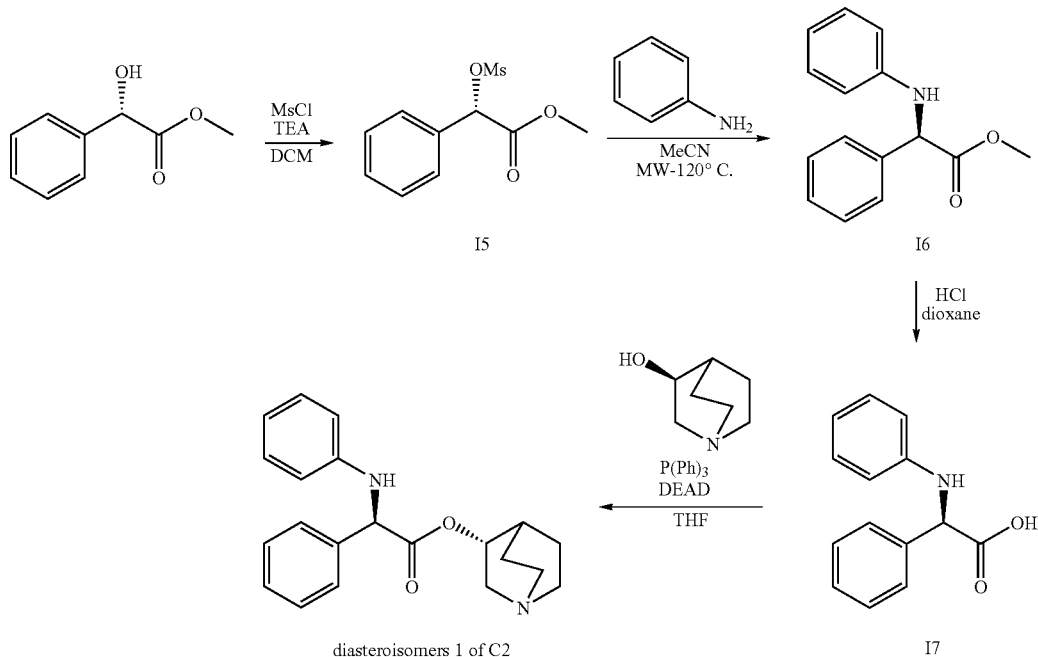

diasteroisomers 1 of C2

Preparation of (S)-methyl 2-(methylsulfonyloxy)-2-phenylacetate (I5)

To a solution of (S)-methyl 2-hydroxy-2-phenylacetate (20.0 g, 120 mmol) in DCM (240 mL) maintained at 0° C. under $N_2$ flowstream, are added mesylchloride (11.2 mL, 144 mmol) and TEA (20.1 mL, 144 mmol) and the mixture is stirred at RT for 1 hour (UPLC-MS monitoring: complete conversion). The mixture is cooled to 0° C., 0.1N HCl (240 mL) is added and the desired compound is extracted with DCM (2×200 mL). The combined DCM phases are dried over $Na_2SO_4$, filtered and evaporated to dryness. The resulting crude is purified by filtration through a silica bed eluting with DCM, obtaining 22.4 g of the title compound as white solid (76% yield).

Preparation of (R)-methyl 2-phenyl-2-(phenylamino)acetate (I6)

Aniline (16.8 mL, 184 mmol) is added to a solution of (S)-methyl 2-(methylsulfonyloxy)-2-phenylacetate (I5) (22.4 g, 92.0 mmol) in $CH_3CN$ (50 mL). The mixture is heated under MW irradiation at 120° C. for 5 minutes (UPLC-MS monitoring: complete conversion). The resulting crude is partitioned between EtOAc (200 mL) and 1N HCl (200 mL) and the aqueous phase is extracted with EtOAc (3×200 mL). The combined organic layers are dried over $Na_2SO_4$, filtered and evaporated under vacuum to obtain 20.3 g of a pale yellow solid (92% yield), which is used in the next step without any additional purification.

in dioxane (85 mL) and the mixture is heated at 70° C. for 18 hours (UPLC-MS monitoring: complete conversion). The dioxane is evaporated, the mixture is cooled to 0° C. and the resulting solid is collected by filtration to obtain 19.1 g of intermediate 17 as a white solid (99% yield).

Preparation of (R)—((R)-quinuclidin-3-yl) 2-phenyl-2-(phenylamino)acetate) (Diasteroisomers 1 of C2)

(R)-2-phenyl-2-(phenylamino)acetic acid (I7) (6.50 g, 28.7 mmol), is dissolved in dry THF (140 mL) under inert atmosphere. 3S-Quinuclidinol (4.0 g, 31.6 mmol), triphenylphosphine (8.90 g, 43.0 mmol) and diethyl azodicarboxylate (6.8 mL, 43.0 mmol) are added and the resulting mixture is refluxed for 30 minutes (UPLC-MS monitoring: complete conversion). The solvent is evaporated and the residue is partitioned between water (100 mL) and EtOAc (100 mL). The aqueous phase is further extracted with EtOAc (3×100 mL). The combined organic layers are dried over $Na_2SO_4$, filtered and evaporated under vacuum. The resulting crude is purified by flash chromatography (DCM/MeOH=95/5) recovering 8.7 g of diastereoisomer 1 of compound C2 as a pale yellow solid (90% yield, single diastereoisomer).

Diastereoisomer 1 of C2:

$^1$H NMR (300 MHz, DMSO-$d_6$) ppm: 7.49-7.58 (m, 2H) 7.25-7.47 (m, 3H) 7.00-7.12 (m, 2H) 6.66-6.78 (m, 2H) 6.51-6.63 (m, 1H) 6.27 (d, 1H) 5.20-5.31 (m, 1H) 4.62-4.73 (m, 1H) 2.95 (ddd, 1H) 2.53-2.68 (m, 3H) 2.17-2.34 (m, 1H) 2.01-2.13 (m, 1H) 1.83-1.93 (m, 1H) 1.38-1.71 (m, 3H) 1.17-1.34 (m, 1H)

LC-MS (ESI POS): 337.2 (MH+).

Example 4

Preparation of (R)-quinuclidin-3-yl 2-(3-fluorophenyl)-2-(3-fluorophenylamino)acetate (Diasteroisomer 1 and 2 of C12)

is heated at 100° C. for 5 minutes under MW irradiation (LC-MS monitoring: complete conversion). The solvent is evaporated and the resulting crude is purified by flash chromatography (Hexane/EtOAc=9/1) in order to obtain 2.00 g of I10 as a yellow oil (99% yield).

Scheme 4

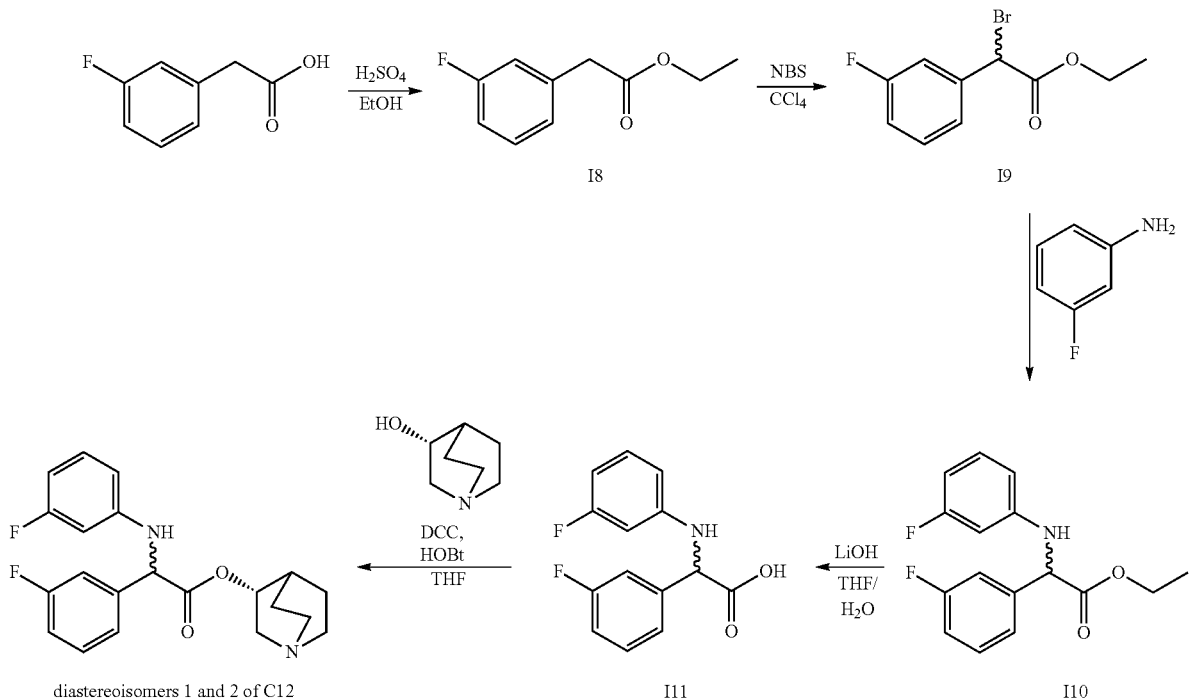

Preparation of ethyl 2-(3-fluorophenyl)acetate (I8)

To a solution of 3-fluorophenyl acetic acid (10.0 g, 64.9 mmol) in ethanol (300 mL), is added a catalytic amount of $H_2SO_4$ (98%, 1 mL) and the mixture reacted for 12 hours at 100° C. (LC-MS monitoring: complete conversion). The solvent is evaporated and the residue is partitioned between EtOAc and water; the organic layer is separated and dried over $Na_2SO_4$ in order to obtain 10.1 g of (I8) as a white solid (85% yield).

Preparation of ethyl 2-bromo-2-(3-fluorophenyl)acetate (I9)

To a solution of ethyl 2-(3-fluorophenyl)acetate (I8) (10.1 g, 55.0 mmol) in $CCl_4$ (250 mL), NBS (9.70 g, 55.0 mmol) is added and the mixture refluxed for 2 hours at 80° C. (LC-MS monitoring: complete conversion). The solvent is evaporated and the resulting crude is dissolved in DCM and purified by filtration on a silica bed in order to obtain 7.80 g of (I9) as a colorless oil (54% yield).

Preparation of ethyl 2-(3-fluorophenyl)-2-(3-fluorophenylamino)-acetate (I10)

A solution of ethyl 2-bromo-2-(3-fluorophenyl)acetate (I9) (1.80 g, 6.84 mmol) in 3-fluoroaniline (6.50 mL, 68.0 mmol)

Preparation of 2-(3-fluorophenyl)-2-(3-fluorophenylamino)acetic acid (I11)

To a solution of ethyl 2-(3-fluorophenyl)-2-(3-fluorophenylamino)-acetate (2.00 g, 6.81 mmol) in THF/$H_2O$ (1:1 mixture, 10 mL), is added LiOH (816 mg, 34.0 mmol) and the mixture is reacted for 2 hours at RT (LC-MS monitoring: complete conversion). 1N HCl (15 mL) is added and the desired compound is extracted with EtOAc. The resulting crude is purified by flash chromatography (Hexane/EtOAc=1/1) in order to obtain 1.79 g of I11 as a pale yellow solid (99% yield).

Preparation of (R)-quinuclidin-3-yl 2-(3-fluorophenyl)-2-(3-fluorophenylamino)acetate (Diasteroisomer 1 and 2 of C12)

To a solution of 2-(3-fluorophenyl)-2-(3-fluorophenylamino)acetic acid (I11) (1.79 g, 6.80 mmol) in dioxane (70 mL), is added a 4M solution of HCl in dioxane (5 mL). The reaction is stirred at RT for 1 hour, then the solvent is evaporated under reduced pressure to obtain a white solid. The compound is dissolved in dry THF (70 mL) and DCC (1.71 g, 8.20 mmol), HOBt (1.10 g, 8.20 mmol) and 3(R)-quinuclidinol (2.60 g, 20.4 mmol) are added. The reaction is stirred at RT for 96 hours under nitrogen flowstream (LC-MS monitoring: complete conversion). The solvent is evaporated and the residue is partitioned between EtOAc and water; the organic layer is separated, dried over Na₂SO₄, filtered and evaporated to dryness. The crude is purified by flash chromatography (DCM/MeOH=97/3) recovering first 150 mg of diastereoisomer 1 of C51 as pale yellow solid (6% yield, single diastereoisomer) and subsequently 830 mg of mixture of diastereoisomers 1 and 2 of C12 as a pale yellow oil (32% yield, mixture of diasteroisomers).

Diastereoisomer 1 of C12 (80 mg) is furthermore purified by preparative LC-MS in order to obtain 53.0 mg of a pale yellow oil (TFA salt).

Diastereoisomer 1 of C12
¹H NMR (300 MHz, DMSO-d6) ppm: 9.48 (br. s., 1H), 7.31-7.58 (m, 3H), 7.15-7.26 (m, 1H), 7.10 (td, 1H), 6.77 (d, 1H), 6.47-6.65 (m, 2H), 6.27-6.47 (m, 1H), 5.48 (d, 1H), 4.95-5.20 (m, 1H), 3.63 (ddd, 1H), 3.07-3.31 (m, 3H), 2.74-2.91 (m, 2H), 2.16-2.33 (m, 1H), 1.65-1.95 (m, 4H);
LC-MS (ESI POS): 373.2 (MH⁺);
$[\alpha]_D = -37.80°$ (c=0.2, MeOH).

Mixture of diastereoisomers 1 and 2 of C12
1H NMR (300 MHz, DMSO-d6) ppm: 9.58 (br. s., 1H), 7.31-7.58 (m, 3H), 7.15-7.26 (m, 1H), 7.10 (td, 1H), 6.77 (d, 1H), 6.47-6.65 (m, 2H), 6.27-6.47 (m, 1H), 5.44 (d, 1H), 4.95-5.20 (m, 1H), 3.67 (ddd, 1H), 3.07-3.31 (m, 3H), 2.74-2.91 (m, 2H), 2.05 (m, 1H), 1.65-1.95 (m, 4H);
LC-MS (ESI POS): 373.2 (MH⁺).

Example 5

Preparation of (R)-1-methylpiperidin-4-yl-2-phenyl-2-(phenylamino)-acetate (C13)

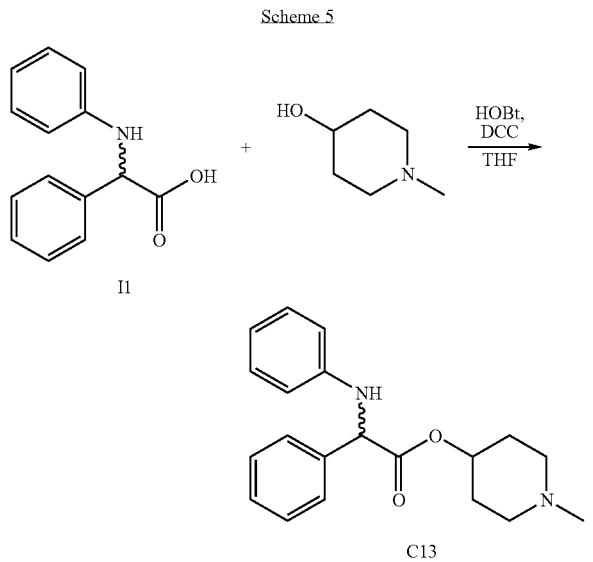

Scheme 5

To a solution of 2-phenyl-2-(phenylamino)acetic acid (I1) (234 mg, 0.91 mmol) in dioxane, is added a 4M solution of HCl in dioxane (5 mL) and the reaction is allowed to stir at RT for 1 hour; the solvent is evaporated under reduced pressure to obtain a white solid which is dissolved in dry THF (10 mL). DCC (222 mg, 1.12 mmol), HOBt (144 mg, 1.14 mmol) and N-methyl-4-piperidinol (307 mg, 2.71 mmol) are added and the mixture is stirred for 96 hours at RT under nitrogen flowstream (LC-MS monitoring: complete conversion). The solvent is evaporated and the residue is partitioned between DCM and water; the organic layer is separated and dried over Na₂SO₄. The crude compound is purified by preparative LC-MS and the collected fractions are portioned between 2M K₂CO₃ and EtOAc. The organic phase is dried over Na₂SO₄, filtered and evaporated to dryness to obtain 20.6 mg of the title compound as a white solid (7% yield, racemic mixture).

¹H NMR (300 MHz, DMSO-d6) ppm: 7.45-7.60 (m, 2H), 7.20-7.45 (m, 3H), 6.95-7.17 (m, 2H), 6.69 (d, 2H), 6.47-6.63 (m, 1H), 6.23 (d, 1H), 5.20 (d, 1H), 4.71 (tt, 1H), 2.34-2.48 (m, 1H), 2.11-2.25 (m, 2H), 2.09 (s, 3H), 1.94-2.08 (m, 1H), 1.71-1.90 (m, 1H), 1.51-1.71 (m, 2H), 1.29-1.51 (m, 1H);
LC-MS (ESI POS): 325.2 (MH⁺).

Example 6

Preparation of (R)-1-methylpyrrolidin-4-yl-2-phenyl-2-(phenylamino)acetate (C14)

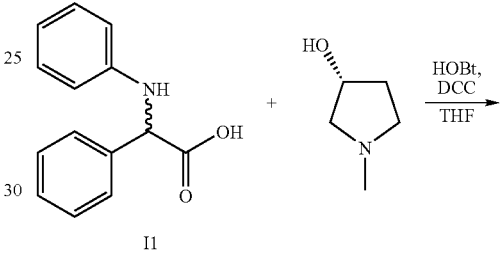

Scheme 6

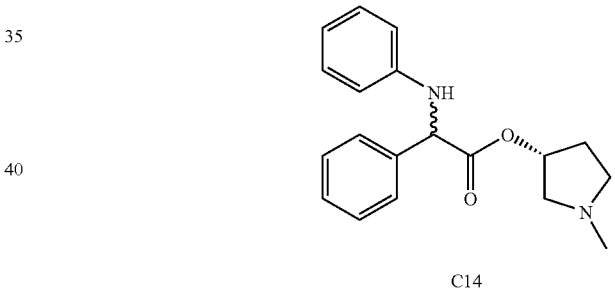

C14

A mixture of 2-phenyl-2-(phenylamino)acetic acid (I1) (200 mg, 0.88 mmol), DCC (218 mg, 1.05 mmol), HOBt (142 mg, 1.05 mmol) and (R)-1-methylpyrrolidin-3-ol (289 uL, 2.64 mmol) in dry THF (10 mL) is stirred at room temperature overnight under nitrogen flowstream (LC-MS monitoring: complete conversion). The solvent is evaporated and the residue is taken up with aq. HCl (pH about 2) and washed with DCM. The aqueous phase is basified with NaHCO₃ and extracted with DCM (three times). The organic layers are combined, dried over Na₂SO₄, filtered and evaporated to dryness. The resulting crude is first purified by flash chromatography (DCM to DCM/MeOH=95/5) and then by preparative LC-MS. The purified compound is partitioned between sat. NaHCO₃ and DCM, the organic phase is dried over Na₂SO₄, filtered and evaporated under vacuum to give 90.8 mg of the title compound as brown oil (33% yield, mixture of diastereoisomers).

¹H NMR (300 MHz, CHLOROFORM-d) ppm
Diastereoisomer 1 of C14: 7.46-7.57 (m, 2H), 7.29-7.45 (m, 3H), 7.08-7.21 (m, 2H), 6.67-6.81 (m, 1H), 6.50-6.67 (m, 2H), 5.20-5.37 (m, 1H), 5.12 (d, 1H), 4.84-5.05 (m, 1H), 2.46-3.04 (m, 4H), 2.44 (s, 3H), 2.10-2.26 (m, 1H), 1.63-1.82 (m, 1H).

Diastereoisomer 2 of C14: 7.46-7.57 (m, 2H), 7.29-7.45 (m, 3H), 7.08-7.21 (m, 2H), 6.67-6.81 (m, 1H), 6.50-6.67 (m, 2H), 5.20-5.37 (m, 1H), 5.12 (d, 1H), 4.84-5.05 (m, 1H), 2.46-3.04 (m, 4H), 2.33 (s, 3H), 2.26-2.40 (m, 1H), 1.86-2.05 (m, 1H);

LC-MS (ESI POS): 311.3 (MH+).

The compounds listed in Table 2 are prepared as previously described for diastereoisomers 1 and 2 of C14, coupling acid I1 with the commercially available (S)-1-methylpyrrolidin-3-ol and (R)-1-methylpiperidin-3-ol respectively.

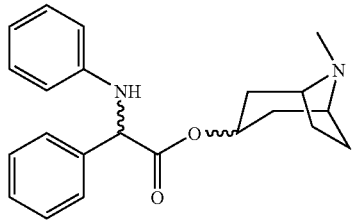

C17

TABLE 2

| Compound | Structure | Yield and appearance | Analytical |
|---|---|---|---|
| C15 | Mixture of diastereoisomers | 28% yield Colorless oil | LC-MS (ESI POS): 311.2 (MH+) <br> 1H NMR (300 MHz, CHLOROFORM-d) ppm <br> Diastereoisomer 1 of C12: 7.46-7.57 (m, 2 H), 7.29-7.45 (m, 3 H), 7.08-7.21 (m, 2 H), 6.67-6.81 (m, 1 H), 6.50-6.67 (m, 2 H), 5.20-5.37 (m, 1 H), 5.12 (d, 1 H), 4.84-5.05 (m, 1 H), 2.46-3.04 (m, 4 H), 2.44 (s, 3 H), 2.10-2.26 (m, 1 H), 1.63-1.82 (m, 1 H) <br> Diastereoisomer 2 of C12: 7.46-7.57 (m, 2 H), 7.29-7.45 (m, 3 H), 7.08-7.21 (m, 2 H), 6.67-6.81 (m, 1 H), 6.50-6.67 (m, 2 H), 5.20-5.37 (m, 1 H), 5.12 (d, 1 H), 4.84-5.05 (m, 1 H), 2.46-3.04 (m, 4 H), 2.33 (s, 3 H), 2.26-2.40 (m, 1 H), 1.86-2.05 (m, 1 H) |
| C16 | Mixture of diastereoisomers | 20% yield Colorless oil | LC-MS (ESI POS): 325.3 (MH+) <br> 1H NMR (300 MHz, DMSO-d6) ppm: 7.45-7.69 (m, 2 H), 7.22-7.45 (m, 3 H), 6.91-7.22 (m, 2 H), 6.66-6.91 (m, 2 H), 6.42-6.66 (m, 1 H), 6.27 (br. s., 1 H), 5.20 (s, 1 H), 4.77 (br. s., 1 H), 2.53-3.00 (m, 2 H), 1.64-2.44 (m, 6 H), 0.90-1.62 (m, 3 H) |

Example 7

Preparation of 8-methyl-8-azabicyclo[3.2.1]octan-3-yl 2-phenyl-2-(phenylamino)acetate (C17)

Scheme 7

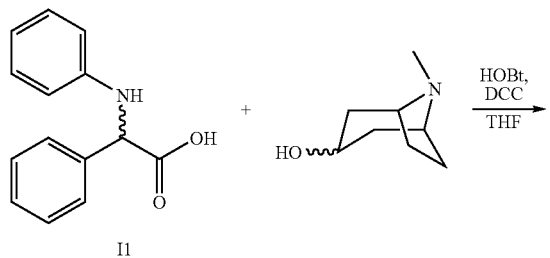

A mixture of 2-phenyl-2-(phenylamino)acetic acid I1 (250 mg, 0.90 mmol), EDC (255 mg, 1.35 mmol), HOBt (245 mg, 1.80 mmol) and 8-methyl-8-azabicyclo[3.2.1]octan-3-ol (380 mg, 2.71 mmol) in dry DMF (10 mL) is heated under microwave irradiation at 100° C. for 1 hour (LC-MS monitoring: complete conversion). The reaction is concentrated under reduced pressure and the residue is portioned between EtOAc and water. The organic phase is dried over Na2SO4, filtered and evaporated to dryness. The resulting crude is purified by preparative HPLC. The collected compound is partitioned between 1N NaHCO3 and DCM, the organic phase is separated dried over Na2SO4, filtered and evaporated under vacuum to give 20.1 mg of the title compound as a colorless oil (7% yield, mixture of diastereoisomers).

1H NMR (300 MHz, CHLOROFORM-d) ppm: 7.45-7.57 (m, 2H), 7.29-7.45 (m, 3H), 7.04-7.21 (m, 2H), 6.65-6.77 (m, 1H), 6.51-6.65 (m, 2H), 5.02-5.13 (m, 2H), 5.00 (d, 1H), 3.07-3.30 (m, 1H), 2.81-3.07 (m, 1H), 2.28 (s, 3H), 2.19-2.27 (m, 1H), 1.84-2.18 (m, 3H), 1.70-1.82 (m, 2H), 1.45 (d, 1H), 1.17 (ddd, 1H);

LC-MS (ESI POS): 351.3 (MH+).

C18 listed in Table 3 is prepared as previously described for C17.

TABLE 3

| Compound | Structure | Yield and appearance | Analytical |
|---|---|---|---|
| C18 | Mixture of diastereoisomers | 5% yield Colorless oil | LC-MS (ESI POS): 365.2 (MH+) <br> 1H NMR (300 MHz, Acetone-d6) ppm: 7.42-7.65 (m, 2 H), 7.26-7.46 (m, 3 H), 7.01-7.15 (m, 2 H), 6.67-6.76 (m, 2 H), 6.56-6.65 (m, 1 H), 5.57-5.65 (m, 1 H), 5.17 (d, 1 H), 4.95 (t, 1 H), 3.05 (dd, 1 H), 2.89 (dd, 1 H), 2.75 (d, 1 H), 2.42 (s, 3 H), 1.87-2.13 (m, 2 H), 1.66 (d, 1 H), 1.28 (d, 1 H). |

Example 8

Preparation of (S)—((R)-quinuclidin-3-yl) 2-amino-3-phenylpropanoate di-trifluoroacetate (Diastereoisomer 1 of C20)

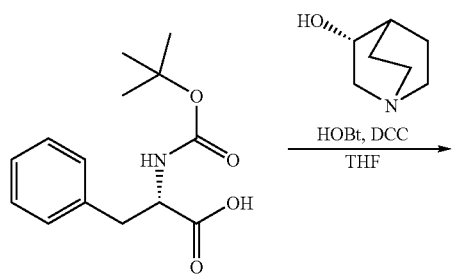

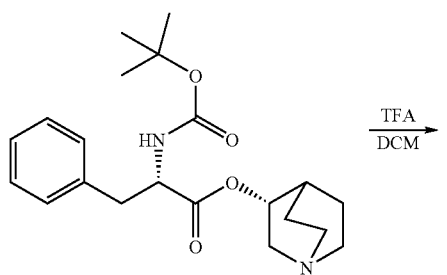

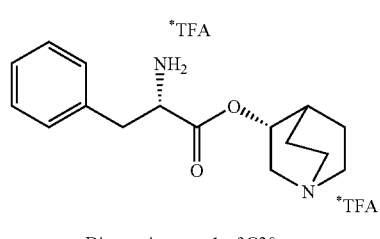

Diastereoisomers 1 of C20

Preparation of (S)—((R)-quinuclidin-3-yl) 2-(tert-butoxycarbonylamino)-3-phenylpropanoate (I19)

To a solution of (S)-2-(tert-butoxycarbonylamino)-3-phenylpropanoic acid (1.03 g, 3.81 mmol) in THF (70 mL), are added DCC (1.03 g, 4.91 mmol), HOBt (660 mg, 4.90 mmol) and 3(R)-quinuclidinol (1.18 g, 9.48 mmol) and the resulting mixture is stirred for 12 hours at RT under nitrogen flow-stream (LC-MS monitoring: complete conversion). The solvent is evaporated and the residue is partitioned between EtOAc (100 mL) and 2M $K_2CO_3$ (50 mL); the organic layer is separated, washed with brine and dried over $Na_2SO_4$. The resulting crude is purified by flash chromatography (DCM/MeOH=95/5, 0.1% $NH_3$ (aq.)) to obtain 1.12 g of I19 (80% yield).

Preparation of (S)—(R)-quinuclidin-3-yl) 2-amino-3-phenylpropanoate di-trifluoroacetate (Diastereoisomer 1 of C20)

To a solution of I19 (220 mg, 0.58 mmol) in DCM (5 mL), trifluoroacetic acid (0.50 mL, 4.41 mmol) is added and the mixture stirred at RT overnight. The solvent is evaporated and the resulting crude is purified by preparative LC-MS in order to obtain 59.4 mg of diastereoisomer 1 of C20 as a brown gummy solid (56% yield, di-trifluoroacetate salt, single diastereoisomer).

1H NMR (300 MHz, DMSO-d6) ppm: 9.81 (br. s., 1H), 8.52 (br. s., 3H), 7.24-7.41 (m, 5H), 5.02-5.09 (m, 1H), 4.20-4.46 (m, 1H), 3.60-3.73 (m, 1H), 3.00-3.33 (m, 7H), 2.01 (br. s., 1H), 1.79-1.95 (m, 1H), 1.76 (br. s., 1H), 1.60 (br. s., 2H); LC-MS (ESI POS): 275.3 (MH+).

Diastereoisomer 2 of C20 listed in Table 4 is prepared as previously described for diastereoisomer 1 of C20, starting from the commercially available (R)-2-(tert-butoxycarbonylamino)-3-phenylpropanoic acid.

TABLE 4

| Compound | Structure | Yield and appearance | Analytical |
|---|---|---|---|
| Diastereoisomer 2 of C20 | (structure shown) 2TFA Single diastereoisomer | 10% overall yield Pale yellow oil | LC-MS (ESI POS): 275.3 (MH+) $^1$H NMR (300 MHz, DMSO-d6) ppm: 8.52 (br. s., 3 H), 7.25-7.41 (m, 5 H), 4.94-5.17 (m, 1 H), 4.37 (dd, 1 H), 3.61 (ddd, 1 H), 3.00-3.30 (m, 5 H), 2.86-2.97 (m, 1 H), 2.82 (ddd, 1 H), 2.08-2.22 (m, 1 H), 1.61-1.94 (m, 4 H) |

Example 9

Preparation of (S)-3-phenyl-2-phenylamino-propionic acid (R)-(1-aza-bicyclo[2.2.2]oct-3-yl) ester (Diasteroisomers 1 of C22)

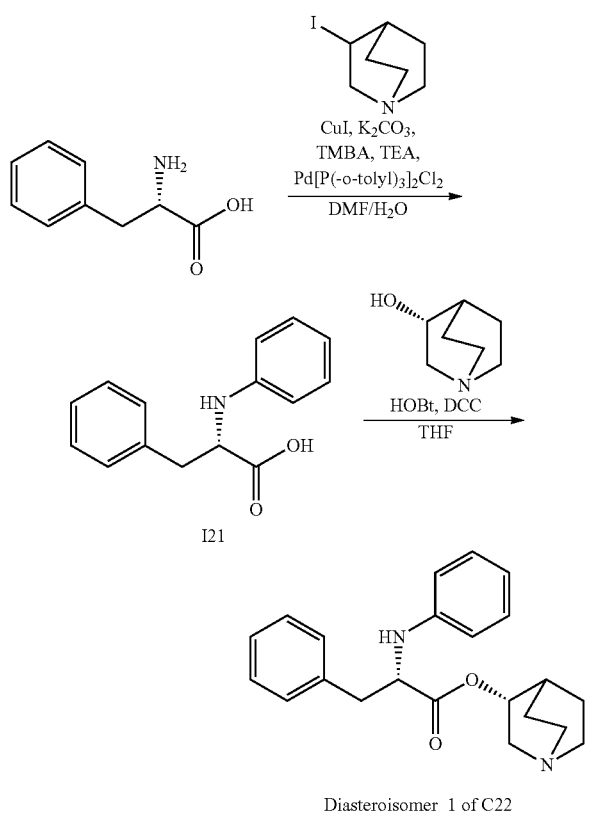

Scheme 9

Diastereoisomer 1 of C22

Preparation of 3-phenyl-2-(phenylamino)propanoic acid (I21)

To a solution of (S)-2-amino-3-phenylpropanoic acid (1.52 g, 9.12 mmol) in a DMF/H$_2$O mixture (10/1, 16.5 mL) maintained under nitrogen flowstream, iodobenzene (1.00 mL, 9.12 mmol), dichlorobis(tri-o-tolylphosphine)palladium(II) (357 mg, 0.42 mmol) CuI (86.4 mg, 0.42 mmol), K$_2$CO$_3$ (1.21 g, 9.12 mmol), rimethylbenzylammonium chloride (286 mg, 1.51 mmol) and triethylamine (TEA) (2.50 mL, 18.0 mmol) are added and the mixture stirred for 24 hours at 100° C. under nitrogen flowstream (LC-MS monitoring: complete conversion). The reaction mixture is partitioned between EtOAc and water; 1N HCl is added until pH=1 and the organic layer is separated, washed with brine and dried over Na$_2$SO$_4$. The resulting crude is purified by flash chromatography (DCM/MeOH=99/1) and 1.21 g of I21 is obtained (56% yield).

Preparation of (S)-3-phenyl-2-phenylamino-propionic acid (R)-(1-aza-bicyclo[2.2.2]oct-3-yl) ester (Diasteroisomers 1 of C22)

To a solution of 3-phenyl-2-(phenylamino)propanoic acid (I21) (1.21 g, 5.01 mmol) in dioxane, a 4M solution of HCl in dioxane (5 mL) is added and the reaction is allowed to stir at RT for 1 hour; the solvent is evaporated under reduced pressure to obtain a white solid which is dissolved in dry THF (70 mL). DCC (1.22 g, 6.01 mmol), HOBt (0.8 g, 6.0 mmol) and 3(R)-quinuclidinol (1.31 g, 10.1 mmol) are added to the resulting solution and the mixture stirred for 24 hours at RT under nitrogen flowstream (LC-MS monitoring: complete conversion). The solvent is evaporated. 1N HCl (20 mL) is added to the resulting crude and the aqueous layer is washed with EtOAc (2×50 mL); NaHCO$_3$ is added to the aqueous layer (pH=7-8) and the product is extracted with DCM and dried over Na$_2$SO$_4$, to obtain 530 mg (35% yield) of diastereoisomer 1 of C22, which is further purified by preparative LC-MS to get the titled product as a brown oil (mixture of diastereoisomers that contains 20% of diastereoisomer 2 of C22, TFA salt).

$^1$H NMR (300 MHz, DMSO-d6) ppm: 9.58 (br. s., 1H), 7.19-7.38 (m, 5H), 6.91-7.15 (m, 2H), 6.55-6.68 (m, 3H), 4.94 (ddd, 1H), 4.34 (t, 1H), 3.62 (ddd, 1H), 2.92-3.25 (m, 7H), 1.63-1.95 (m, 3H), 1.36-1.63 (m, 2H);

LC-MS (ESI POS): 351.3 (MH+).

Diastereoisomer 2 of C22 listed in Table 5 is obtained as previously described for diastereoisomer 1 of C22, starting from the commercially available (R)-2-amino-3-phenylpropanoic acid.

TABLE 5

| Compound | Structure | Yield and ppearance | Analytical |
|---|---|---|---|
| Diastereoisomer 2 of C22 | 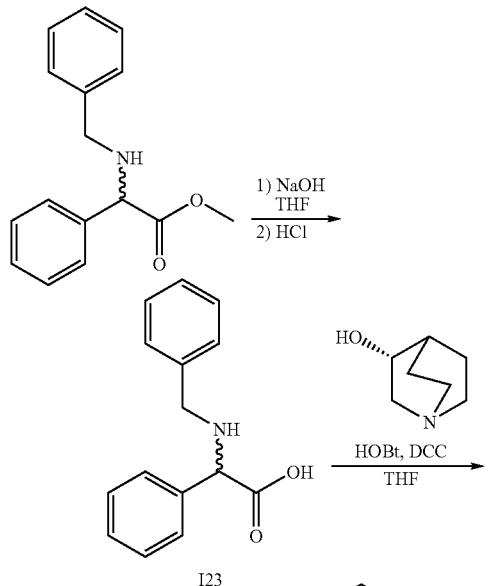  TFA  Single diastereoisomer | 7% overall yield Brown oil | LC-MS (ESI POS): 351.3 (MH+)  $^1$H NMR (300 MHz, DMSO-d6 + $Na_2CO_3$) ppm: 7.15-7.43 (m, 5 H), 6.96-7.15 (m, 2 H), 6.47-6.69 (m, 3 H), 6.03 (d, 1 H), 4.43-4.67 (m, 1 H), 4.10-4.41 (m, 1 H), 2.95-3.18 (m, 2 H), 2.80-2.95 (m, 1 H), 2.54-2.63 (m, 3 H), 2.30-2.45 (m, 1 H), 1.89-2.06 (m, 1 H), 1.69-1.84 (m, 1 H), 1.39-1.58 (m, 3 H) |

Example 10

Preparation of (R)-quinuclidin-3-yl 2-(benzylamino)-2-phenylacetate (C24)

Scheme 10

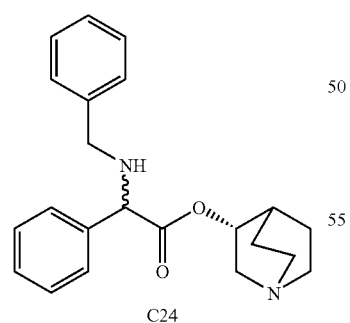

Preparation of 2-(benzylamino)-2-phenylacetic acid (I23)

A solution of methyl 2-(benzylamino)-2-phenylacetate (1.00 g, 3.90 mmol) in THF (90 mL) and 1N NaOH (10 mL) is stirred at room temperature overnight (LC-MS monitoring: complete conversion). The solvent is removed under reduced pressure and the crude is portioned between EtOAc and water. The aqueous phase is acidified with conc. HCl (pH about 3) and then extracted with EtOAc (three times). The organic phase is dried over $Na_2SO_4$, filtered and evaporated to dryness to give the title compound as a white solid (940 mg, quantitative yield), which is used in the next step without any further purification.

Preparation of (R)-quinuclidin-3-yl 2-(benzylamino)-2-phenylacetate (Diasteroisomers 1 and 2 of C24)

A mixture of 2-(benzylamino)-2-phenylacetic acid (I23) (0.94 g, 3.90 mmol), DCC (0.97 g, 4.70 mmol), HOBt (0.63 g, 4.07 mmol) and 3(R)-quinuclidinol (1.51 g, 11.7 mmol) in dry THF (30 mL) is stirred at room temperature overnight under nitrogen flowstream (LC-MS monitoring: complete conversion). The solvent is evaporated and the residue is taken up with EtOAc and washed twice with water. The organic phase is dried over $Na_2SO_4$, filtered and evaporated to dryness. The resulting crude is purified by flash chromatography (DCM/MeOH=98/2, 0.2% $NH_{3(aq.)}$ to 95/5, 0.5% $NH_{3(aq.)}$) to give a mixture of diastereoisomers 1 and 2 of C24 (231 mg, 52% yield, mixture of diasteroisomers).

The mixture of diastereoisomers 1 and 2 of C24 (55 mg) is furthermore purified by preparative HPLC.

$^1$H NMR (300 MHz, DMSO-d6+$Na_2CO_3$) ppm: 7.20-7.45 (m, 11H), 4.55-4.79 (m, 1H), 4.35 (s, 1H), 3.67 (d, 2H), 2.85-3.14 (m, 2H), 2.56-2.71 (m, 2H), 2.31-2.46 (m, 1H), 2.07-2.23 (m, 1H), 1.82-1.93 (m, 1H), 1.32-1.79 (m, 4H);
LC-MS (ESI POS): 351.2 (MH+).

Example 11

Preparation of (R)-quinuclidin-3-yl 2-(cyclopentylamino)-2-phenylacetate di-trifluoroacetate (C26)

Scheme 11

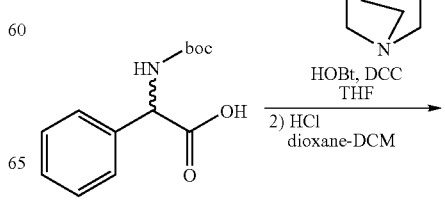

Preparation of (R)-quinuclidin-3-yl 2-(cyclopenty-lamino)-2-phenylacetate di-trifluoroacetate (C26)

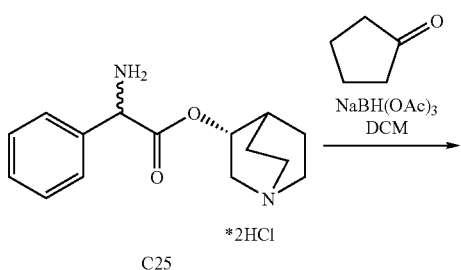

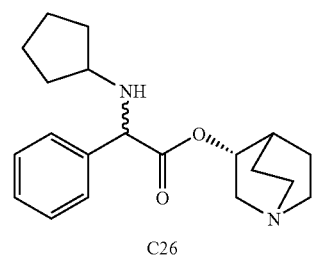

(R)-Quinuclidin-3-yl 2-amino-2-phenylacetate (C25) (200 mg, 0.60 mmol) is dissolved in dry DCM (10 mL) and treated with sodium triacetoxyborohydride (508 mg, 2.40 mmol). The reaction is stirred at room temperature for 30 minutes and then cyclopentanone (106 uL, 1.20 mmol) is added and the reaction is stirred at room temperature for additional 16 hours (LC-MS monitoring: complete conversion). The reaction is diluted with DCM and washed twice with 1N NaOH, the organic layer is dried over $Na_2SO_4$, filtered and evaporated to dryness. The crude compound is purified by preparative HPLC to give C26 as a white solid (53.1 mg, 16% yield, di trifluoroacetate salt, mixture of diastereoisomers).

$^1$H NMR (300 MHz, DMSO-d6) ppm: 10.02 (br. s., 2H), 9.75 (br. s., 1H), 7.43-7.76 (m, 5H), 5.24-5.49 (m, 1H), 5.01-5.24 (m, 1H), 3.51-3.79 (m, 1H), 3.12-3.37 (m, 4H), 2.93-3.12 (m, 1H), 2.75-2.94 (m, 1H), 2.20-2.39 (m, 1H), 1.78-2.14 (m, 4H), 1.61-1.77 (m, 5H), 1.31-1.57 (m, 3H);

LC-MS (ESI POS): 329.2 (MH$^+$).

C27 listed in Table 6 is obtained as previously described for C26, using cyclohexanone instead of cyclopentanone.

TABLE 6

| Compound | Structure | Yield and appearance | Analytical |
|---|---|---|---|
| C27 | <br><br>Mixture of diastereoisomers | 24% yield<br>White solid | LC-MS (ESI POS): 343.2 (MH$^+$)<br>$^1$H NMR (300 MHz, DMSO-d6) ppm: 9.47-9.79 (m, 3 H), 7.36-7.85 (m, 5 H), 5.37-5.54 (m, 1 H), 5.10-5.20 (m, 1 H), 3.56-3.82 (m, 1 H), 2.68-3.28 (m, 5 H), 1.97-2.33 (m, 3 H), 1.66-1.94 (m, 5 H), 1.56 (br. s., 2 H), 1.29 (br. s., 2 H), 1.12 (br. S., 3 H) |

Preparation of (R)-quinuclidin-3-yl 2-amino-2-phenylacetate di-hydrochloride (C25)

A mixture of 2-(tert-butoxycarbonylamino)-2-phenylacetic acid (0.90 g, 4.18 mmol), HOBt (0.68 g, 12.5 mmol), DCC (1.29 g, 6.27 mmol) and 3(R)-quinuclidinol (1.59 g, 12.5 mmol) in dry THF (50 mL) is stirred at room temperature for 16 hours (LC-MS monitoring: complete conversion). The solvent is removed under reduced pressure, the residue is taken up with EtOAc and washed twice with 2M $K_2CO_3$. The organic phase is dried over $Na_2SO_4$, filtered and evaporated to dryness. The compound is triturated with hexane to give (R)-quinuclidin-3-yl 2-(tert-butoxycarbonylamino)-2-phenylacetate as a white solid (1.46 g; 97% yield, mixture of diastereoisomers). This compound is dissolved in DCM (50 mL) and 4N HCl in dioxane (5 mL) is added. The reaction is stirred at room temperature for 1 hour (LC-MS monitoring: complete conversion) and then solvent is separated. The gummy solid is triturated with hexane to give C25 as a white solid (1.26 g, 94% yield, di hydrochloride, mixture of diastereoisomers).

Example 12

Preparation of ((4-chloro-phenylamino)-phenyl-acetic acid (R)-(1-aza-bicyclo[2.2.2]oct-3-yl) ester (C29)

Scheme 12

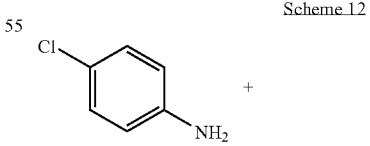

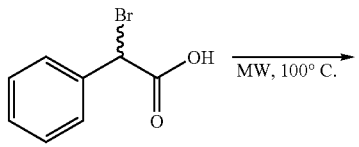

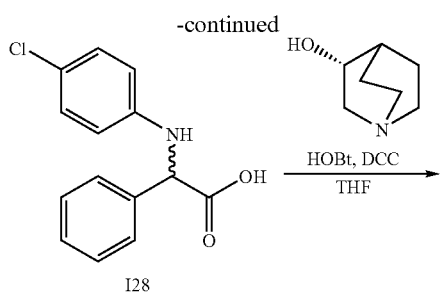

I28

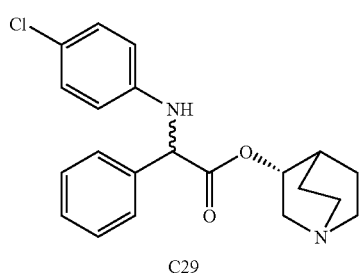

C29

Preparation of (4-chloro-phenylamino)-phenyl-acetic acid (I28)

To a solution of α-bromophenylacetic acid (1.00 g, 4.65 mmol) in acetonitrile (20 mL), is added 4-chloro-phenylamine (1.18 g, 9.30 mmol) and the mixture reacted in a closed vessel under MW irradiation at 100° C. for 1 hour (UPLC-MS monitoring: complete conversion). Solvent is evaporated and residue is portioned between EtOAc and 1N HCl. The organic phase is dried over $Na_2SO_4$, filtered and evaporated to dryness to get intermediate 176 as a yellow solid (0.57 g; 47% yield).

Preparation of ((4-chloro-phenylamino)-phenyl-acetic acid (R)-(1-aza-bicyclo[2.2.2]oct-3-yl) ester (C29)

To a solution of (4-chloro-phenylamino)-phenyl-acetic acid (I28) (574 mg, 2.20 mmol) in dry THF (20 mL), are added DCC (543 mg, 2.64 mmol), HOBt (359 mg, 2.64 mmol) and 3(R)-quinuclidinol (558 mg, 4.40 mmol). The resulting mixture is stirred at RT overnight (UPLC-MS monitoring: complete conversion). The solvent is evaporated and the residue is portitioned between EtOAc and 2M $K_2CO_3$. The organic phase is dried over $Na_2SO_4$, filtered and evaporated to dryness. The resulting crude is purified by flash chromatography (DCM/MeOH=99/1 to 85/15) to obtain the title compound as a white solid (306 mg, 37% yield, mixture of diastereoisomers).

$^1$H NMR (300 MHz, DMSO-d6) ppm: 7.46-7.59 (m, 2H), 7.22-7.45 (m, 3H), 6.99-7.18 (m, 2H), 6.65-6.80 (m, 2H), 6.52 (d, 1H), 5.28 (d, 1H), 4.60-4.82 (m, 1H), 3.04 (ddd, 1H), 2.54-2.70 (m, 4H), 2.03-2.36 (m, 1H), 1.67-1.97 (m, 1H), 1.36-1.68 (m, 2H), 1.05-1.35 (m, 2H);

LC-MS (ESI POS): 371.1 (MH$^+$).

The compounds listed in Table 7 are obtained as previously described for C29, starting from the suitable commercially available 2-bromo-phenylacetic acid derivatives and anilines.

TABLE 7

| Compound | Structure | Yield and appearance | Analytical |
|---|---|---|---|
| C30<br><br>Mixture of diastereoisomers | | 9% yield<br>White solid | LC-MS (ESI POS): 395.1 (MH$^+$)<br>$^1$H NMR (300 MHz, DMSO-d6) ppm: 7.68 (m, 2 H), 7.47-7.58 (m, 2 H), 7.23-7.47 (m, 3 H), 7.15 (d, 1 H), 6.62-6.80 (m, 2 H), 5.39 (d, 1 H), 4.75 (ddd, 1 H), 3.74 (s, 3 H), 2.86-3.19 (m, 1 H), 2.54-2.69 (m, 4 H), 1.84-2.26 (m, 1 H), 1.35-1.80 (m, 3 H), 0.99-1.34 (m, 2 H) |
| Diastereoisomer 1 of C31<br><br>Single diastereoisomer | | 28% yield<br>Pale yellow solid | LC-MS (ESI POS): 401.1 (MH$^+$)<br>$^1$H NMR (300 MHz, DMSO-d6) ppm: 7.76 (d, 1 H), 7.64 (d, 1 H), 7.22-7.54 (m, 5 H), 6.71 (d, 1 H), 5.60 (d, 1 H), 4.58-4.89 (m, 1 H), 3.78 (s, 3 H), 2.98 (ddd, 1 H), 2.54-2.69 (m, 3 H), 2.13-2.27 (m, 1 H), 1.96-2.09 (m, 1 H), 1.85-1.96 (m, 1 H), 1.51-1.73 (m, 2 H), 1.21-1.51 (m, 2 H) |

TABLE 7-continued

| Compound | Structure | Yield and appearance | Analytical |
|---|---|---|---|
| Diastereoisomer 2 of C31 | Single diastereoisomer | 35% yield Pale yellow solid | LC-MS (ESI POS): 401.1 (MH$^+$) $^1$H NMR (300 MHz, DMSO-d6) ppm: 7.78 (d, 1 H) 7.66 (d, 1 H) 7.17-7.53 (m, 5 H) 6.68 (d, 1 H) 5.63 (d, 1 H) 4.72-5.09 (m, 1 H) 3.78 (s, 3 H) 2.71-3.04 (m, 5 H) 1.10-2.07 (m, 6 H) |
| C32 | Mixture of diastereoisomer | 17% yield over two steps yellow solid | LC-MS (ESI POS): 355.1 (MH$^+$) $^1$H NMR (300 MHz, DMSO-d$_6$) ppm: 9.38 (br. s., 1 H) 7.47-7.61 (m, 2 H), 7.28-7.46 (m, 3 H), 6.86-7.03 (m, 2 H), 6.64-6.79 (m, 2 H), 6.32 (br. s., 1 H), 5.32 (br. s., 1 H), 4.86-5.10 (m, 1 H), 3.55-3.70 (m, 1 H), 2.91-3.33 (m, 4 H), 2.64-2.73 (m, 1 H), 2.13-2.28 (m, 1 H), 1.46-2.01 (m, 4 H) |
| C33 | Mixture of diastereoisomer | 11% yield over two steps Pale yellow solid | LC-MS (ESI POS): 355.2 (MH$^+$) $^1$H NMR (300 MHz, DMSO-d$_6$) ppm: 7.36-7.66 (m, 2 H), 7.15-7.28 (m, 2 H), 7.00-7.12 (m, 2 H), 6.64-6.81 (m, 2 H), 6.50-6.64 (m, 1 H), 6.29 (d, 1 H), 5.29 (d, 1 H), 4.39-4.82 (m, 1 H), 3.01-3.12 (m, 1 H), 2.53-2.69 (m, 5 H), 1.67-1.80 (m, 1 H), 0.97-1.58 (m, 4 H) |

Example 13

Preparation of 2-({[(R)-(1-aza-bicyclo[2.2.2]oct-3-yl)oxycarbonyl]-phenyl-methyl}-amino)-benzoic acid methyl ester (C35)

Scheme 13

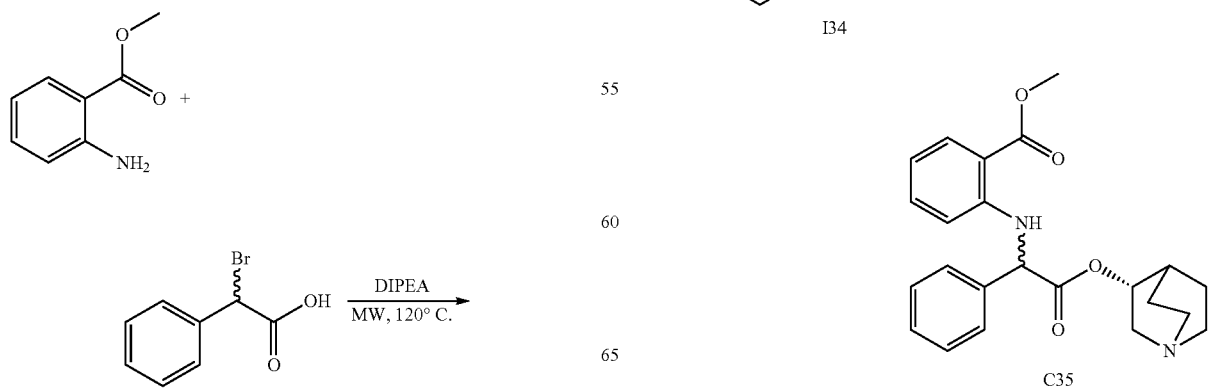

Preparation of N-ethyl-N-isopropylpropan-2-amine 2-[(carboxy-phenyl-methyl)-amino]-benzoic acid methyl ester (I34)

2-Bromo-2-phenylacetic acid (400 mg, 1.86 mmol), methyl 2-aminobenzoate (0.26 mL, 2.05 mmol), and N,N-diisopropylethylamine (DIPEA) (0.65 mL, 3.72 mmol) are dissolved in acetonitrile (8 mL). The resulting solution is heated under MW irradiation into a sealed vial at 100° C. for 20 minutes. The mixture is evaporated and the crude residue is purified by flash chromatography (DCM/MeOH=97/3) affording intermediate 182 as a white solid (611 mg, 79% yield, DIPEA salt).

Preparation of 2-({[(R)-(1-aza-bicyclo[2.2.2]oct-3-yl)oxycarbonyl]-phenyl-methyl}-amino)-benzoic acid methyl ester (C35)

N-ethyl-N-isopropylpropan-2-amine 2-(2-(methoxycarbonyl)phenylamino)-2-phenylacetate (I34) (611 mg, 1.47 mmol), 2-(1H-benzo[d][1,2,3]triazol-1-yl)-1,1,3,3-tetramethylisouronium hexafluorophosphate (V) (559 mg, 1.47 mmol), and HOBT (226 mg, 1.47 mmol) are dissolved in THF (7 mL) and MeCN (3 mL). (R)-Quinuclidin-3-ol (375 mg, 2.95 mmol) is added and the mixture is stirred at RT for 1 hour. Solvents are evaporated, the residue is dissolved in EtOAc and washed with sat. NaHCO$_3$, water and brine. The organic layer is recovered, dried over Na$_2$SO$_4$, filtered and evaporated. The crude is purified by preparative HPLC and the collected fractions are evaporated, the residue is dissolved in EtOAc and washed with NaHCO$_3$ and brine. The organic layer is recovered, dried over Na$_2$SO$_4$, filtered and evaporated to afford compound the title compound as a colorless compound (95 mg, 16% yield, mixture of diastereoisomers).

$^1$H NMR (300 MHz, DMSO-d$_6$) ppm: 8.56-8.92 (m, 1H), 7.80-7.94 (m, 1H), 7.46-7.58 (m, 2H), 7.22-7.45 (m, 4H), 6.31-6.78 (m, 2H), 5.53 and 5.51 (d, 1H), 4.47-4.87 (m, 1H), 3.86 (s, 3H), 3.07 and 2.97 (ddd, 1H), 2.54-2.68 (m, 4H), 0.95-2.34 (m, 6H);

LC-MS (ESI POS): 395.3 (MH+).

Example 14

Preparation of (2-methoxy-phenylamino)-phenyl-acetic acid (R)-(1-aza-bicyclo[2.2.2]oct-3-yl) ester (C37)

Scheme 14

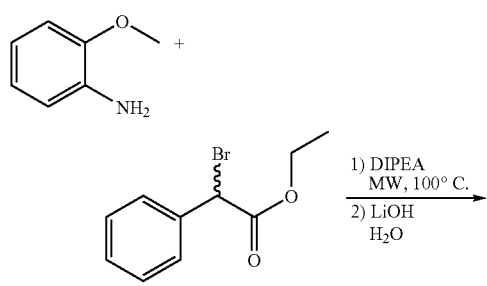

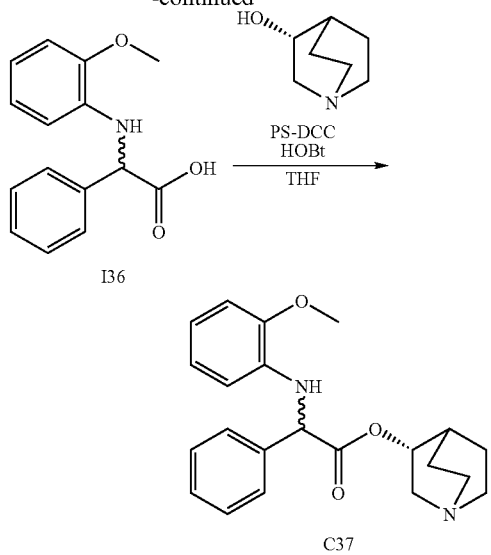

Preparation of (2-methoxy-phenylamino)-phenyl-acetic acid hydrochloride (I36)

Ethyl 2-bromo-2-phenylacetate (500 mg, 2.06 mmol), 2-methoxyaniline (0.28 mL, 2.47 mmol) and DIPEA (0.47 ml, 2.67 mmol) are dissolved in acetonitrile (10 mL). The resulting solution is heated under microwave irradiation at 100° C. for 30 minutes. DIPEA (47 ul, 0.27 mmol) and 2-methoxyaniline (28 uL, 0.25 mmol) are added and microwave heating is carried out for others 15 minutes. Water (5 mL) and lithium hydroxide hydrate (259 mg, 6.17 mmol) are directly added to the reaction solution and the resulting mixture is vigorously stirred at RT for 1 hour. Acetonitrile is evaporated, the remaining water phase is cooled at 0° C. and 4M HCl in 1,4-dioxane is added until pH is about 1. The solid obtained is collected by filtration and washed with water. The solid-cake is recovered and dried under vacuum to obtain intermediate 184 as a brown solid (377 mg, 62% yield).

Preparation of (2-methoxy-phenylamino)-phenyl-acetic acid (R)-(1-aza-bicyclo[2.2.2]oct-3-yl) ester (C37)

PS-DCC (2.05 g, 2.57 mmol, loading: 1.25 mmol/g) is suspended in THF (15 mL) and shaken for few minutes. Then (2-methoxy-phenylamino)-phenyl-acetic acid hydrochloride (I36) (377 mg, 1.28 mmol) and HOBT (393 mg, 2.57 mmol) are added. After 10 minutes, (R)-quinuclidin-3-ol (490 mg, 3.85 mmol) is added and the mixture is shaken at RT for 16 hours (Conversion complete by UPLC/MS-UV). PS-DCC is filtered off and the filtrate is evaporated to dryness. The residue is dissolved in EtOAc and washed with sat. NaHCO$_3$, water and brine. The organic layer is recovered, dried over Na$_2$SO$_4$, filtered and evaporated to afford the title compound as a yellow oil (548 mg, quantitative yield, mixture of diastereoisomers).

$^1$H NMR (300 MHz, DMSO-d6) ppm: 7.45-7.55 (m, 2H), 7.13-7.43 (m, 3H), 6.78-6.93 (m, 1H), 6.64 (m, 2H), 6.29-6.51 (m, 1H), 5.40 (d, 1H), 5.31 (d, 1H), 4.58-4.85 (m, 1H), 3.84 (s, 3H), 2.91-3.14 (m, 1H), 2.54-2.72 (m, 3H), 1.95-2.47 (m, 2H), 0.98-1.92 (m, 5H);

LC-MS (ESI POS): 367.3 (MH+).

Example 15

Preparation of phenyl-o-methylphenylamino-acetic acid (R)-(1-aza-bicyclo[2.2.2]oct-3-yl) ester (C39)

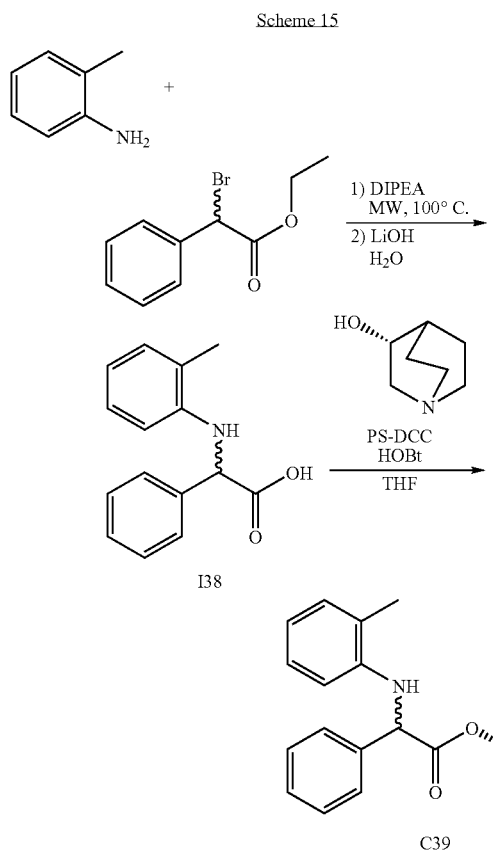

Preparation of phenyl-o-methyl phenylamino-acetic acid hydrochloride (I38)

Ethyl 2-bromo-2-phenylacetate (0.28 mL, 1.64 mmol), ortho-toluidine (0.26 mL, 2.47 mmol) and DIPEA (0.43 mL, 2.47 mmol) are dissolved in acetonitrile (5 mL) and stirred under MW irradiation at 100° C. for 1 hour (Conversion complete by UPLC/MS-UV). Lithium hydroxide hydrate (207 mg, 4.94 mmol) and water (3 mL) are added and the mixture is stirred at RT for 16 hours. 4M HCl in dioxane is added until pH is about 1, then the solvents are evaporated, the residue is suspended in water, sonicated, cooled at 0° C. and the resulting solid is recovered by filtration and dried under vacuum to get intermediate 186 as a off-white solid (290 mg, 63% yield).

Preparation of phenyl-o-methyl phenylamino-acetic acid (R)-(1-aza-bicyclo[2.2.2]oct-3-yl)ester (C39)

PS-DCC (1.15 g, 1.44 mmol, loading: 1.25 mmol/g) is suspended in THF (15 mL). Phenyl-o-methylphenylamino-acetic acid hydrochloride (I38) (200 mg, 0.72 mmol) and HOBT (221 mg, 1.44 mmol) are added, followed by (R)-quinuclidin-3-ol (275 mg, 2.16 mmol) and the mixture is shaken for 16 hours at RT. PS-DCC is filtered off and the filtrate is evaporated. The resulting residue is dissolved in EtOAc and washed sequentially with water, sat. NaHCO$_3$, water and brine. The organic layer is dried over Na$_2$SO$_4$, filtered and evaporated to give the title compound as a colorless oil (260 mg, quantitative yield, mixture of diastereoisomers).

$^1$H NMR (300 MHz, DMSO-d6) ppm: 7.50-7.62 (m, 2H), 7.25-7.46 (m, 3H), 7.00-7.07 (m, 1H), 6.82-6.98 (m, 1H), 6.51-6.66 (m, 1H), 6.30-6.49 (m, 1H), 5.32 (d, 1H), 5.10 (d, 1H), 4.65-4.85 (m, 1H), 2.85-3.16 (m, 1H), 2.56-2.69 (m, 3H), 2.23 (s, 3H), 2.13-2.46 (m, 2H), 0.95-1.97 (m, 5H);

LC-MS (ESI POS): 351.2 (MH+).

Example 16

Preparation of phenyl-(3-trifluoromethoxy-phenylamino)-acetic acid (R)-(1-aza-bicyclo[2.2.2]oct-3-yl) ester (C41)

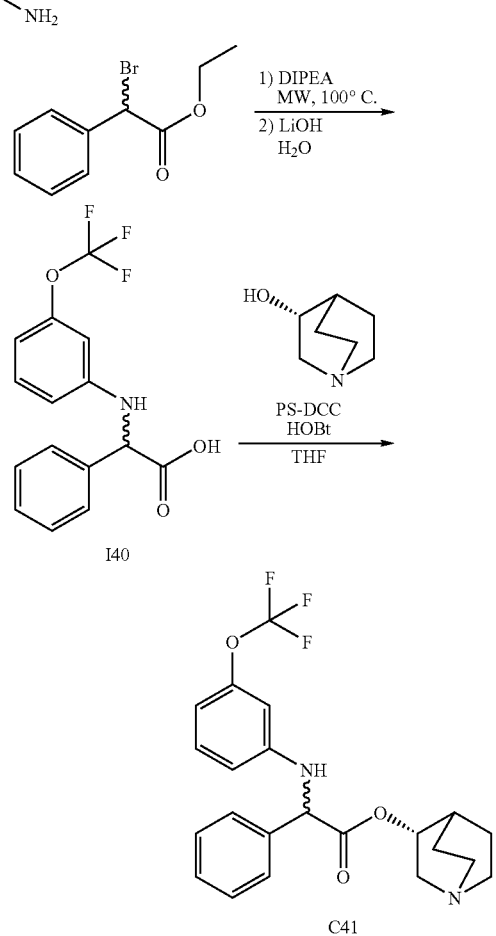

Preparation of phenyl-(3-trifluoromethoxy-phenylamino)-acetic acid hydrochloride (I40)

Ethyl 2-bromo-2-phenylacetate (400 mg, 1.64 mmol), 3-(trifluoromethoxy)aniline (0.33 mL, 2.47 mmol), and DIPEA (0.43 mL, 2.47 mmol) are dissolved in acetonitrile (5 mL) and heated under MW irradiation at 100° C. for 1 hour (Conversion complete by UPLC/MS-UV). Water (5 mL) and lithium hydroxide hydrate (207 mg, 4.94 mmol) are directly added and the resulting mixture is stirred at RT for 1 hour. Then 4M HCl in dioxane is added until pH 1, the organic solvents are evaporated and the resulting crude oil is purified by filtration through a silica pad using DCM/MeOH=9/1 as the eluent. Intermediate 188 is collected as a brown oil (569 mg, quantitative yield).

Preparation of phenyl-(3-trifluoromethoxy-phenylamino)-acetic acid (R)-(1-aza-bicyclo[2.2.2]oct-3-yl) ester (C41)

PS-DCC (920 mg, 1.15 mmol, loading: 1.25 mmol/g) is suspended in THF (15 mL). Phenyl-(3-trifluoromethoxy-phenylamino)-acetic acid hydrochloride (I40) (200 mg, 0.57 mmol) and HOBT (176 mg, 1.15 mmol) are added, followed by (R)-quinuclidin-3-ol (219 mg, 1.73 mmol) and the mixture is shaken for 16 hours at RT. PS-DCC is filtered off and the filtrate is evaporated. The resulting residue is dissolved in EtOAc and washed with water, sat. NaHCO₃, water and brine. The organic phase is dried over Na₂SO₄, filtered and evaporated to give the title compound as a colorless oil (206 mg, 85% yield, mixture of diastereoisomers).

$^1$H NMR (300 MHz, DMSO-d6) ppm: 7.26-7.62 (m, 5H), 7.16 (t, 1H), 6.79 (d, 1H), 6.38-6.75 (m, 3H), 5.34 (d, 1H), 4.66-4.80 (m, 1H), 2.91-3.24 (m, 1H), 2.53-2.76 (m, 3H), 1.97-2.39 (m, 2H), 1.67-1.96 (m, 1H), 0.99-1.67 (m, 4H);

LC-MS (ESI POS): 421.2 (MH$^+$).

Example 17

Preparation of (3-ethyl-phenylamino)-phenyl-acetic acid (R)-(1-aza-bicyclo[2.2.2]oct-3-yl) ester (C43)

Scheme 17

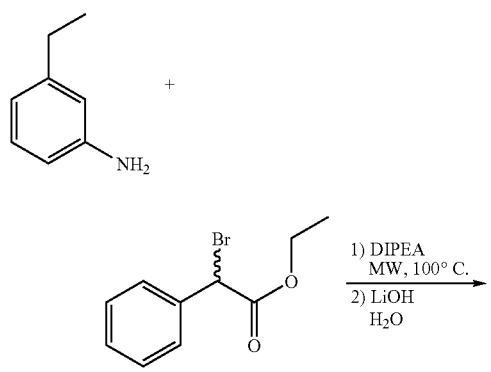

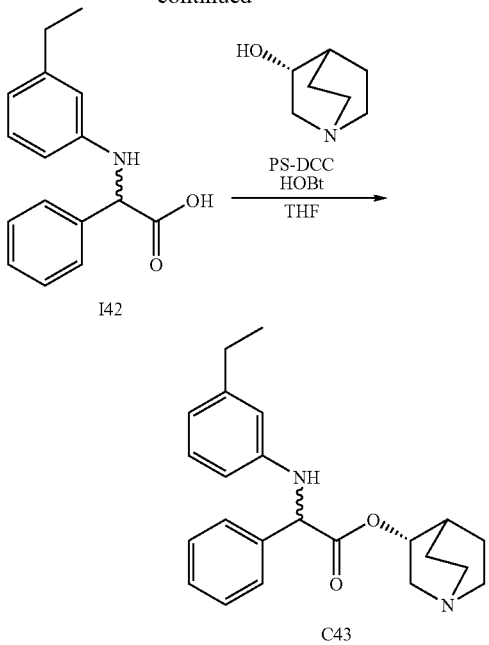

Preparation of (3-ethyl-phenylamino)-phenyl-acetic acid hydrochloride (I42)

Ethyl 2-bromo-2-phenylacetate (0.29 mL, 1.64 mmol), 3-ethylaniline (0.31 mL, 2.47 mmol), and N-ethyl-N-isopropylpropan-2-amine (0.43 mL, 2.47 mmol) are dissolved in acetonitrile (5 mL) and stirred under MW irradiation at 100° C. for 1 hour (Conversion complete by UPLC/MS-UV). Lithium hydroxide hydrate (207 mg, 4.94 mmol) and water (3 mL) are added and the mixture is stirred at RT for 16 hours. 4M HCl in dioxane is added until pH 1 and the solvents are evaporated. The residue is suspended in water, sonicated, cooled at 0° C. and filtered under suction. The recovered white solid is dried under vacuum at 40° C. overnight (414 mg, 86% yield).

Preparation of (3-ethyl-phenylamino)-phenyl-acetic acid (R)-(1-aza-bicyclo[2.2.2]oct-3-yl)ester (C43)

PS-DCC (1097 mg, 1.371 mmol, loading: 1.25 mmol/g) is suspended in THF (15 mL). HOBT (210 mg, 1.37 mmol), (3-ethyl-phenylamino)-phenyl-acetic acid hydrochloride (I42) (200 mg, 0.68 mmol), and (R)-quinuclidin-3-ol (262 mg, 2.06 mmol) are added and the suspension is shaken at RT for 16 hours. PS-DCC is filtered off and the filtrate is evaporated. The resulting residue is dissolved in EtOAc and washed with water, sat. NaHCO₃, water and brine. The organic phase is dried over Na₂SO₄, filtered and evaporated. The crude is purified by flash chromatography (DCM/MeOH=95/5) to obtain the title compound as a colorless oil (72 mg, 30% yield, mixture of diastereoisomers).

$^1$H NMR (300 MHz, DMSO-d$_6$) ppm: 7.45-7.60 (m, 2H), 7.21-7.47 (m, 3H), 6.96 (t, 1H), 6.56-6.66 (m, 1H), 6.47-6.56 (m, 1H), 6.38-6.47 (m, 1H), 6.17 (d, 1H), 5.16-5.39 (m, 1H), 4.60-4.79 (m, 1H), 2.89-3.16 (m, 1H), 2.54-2.70 (m, 3H), 2.45 (q, 2H), 1.98-2.34 (m, 2H), 1.66-1.96 (m, 1H), 1.20-1.66 (m, 4H), 1.11 (t, 3H);

LC-MS (ESI POS): 365.3 (MH+).

Example 18

Preparation of (3-acetylamino-phenylamino)-phenyl-acetic acid (R)-(1-aza-bicyclo[2.2.2]oct-3-yl) ester (C46)

Scheme 18

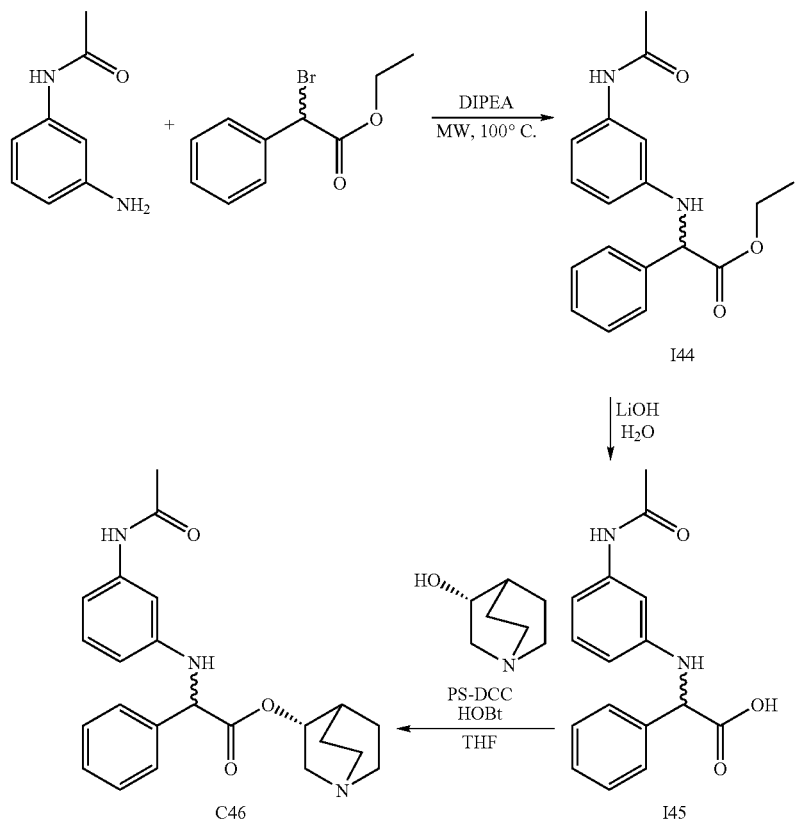

Preparation of (3-acetylamino-phenylamino)-phenyl-acetic acid ethyl ester (I44)

N-(3-Aminophenyl)acetamide (371 mg, 2.47 mmol), ethyl 2-bromo-2-phenylacetate (0.29 mL, 1.64 mmol), and DIPEA (0.43 mL, 2.47 mmol) are dissolved in acetonitrile (5 mL). The reaction is heated under MW irradiation at 100° C. for 30 minutes. Conversion complete by UPLC/MS-UV. Acetonitrile is evaporated and the crude residue is purified by flash chromatography (DCM/EtOAc=8/2) to obtain intermediate 192 as a colorless oil (440 mg, 86% yield).

Preparation of (3-acetylamino-phenylamino)-phenyl-acetic acid hydrochloride (I45)

(3-Acetylamino-phenylamino)-phenyl-acetic acid ethyl ester (I44) (440 mg, 1.41 mmol) and lithium hydroxide hydrate (118 mg, 2.82 mmol) are dissolved in THF (5 mL) and water (3 mL). The reaction is stirred at RT for 2 hours. THF is evaporated, the resulting aqueous solution is cooled at 0° C. and 1M HCl is added until pH is about 2. The precipitated is recovered by filtration, washed with cool water and dried under vacuum overnight to obtain intermediate 193 as a yellow solid (190 mg, 42% yield).

Preparation of (3-acetylamino-phenylamino)-phenyl-acetic acid (R)-(1-aza-bicyclo[2.2.2]oct-3-yl) ester (C46)

PS-DCC (798 mg, 0.10 mmol, loading: 1.25 mmol/g) is suspended in dry THF (10 mL). (3-Acetylamino-phenylamino)-phenyl-acetic acid hydrochloride (I45) (160 mg, 0.50 mmol), HOBT (153 mg, 0.10 mmol), and (R)-quinuclidin-3-ol (190 mg, 1.50 mmol) are added and the mixture is shaken for 16 hours at RT (Conversion complete by UPLC/MS-UV). PS-DCC is filtered off and washed with THF and then with EtOAc. The filtrate is evaporated, the resulting residue is taken up with EtOAc and washed with 5% NaHCO$_3$, water and brine. The organic layer is separated, dried over Na$_2$SO$_4$, filtered and evaporated to afford the title compound as a yellow oil (196 mg, quantitative yield, mixture of diastereoisomers).

$^1$H NMR (300 MHz, DMSO-d$_6$) ppm: 9.62 (s, 1H), 7.47-7.60 (m, 2H), 7.25-7.47 (m, 3H), 7.01-7.11 (m, 1H), 6.96 (t, 1H), 6.66-6.83 (m, 1H), 6.36-6.46 (m, 1H), 6.30 (d, 1H), 5.15 (d, 1H), 4.58-4.78 (m, 1H), 2.95 and 3.06 (ddd, 1H), 2.54-2.70 (m, 5H), 1.99 (s, 3H), 1.23-1.95 (m, 5H);

LC-MS (ESI POS): 394.2 (MH+).

C47 listed in Table 8 is prepared as previously described for C46, using 3-amino-N-methyl-benzamide instead of N-(3-aminophenyl)acetamide.

TABLE 8

| Compound | Structure | Yield and appearance | Analytical |
|---|---|---|---|
| C47 | 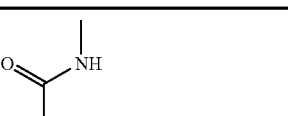 Mixture of stereoisomer | Quantitative yield Yellow oil | LC-MS (ESI POS): 394.2 (MH+) <br> ¹H NMR (300 MHz, DMSO-$d_6$) ppm: 8.17 (q, 1 H), 7.48-7.59 (m, 2 H), 7.25-7.48 (m, 3 H), 7.17-7.23 (m, 1 H), 7.13 (t, 1 H), 6.99-7.08 (m, 1 H), 6.80-6.94 (m, 1 H), 6.49 (d, 1 H), 5.32 (d, 1 H), 4.59-4.79 (m, 1 H), 2.89-3.15 (m, 1 H), 2.74 (d, 3 H), 2.54-2.68 (m, 5 H), 1.07-1.96 (m, 5 H) |

Example 19

Preparation of (3-fluoro-4-methyl-phenylamino)-phenyl-acetic acid (R)-(1-aza-bicyclo[2.2.2]oct-3-yl) ester (C49)

Scheme 19

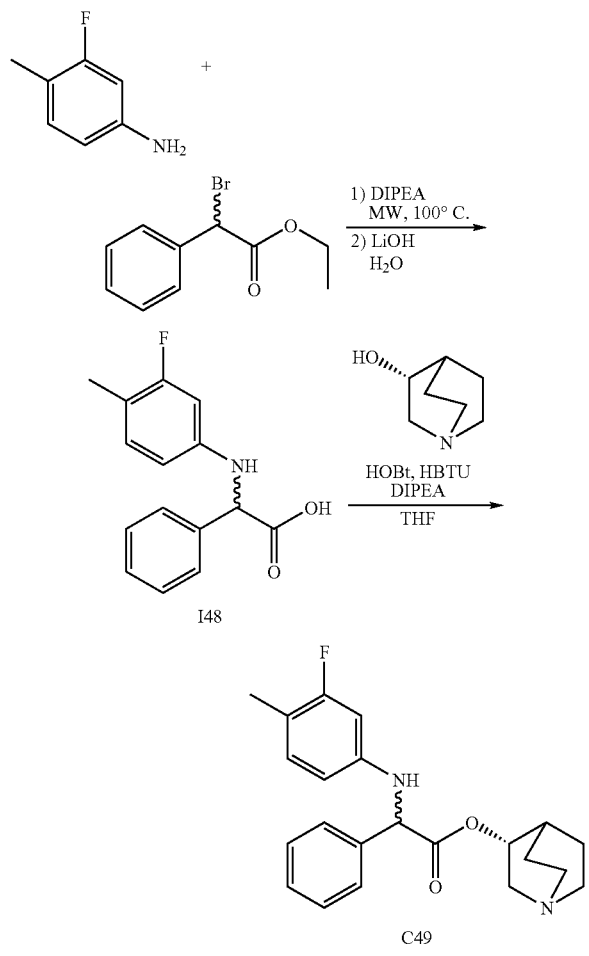

Preparation of (3-fluoro-4-methyl-phenylamino)-phenyl-acetic acid hydrochloride (I48)

Ethyl 2-bromo-2-phenylacetate (0.29 mL, 1.64 mmol), 3-fluoro-4-methylaniline (247 mg, 1.97 mmol) and DIPEA (0.37 mL, 2.14 mmol) are dissolved in acetonitrile (8 mL). The reaction is heated in a microwave oven at 100° C. for 1 hour and 15 minutes. Then, a solution of lithium hydroxide hydrate (207 mg, 4.94 mmol) in water (5 mL) is added and the mixture is stirred at RT for 2 hours. Acetonitrile is evaporated under vacuum, the remaining aqueous solution is cooled at 0° and the pH is adjusted to 2 with 4M HCl in dioxane. The resulting white solid is recovered by filtration and dried at 45° C. under vacuum overnight (367 mg, 75% yield).

Preparation of (3-fluoro-4-methyl-phenylamino)-phenyl-acetic acid (R)-(1-aza-bicyclo[2.2.2]oct-3-yl) ester (C49)

(3-Fluoro-4-methyl-phenylamino)-phenyl-acetic acid hydrochloride (I48) (250 mg, 0.84 mmol), 2-(1H-benzo[d][1,2,3]triazol-1-yl)-1,1,3,3-tetramethylisouronium hexafluorophosphate (V) (321 mg, 0.84 mmol), and HOBT (129 mg, 0.84 mmol) are dissolved in acetonitrile (6 mL). DIPEA (0.29 mL, 1.69 mmol) is added, followed by (R)-quinuclidin-3-ol (215 mg, 1.69 mmol) and the resulting yellow solution is stirred at RT overnight (Conversion complete by UPLC/MS-UV). MeCN is evaporated, the residue is dissolved in EtOAc and washed with sat. NaHCO₃, water and brine. The organic layer is recovered, dried over Na₂SO₄, filtered and evaporated. The crude compound is purified by filtration through a pad of silica using DCM/MeOH=9/1 as the eluent to obtain the title compound as a yellow oil (311 mg, quantitative yield, mixture of diastereoisomers).

¹H NMR (300 MHz, DMSO-$d_6$) ppm: 7.26-7.65 (m, 5H), 6.94 (td, 1H), 6.34-6.61 (m, 3H), 5.25-5.33 (m, 1H), 4.78-5.01 (m, 1H), 3.42 and 3.52 (ddd, 1H), 2.82-3.22 (m, 4H), 2.54-2.66 (m, 1H), 1.92-1.99 and 2.10-2.21 (m, 1H), 2.04 (s, 3H), 1.31-1.87 (m, 4H);

LC-MS (ESI POS): 369.2 (MH+).

Example 20

Preparation of (3-methylsulfanyl-phenylamino)-phenyl-acetic acid (R)-(1-aza-bicyclo[2.2.2]oct-3-yl) ester (C52)

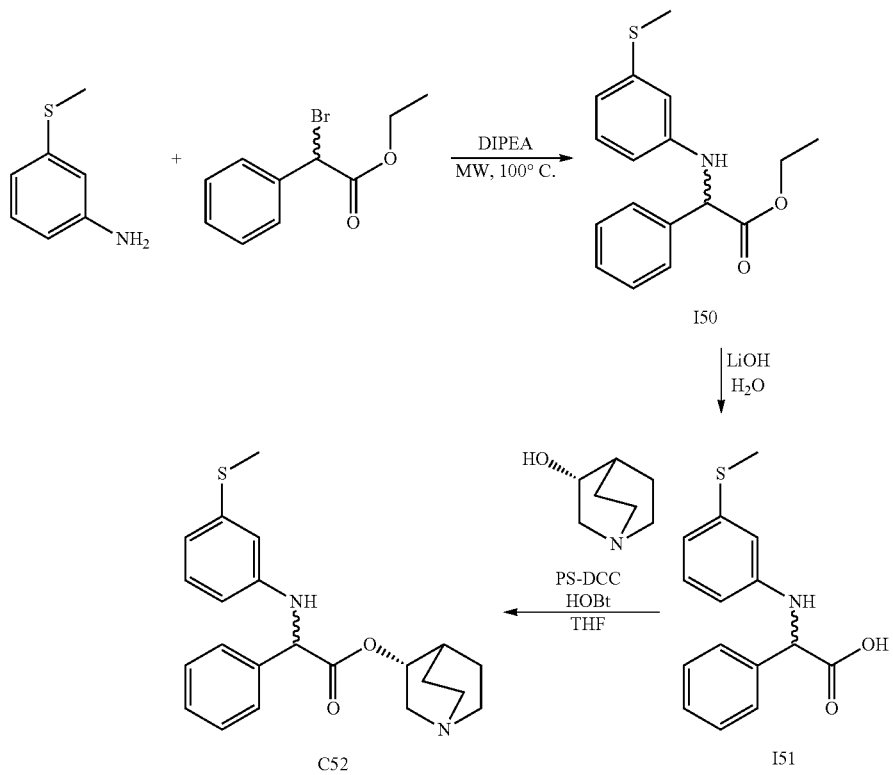

Scheme 20

Preparation of (3-methylsulfanyl-phenylamino)-phenyl-acetic acid ethyl ester (I50)

Ethyl 2-bromo-2-phenylacetate (0.22 mL, 1.23 mmol), 3-(methylthio)aniline (0.22 mL, 1.85 mmol), and DIPEA (0.32 mL, 1.85 mmol) are dissolved in acetonitrile (3 mL) and heated under microwave irradiation at 100° C. for 1 hour. Acetonitrile is evaporated and the crude residue is purified by flash chromatography (petroleum ether/EtOAc=85/15) to obtain intermediate I98 as a colorless oil (292 mg, 79% yield).

Preparation of (3-methylsulfanyl-phenylamino)-phenyl-acetic acid hydrochloride (I51)

(3-Methylsulfanyl-phenylamino)-phenyl-acetic acid ethyl ester (I50) (292 mg, 0.97 mmol) and lithium hydroxide hydrate (81 mg, 1.94 mmol) are dissolved in THF (7 mL) and water (3 mL) and stirred at RT for 2 hours. THF is evaporated, the solution is cooled at 0° C. and 1M HCl is added dropwise until pH 1. The resulting mixture is concentrated and extracted several times with DCM. The collected organic phases are dried over $Na_2SO_4$, filtered and evaporated to afford intermediate I99 as a brown-solid (248 mg, 83% yield).

Preparation of (3-methylsulfanyl-phenylamino)-phenyl-acetic acid (R)-(1-aza-bicyclo[2.2.2]oct-3-yl) ester (C52)

PS-DCC (602 mg, 0.80 mmol, loading: 1.33 mmol/g) is suspended in dry THF (15 mL). (3-Methylsulfanyl-phenylamino)-phenyl-acetic acid hydrochloride (I51) (124 mg, 0.40 mmol), HOBT (123 mg, 0.80 mmol), and (R)-quinuclidin-3-ol (153 mg, 1.20 mmol) are added and the suspension is shaken at RT overnight (16 hours). PS-DCC is filtered off, washed with THF and the filtrate is evaporated. The resulting residue is dissolved in EtOAc and washed with sat. $NaHCO_3$, water and brine. The organic layer is recovered, dried over $Na_2SO_4$, filtered and evaporated to afford the title compound as a brown oil (153 mg, quantitative yield, mixture of diastereoisomers).

$^1$H NMR (300 MHz, DMSO-$d_6$) ppm: 7.49-7.58 (m, 2H), 7.28-7.48 (m, 3H), 6.99 (t, 1H), 6.58-6.69 (m, 1H), 6.43-6.56 (m, 2H), 6.38 (d, 1H), 5.29 (d, 1H), 4.59-4.78 (m, 1H), 2.88-3.13 (m, 1H), 2.54-2.69 (m, 3H), 2.37 (s, 3H), 1.68-2.24 (m, 3H), 0.98-1.65 (m, 4H);

LC-MS (ESI POS): 383.2 (MH+).

C53 listed in Table 9 is prepared as previously described for C52, using 1-(3-amino-phenyl)-ethanone instead of 3-(methylthio)aniline.

TABLE 9

| Compound | Structure | Yield and appearance | Analytical |
|---|---|---|---|
| C53 | Mixture of stereoisomer | Quantitative yield Yellow oil | LC-MS (ESI POS): 379.3 (MH+)<br>$^1$H NMR (300 MHz, DMSO-$d_6$) ppm: 7.49-7.64 (m, 2 H), 7.25-7.48 (m, 4 H), 7.13-7.26 (m, 2 H), 6.87-7.04 (m, 1 H), 6.63 (d, 1 H), 5.35 (d, 1 H), 4.56-4.82 (m, 1 H), 2.96 (ddd, 1 H), 2.55-2.68 (m, 4 H), 2.48 (s, 3 H), 2.02-2.32 (m, 1 H), 0.98-1.97 (m, 5 H) |

Example 21

Preparation of (2,5-dimethoxy-phenylamino)-phenyl-acetic acid (R)-(1-aza-bicyclo[2.2.2]oct-3-yl) ester (C55)

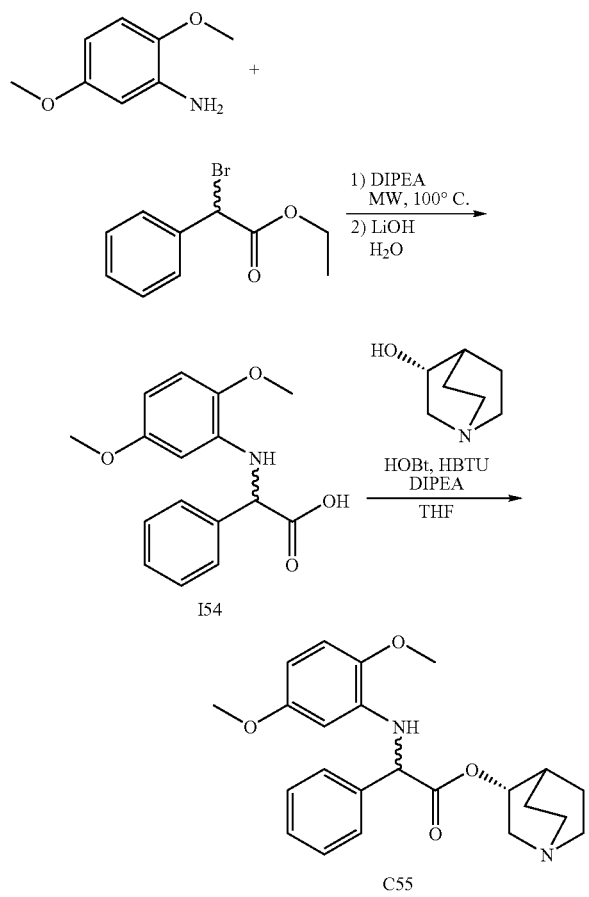

Scheme 21

Preparation of (2,5-dimethoxy-phenylamino)-phenyl-acetic acid hydrochloride (I54)

2,5-Dimethoxyaniline (284 mg, 1.85 mmol), ethyl 2-bromo-2-phenylacetate (0.22 ml, 1.23 mmol), and DIPEA (0.32 mL, 1.85 mmol) are dissolved in acetonitrile (5 mL) and stirred under MW heating at 100° C. for 1 hour. Water (2 mL, 111 mmol) and lithium hydroxide hydrate (104 mg, 2.47 mmol) are directly added and the resulting mixture is stirred at RT overnight. Acetonitrile is evaporated, 1M HCl is added and the acid aqueous phase is extracted with DCM. The collected organic phases are washed with brine, dried (Na$_2$SO$_4$), filtered and evaporated to obtain intermediate I102 as a white solid (154 mg, 38% yield).

Preparation of (2,5-Dimethoxy-phenylamino)-phenyl-acetic acid (R)-(1-aza-bicyclo[2.2.2]oct-3-yl) ester (C55)

PS-DCC (715 mg, 0.951 mmol, loading: 1.33 mmol/g) is suspended in dry THF (10 mL). (2,5-Dimethoxy-phenylamino)-phenyl-acetic acid hydrochloride (I54) (154 mg, 0.48 mmol), HOBT (146 mg, 0.95 mmol) and (R)-quinuclidin-3-ol (181 mg, 1.43 mmol) are added and the mixture is shaken at RT overnight. PS-DCC is filtered off and the filtrate is evaporated. The residue is dissolved in EtOAc and washed with sat. NaHCO$_3$, water and brine. The organic layer is dried over Na$_2$SO$_4$, filtered and evaporated to dryness. The crude compound is purified by flash chromatography (DCM/MeOH=95/5) to achieve the title compound as a colorless oil (108 mg, 57% yield, mixture of diastereoisomers).

$^1$H NMR (300 MHz, DMSO-$d_6$) ppm: 7.23-7.59 (m, 5H), 6.74 (d, 1H), 6.09-6.20 (m, 1H), 6.04 (d, 1H), 5.42 (d, 1H), 5.33 (d, 1H), 4.64-4.83 (m, 1H), 3.79 (s, 3H), 3.56 (s, 3H), 2.90-3.03 and 3.04-3.15 (m, 1H), 2.54-2.67 (m, 4H), 1.96-2.25 (m, 1H), 1.65-1.73 and 1.89-1.96 (m, 1H), 0.98-1.66 (m, 4H);

LC-MS (ESI POS): 397.3 (MH+).

Example 22

Preparation of (2,5-difluoro-phenylamino)-phenyl-acetic acid (R)-(1-aza-bicyclo[2.2.2]oct-3-yl)ester (C58)

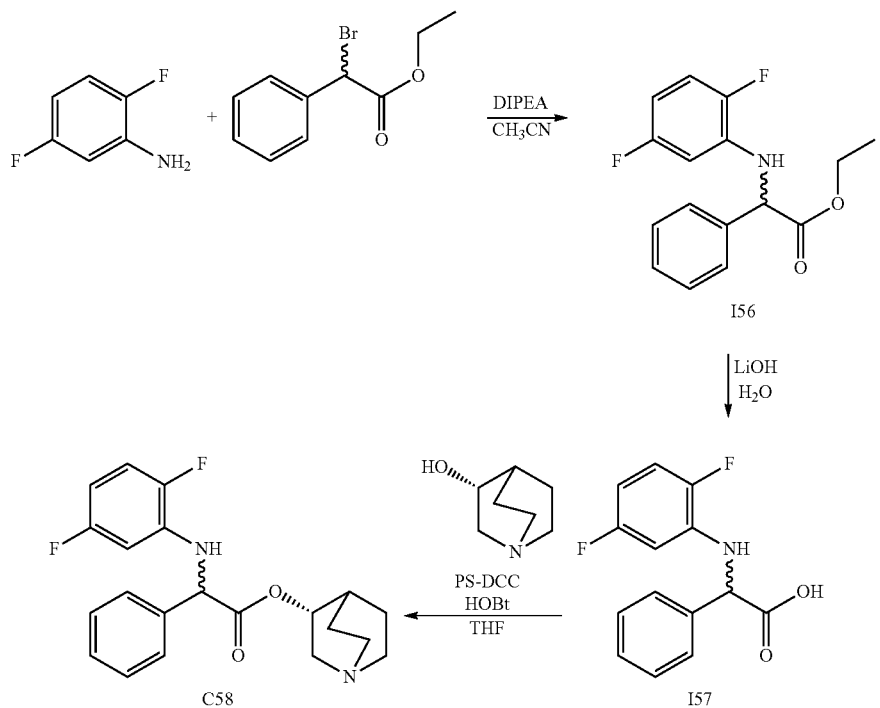

Scheme 22

Preparation of (2,5-difluoro-phenylamino)-phenyl-acetic acid ethyl ester (I56)

2,5-Difluoroaniline (0.19 mL, 1.85 mmol), ethyl 2-bromo-2-phenylacetate (0.22 mL, 1.23 mmol), and DIPEA (0.32 mL, 1.85 mmol) are dissolved in acetonitrile (3 mL) and heated under MW irradiation at 100° C. for 6 hours and then at 110° C. for 4 hours. Acetonitrile is evaporated and the crude is purified by flash chromatography (Petroleum ether/EtOAc=97/3) to obtain intermediate I104 as a white solid (240 mg, 67% yield).

Preparation of (2,5-difluoro-phenylamino)-phenyl-acetic acid hydrochloride (I57)

(2,5-Difluoro-phenylamino)-phenyl-acetic acid ethyl ester (I56) (240 mg, 0.82 mmol) is dissolved in THF/water (7/3 mL). Lithium hydroxide hydrate (69.1 mg, 1.65 mmol) is added and the resulting mixture is stirred at RT for 16 hours. THF is evaporated under reduced pressure, the solution is cooled at 0° C. and 1M HCl is added dropwise until pH 1. The white solid is recovered by filtration, washed with cold water and dried under vacuum at 40° C. overnight to obtain intermediate I105 as a white solid (198 mg, 80% yield).

Preparation of (2,5-difluoro-phenylamino)-phenyl-acetic acid (R)-(1-aza-bicyclo[2.2.2]oct-3-yl)ester (C58)

PS-DCC (914 mg, 1.301 mmol, loading: 1.33 mmol/g) is suspended in dry THF (15 mL). (2,5-Difluoro-phenylamino)-phenyl-acetic acid hydrochloride (I57) (195 mg, 0.65 mmol), HOBT (199 mg, 1.30 mmol), and (R)-quinuclidin-3-ol (248 mg, 1.95 mmol) are added and the suspension is shaken at RT for 16 hours (Conversion complete by UPLC/MS-UV). PS-DCC is filtered off under suction and the filtrate is evaporated. The resulting residue is dissolved in EtOAc and washed with sat. $NaHCO_3$, water and brine. The organic layer is separated, dried over $Na_2SO_4$, filtered and evaporated. The crude is purified by filtration through a silica-pad using DCM/MeOH=95/5 as the eluent. The title compound is collected as a colorless oil (195 mg, 80% yield, mixture of diastereoisomers).

$^1$H NMR (300 MHz, DMSO-$d_6$) ppm: 7.49-7.62 (m, 2H) 7.28-7.47 (m, 3H) 7.02-7.15 (m, 1H) 6.46-6.60 (m, 1H) 6.32-6.46 (m, 1H) 5.85-6.00 (m, 1H) 5.43 and 5.45 (d, 1H) 4.66-4.82 (m, 1H) 2.99 and 3.09 (ddd, 1H) 2.54-2.69 (m, 4H) 2.01-2.31 (m, 1H) 1.85-1.96 and 1.65-1.75 (m, 1H) 0.92-1.66 (m, 4H);

LC-MS (ESI POS): 373.2 (MH+).

C59 listed in Table 10 is prepared as previously described for C58, using 2,6-dimethyl-phenylamine instead of 2,5-difluoroaniline.

TABLE 10

| Compound | Structure | Yield and appearance | Analytical |
|---|---|---|---|
| C59 | 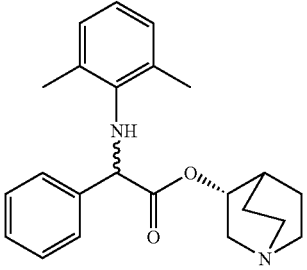<br>Mixture of diastereoisomer | 34% yield<br>Colorless oil | LC-MS (ESI POS): 365.1 (MH+)<br>$^1$H NMR (300 MHz, DMSO-d$_6$) ppm: 7.44-7.59 (m, 2 H), 7.25-7.44 (m, 3 H), 6.91 (d, 2 H), 6.60-6.79 (m, 1 H), 4.95 and 4.96 (d, 1 H), 4.62-4.82 (m, 2 H), 2.82-3.11 (m, 1 H), 2.55-2.61 (m, 3 H), 2.30-2.38 (m, 1 H), 2.22 (s, 6 H), 1.98-2.12 (m, 1 H), 1.70-1.75 and 1.77-1.89 (m, 1 H), 1.01-1.62 (m, 4 H) |

Example 23

Preparation of (2-ethyl-phenylamino)-phenyl-acetic acid (R)-(1-aza-bicyclo[2.2.2]oct-3-yl)ester (C61)

Scheme 23

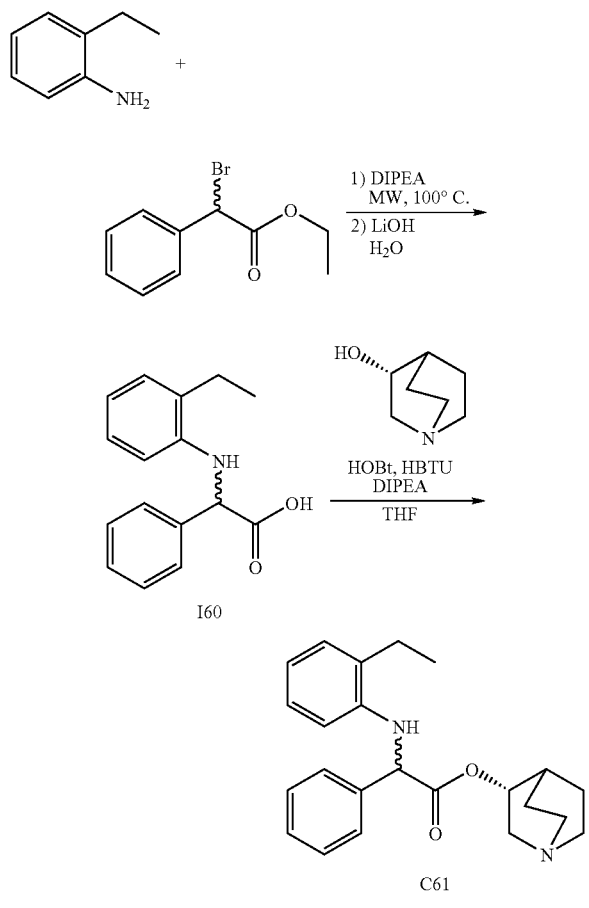

Preparation of (2-ethyl-phenylamino)-phenyl-acetic acid hydrochloride (I60)

2-Ethylaniline (0.23 mL, 1.85 mmol), ethyl 2-bromo-2-phenylacetate (0.22 mL, 1.23 mmol), and DIPEA (0.32 mL, 1.85 mmol) are dissolved in acetonitrile (3 mL) and stirred under MW irradiation at 100° C. for 1 hour. Water (2 ml, 111 mmol) and lithium hydroxide hydrate (104 mg, 2.47 mmol) are added to the reaction and the resulting mixture is stirred at RT overnight (16 hours). Acetonitrile is evaporated and 1M HCl is added until pH 1. The aqueous phase is extracted several times with DCM and the organic phases are collected and washed with water and brine, dried (Na$_2$SO$_4$), filtered and evaporated to give intermediate I108 as an off-white solid (316 mg, 88% yield).

Preparation of (2-ethyl-phenyl amino)-phenyl-acetic acid (R)-(1-aza-bicyclo[2.2.2]oct-3-yl)ester (C61)

PS-DCC (962 mg, 1.37 mmol, loading: 1.33 mmol/g) is suspended in THF (10 mL). HOBT (210 mg, 1.37 mmol), (2-ethyl-phenylamino)-phenyl-acetic acid hydrochloride (I60) (200 mg, 0.68 mmol), and (R)-quinuclidin-3-ol (262 mg, 2.06 mmol) are added and the mixture is shaken at RT overnight. PS-DCC is filtered off and washed with THF and the filtrate is evaporated under reduced pressure. The resulting residue is dissolved in EtOAc and washed with sat. NaHCO$_3$, water and brine. The organic layer is separated, dried over Na$_2$SO$_4$, filtered and evaporated. The residue is first purified by flash chromatography (DCM/MeOH=9/1) and then by preparative HPLC. The fractions containing the product are pooled, concentrated under vacuum, basified with sat. NaHCO$_3$ and extracted with EtOAc. The organic layer is dried (Na$_2$SO$_4$), filtered and evaporated to afford the title compound as a colorless oil (52 mg, 21% yield, mixture of diastereoisomers).

$^1$H NMR (300 MHz, DMSO-d$_6$) ppm: 7.47-7.60 (m, 2H), 7.23-7.46 (m, 3H), 7.00-7.08 (m, 1H), 6.86-6.96 (m, 1H), 6.53-6.66 (m, 1H), 6.34-6.48 (m, 1H), 5.32 and 5.33 (d, 1H), 5.17 and 5.18 (d, 1H), 4.66-4.84 (m, 1H), 2.96 and 3.07 (ddd, 1H), 2.61 (q, 2H), 2.55-2.69 (m, 3H), 1.98-2.39 (m, 2H), 1.65-1.73 and 1.85-1.96 (m, 1H), 1.24 (t, 3H), 1.02-1.77 (m, 4H);

LC-MS (ESI POS): 365.1 (MH+).

Example 24

Preparation of (2-acetyl-phenylamino)-phenyl-acetic acid (R)-(1-aza-bicyclo[2.2.2]oct-3-yl)ester (C64)

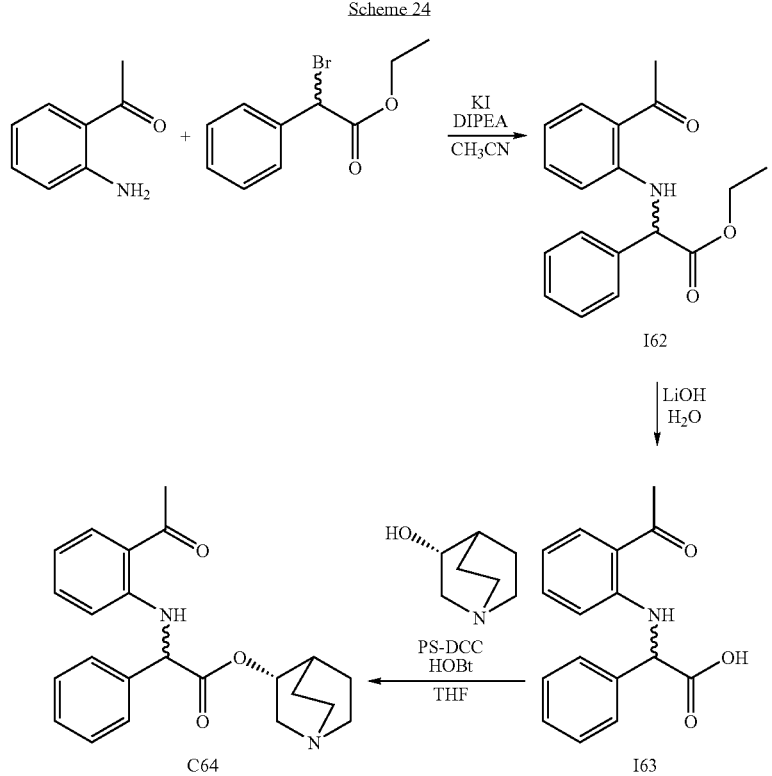

Scheme 24

Preparation of (2-acetyl-phenylamino)-phenyl-acetic acid ethyl ester (I62)

1-(2-Aminophenyl)ethanone (250 mg, 1.85 mmol), ethyl 2-bromo-2-phenylacetate (0.22 ml, 1.23 mmol), DIPEA (0.32 mL, 1.85 mmol) and a catalytic amount of potassium iodide are dissolved in acetonitrile (4 mL) and heated under MW irradiation at 100° C. for 2 hours and then at 120° C. for 1 hour. Acetonitrile is evaporated and the crude is purified by flash chromatography (petroleum ether/EtOAc=93/7) to obtain intermediate I110 as a yellow oil (367 mg, quantitative yield).

Preparation of (2-acetyl-phenylamino)-phenyl-acetic acid hydrochloride (I63)

(2-Acetyl-phenylamino)-phenyl-acetic acid ethyl ester (I62) (367 mg, 1.23 mmol) and lithium hydroxide hydrate (104 mg, 2.47 mmol) are dissolved in water (1.7 mL) and acetonitrile (5 mL). The reaction is stirred at RT overnight and then the solvents are evaporated. The residue is dissolved in EtOAc and washed several times with 1M HCl. The organic phase is recovered, dried ($Na_2SO_4$), filtered and evaporated to afford intermediate I111 as a brown solid (181 mg, 48% yield).

Preparation of (2-acetyl-phenylamino)-phenyl-acetic acid (R)-(1-aza-bicyclo[2.2.2]oct-3-yl)ester (C64)

PS-DCC (890 mg, 1.184 mmol, loading: 1.33 mmol/g) is suspended in dry THF (10 mL). (2-Acetyl-phenylamino)-phenyl-acetic acid hydrochloride (I63) (181 mg, 0.59 mmol), HOBt (181 mg, 1.18 mmol), and (R)-quinuclidin-3-ol (226 mg, 1.78 mmol) are added and the mixture is shaken at RT overnight. PS-DCC is filtered off and the filtrate is evaporated. The residue is dissolved in EtOAc and washed with sat. $NaHCO_3$, water and brine, dried over $Na_2SO_4$, filtered and evaporated. The resulting crude oil is purified by flash chromatography (DCM/MeOH=9/1) to afford the title compound as a colorless oil (239 mg, quantitative yield, mixture of diastereoisomers).

$^1$H NMR (300 MHz, DMSO-$d_6$) ppm: 9.81 and 9.82 (d, 1H), 7.83-7.94 (m, 1H), 7.44-7.54 (m, 2H), 7.22-7.44 (m, 4H), 6.54-6.73 (m, 2H), 5.52 and 5.53 (d, 1H), 4.61-4.87 (m, 1H), 2.99 and 3.10 (ddd, 1H), 2.59 (s, 3H), 2.54-2.69 (m, 3H), 2.02-2.39 (m, 2H), 1.69-1.78 and 1.87-1.97 (m, 1H), 0.94-1.70 (m, 4H);

LC-MS (ESI POS): 379.3 (MH+).

C65 listed in Table 11 is prepared as previously described for C64, using 3,5-difluoro-phenylamine instead of 1-(2-aminophenyl)ethanone.

TABLE 11

| Compound | Structure | Yield and appearance | Analytical |
|---|---|---|---|
| C65 | (3,5-difluorophenyl-NH-CH(phenyl)-C(=O)-O-quinuclidin-3-yl); Mixture of stereoisomer | 86% yield White foam | LC-MS (ESI POS): 373.3 (MH+)<br>$^1$H NMR (300 MHz, DMSO-$d_6$) ppm: 7.48-7.57 (m, 2 H), 7.28-7.46 (m, 3 H), 7.02 (d, 1 H), 6.19-6.49 (m, 3 H), 5.38 (d, 1 H), 4.66-4.80 (m, 1 H), 2.98 and 3.10 (ddd, 1 H), 2.54-2.69 (m, 3 H), 2.20-2.34 (m, 1 H), 2.01-2.13 (m, 1 H), 1.84-1.97 (m, 1 H), 1.05-1.78 (m, 4 H) |

Example 25

Preparation of 3-({[(R)-(1-aza-bicyclo[2.2.2]oct-3-yl)oxycarbonyl]-phenyl-methyl}-amino)-benzoic acid ethyl ester (C67)

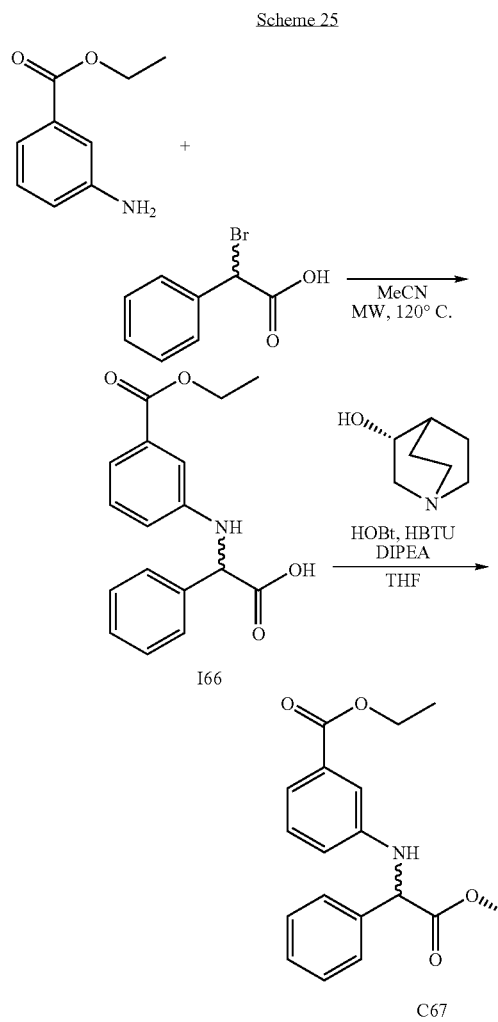

Scheme 25

Preparation of 3-[(carboxy-phenyl-methyl)-amino]-benzoic acid ethyl ester hydrochloride (I66)

Ethyl 3-aminobenzoate (0.52 mL, 3.49 mmol), 2-bromo-2-phenylacetic acid (250 mg, 1.16 mmol), and DIPEA (0.41 mL, 2.32 mmol) are dissolved in acetonitrile (4 mL) and heated under MW irradiation at 100° C. into a sealed vial for 30 minutes. Acetonitrile is evaporated and the crude is dissolved in DCM and washed with 1M HCl, water and brine. The organic layer is separated, dried (Na$_2$SO$_4$) and evaporated to obtain intermediate I114 as clear-brown oil (348 mg, 89% yield).

Preparation of 3-({[(R)-(1-aza-bicyclo[2.2.2]oct-3-yl)oxycarbonyl]-phenyl-methyl}-amino)-benzoic acid ethyl ester (C67)

3-[(Carboxy-phenyl-methyl)-amino]-benzoic acid ethyl ester hydrochloride (I66) (161 mg, 0.48 mmol), 2-(1H-benzo[d][1,2,3]triazol-1-yl)-1,1,3,3-tetramethylisouronium hexafluorophosphate (V) (218 mg, 0.57 mmol), and HOBT (88 mg, 0.57 mmol) are dissolved in dry THF (10 mL). (R)-Quinuclidin-3-ol (61.0 mg, 0.48 mmol) and DIPEA (0.17 mL, 0.96 mmol) are added and the mixture is stirred under inert atmosphere overnight. THF is evaporated and the crude residue is dissolved in EtOAc and washed with sat. NaHCO$_3$, water and brine. The recovered organic layer is dried (Na$_2$SO$_4$), filtered and evaporated. The crude is purified by flash chromatography (DCM/MeOH=95/5) to afford the title compound as a yellow oil (154 mg, 79% yield, mixture of diastereoisomers).

$^1$H NMR (300 MHz, DMSO-d6) ppm: 7.50-7.61 (m, 2H), 7.29-7.48 (m, 4H), 7.14-7.29 (m, 2H), 6.92-7.02 (m, 1H), 6.70 (d, 1H), 5.35 (d, 1H), 4.56-4.92 (m, 1H), 4.26 (q, 2H), 3.09-3.25 (m, 1H), 2.65-2.95 (m, 4H), 2.21-2.38 (m, 1H), 1.79-2.10 (m, 1H), 1.36-1.80 (m, 4H), 1.30 (t, 3H);

LC-MS (ESI POS): 409.3 (MH+).

Example 26

Preparation of (3-methoxy-phenylamino)-phenyl-acetic acid (R)-(1-aza-bicyclo[2.2.2]oct-3-yl)ester (C69)

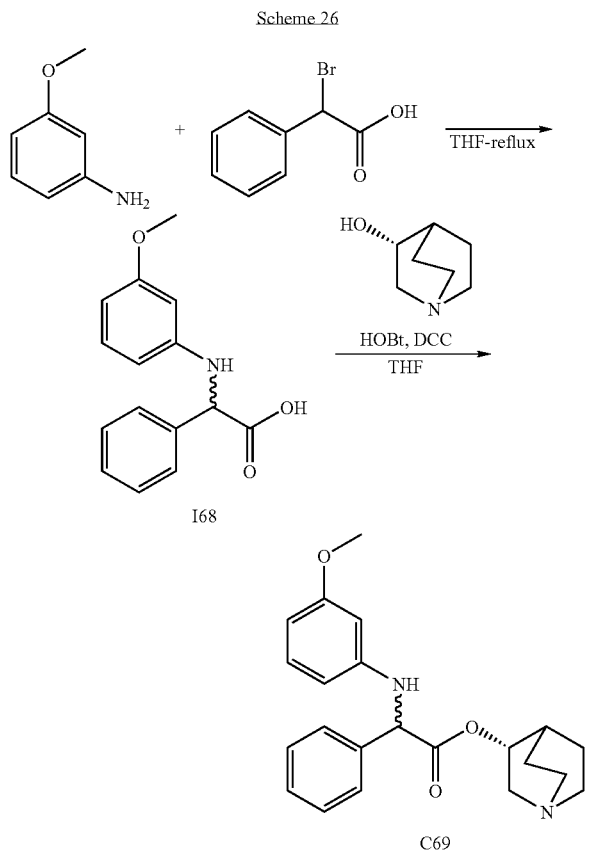

Preparation of (3-methoxy-phenylamino)-phenyl-acetic acid (I68)

A solution of 2-bromo-2-phenylacetic acid (0.5 g, 2.28 mmol) and 3-methoxyaniline (0.54 mL, 4.56 mmol) in THF (12 mL) is refluxed for 4 hours. Solvent is removed under vacuum, the residue is taken up with 1M HCl and extracted with EtOAc. The organic phase is dried ($Na_2SO_4$), filtered and evaporated. The crude is purified by flash chromatography (DCM/MeOH=98/2 to 9/1) to obtain intermediate I116 as a white solid (0.58 g, 99% yield).

Preparation of (3-methoxy-phenylamino)-phenyl-acetic acid (R)-(1-aza-bicyclo[2.2.2]oct-3-yl)ester (C69)

(3-Methoxy-phenylamino)-phenyl-acetic acid (0.58 g, 2.25 mmol), HOBT (0.45 g, 2.93 mmol) and DCC (0.60 g, 2.93 mmol) are dissolved in THF (100 mL) and stirred at RT for 20 minutes. Then, (R)-quinuclidin-3-ol (0.57 g, 4.51 mmol) is added and the resulting reaction is stirred at the same temperature for one day. The solvent is evaporated, the residue is taken up with EtOAc and the insoluble is filtered off. The organic solution is washed with 1M $K_2CO_3$ and then with brine. The crude is purified by flash chromatography (DCM/MeOH=99/1 to 80:20) to obtain the title compound as a yellow solid (0.43 g, 52% yield, mixture of diastereoisomers).

$^1$H NMR (300 MHz, DMSO-$d_6$) ppm:

Diastereoisomer 1: 7.48-7.64 (m, 2H), 7.22-7.47 (m, 3H), 6.95 (t, 1H), 6.23-6.38 (m, 3H), 6.09-6.19 (m, 1H), 5.25 (d, 1H), 4.50-4.79 (m, 1H), 3.64 (s, 3H), 2.97 (ddd, 1H), 2.20-2.71 (m, 4H), 2.03-2.13 (m, 1H), 1.83-1.95 (m, 1H), 1.19-1.67 (m, 4H);

Diastereoisomer 2: 7.48-7.64 (m, 2H), 7.22-7.47 (m, 3H), 6.95 (t, 1H), 6.23-6.38 (m, 3H), 6.09-6.19 (m, 1H), 5.24 (d, 1H), 4.50-4.79 (m, 1H), 3.64 (s, 3H), 3.04-3.14 (m, 1H), 2.20-2.71 (m, 5H), 1.68-1.74 (m, 1H), 1.19-1.67 (m, 4H);

LC-MS (ESI POS): 367.1 (MH+).

Example 27

Preparation of [(4-fluoro-phenyl)-methyl-amino]-phenyl-acetic acid (R)-(1-aza-bicyclo[2.2.2]oct-3-yl) ester (C72)

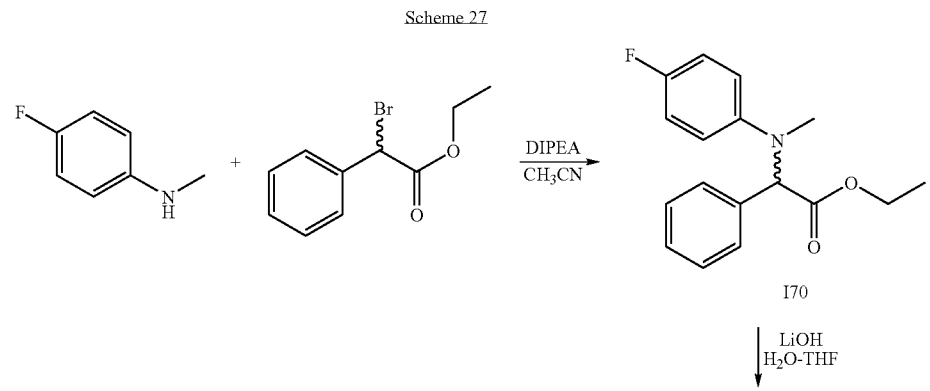

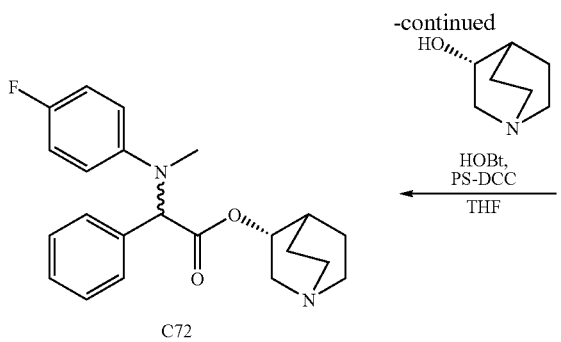
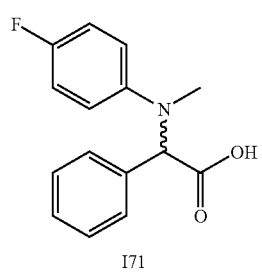

Preparation of [(4-fluoro-phenyl)-methyl-amino]-phenyl-acetic acid ethyl ester (I70)

4-Fluoro-N-methylaniline (0.33 g, 2.67 mmol) is added to a solution of ethyl 2-bromo-2-phenylacetate (0.36 mL, 2.06 mmol) in acetonitrile (6.86 mL) and DIPEA (0.47 ml, 2.67 mmol). The dark solution is stirred at 100° C. under microwave irradiation for 1 hour. Then solvent is evaporated and the crude is purified by flash chromatography (Petroleum ether/EtOAc=97/3) to obtain intermediate I118 as a yellow solid (0.59 g, 100% yield).

Preparation of [(4-fluoro-phenyl)-methyl-amino]-phenyl-acetic acid hydrochloride (I71)

To a solution of [(4-fluoro-phenyl)-methyl-amino]-phenyl-acetic acid ethyl ester (I70) (0.59 g, 2.05 mmol) in THF (10 mL) and water (10 mL), is added lithium hydroxide hydrate (0.26 g, 6.14 mmol). The reaction is stirred at RT for 3.5 hours and then at 70° C. for 24 hours. 3N HCl is added till pH is about 1 and the mixture is evaporated. Water (15 mL) is added and the residue is triturated obtaining a pale brown suspension that is filtered on a buckner funnel, washed with water and then with acetonitrile. The solid is dried under vacuum at 40° C. overnight to obtain intermediate I119 as a pale brown powder (0.44 g, 72% yield).

Preparation of [(4-fluoro-phenyl)-methyl-amino]-phenyl-acetic acid (R)-(1-aza-bicyclo[2.2.2]oct-3-yl)ester (C72)

PS-DCC (1.02 g, 1.35 mmol, loading: 1.33 mmol/g) is suspended in dry THF (13.5 mL). Then HOBT (0.21 g, 1.35 mmol), [(4-fluoro-phenyl)-methyl-amino]-phenyl-acetic acid hydrochloride (I71) (0.20 g, 0.68 mmol) and (R)-quinuclidin-3-ol (0.26 g, 2.03 mmol) are added. The mixture is shaken at RT overnight. PS-DCC is filtered off, washed with EtOAc and THF. The solution is evaporated and the residue is portioned between EtOAc and water. The organic phase is washed with sat. NaHCO$_3$, dried (Na$_2$SO$_4$) and evaporated. The crude is purified by flash chromatography (DCM/MeOH=95/5) to afford the title compound as a colorless oil (209 mg, 84% yield, mixture of diastereoisomers).

$^1$H NMR (300 MHz, DMSO-d$_6$) ppm: 7.26-7.49 (m, 5H) 6.99-7.13 (m, 2H) 6.83-6.99 (m, 2H) 5.78 (d, 1H) 4.74-4.88 (m, 1H) 3.02-3.18 (m, 2H) 2.56-2.79 (m, 5H) 2.29-2.46 (m, 2H) 1.76-1.93 (m, 1H) 1.41-1.63 (m, 3H) 1.19-1.39 (m, 1H); LC-MS (ESI POS): 369.2 (MH+).

Example 28

Preparation of (methyl-phenyl-amino)-phenyl-acetic acid (R)-(1-aza-bicyclo[2.2.2]oct-3-yl)ester (C75)

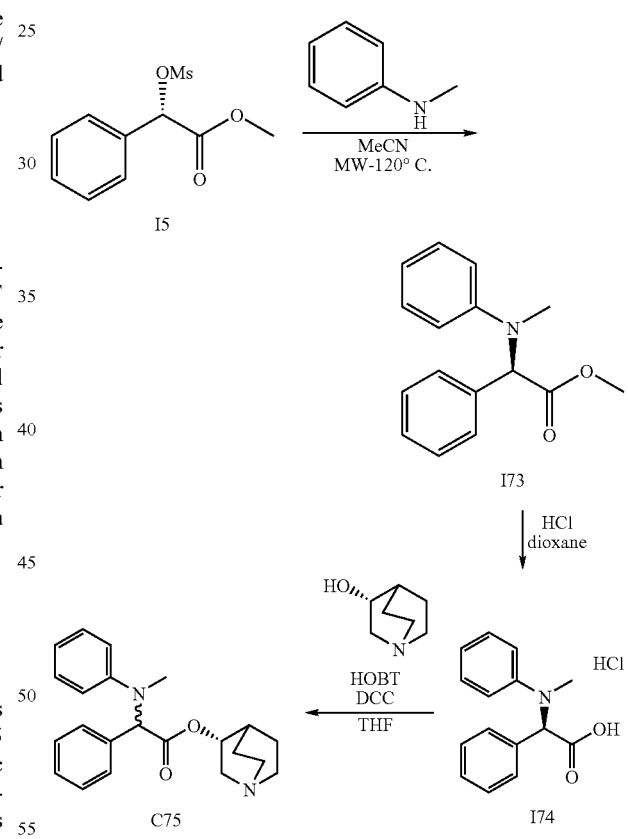

Preparation of (R)-(methyl-phenyl-amino)-phenyl-acetic acid methyl ester (I73)

N-methylaniline (299 ul, 2.76 mmol) is added to a solution of (S)-methyl 2-(methylsulfonyloxy)-2-phenylacetate (I5) (450 mg, 1.84 mmol) in acetonitrile (10 mL). The reaction is heated at 120° C. for 15 minutes (microwave irradiation). 2N HCl (5 mL) is added and the mixture is extracted with EtOAc. The organic phase is dried over sodium sulphate and the solvent is evaporated to dryness. The crude is purified by flash chromatography on silica gel (Petroleum ether/Et2O=9/1) to obtain intermediate I121 as an orange amorphous solid (125 mg, 27% yield).

Preparation of (R)-(methyl-phenyl-amino)-phenyl-acetic acid hydrochloride (I74)

(R)-(Methyl-phenyl-amino)-phenyl-acetic acid methyl ester (I73) (125 mg, 0.49 mmol) is dissolved in dioxane (2 mL). 37% Hydrogen chloride in water (3.00 mL, 36.5 mmol) is added and the mixture is stirred at 70° C. for 18 hours. Then a second portion of 37% hydrogen chloride in water (1.00 mL, 12.2 mmol) is added and the mixture is stirred at 70° C. for additional 36 hours. The mixture is cooled to RT and the white precipitate is filtered and washed with dioxane and Et2O to obtain intermediate I122 as a white solid (97 mg, 71% yield).

Preparation of (methyl-phenyl-amino)-phenyl-acetic acid (R)-(1-aza-bicyclo[2.2.2]oct-3-yl)ester (C75)

(R)-(Methyl-phenyl-amino)-phenyl-acetic acid hydrochloride (I74) (97 mg, 0.35 mmol), HOBT (107 mg, 0.70 mmol), DCC (144 mg, 0.70 mmol) and (R)-quinuclidin-3-ol (89 mg, 0.70 mmol) are dissolved in dioxane (5 mL) and the mixture is stirred at RT for 15 hours. The white precipitate is filtered and discarded whereas the clear solution is evaporated to dryness. The residue is dissolved in EtOAc and washed with sat. $Na_2CO_3$ and then brine. The organic phase is dried over sodium sulphate, filtered and evaporated to dryness. The resulting crude is purified by flash chromatography on silica gel (DCM/MeOH=97/3 to 95/5) to obtain the title compound as a pale yellow oil (46 mg, 38% yield, mixture of diastereoisomers).

$^1$H NMR (300 MHz, DMSO-$d_6$) ppm: 7.29-7.53 (m, 5H) 7.14-7.29 (m, 2H) 6.86-6.99 (m, 2H) 6.67-6.80 (m, 1H) 5.84 and 5.83(s, 1H) 4.73-4.88 (m, 1H) 2.99-3.16 (m, 1H) 2.75 and 2.71 (s, 3H) 2.53-2.69 (m, 3H) 2.29-2.47 (m, 2H) 1.74-1.95 (m, 1H) 1.32-1.63 (m, 3H) 1.12-1.30 (m, 1H);

LC-MS (ESI POS): 351.3 (MH$^+$).

Example 29

Preparation of (4-methyl-benzylamino)-phenyl-acetic acid (R)-(1-aza-bicyclo[2.2.2]oct-3-yl)ester (C77)

Scheme 29

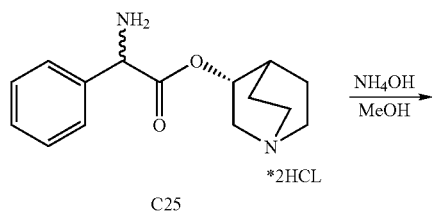

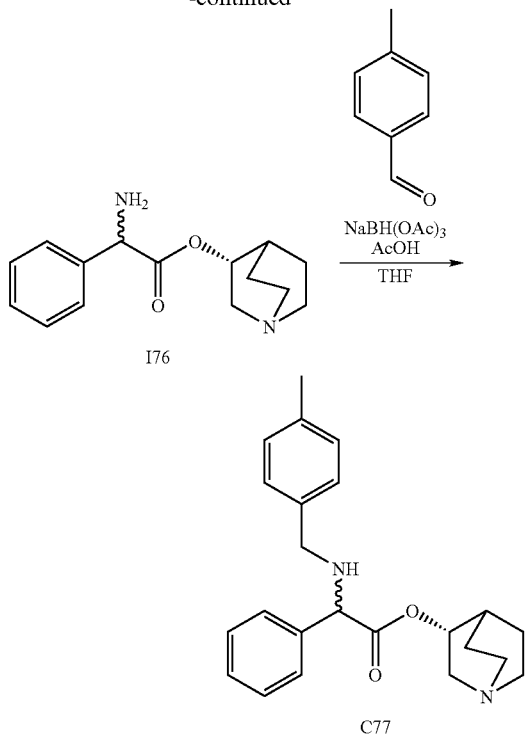

Preparation of amino-phenyl-acetic acid (R)-(1-aza-bicyclo[2.2.2]oct-3-yl)ester (I76)

(R)-Quinuclidin-3-yl 2-amino-2-phenylacetate dihydrochloride (C25) (1.11 g, 3.33 mmol) is dissolved in MeOH (10 mL) and 32% $NH_4OH$ (2.0 mL, 16.07 mmol) is added. The solution is stirred at RT for 30 seconds and then is evaporated under vacuum. The residue is dissolved in DCM/MeOH (4.5/0.5 mL) and about 1 g of $SiO_2$ is added. The suspension is evaporated and the residue is loaded on a silica gel column and purified eluting with DCM/MeOH/NH4OH=9.2/0.8/0.1 to 9/1/0.1 to collect intermediate I124 as a pale yellow oil (635 mg, 73% yield).

Preparation of (4-methyl-benzylamino)-phenyl-acetic acid (R)-(1-aza-bicyclo[2.2.2]oct-3-yl)ester (C77)

To a solution of amino-phenyl-acetic acid (R)-(1-aza-bicyclo[2.2.2]oct-3-yl)ester (I76) (100 mg, 0.38 mmol) in dry THF (3.84 mL), are added 4-methylbenzaldehyde (68 mL, 0.57 mmol) and AcOH (0.5 mL, 8.73 mmol). The mixture is stirred at RT and sodium triacetoxyborohydride (163 mg, 0.77 mmol) is added. The reaction is stirred at RT for 1.5 hours then cyclohexane is added and the mixture is evaporated to dryness. The crude is purified by flash chromatography (DCM/MeOH/NH4OH=95/5/0.5) to obtain the title compound as a colorless oil (76 mg, 54% yield, mixture of diastereoisomers).

$^1$H NMR (300 MHz, DMSO-d6) ppm: 7.25-7.51 (m, 5H), 7.15-7.23 (m, 2H), 7.03-7.15 (m, 2H), 4.51-4.81 (m, 1H), 4.33 (d, 1H), 3.61 (s, 2H), 2.85-3.19 (m, 1H), 2.57-2.69 (m, 5H), 2.28 (s, 3H), 1.68-1.92 (m, 1H), 0.91-1.64 (m, 4H);

LC-MS (ESI POS): 365.2 (MH+).

The compounds listed in Table 12 are prepared as previously described for C77, using 4-fluorobenzaldehyde, 4-methoxybenzaldehyde and benzaldehyde instead of 4-methylbenzaldehyde.

TABLE 12

| Compound | Structure | Yield and appearance | Analytical |
|---|---|---|---|
| C78 | Mixture of stereoisomer | 64% yield Colorless oil | LC-MS (ESI POS): 369.1 (MH+) <br> $^1$H NMR (300 MHz, DMSO-d$_6$) ppm: 7.23-7.61 (m, 7 H), 7.01-7.23 (m, 2 H), 4.58-4.79 (m, 1 H), 4.34 (s, 1 H), 3.64 (s, 2 H), 2.99 and 3.07 (ddd, 1 H), 2.54-2.69 (m, 3 H), 2.08-2.46 (m, 2 H), 1.69-1.79 and 1.83-1.90 (m, 1 H), 1.03-1.64 (m, 4 H) |
| C79 | Mixture of stereoisomer | 55% yield Colorless oil | LC-MS (ESI POS): 381.2 (MH+) <br> $^1$H NMR (300 MHz, DMSO-d6) ppm: 7.25:-7.50 (m, 5 H) 7.16-7.25 (m, 2 H) 6.81-6.92 (m, 2 H) 4.58-4.76 (m, 1 H) 4.32 (d, 1 H) 3.73 (s, 3 H) 3.59 (d, 2 H) 2.86-3.13 (m, 1 H) 2.53-2.67 (m, 5 H) 2.06-2.20 (m, 1 H) 1.68-1.90 (m, 1 H) 1.05-1.64 (m, 4 H) |
| C80 | Mixture of stereoisomer | 64% yield Pale yellow oil | LC-MS (ESI POS): 351.3 (MH+) <br> $^1$H NMR (300 MHz, DMSO-d6) ppm: 7.07-7.54 (m, 10 H), 4.59-4.79 (m, 1 H), 4.35 (s, 1 H), 3.66 (s, 2 H), 2.97-3.14 (m, 1 H), 2.56-2.70 (m, 4 H), 2.17-2.40 (m, 1 H), 1.71-1.97 (m, 1 H), 0.99-1.69 (m, 4 H) |

Example 30

Alternative preparation of (4-fluoro-benzylamino)-phenyl-acetic acid (R)-(1-aza-bicyclo[2.2.2]oct-3-yl) ester (C82)

Scheme 30

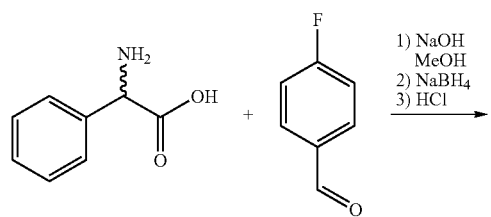

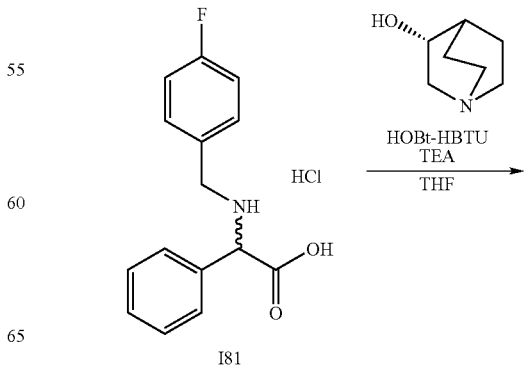

-continued

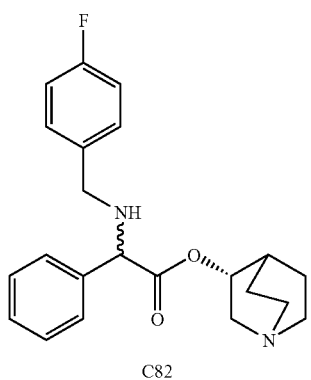

C82

Preparation of (4-fluoro-benzylamino)-phenyl-acetic acid hydrochloride (I81)

4-Fluorobenzaldehyde (0.25 mL, 2.38 mmol), 2-amino-2-phenylacetic acid (300 mg, 1.98 mmol) and NaOH (79 mg, 1.98 mmol) are dissolved in MeOH (20 mL) and stirred at RT overnight. The reaction is cooled at 0° C. and NaBH$_4$ (150 mg, 3.97 mmol) is added. After being stirred at 0° C. for 30 minutes, the reaction is judged complete by UPLC-MS analysis. 4M HCl in dioxane is added dropwise till pH 5 and the precipitate is collected by suction filtration, washed with Et$_2$O and dried under vacuum at 40° C. to obtain intermediate I129 as a white solid (587 mg, quantitative yield).

Preparation of (4-fluoro-benzylamino)-phenyl-acetic acid (R)-(1-aza-bicyclo[2.2.2]oct-3-yl)ester (C82)

A mixture of (4-fluoro-benzylamino)-phenyl-acetic acid hydrochloride (233 mg, 0.79 mmol), (R)-quinuclidin-3-ol (200 mg, 1.57 mmol), 2-(1H-benzo[d][1,2,3]triazol-1-yl)-1,1,3,3-tetramethylisouronium hexafluorophosphate (V) (596 mg, 1.57 mmol), TEA (0.22 mL, 1.57 mmol) and HOBT (241 mg, 1.57 mmol) in acetonitrile (10 mL) is stirred at RT for 48 hours. THF is removed under vacuum and the crude is partitioned between EtOAc and water. The organic phase is dried over sodium sulphate, filtered and evaporated to dryness. The crude is purified by preparative HPLC. The combined fractions are dried and partitioned between EtOAc and 2M K$_2$CO$_3$. The organic phase is dried over sodium sulphate, filtered and evaporated to dryness to achieve the title compound as colorless oil (61 mg, 21% yield, mixture of diastereoisomers).

$^1$H NMR (300 MHz, DMSO-d$_6$) ppm: 7.25-7.63 (m, 7H), 7.00-7.24 (m, 2H), 4.58-4.79 (m, 1H), 4.34 (s, 1H), 3.64 (s, 2H), 2.80 and 3.07 (ddd, 1H), 2.54-2.69 (m, 3H), 2.08-2.46 (m, 2H), 1.69-1.79 and 1.83-1.90 (m, 1H), 1.03-1.64 (m, 4H); LC-MS (ESI POS): 369.1 (MH$^+$).

Example 31

Preparation of (4-fluoro-phenyl)-(3-fluoro-phenylamino)-acetic acid (R)-(1-aza-bicyclo[2.2.2]oct-3-yl)ester (C84)

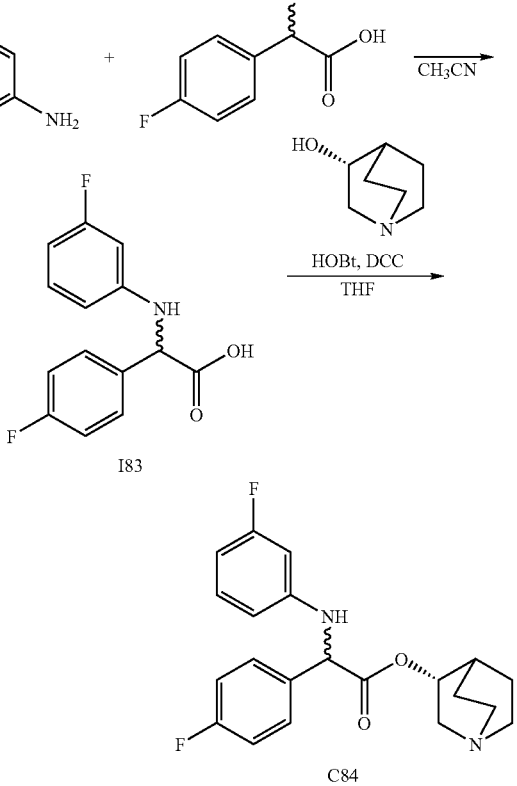

Preparation of (4-fluoro-phenyl)-(3-fluoro-phenylamino)-acetic acid (I83)

A mixture of 2-bromo-2-(4-fluorophenyl)acetic acid (500 mg, 2.15 mmol) and 3-fluoroaniline (477 mg, 4.29 mmol) in acetonitrile (8 mL) is heated under microwave irradiation at 100° C. for 50 minutes. Then 3-fluoroaniline (238 mg, 2.15 mmol) is added again and reaction is heated at 120° C. for 45 minutes in a microwave oven (LC-MS monitoring: complete conversion). The organic solution is diluted with EtOAc and washed with 2N HCl and then with brine. The organic phase is dried over Na$_2$SO$_4$, filtered and the solvent is evaporated to give intermediate I131 as a white solid (510 mg, 90% yield).

Preparation of (4-fluoro-phenyl)-(3-fluoro-phenylamino)-acetic acid (R)-(1-aza-bicyclo[2.2.2]oct-3-yl)ester (C84)

A mixture of (4-fluoro-phenyl)-(3-fluoro-phenylamino)-acetic acid (I83) (510 mg, 1.94 mmol), (R)-quinuclidin-3-ol (246 mg, 1.94 mmol), HOBT (356 mg, 2.32 mmol) and DCC (480 mg, 2.32 mmol) in THF (10 mL) is stirred at RT overnight (UPLC-MS monitoring: complete conversion). The solvent is evaporated, the crude is dissolved in EtOAc and the insoluble is filtered off The clear solution is washed with 1N K$_2$CO$_3$ and then with brine. The organic layer is dried over Na$_2$SO$_4$, filtered and evaporated. The crude is purified by silica gel chromatography (EtOAc/MeOH=8/2) to give the title compound as a yellow oil (360 mg, 50% yield, mixture of diastereoisomers).

$^1$H NMR (300 MHz, DMSO-d6):

Diastereoisomer 1 of C84: 7.41-7.65 (m, 2H), 7.15-7.33 (m, 2H), 6.96-7.14 (m, 1H), 6.67 (d, 1H), 6.43-6.59 (m, 2H), 6.20-6.42 (m, 1H), 5.36 (d, 1H), 4.46-4.88 (m, 1H), 2.97 (ddd, 1H), 2.53-2.72 (m, 3H), 2.18-2.39 (m, 1H), 2.01-2.16 (m, 1H), 1.80-1.96 (m, 1H), 1.21-1.66 (m, 4H).

Diastereoisomer 2 of C84: 7.41-7.65 (m, 2H), 7.15-7.33 (m, 2H), 6.96-7.14 (m, 1H), 6.67 (d, 1H), 6.43-6.59 (m, 2H), 6.20-6.42 (m, 1H), 5.35 (d, 1H), 4.46-4.88 (m, 1H), 3.08 (ddd, 1H), 2.53-2.72 (m, 5H), 1.66-1.76 (m, 1H), 1.21-1.66 (m, 4H);

LC-MS (ESI POS): 373 (MH+).

C85 listed in Table 13 is prepared as previously described for C84, using 2-fluoroaniline instead of 3-fluoroaniline.

TABLE 13

| Compound | Structure | Yield and appearance | Analytical |
| --- | --- | --- | --- |
| C85 | 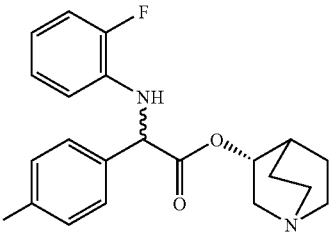<br>Mixture of stereoisomer | 53% yield<br>White solid | LC-MS (ESI POS): 373.1 (MH$^+$)<br>$^1$H NMR (300 MHz, DMSO-d$_6$) ppm: 7.49-7.66 (m, 2 H), 7.15-7.28 (m, 2 H), 7.07 (ddd, 1 H), 6.81-6.95 (m, 1 H), 6.50-6.78 (m, 2 H), 5.67 (d, 1 H), 5.40 (d, 1 H), 4.58-4.84 (m, 1 H), 3.07 (ddd, 1 H), 2.54-2.68 (m, 5 H), 1.64-1.77 (m, 1 H), 1.04-1.65 (m, 4 H) |

Example 32

Preparation of (R)-quinuclidin-3-yl 2-(phenylamino)-2-(thiophen-2-yl)acetate hydrochloride (C90)

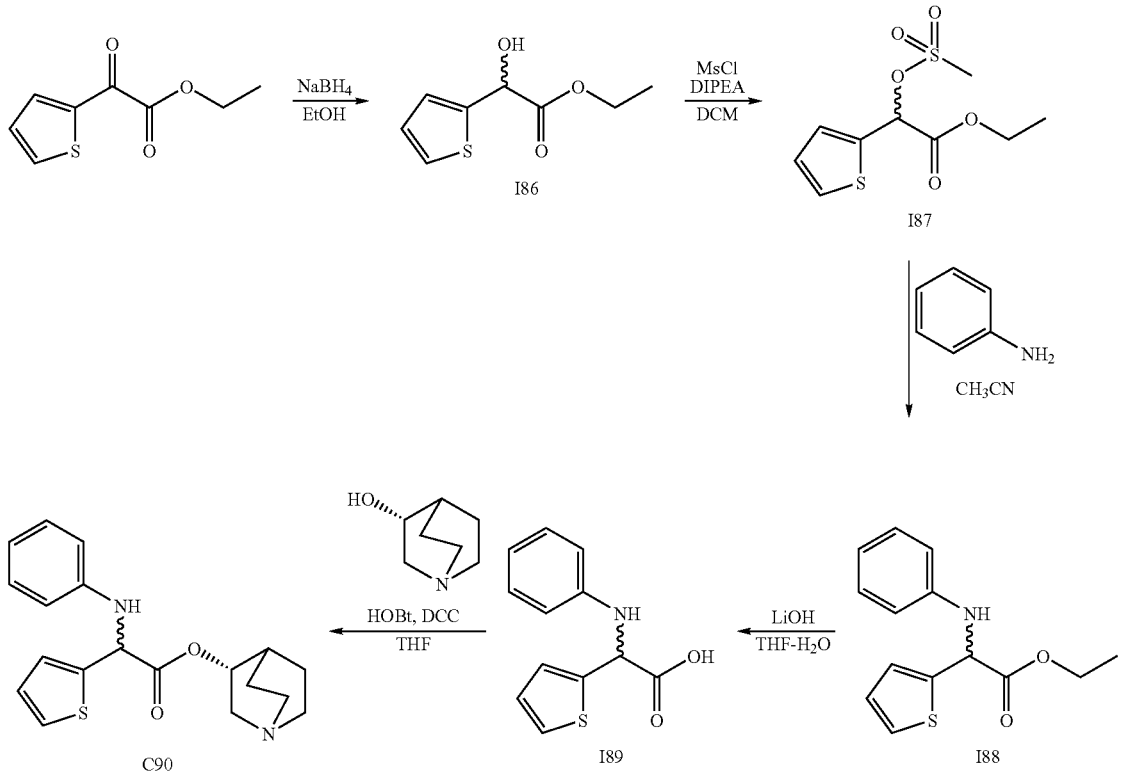

Preparation of hydroxy-thiophen-2-yl-acetic acid ethyl ester (I86)

A solution of ethyl 2-oxo-2-(thiophen-2-yl)acetate (5.00 g, 27.1 mmol) in ethanol (50 mL) is cooled at 0° C. with an ice bath. $NaBH_4$ (0.31 g, 8.14 mmol) is added in four portions under stirring. The mixture is stirred at 0° C. for 10 minutes, then allowed to warm at RT and stirred for additional 30 minutes. Reaction is concentrated under vacuum and the residue is partitioned between $Et_2O$ and ice-cooled water. The organic layer is separated, washed with water and brine, dried over $Na_2SO_4$, filtered and evaporated to give a colorless liquid (5.05 g, 91% yield).

Preparation of ethyl 2-(methylsulfonyloxy)-2-(thiophen-2-yl)acetate (I87)

Hydroxy-thiophen-2-yl-acetic acid ethyl ester (4.58 g, 24.6 mmol) is dissolved in dry DCM (125 mL) and cooled at 0° C. DIPEA (5.15 mL, 29.5 mmol) and methanesulphonyl chloride (2.11 mL, 27.1 mmol) are added and the resulting solution is stirred at RT for 1 hour. DIPEA (0.859 ml, 4.92 mmol) and methanesulphonyl chloride (0.19 mL, 2.46 mmol) are added again. After being stirred at room temperature for 1 additional hour, a third portion of DIPEA (0.43 mL, 2.46 mmol) and methanesulphonyl chloride (77 ul, 0.98 mmol) is added. After 1 hour the reaction is completed. The mixture is diluted with DCM, washed with sat. $NaHCO_3$, water and brine, dried ($Na_2SO_4$), filtered and evaporated. The resulting yellow oil is used in the next step without any further purification.

Preparation of ethyl 2-(phenylamino)-2-(thiophen-2-yl)acetate (I88)

Ethyl 2-(methylsulfonyloxy)-2-(thiophen-2-yl)acetate (I87) (5.7 g, 21.6 mmol), aniline (2.16 mL, 23.7 mmol) and DIPEA (4.52 mL, 25.9 mmol) are dissolved in acetonitrile (20 mL) to give a yellow solution which is heated under microwave irradiation into a sealed vial at 100° C. for 15 minutes. Conversion complete by UPLC/MS-UV. Solvent is evaporated and the residue is dissolved in DCM and washed with water and brine, dried ($Na_2SO_4$), filtered and evaporated to dryness. The resulting crude is purified by flash chromatography (Petroleum ether/EtOAc=85/15) to get desired compound as a yellow solid (4.33 g, 77% yield).

Preparation of 2-(phenylamino)-2-(thiophen-2-yl) acetic acid hydrochloride (I89)

Ethyl 2-(phenylamino)-2-(thiophen-2-yl)acetate (I88) (3.86 g, 14.8 mmol) and lithium hydroxide hydrate (1.24 g, 29.5 mmol) are dissolved in THF/water (20 mL/20 mL) and stirred at RT for 4 hours. THF is evaporated, the mixture is cooled to 0° C. and 4M HCl in dioxane is added until pH is about 1. The resulting precipitate is collected by suction filtration and washed with water. The white solid is dried under vacuum at 40° C. for 18 h (3.09 g, 78% yield).

Preparation of (R)-quinuclidin-3-yl-2-(phenylamino)-2-(thiophen-2-yl)acetate hydrochloride (C90)

2-(Phenylamino)-2-(thiophen-2-yl)acetic acid hydrochloride (I89) (359 mg, 1.33 mmol), DCC (330 mg, 1.60 mmol) and HOBT (245 mg, 1.60 mmol) are dissolved in THF (15 mL). (R)-quinuclidin-3-ol (339 mg, 2.66 mmol) is added and the reaction mixture is stirred at RT for 16 hours. HOBT (20.4 mg, 0.13 mmol) and DCC (33.0 mg, 0.16 mmol) are added again and the mixture is stirred for additional 8 hours. HOBT (20.4 mg, 0.13 mmol), DCC (33.0 mg, 0.16 mmol), (R)-quinuclidin-3-ol (16.9 mg, 0.13 mmol) are added and the mixture is stirred for additional 16 hours. THF is evaporated and the resulting crude oil is dissolved in EtOAc and washed with water and brine. The organic phase is recovered, dried over $Na_2SO_4$, filtered and evaporated. The crude is first purified by flash chromatography (DCM/MeOH=9/1) and then by preparative HPLC. The pure fractions are collected and evaporated. The resulting TFA salt is dissolved in THF and passed through a PL-$HCO_3$ cartridge (Varian, 200 mg, 1.8 mmol/g $HCO_3^-$). THF is evaporated, the product is dissolved in dioxane (2 mL) and 4M HCl in dioxane (2 mL) is added. The solvent is evaporated and the residue is dried under vacuum for 24 h to obtain the title compound as a brown solid (33 mg, 7% yield, mixture of disatereoisomers).

$^1$NMR (300 MHz, DMSO-$d_6$) ppm: 10.01 (br. s., 1H) 7.47-7.56 (m, 1H) 7.21-7.29 (m, 1H) 6.99-7.16 (m, 3H) 6.71-6.82 (m, 2H) 6.53-6.70 (m, 1H) 5.64 and 5.61 (s, 1H) 4.99-5.13 (m, 1H) 3.03-3.28 (m, 4H) 2.71-2.92 (m, 2H) 1.42-2.28 (m, 5H); LC-MS (ESI POS): 343.1 (MH+).

Example 33

Preparation of (4-methoxy-phenyl)-phenylamino-acetic acid (R)-(1-aza-bicyclo[2.2.2]oct-3-yl)ester (C93)

Scheme 33

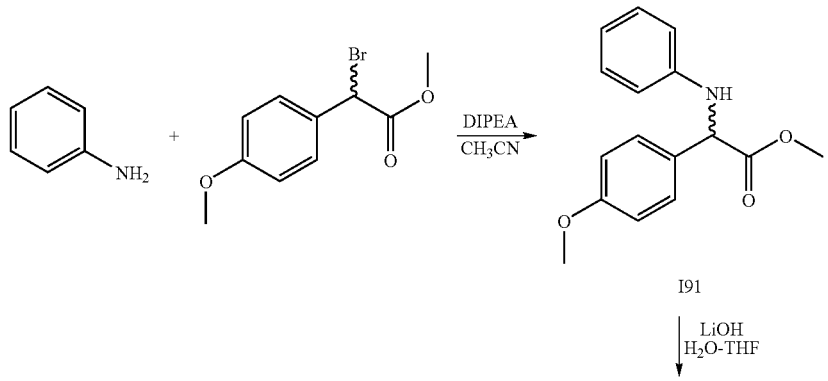

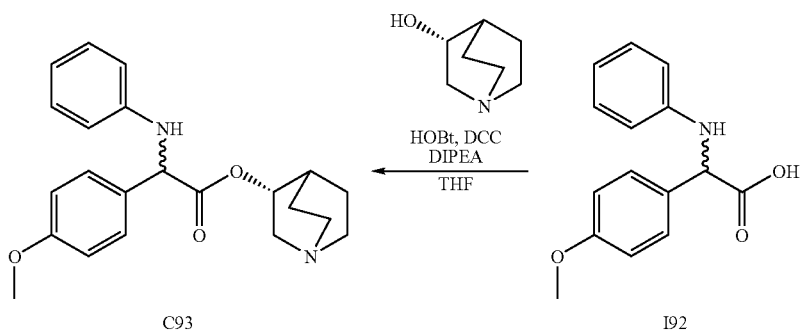

Preparation of (4-methoxy-phenyl)-phenylamino-acetic acid methyl ester (I91)

Methyl 2-bromo-2-(4-methoxyphenyl)acetate (1.10 g, 4.25 mmol), DIPEA (0.89 mL, 5.09 mmol), and aniline (0.43 mL, 4.67 mmol) are dissolved in acetonitrile (12 mL). The reaction is heated for 18 minutes at 100° C. under microwave irradiation. Acetonitrile is evaporated and the residue is diluted with DCM and washed with water and brine, dried over Na$_2$SO$_4$, filtered and evaporated to dryness. The crude is purified by flash chromatography (Petroleum Ether/EtOAc=9/1) to give intermediate I139 as a yellow oil (745 mg, 65% yield).

Preparation of (4-methoxy-phenyl)-phenylamino-acetic acid hydrochloride (I92)

(4-Methoxy-phenyl)-phenylamino-acetic acid methyl ester (953 mg, 3.51 mmol) and lithium hydroxide hydrate (295 mg, 7.03 mmol) are dissolved in THF (5 mL) and water (5 mL) and the resulting reaction is stirred overnight at RT (Conversion complete by UPLC-MS/UV). THF is evaporated, the aqueous phase is cooled at 0° C. and acidified till pH 1 with 4M HCl in 1.4 dioxane. The precipitate is collected by suction filtration and the white solid is dried overnight at 45° C. under vacuum (718 mg, 70% yield).

Preparation of (4-methoxy-phenyl)-phenylamino-acetic acid (R)-(1-aza-bicyclo[2.2.2]oct-3-yl)ester (C93)

(4-Methoxy-phenyl)-phenylamino-acetic acid hydrochloride (I92) (300 mg, 1.02 mmol), DCC (253 mg, 1.23 mmol), and HOBT (188 mg, 1.23 mmol) are dissolved in THF (10 mL). DIPEA (0.36 mL, 2.04 mmol) and (R)-quinuclidin-3-ol (130 mg, 1.02 mmol) are added. The mixture is stirred ad RT for 16 hours. Then DCC (25.3 mg, 0.12 mmol), HOBT (18.8 mg, 0.12 mmol), DIPEA (36 uL, 0.204 mmol) and (R)-quinuclidin-3-ol (13.0 mg, 0.10 mmol) are added again and reaction is stirred for additional 32 hours. THF is evaporated and the residue is dissolved in EtOAc and washed with sat. NaHCO$_3$, H$_2$O and brine. The organic layer is dried (Na$_2$SO$_4$), filtered and evaporated. The crude residue is purified by flash chromatography (DCM/MeOH=97/3 to 92/8) to obtain the title compound as a yellow solid (90 mg, 24% yield, mixture of diastereoisomers).

$^1$H NMR (300 MHz, DMSO-d$_6$) ppm: 7.34-7.63 (m, 2H), 7.01-7.15 (m, 2H), 6.87-7.01 (m, 2H), 6.63-6.74 (m, 2H), 6.52-6.62 (m, 1H), 6.19 (d, 1H), 5.17 (d, 1H), 4.55-4.85 (m, 1H), 3.74 (s, 3H), 2.83-3.20 (m, 1H), 2.03-2.69 (m, 5H), 1.65-1.94 (m, 1H), 0.93-1.63 (m, 4H);
LC-MS (ESI POS): 367.3 (MH+).

Example 34

Preparation of 4-{[(R)-(1-aza-bicyclo[2.2.2]oct-3-yl)oxycarbonyl]-phenylamino-methyl}-benzoic acid methyl ester (C95)

Scheme 34

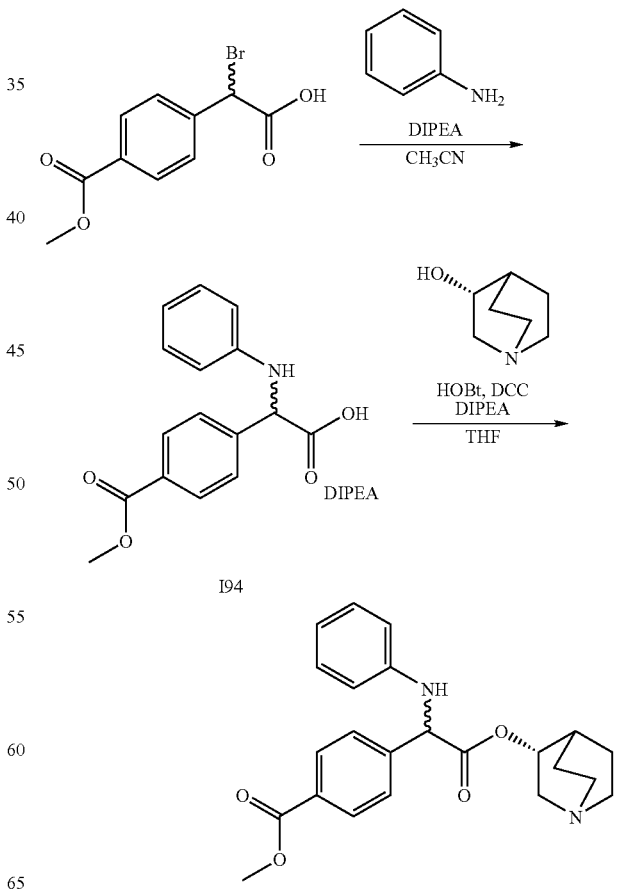

Preparation of N-ethyl-N-isopropylpropan-2-amine 2-(4-(methoxycarbonyl)phenyl)-2-(phenylamino) acetate (I94)

2-Bromo-2-(4-(methoxycarbonyl)phenyl)acetic acid (700 mg, 2.56 mmol), aniline (0.23 mL, 2.56 mmol), and DIPEA (0.94 mL, 5.38 mmol) are dissolved in acetonitrile (5 mL). The reaction is stirred at 100° C. under microwave irradiation for 15 minutes. Acetonitrile is evaporated and the residue is dissolved in DCM and washed with water and brine. The organic layer is dried ($Na_2SO_4$), filtered and evaporated. The crude compound is purified by flash chromatography (DCM/MeOH=9/1) to obtain intermediate I142 as a white solid (381 mg, 37% yield).

Preparation of 4-{[(R)-(1-aza-bicyclo[2.2.2]oct-3-yl) oxycarbonyl]-phenylamino-methyl}-benzoic acid methyl ester (C95)

N-Ethyl-N-isopropylpropan-2-amine 2-(4-(methoxycarbonyl)phenyl)-2-(phenylamino)acetate (I94) (212 mg, 0.51 mmol), DCC (158 mg, 0.77 mmol), and HOBT (117 mg, 0.77 mmol) are dissolved in dry THF (5 mL). (R)-Quinuclidin-3-ol (195 mg, 1.53 mmol) is added and the mixture is stirred at RT for 2 days. A second portion of DCC (79 mg, 0.38 mmol), HOBT (58.7 mg, 0.38 mmol) and (R)-quinuclidin-3-ol (98 mg, 0.77 mmol) are added and the mixture is further stirred for 24 hours. Then THF is evaporated, the residue is dissolved in EtOAc and washed with $NaHCO_3$, water and brine. The organic phase is dried ($Na_2SO_4$), filtered and evaporated. The crude is purified by preparative HPLC. The recovered fractions are evaporated, dissolved in EtOAc and washed with sat. $NaHCO_3$. The organic phase is dried ($Na_2SO_4$), filtered and evaporated to afford the desired compound as a colorless oil (42 mg, 21% yield, mixture of diastereoisomers).

$^1$H NMR (300 MHz, DMSO-$d_6$) ppm: 7.88-8.05 (m, 2H), 7.51-7.76 (m, 2H), 6.91-7.13 (m, 2H), 6.71 (dd, 2H), 6.50-6.64 (m, 1H), 6.38 (d, 1H), 5.42 (d, 1H), 4.39-4.86 (m, 1H), 3.85 (s, 3H), 2.84-3.15 (m, 1H), 2.54-2.67 (m, 4H), 0.76-2.16 (m, 6H);

LC-MS (ESI POS): 395.4 (MH+).

Example 35

Preparation of (3-fluoro-phenyl)-phenylamino-acetic acid (R)-(1-aza-bicyclo[2.2.2]oct-3-yl)ester (C99)

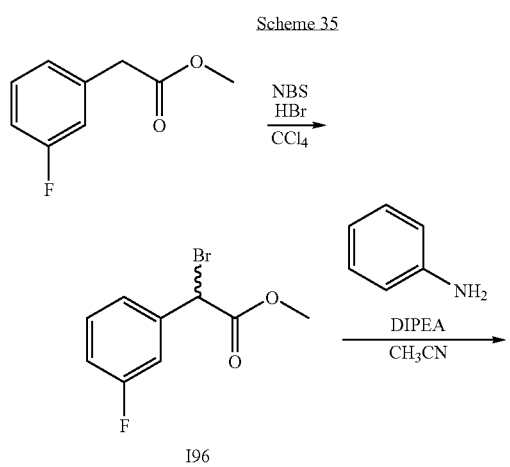

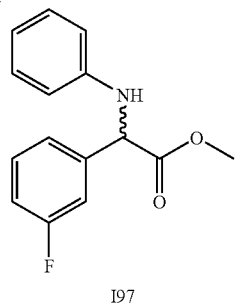

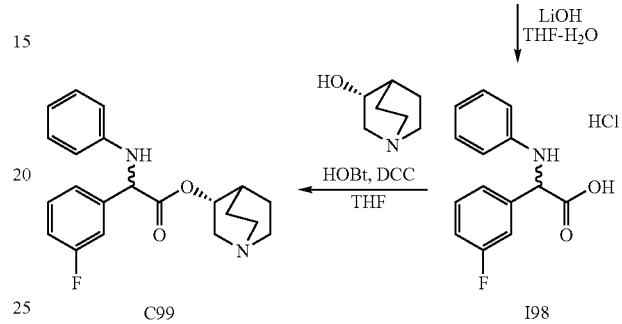

Preparation of bromo-(3-fluoro-phenyl)-acetic acid methyl ester (I96)

Methyl 2-(3-fluorophenyl)acetate (1.90 g, 11.3 mmol) and N-bromo succinimide (2.01 g, 11.3 mmol) are dissolved in $CCl_4$ (80 mL). HBr (64 ul, 0.56 mmol) is added and the mixture is stirred under reflux overnight. The mixture is cooled at RT, diluted with DCM and washed with sat. $NaHCO_3$, water and brine. The organic layer is dried ($Na_2SO_4$), filtered and evaporated obtaining intermediate I144 as a yellow oil (2.68 g, 96% yield).

Preparation of (3-fluoro-phenyl)-phenylamino-acetic acid methyl ester (I97)

Bromo-(3-fluoro-phenyl)-acetic acid methyl ester (I96) (300 mg, 1.21 mmol), DIPEA (0.32 mL, 1.82 mmol), and aniline (0.17 mL, 1.82 mmol) are dissolved in acetonitrile (4 mL) and heated under MW irradiation at 100° C. for 1 hour. Acetonitrile is evaporated and the residue is purified by flash chromatography (Petroleum ether/EtOAc=95/5) to obtain intermediate I145 as a colorless oil (229 mg, 73% yield).

Preparation of (3-fluoro-phenyl)-phenylamino-acetic acid (I98)

(3-Fluoro-phenyl)-phenylamino-acetic acid methyl ester (I97) (229 mg, 0.88 mmol) and lithium hydroxide hydrate (74.1 mg, 1.77 mmol) are dissolved in THF/water (6 mL/2 mL) and stirred at RT for 2 hours. THF is evaporated, the resulting basic aqueous solution is acidified till pH 1 with 1M HCl. The precipitate is recovered by suction filtration and washed with 1M HCl. The compound is dried at 40° C. under vacuum overnight to get intermediate I146 as a white solid (186 mg, 75% yield).

Preparation of (3-fluoro-phenyl)-phenylamino-acetic acid (R)-(1-aza-bicyclo[2.2.2]oct-3-yl)ester (C99)

PS-DCC (982 mg, 1.31 mmol, loading: 1.33 mmol/g) is suspended in dry THF (15 mL). (3-fluoro-phenyl)-phenylamino-acetic acid hydrochloride (I98) (184 mg, 0.65 mmol), HOBT (200 mg, 1.31 mmol), and (R)-quinuclidin-3-ol (249 mg, 1.96 mmol) are added and the mixture is shaken at RT overnight. PS-DCC is filtered off and the filtrate is evaporated. The residue is dissolved in EtOAc and washed with NaHCO₃, water and brine. The organic layer is dried over Na₂SO₄, filtered and evaporated to dryness. The crude compound is purified by filtration through a pad of silica-gel using DCM/MeOH=9/1 as the eluent. The title compound is obtained as a colorless oil (129 mg, 56% yield, mixture of diastereoisomers).

$^1$H NMR (300 MHz, DMSO-d6) ppm: 7.31-7.52 (m, 3H), 7.11-7.23 (m, 1H), 6.98-7.11 (m, 2H), 6.67-6.76 (m, 2H), 6.51-6.63 (m, 1H), 6.35 (d, 1H), 5.35 and 5.36 (d, 1H), 4.59-4.80 (m, 1H), 2.97 and 3.07 (ddd, 1H), 2.55-2.67 (m, 5H), 1.67-1.74 and 1.81-1.95 (m, 1H), 1.10-1.66 (m, 4H);

LC-MS (ESI POS): 355.2 (MH⁺).

C100 listed in Table 14 is alternatively prepared as previously described for C99, using methyl 2-(4-fluorophenyl)acetate instead of methyl 2-(3-fluorophenyl)acetate.

TABLE 14

| Compound | Structure | Yield and appearance | Analytical |
|---|---|---|---|
| C100 | Mixture of diastereoisomers | 44% yield White solid | LC-MS (ESI POS): 355.0 (MH⁺) $^1$H NMR (300 MHz, DMSO-d₆) ppm: 7.69-7.83 (m, 4 H), 7.01-7.16 (m, 2 H), 6.65-6.79 (m, 2 H), 6.53-6.64 (m, 1 H), 6.42 (d, 1 H), 5.46 and 5.47 (d, 1 H), 4.66-4.81 (m, 1 H), 2.99 and 3.10 (ddd, 1 H), 2.54-2.88 (m, 4 H), 2.04-2.41 (m, 1 H), 0.92-1.97 (m, 5 H) |

Example 36

Preparation of phenylamino-(4-trifluoromethyl-phenyl)-acetic acid (R)-(1-aza-bicyclo[2.2.2]oct-3-yl) ester (C105)

Scheme 36

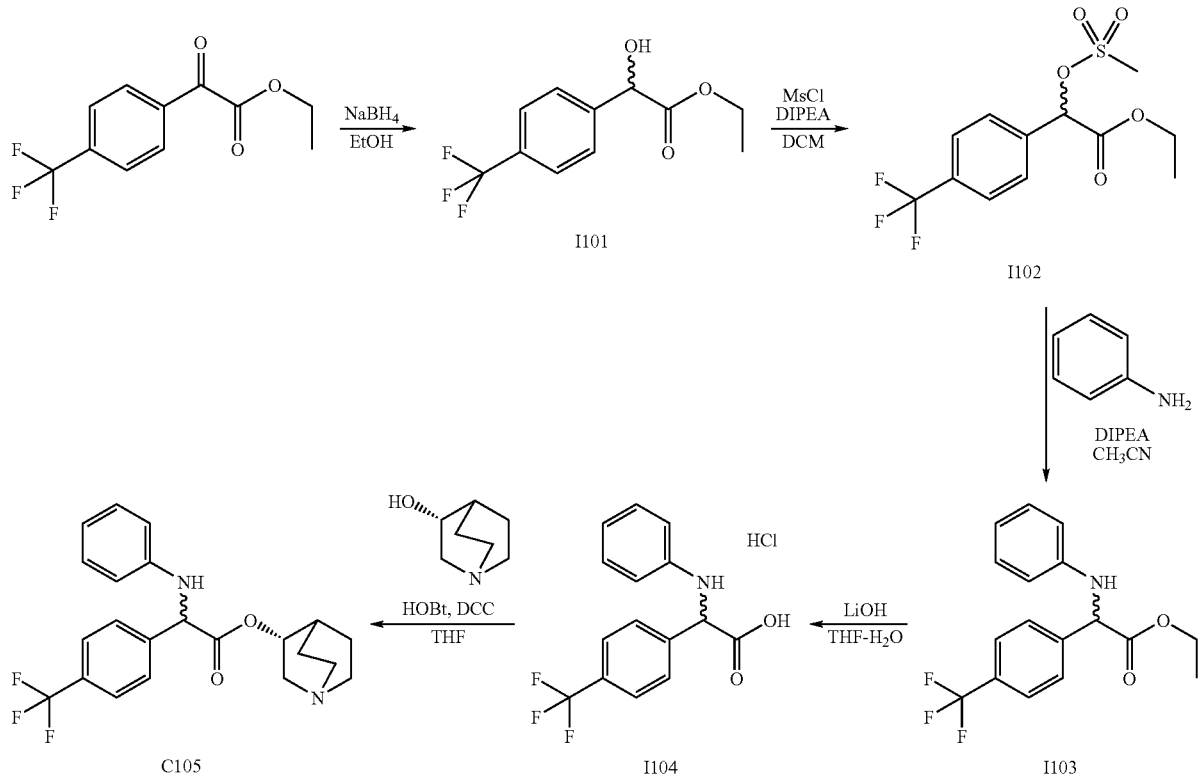

Preparation of hydroxy-(4-trifluoromethyl-phenyl)-acetic acid ethyl ester (I101)

Ethyl 2-oxo-2-(4-(trifluoromethyl)phenyl)acetate (500 mg, 2.03 mmol) is dissolved in absolute EtOH (10 mL) and cooled at 0° C. under $N_2$. $NaBH_4$ (38.4 mg, 1.02 mmol) is added in two portions and the resulting suspension is allowed to warm to RT and stirred for 45 minutes. The solvent is evaporated, the resulting residue is diluted with $Et_2O$ and cool water is added. The organic layer is separated, washed with water and brine, dried over $Na_2SO_4$, filtered and evaporated obtaining intermediate I149 as a colorless oil (440 mg, 87% yield).

Preparation of methanesulfonyloxy-(4-trifluoromethyl-phenyl)-acetic acid ethyl ester (I102)

Hydroxy-(4-trifluoromethyl-phenyl)-acetic acid ethyl ester (I101) (440 mg, 1.77 mmol) and DIPEA (0.43 mL, 2.48 mmol) are dissolved in dry DCM (17 mL) and cooled at 0° C. under $N_2$. Methansulfonyl chloride (0.18 mL, 2.30 mmol) is added dropwise to the solution and the resulting mixture is allowed to warm to RT and stirred for 3 hours. The mixture is diluted with DCM and washed with sat. $NaHCO_3$, water and brine. The organic layer is dried ($Na_2SO_4$), filtered and evaporated to obtain intermediate I150 as a yellow oil (578 mg, quantitative yield), which is used in the next step without any further purification.

Preparation of phenylamino-(4-trifluoromethyl-phenyl)-acetic acid ethyl ester (I103)

Methanesulfonyloxy-(4-trifluoromethyl-phenyl)-acetic acid ethyl ester (I102) (594 mg, 1.82 mmol), aniline (0.25 mL, 2.73 mmol), and DIPEA (0.48 mL, 2.73 mmol) are dissolved in acetonitrile (4 mL). The reaction is heated under microwave irradiation at 100° C. for 1 hour and 30 minutes. Aniline (0.17 mL, 1.820 mmol) is added again and the reaction is heated under microwave irradiation at 100° C. for 3 hours. Acetonitrile is removed under vacuum and the residue is purified by flash chromatography (Petroleum ether/DCM=75/25) to afford intermediate I151 as a yellow oil (195 mg, 60% yield).

Preparation of phenylamino-(4-trifluoromethyl-phenyl)-acetic acid hydrochloride (I104)

Phenylamino-(4-trifluoromethyl-phenyl)-acetic acid ethyl ester (I103) (195 mg, 0.60 mmol) and lithium hydroxide hydrate (50.6 mg, 1.21 mmol) are dissolved in THF/water (9 mL/3 mL) and stirred at RT for 4 hours and then at 40° C. for 1 hour. THF is evaporated and the remaining aqueous solution is acidified with 1M HCl till pH 1. The resulting precipitate is recovered by suction filtration, washed with 1M HCl and dried under vacuum at 40° C. overnight to obtain intermediate I152 as a white solid (200 mg, quantitative yield).

Preparation of phenylamino-(4-trifluoromethyl-phenyl)-acetic acid (R)-(1-aza-bicyclo[2.2.2]oct-3-yl) ester (C105)

PS-DCC (907 mg, 1.21 mmol, loading: 1.33 mmol/g) is suspended in dry THF (10 mL). Phenylamino-(4-trifluoromethyl-phenyl)-acetic acid hydrochloride (I104) (200 mg, 0.60 mmol), HOBT (185 mg, 1.21 mmol), and (R)-quinuclidin-3-ol (230 mg, 1.81 mmol) are added and the mixture is shaken at RT overnight. PS-DCC is filtered off, the filtrate is evaporated and the residue is dissolved in EtOAc and washed with $NaHCO_3$, water and brine. The organic layer is dried over $Na_2SO_4$, filtered and evaporated to dryness. The resulting crude compound is purified by filtration through a pad of silica-gel using DCM/MeOH=9/1 as the eluent. The title compound is obtained as a colorless oil (110 mg, 45% yield, mixture of diastereoisomers).

$^1$H NMR (300 MHz, DMSO-$d_6$) ppm: 7.69-7.83 (m, 4H), 7.01-7.16 (m, 2H), 6.65-6.79 (m, 2H), 6.53-6.64 (m, 1H), 6.42 (d, 1H), 5.46 and 5.47 (d, 1H), 4.66-4.81 (m, 1H), 2.99 and 3.10 (ddd, 1H), 2.54-2.88 (m, 4H), 2.04-2.41 (m, 1H), 0.92-1.97 (m, 5H);

LC-MS (ESI POS): 405.2 (MH$^+$).

Example 37

Preparation of (S)-quinuclidin-3-yl 2-phenyl-2-(phenylamino)-acetate (C106)

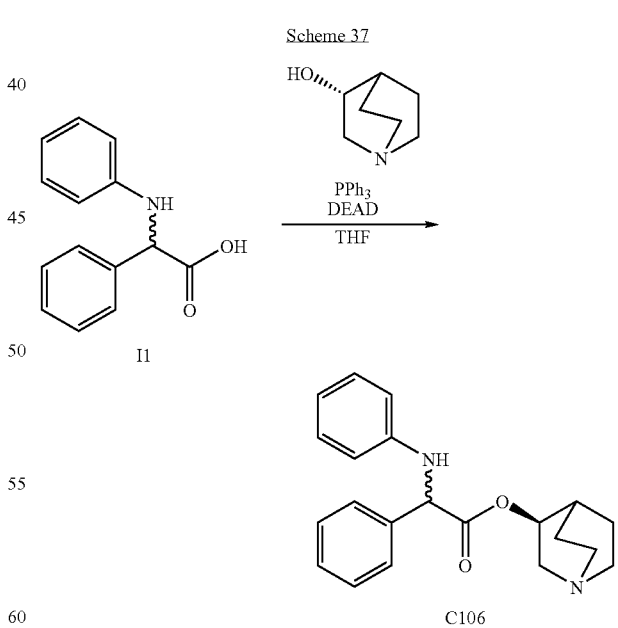

Scheme 37

To a solution of 2-phenyl-2-(phenylamino)acetic acid (I1) (500 mg, 2.20 mmol), (R)-quinuclidin-3-ol (280 mg, 2.20 mmol) and triphenylphosphine (577 mg, 2.20 mmol) in dry THF (7 mL) cooled at 0° C., is added (E)-diethyl diazene-1,2-dicarboxylate (0.35 mL, 2.20 mmol) and the reaction is stirred for 2 hours at RT. The solvent is removed under vacuum and the residue is taken up with EtOAc, washed with 5% NaHCO₃ and brine, dried over Na₂SO₄ and evaporated to dryness. The resulting yellow oil is purified by flash chromatography (EtOAc/MeOH/NH₄OH=90/10/0.1 to 70/30/0.1) to obtain desired product as a white powder (78.0 mg, 10% yield, mixture of diasteroisomer).

¹H NMR (300 MHz, DMSO-d₆) ppm

Diastereoisomer 1 of C106: 7.48-7.62 (m, 2H), 7.24-7.45 (m, 3H), 6.98-7.11 (m, 2H), 6.66-6.75 (m, 2H), 6.51-6.62 (m, 1H), 6.27 (d, 1H), 5.25 (d, 1H), 4.58-4.82 (m, 1H), 3.08 (dd, 1H), 2.54-2.70 (m, 5H), 1.62-1.75 (m, 1H), 0.97-1.60 (m, 4H);

Diastereoisomer 2 of C106: 7.48-7.62 (m, 2H), 7.24-7.45 (m, 3H), 6.98-7.11 (m, 2H), 6.66-6.75 (m, 2H), 6.51-6.62 (m, 1H), 6.27 (d, 1H), 5.26 (d, 1H), 4.58-4.82 (m, 1H), 2.95 (m, 1H), 2.54-2.70 (m, 4H), 2.02-2.14 (m, 1H), 1.86-1.95 (m, 1H), 0.97-1.60 (m, 4H);

LC-MS (ESI POS): 337.2 (MH+).

Example 38

Preparation of phenyl-phenylamino-acetic acid 1-methyl-azepan-4-yl ester (C107)

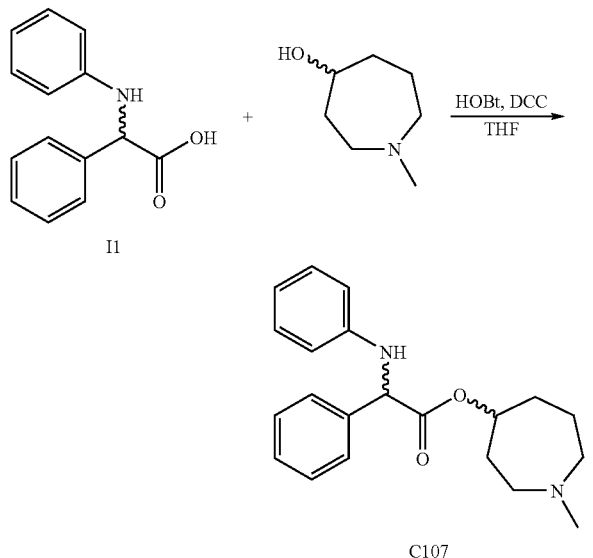

A mixture of 2-phenyl-2-(phenylamino)acetic acid (I1) (175 mg, 0.77 mmol), DCC (192 mg, 0.92 mmol), HOBt (124 mg, 0.92 mmol) and 1-methyl-azepan-4-ol (100 mg, 0.77 mmol) in dry THF (100 mL) is stirred at RT overnight under nitrogen flowstream (UPLC-MS monitoring: complete conversion). The solvent is evaporated and the residue is taken up with aq. HCl and washed with EtOAc. The aqueous phase is basified with NaHCO₃ and extracted with DCM (three times). The organic layers are combined, dried over Na₂SO₄, filtered and evaporated to dryness. The resulting crude is first purified by flash chromatography (DCM to DCM/MeOH=95/5) and then by preparative LC-MS. The purified compound is partitioned between sat. NaHCO₃ and DCM, the organic phase is dried over Na₂SO₄, filtered and evaporated under vacuum to give 53 mg of the title compound as brown oil (20% yield, mixture of diastereoisomers).

¹H NMR (300 MHz, CHLOROFORM-d) ppm: 12.76 (br. s., 1H), 7.30-7.62 (m, 6H), 7.07-7.23 (m, 2H), 6.50-6.84 (m, 3H), 5.15-5.39 (m, 1H), 5.09 (d, 1H), 3.21-3.79 (m, 2H), 2.60 (d, 3H), 1.80-3.15 (m, 8H);

LC-MS (ESI POS): 339.2 (MH⁺).

Example 39

Preparation of (R)-1-(2-phenoxy-ethyl)-3-((R)-2-phenyl-2-phenylamino-acetoxy)-1-azonia-bicyclo[2.2.2]octane (Diastereoisomer 1 of C108)

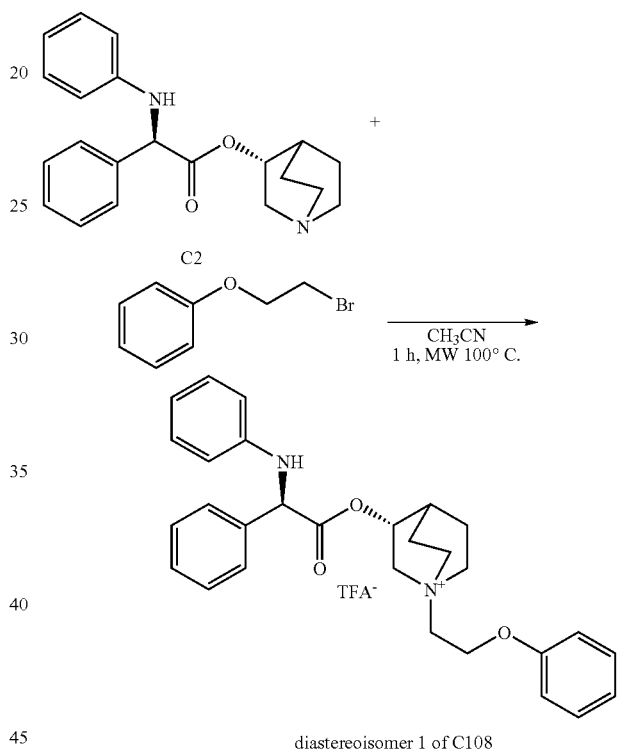

To a solution of (R)-quinuclidin-3-yl 2-phenyl-2-(phenylamino)acetate (diastereoisomer 1 of C2) (127 mg, 0.38 mmol), α-bromophenethole is added (91.2 mg, 0.45 mmol) and the mixture reacted in a closed vessel under MW irradiation for 1 hour at 100° C. (LC-MS monitoring: complete conversion). The resulting crude is purified by preparative LC-MS to obtain the title compound as a pale yellow solid (18.9 mg, 14% yield, trifluoroacetate salt, single diasteroisomer).

¹H NMR (300 MHz, DMSO-d6+Na₂CO₃) ppm: 7.46-7.69 (m, 2H), 7.21-7.46 (m, 5H), 6.89-7.16 (m, 5H), 6.66-6.80 (m, 2H), 6.58 (t, 1H), 6.36 (d, 1H), 5.34 (d, 1H), 4.99-5.21 (m, 1H), 4.34 (t, 2H), 3.86-4.08 (m, 1H), 3.39-3.72 (m, 5H), 3.11 (d, 1H), 2.78-3.02 (m, 1H), 2.20-2.39 (m, 1H), 1.61-2.15 (m, 4H);

LC-MS (ESI POS): 457.3 (MH⁺).

Final compounds listed in Table 15 are prepared as previously described for C108, by alkylation of suitable compounds (Diastereoisomer 1 of C2, Diastereoisomer 2 of C2, C2, Diastereoisomer 1 of C3, Diastereoisomer 2 of C3, C12, C4, Diastereoisomer 2 of C22, C43 and C30) and the commercially available alkylating agents.

TABLE 15

| Compound | Structure | Yield and Appearance | Analytical |
|---|---|---|---|
| Diastereo-isomer 1 of C109 | Single diastereoisomer | 16% yield Pale yellow oil | LC-MS (ESI POS): 461.2 (MH+)<br>¹H NMR (300 MHz, DMSO-d6)<br>ppm: 8.21 (dd, 1 H), 8.05 (dd, 1 H), 7.49-7.63 (m, 2 H), 7.27-7.48 (m, 4 H), 6.98-7.17 (m, 2 H), 6.67-6.79 (m, 2 H), 6.59 (t, 1 H), 5.38 (s, 1 H), 5.12-5.27 (m, 1 H), 4.97 (s, 2 H), 4.07 (ddd, 1 H), 3.42-3.78 (m, 4 H), 3.15-3.42 (m, 1 H), 2.30-2.44 (m, 1 H), 1.81-2.14 (m, 4 H) |
| C109 | Mixture of diastereoisomers | 61% yield Pale yellow oil | LC-MS (ESI POS): 461.2 (MH+)<br>¹H NMR (300 MHz, DMSO-d₆)<br>ppm: 8.21 (dd, 1 H), 8.07 (dd, 1 H), 7.50-7.65 (m, 2 H), 7.23-7.48 (m, 4 H), 6.96-7.19 (m, 2 H), 6.65-6.80 (m, 2 H), 6.52-6.65 (m, 1 H), 5.34 (s, 1 H), 5.12-5.27 (m, 1 H), 5.00-5.07 (m, 2 H), 4.00-4.17 (m, 1 H), 3.31-3.97 (m, 5 H), 2.10-2.15 (m, 1 H), 1.88-2.04 (m, 2 H), 1.63-1.83 (m, 1 H), 1.36-1.63 (m, 1 H) |
| Diastereo-isomer 1 of C110 | Single diastereoisomer | 33% yield Brownish oil | LC-MS (ESI POS): 471.3 (MH+)<br>¹H NMR (300 MHz, DMSO-d6 + Na₂CO₃)<br>ppm: 7.50-7.65 (m, 2 H), 7.25-7.50 (m, 5 H), 7.03-7.25 (m, 2 H), 6.87-7.03 (m, 3 H), 6.69-6.83 (m, 2 H), 6.61 (t, 1 H), 6.37 (d, 1 H), 5.35 (d, 1 H), 5.01-5.22 (m, 1 H), 4.01 (t, 2 H), 3.72-3.91 (m, 1 H), 3.36-3.50 (m, 3 H), 3.10-3.25 (m, 2 H), 2.89 (d, 1 H), 2.67-2.82 (m, 1 H), 2.22-2.38 (m, 1 H), 1.56-2.15 (m, 6 H) |
| Diastereo-isomer 2 of C110 | Single diastereoisomer | 79% yield Pale yellow oil | LC-MS (ESI POS): 471.3 (MH+)<br>¹H NMR (300 MHz, DMSO-d₆)<br>ppm: 7.56 (dd, 2 H), 7.24-7.49 (m, 5 H), 7.05-7.13 (m, 2 H), 6.92-7.00 (m, 3 H), 6.66-6.80 (m, 2 H), 6.53-6.66 (m, 1 H), 5.31 (s, 1 H), 5.01-5.21 (m, 1 H), 3.88-4.16 (m, 3 H), 3.21-3.52 (m, 7 H), 1.77-2.42 (m, 5 H), 1.58-1.73 (m, 1 H), 1.36-1.57 (m, 1 H)<br>[α]$_D$ = −24.48° (c = 0.14, MeOH) |

TABLE 15-continued

| Compound | Structure | Yield and Appearance | Analytical |
|---|---|---|---|
| Diastereo-isomer 1 of C111 | Single diastereoisomer | 28% yield Brownish oil | LC-MS (ESI POS): 351.3 (MH$^+$) $^1$H NMR (300 MHz, DMSO-d6) ppm: 7.50-7.64 (m, 2 H), 7.29-7.50 (m, 3 H), 7.01-7.23 (m, 2 H), 6.68-6.83 (m, 2 H), 6.53-6.68 (m, 1 H), 5.34 (s, 1 H), 5.00-5.24 (m, 1 H), 3.80 (ddd, 1 H), 3.21-3.42 (m, 3 H), 2.97 (dt, 1 H), 2.86 (s, 3 H), 2.79-2.92 (m, 1 H), 2.20-2.36 (m, 1 H), 1.75-2.01 (m, 4 H) |
| Diastereo-isomer 2 of C111 | Single diastereoisomer | 72% yield Pale yellow oil | LC-MS (ESI POS): 351.3 (MH$^+$) $^1$H NMR (300 MHz, DMSO-d$_6$) ppm: 7.48-7.63 (m, 2 H), 7.24-7.48 (m, 3 H), 6.99-7.17 (m, 2 H), 6.50-6.80 (m, 3 H), 5.29 (s, 1 H), 4.99-5.19 (m, 1 H), 3.71-3.94 (m, 1 H), 3.08-3.54 (m, 5 H), 2.95 (s, 3 H), 1.94 2.15 (m, 1 H), 1.68-1.94 (m, 2 H), 1.56-1.68 (m, 1 H), 1.29-1.56 (m, 1 H) $[\alpha]_D = -6.43°$ (c = 0.14, MeOH) |
| Diastereo-isomer 2 of C112 | Single diastereoisomer | 65% yield Pale yellow oil | LC-MS (ESI POS): 457.3 (MH$^+$) $^1$H NMR (300 MHz, DMSO-d$_6$) ppm: 7.47-7.65 (m, 2 H), 7.22-7.47 (m, 5 H), 6.86-7.19 (m, 5 H), 6.65-6.81 (m, 2 H), 6.50-6.65 (m, 1 H), 6.34 (br. s., 1 H), 5.31 (s, 1 H), 5.01-5.21 (m, 1 H), 4.40-4.46 (m, 2 H), 3.88-4.13 (m, 1 H), 3.66-3.74 (m, 2 H), 3.43-3.51 (m, 5 H), 2.02-2.17 (m, 1 H), 1.72-2.02 (m, 3 H), 1.39-1.72 (m, 1 H) $[\alpha]_D = -26.00°$ (c = 0.14, MeOH) |
| C113 | Mixture of diastereoisomers | 69% yield Pale yellow oil | LC-MS (ESI POS): 455.3 (MH$^+$) $^1$H NMR (300 MHz, DMSO-d$_6$) ppm: 9.38 (br. s., 1 H), 7.50-7.72 (m, 2 H), 7.26-7.50 (m, 3 H), 6.98-7.25 (m, 2 H), 6.68-6.83 (m, 2 H), 6.52-6.68 (m, 1 H), 5.34 (s, 1 H), 4.92-5.18 (m, 1 H), 3.57-3.67 (m, 1 H), 3.05-3.33 (m, 3 H), 2.57-2.81 (m, 2 H), 2.08-2.30 (m, 1 H), 1.63-1.94 (m, 4 H) |

TABLE 15-continued

| Compound | Structure | Yield and Appearance | Analytical |
|---|---|---|---|
| Diastereo-isomer 1 of C114 | Single diastereoisomer | 14% yield brown oil | LC-MS (ESI POS): 461.1 (MH+)<br>$^1$H NMR (300 MHz, DMSO-d6) ppm: 8.60 (dd, 1 H), 7.74 (dd, 1 H), 7.50-7.64 (m, 3 H), 7.26-7.49 (m, 3 H), 6.95-7.22 (m, 2 H), 6.66-6.81 (m, 2 H), 6.51-6.66 (m, 1 H), 6.36 (br. S., 1 H), 5.38 (s, 1 H), 5.12-5.29 (m, 1 H), 4.94 (s, 2 H), 3.95-4.17 (m, 1 H), 3.50-3.82 (m, 5 H), 2.31-2.43 (m, 1 H), 1.69-2.21 (m, 4 H) |
| Diastereo-isomer 1 of C115 | Single diastereoisomer | 59% yield colorless oil | LC-MS (ESI POS): 473.2 (MH+)<br>$^1$H NMR (300 MHz, DMSO-d6) ppm: 7.94-8.19 (m, 2 H), 7.53-7.68 (m, 2 H), 7.26-7.53 (m, 5 H), 7.00-7.22 (m, 2 H), 6.68-6.84 (m, 2 H), 6.52-6.68 (m, 1 H), 6.36 (br. S., 1 H), 5.38 (s, 1 H), 5.17-5.30 (m, 1 H), 5.07 (s, 2 H), 4.06 (ddd, 1 H), 3.54-3.74 (m, 3 H), 3.48 (d, 1 H), 3.30-3.43 (m, 1 H), 2.30-2.42 (m, 1 H), 1.85-2.14 (m, 4 H)<br>$[\alpha]_D = -46.15°$ (c = 0.26, MeOH) |
| C116 | Mixture of diastereoisomers | 67% yield colorless oil | LC-MS (ESI POS): 441.2 (MH+)<br>$^1$H NMR (300 MHz, DMSO-d6) ppm: 7.52-7.64 (m, 2 H), 7.21-7.51 (m, 8 H), 6.99-7.20 (m, 2 H), 6.67-6.83 (m, 2 H), 6.52-6.67 (m, 1 H), 6.35 (br. s., 1 H), 5.35 (s, 1 H), 5.07-5.24 (m, 1 H), 3.77-3.88 (m, 1 H), 3.43-3.57 (m, 1 H), 3.17-3.43 (m, 4 H), 2.92-3.12 (m, 2 H), 2.76-2.92 (m, 2 H), 2.32 (br. s., 1 H), 1.34-2.16 (m, 4 H) |

TABLE 15-continued

| Compound | Structure | Yield and Appearance | Analytical |
|---|---|---|---|
| Diastereo-isomer 1 of C117 | Single diastereoisomer | 13% yield brown amorphous solid | LC-MS (ESI POS): 511.2 (MH$^+$)<br>$^1$H NMR (300 MHz, DMSO-d6) ppm: 8.46 (d, 1 H), 8.04-8.22 (m, 2 H), 7.49-7.69 (m, 4 H), 7.28-7.49 (m, 3 H), 7.00-7.18 (m, 2 H), 6.69-6.80 (m, 2 H), 6.54-6.67 (m, 1 H), 6.36 (d, 1 H), 5.39 (d, 1 H), 5.17-5.30 (m, 1 H), 5.11 (s, 2 H), 3.94-4.19 (m, 1 H), 3.37-3.77 (m, 5 H), 2.31-2.43 (m, 1 H), 1.88-2.12 (m, 4 H)<br>$[\alpha]_D = -47.81°$ (c = 0.21, MeOH) |
| Diastereo-isomer 1 of C118 | Single diastereoisomer | 22% yield Yellow oil | LC-MS (ESI POS): 497.1 (MH$^+$)<br>$^1$H NMR (300 MHz, DMSO-d$_6$) ppm: 8.20 (dd, 1 H) 8.04 (dd, 1 H) 7.53-7.68 (m, 2 H) 7.34 (dd, 1 H) 7.17-7.30 (m, 2 H) 6.85-7.00 (m, 2 H) 6.63-6.79 (m, 2 H) 5.40 (s, 1 H) 5.13-5.26 (m, 1 H) 4.89-5.07 (m, 2 H) 3.97-4.13 (m, 1 H) 3.34-3.73 (m, 5 H) 2.35 (br. s., 1 H) 1.83-2.16 (m, 4 H)<br>$[\alpha]_D = -33.13°$ (c = 0.23, MeOH) |
| Diastereo-isomer 1 of C119 | Single diastereoisomer | 16% yield Yellow oil | LC-MS (ESI POS): 491.2 (MH$^+$)<br>$^1$H NMR (300 MHz, DMSO-d$_6$) ppm: 7.91-8.00 (m, 2 H) 7.70-7.82 (m, 1 H) 7.55-7.69 (m, 4 H) 7.20-7.32 (m, 2 H) 6.84-7.01 (m, 2 H) 6.65-6.80 (m, 2 H) 5.41 (s, 1 H) 5.18-5.27 (m, 1 H) 5.10 (s, 2 H) 3.97-4.13 (m, 1 H) 3.33-3.73 (m, 6 H) 2.37 (br. s., 1 H) 1.80-2.16 (m, 4 H)<br>$[\alpha]_D = -57.20°$ (c = 0.20, MeOH) |
| Diastereo-isomer 1 of C120 | Single diastereoisomer | 19% yield Brown oil | LC-MS (ESI POS): 387.2 (MH$^+$)<br>$^1$H NMR (300 MHz, DMSO-d6) ppm: 7.52-7.70 (m, 2 H), 7.13-7.35 (m, 2 H), 6.85-7.04 (m, 2 H), 6.61-6.82 (m, 2 H), 6.34 (br. s., 1 H), 5.35 (s, 1 H), 4.93-5.21 (m, 1 H), 3.72-3.91 (m, 1 H), 3.16-3.32 (m, 3 H), 2.94-3.11 (m, 2 H), 2.90 (s, 3 H), 2.24-2.31 (m, 1 H), 1.74-2.02 (m, 4 H) |

TABLE 15-continued

| Compound | Structure | Yield and Appearance | Analytical |
|---|---|---|---|
| C121 | Mixture of diastereoisomers | 23% yield Pale yellow oil | LC-MS (ESI POS): 491.6 (MH$^+$)<br>$^1$H NMR (300 MHz, DMSO-d6) ppm: 7.90-8.04 (m, 2 H), 7.69-7.83 (m, 1 H), 7.55-7.68 (m, 2 H), 7.34-7.55 (m, 3 H), 7.01-7.28 (m, 2 H), 6.79 (br. s., 1 H), 6.50-6.69 (m, 2 H), 6.29-6.50 (m, 1 H), 5.55 (br. s., 1 H), 5.21-5.32 (m, 1 H), 5.12 (s, 2 H), 3.99-4.13 (m, 1 H), 3.46-3.72 (m, 5 H), 2.31-2.45 (m, 1 H), 1.51-2.22 (m, 4 H) |
| C122 | Mixture of diastereoisomers | 49% yield Pale yellow oil | LC-MS (ESI POS): 475.2 (MH$^+$)<br>$^1$H NMR (300 MHz, DMSO-d$_6$ + TFA) ppm: 8.21 (dd, 1 H) 8.06 (dd, 1 H) 7.31-7.50 (m, 6 H) 7.17-7.30 (m, 2 H) 6.89-6.99 (m, 2 H) 6.70-6.80 (m, 1 H) 5.96 (s, 1 H) 5.25-5.37 (m, 1 H) 5.03 (d, 2 H) 4.08-4.24 (m, 1 H) 3.53-3.74 (m, 4 H) 3.39-3.51 (m, 1 H) 2.76 (s, 3 H) 2.21-2.33 (m, 1 H) 1.92-2.11 (m, 2 H) 1.67-1.90 (m, 1 H) 1.47-1.65 (m, 1 H) |
| C123 | Mixture of diastereoisomers | 56% yield Yellow oil | LC-MS (ESI POS): 469.3 (MH$^+$)<br>$^1$H NMR (300 MHz, DMSO-d6) ppm: 7.89-8.06 (m, 2 H), 7.69-7.89 (m, 1 H), 7.55-7.69 (m, 2 H), 7.32-7.55 (m, 5 H), 7.18-7.32 (m, 2 H), 6.89-7.07 (m, 2 H), 6.67-6.86 (m, 1 H), 5.98 (s, 1 H), 5.26-5.44 (m, 1 H), 5.15 (br. s., 2 H), 4.02-4.30 (m, 1 H), 3.43-3.76 (m, 5 H), 2.77 (s, 3 H), 2.18-2.39 (m, 1 H), 1.41-2.15 (m, 4 H) |
| C124 | Mixture of diastereoisomers | 60% yield Brown oil | LC-MS (ESI POS): 471.3 (MH$^+$)<br>$^1$H NMR (300 MHz, DMSO-d$_6$) ppm: 7.15-7.46 (m, 7 H), 6.88-7.15 (m, 5 H), 6.44-6.74 (m, 3 H), 4.89-5.15 (m, 1 H), 4.38-4.47 (m, 2 H), 4.35 (t, 1 H), 3.96 (ddd, 1 H), 3.60-3.76 (m, 2 H), 3.41-3.60 (m, 3 H), 3.21-3.41 (m, 2 H), 3.09 (d, 2 H), 1.76-2.09 (m, 3 H), 1.44-1.76 (m, 2 H) |

TABLE 15-continued

| Compound | Structure | Yield and Appearance | Analytical |
|---|---|---|---|
| Diastereo-isomer 1 of C125 | Single diastereoisomer | 35% yield Brown oil | LC-MS (ESI POS): 475.2 (MH+) <br> $^1$H NMR (300 MHz, DMSO-d$_6$) ppm: 8.21 (dd, 1 H), 8.07 (dd, 1 H), 7.18-7.40 (m, 6 H), 6.96-7.17 (m, 2 H), 6.48-6.74 (m, 3 H), 5.08-5.19 (m, 1 H), 5.05 (d, 1 H), 4.99 (d, 1 H), 4.23-4.48 (m, 1 H), 4.05 (dd, 1 H), 3.26-3.83 (m, 5 H), 2.94-3.24 (m, 2 H), 1.84-2.06 (m, 3 H), 1.60-1.84 (m, 2 H) <br> $[\alpha]_D = -13.26°$ (c = 0.35, MeOH) |
| C126 | Mixture of diastereoisomers | 49% yield Brown oil | LC-MS (ESI POS): 365.3 (MH+) <br> $^1$H NMR (300 MHz, DMSO-d$_6$) ppm: 7.17-7.45 (m, 5 H), 6.98-7.17 (m, 2 H), 6.56-6.67 (m, 3 H), 4.85-5.14 (m, 1 H), 4.23-4.43 (m, 1 H), 3.80 (ddd, 1 H), 3.14-3.51 (m, 5 H), 3.09 (d, 2 H), 2.92 (s, 3 H), 1.71-1.98 (m, 3 H), 1.39-1.69 (m, 2 H) |
| Diastereo-isomer 1 of C127 | Single diastereoisomer | 25% yield Pale yellow oil | LC-MS (ESI POS): 469.2 (MH+) <br> 1H NMR (300 MHz, DMSO-d6) ppm: 7.88-8.05 (m, 2 H), 7.70-7.84 (m, 1 H), 7.51-7.70 (m, 2 H), 7.18-7.44 (m, 5 H), 6.98-7.18 (m, 2 H), 6.49-6.81 (m, 3 H), 6.12 (d, 1 H), 5.14 (s, 2 H), 5.02-5.14 (m, 1 H), 4.26-4.55 (m, 1 H), 3.92-4.21 (m, 1 H), 3.50-3.73 (m, 5 H), 3.14 (dd, 1 H), 3.08 (dd, 1 H), 1.82-2.07 (m, 3 H), 1.58-1.82 (m, 2 H) <br> $[\alpha]_D = -15.84°$ (c = 0.365, MeOH) |
| C128 | Mixture of diastereoisomers | 22% yield Colorless oil | LC-MS (ESI POS): 469.3 (MH+) <br> $^1$H NMR (300 MHz, DMSO-d6) ppm: 7.88-8.11 (m, 2 H), 7.69-7.88 (m, 1 H), 7.38-7.66 (m, 12 H), 5.25-5.46 (m, 2 H), 4.98-5.25 (m, 2 H), 3.95-4.28 (m, 3 H), 3.77 (d, 1 H), 3.43-3.70 (m, 4 H), 1.31-2.43 (m, 5 H) |

TABLE 15-continued

| Compound | Structure | Yield and Appearance | Analytical |
|---|---|---|---|
| Diastereo-isomer 1 of C129 | Single diastereoisomer | 45% yield amorphous brown solid | LC-MS (ESI POS): 456.1 (MH+)<br>$^1$H NMR (300 MHz, DMSO-d6) ppm: 8.80-9.01 (m, 2 H), 7.71-7.92 (m, 2 H), 7.51-7.67 (m, 2 H), 7.27-7.51 (m, 3 H), 7.01-7.18 (m, 2 H), 6.68-6.83 (m, 2 H), 6.51-6.67 (m, 1 H), 5.39 (s, 1 H), 5.15-5.30 (m, 1 H), 5.09 (s, 2 H), 3.97-4.16 (m, 1 H), 3.51-3.69 (m, 3 H), 3.32-3.49 (m, 2 H), 2.31-2.43 (m, 1 H), 1.82-2.15 (m, 4 H)<br>$[\alpha]_D = -36.13°$ (c = 0.3, MeOH) |
| Diastereo-isomer 1 of C130 | Single diastereoisomer | 25% yield Light brown oil | LC-MS (ESI POS): 494.9 (MH+)<br>$^1$H NMR (300 MHz, DMSO-d$_6$) ppm: 8.23 (d, 1 H), 7.53-7.62 (m, 2 H), 7.28-7.49 (m, 4 H), 6.99-7.18 (m, 2 H), 6.68-6.83 (m, 2 H), 6.60 (m, 1 H), 6.26-6.46 (m, 1 H), 5.32-5.47 (m, 1 H), 5.13-5.25 (m, 1 H), 4.94 (s, 2 H), 3.98-4.21 (m, 1 H), 3.51-3.69 (m, 2 H), 3.13-3.36 (m, 3 H), 2.32-2.41 (m, 1 H), 1.78-2.16 (m, 4 H) |
| Diastereo-isomer 1 of C131 | Single diastereoisomer | 22% yield Yellow oil | LC-MS (ESI POS): 475.03 (MH+)<br>$^1$H NMR (300 MHz, DMSO-d$_6$) ppm: 7.89 (d, 1 H), 7.50-7.62 (m, 2 H), 7.27-7.48 (m, 3 H), 6.99-7.18 (m, 3 H), 6.67-6.82 (m, 2 H), 6.52-6.65 (m, 1 H), 6.24-6.46 (m, 1 H), 5.30-5.43 (m, 1 H), 5.15-5.27 (m, 1 H), 4.88 (s, 2 H), 3.97-4.13 (m, 1 H), 3.56-3.72 (m, 3 H), 3.10-3.38 (m, 2 H), 2.57 (s, 3 H), 2.31-2.41 (m, 1 H), 1.74-2.15 (m, 4 H) |
| Diastereo-isomer 1 of C132 | Single diastereoisomer | 21% yield Brown oil | LC-MS (ESI POS): 458.1 (MH+)<br>$^1$H NMR (300 MHz, DMSO-d$_6$) ppm: 7.50-7.62 (m, 2 H), 7.29-7.48 (m, 4 H), 7.22 (dd, 1 H), 7.04-7.13 (m, 2 H), 6.69-6.78 (m, 2 H), 6.52-6.63 (m, 1 H), 6.39 (br. s., 1 H), 6.24 (dd, 1 H), 5.37 (br. s., 1 H), 5.08-5.23 (m, 1 H), 4.64 (s, 2 H), 3.94-4.16 (m, 1 H), 3.88 (s, 3 H), 3.62-3.79 (m, 2 H), 3.20-3.44 (m, 3 H), 2.31-2.41 (m, 1 H), 1.79-2.13 (m, 4 H) |

TABLE 15-continued

| Compound | Structure | Yield and Appearance | Analytical |
|---|---|---|---|
| Diastereo-isomer 1 of C133 | Single diastereoisomer | 18% yield Brown oil | LC-MS (ESI POS): 474.1 (MH+)<br>¹H NMR (300 MHz, DMSO-d₆) ppm: 7.53-7.63 (m, 2 H), 7.32-7.48 (m, 3 H), 7.10 (m, 2 H), 6.69-6.80 (m, 2 H), 6.50-6.65 (m, 1 H), 6.38 (s, 1 H), 5.29-5.49 (m, 1 H), 5.10-5.29 (m, 1 H), 4.74 (s, 2 H), 3.91-4.16 (m, 1 H), 3.40-3.70 (m, 5 H), 2.48 (br. s., 3 H), 2.41 (s, 3 H), 2.31-2.39 (m, 1 H), 1.66-2.07 (m, 4 H) |
| Diastereo-isomer 1 of C134 | Single diastereoisomer | 37% yield Pale yellow oil | LC-MS (ESI POS): 487.04 (MH+)<br>¹H NMR (300 MHz, DMSO-d₆) ppm: 7.50-7.59 (m, 2 H), 7.20-7.48 (m, 9 H), 6.99-7.13 (m, 2 H), 6.67-6.81 (m, 2 H), 6.53-6.65 (m, 1 H), 6.36 (d, 1 H), 5.34 (d, 0 H), 4.93-5.16 (m, 0 H), 3.66-3.92 (m, 1 H), 3.14-3.39 (m, 8 H), 2.91-3.06 (m, 1 H), 1.32-2.16 (m, 7 H)<br>formiate ion: 8.36 (s, 2 H)<br>[α]$_D$ = −24.14° (c = 0.29, MeOH) |
| C135 | Mixture of diastereoisomer | 18% yield Colorless oil | LC-MS (ESI POS): 483.2 (MH+)<br>¹H NMR (300 MHz, DMSO-d₆) ppm: 8.51 (s, 1 H), 7.91-8.04 (m, 2 H), 7.67-7.82 (m, 1 H), 7.50-7.67 (m, 4 H), 7.30-7.49 (m, 3 H), 7.00 (t, 1 H), 6.59-6.66 (m, 1 H), 6.50-6.58 (m, 1 H), 6.44-6.50 (m, 1 H), 6.30 (d, 1 H), 5.29-5.44 (m, 1 H), 5.21-5.27 (m, 1 H), 5.12 and 5.20 (s, 2 H), 4.00-4.24 (m, 1 H), 3.45-3.85 (m, 5 H), 2.47 (q, 2 H), 2.10-2.17 and 2.31-2.40 (m, 1 H), 1.43-2.09 (m, 4 H), 1.12 (t, 3 H) |
| C136 | Mixture of diastereoisomers | 41% yield Pale yellow solid | LC-MS (ESI POS): 513.2 (MH+)<br>¹H NMR (300 MHz, DMSO-d6) ppm: 7.89-8.07 (m, 2 H), 7.68-7.85 (m, 2 H), 7.52-7.67 (m, 5 H), 7.31-7.49 (m, 3 H), 7.06-7.28 (m, 1 H), 6.55-6.98 (m, 2 H), 5.37-5.60 (m, 1 H), 5.20-5.32 (m, 1 H), 4.99-5.20 (m, 2 H), 3.98-4.27 (m, 1 H), 3.75 (s, 3 H), 3.39-3.71 (m, 5 H), 2.07-2.45 (m, 1 H), 1.43-2.07 (m, 4 H) |

The compounds listed in Table 16 are prepared as previously described for C108 by reaction of an equimolar mixture of diastereoisomer 1 and 2 of C2 with the suitable alkylating reagent.

TABLE 16

| Compound | Structure | Yield and Appearance | Analytical |
|---|---|---|---|
| C137 | Mixture of diastereoisomers | 10% yield Pale yellow oil | LC-MS (ESI POS): 473.2 (MH$^+$) $^1$H NMR (300 MHz, DMSO-d6) ppm: 7.50-7.63 (m, 2 H), 7.20-7.50 (m, 8 H), 7.07 (dd, 2 H), 6.64-6.83 (m, 2 H), 6.48-6.64 (m, 1 H), 6.35 (d, 1 H), 5.33 (d, 1 H), 5.00-5.20 (m, 1 H), 3.74-3.93 (m, 1 H), 3.36-3.55 (m, 9 H), 2.87-3.02 (m, 1 H), 2.31-2.45 (m, 1 H), 2.04-2.07 (m, 1 H), 1.75-2.01 (m, 4 H) |
| C138 | Mixture of diastereoisomers | 15% yield Pale yellow oil | LC-MS (ESI POS): 433.2 (MH$^+$) $^1$H NMR (300 MHz, DMSO-d6) ppm: 7.48-7.65 (m, 2 H), 7.26-7.48 (m, 3 H), 6.93-7.21 (m, 2 H), 6.67-6.83 (m, 2 H), 6.55-6.67 (m, 1 H), 5.33 (s, 1 H), 5.00-5.19 (m, 1 H), 3.68-4.01 (m, 1 H), 3.36 (br. s., 4 H), 2.66-3.14 (m, 3 H), 1.41-2.15 (m, 10 H), 0.87-1.42 (m, 7 H) |
| C139 | Mixture of diastereoisomers | 15% yield Pale yellow oil | LC-MS (ESI POS): 419.3 (MH$^+$) $^1$H NMR (300 MHz, DMSO-d6) ppm: 7.51-7.67 (m, 2 H), 7.28-7.49 (m, 3 H), 6.99-7.19 (m, 2 H), 6.67-6.85 (m, 2 H), 6.52-6.67 (m, 1 H), 5.33 (s, 1 H), 5.07-5.21 (m, 1 H), 4.87-5.07 (m, 1 H), 3.66-3.94 (m, 1 H), 3.28-3.55 (m, 3 H), 3.09-3.28 (m, 2 H), 2.82-3.08 (m, 2 H), 1.74-2.43 (m, 7 H), 1.63 (s, 3 H), 1.69 (s, 3 H) |
| C140 | Mixture of diastereoisomers | 16% yield Pale yellow oil | LC-MS (ESI POS): 523.3 (MH$^+$) $^1$H NMR (300 MHz, DMSO-d6) ppm: 8.16-8.27 (m, 1 H), 7.92 (d, 2 H), 7.53-7.66 (m, 2 H), 7.27-7.49 (m, 3 H), 7.00-7.16 (m, 2 H), 6.68-6.81 (m, 2 H), 6.52-6.66 (m, 1 H), 5.37 (s, 1 H), 5.17-5.27 (m, 1 H), 4.94-5.17 (m, 2 H), 3.92-4.25 (m, 1 H), 3.65-3.81 (m, 1 H), 3.54-3.69 (m, 3 H), 3.30-3.54 (m, 1 H), 1.38-2.45 (m, 5 H) |

Example 40

Preparation of (R)-1-(2-oxo-2-phenyl-ethyl)-3-(((R)-2-phenyl-2-phenylamino-acetoxy)-1-azonia-bicyclo[2.2.2]octane (Diastereoisomer 1 of C141)

Scheme 40

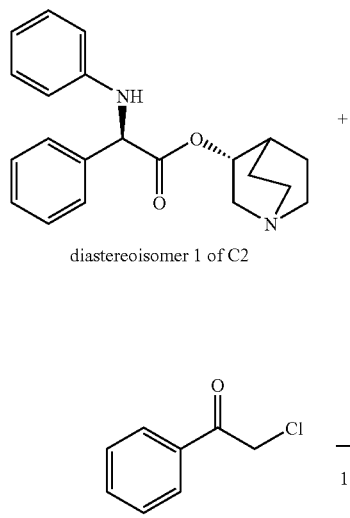

diastereoisomer 1 of C2

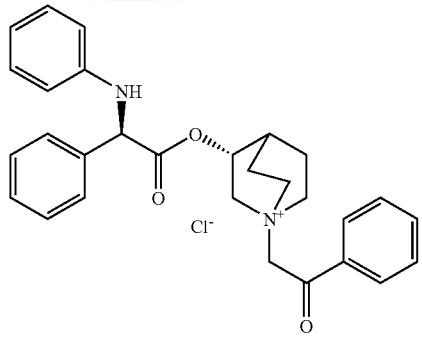

diastereoisomer 1 of C141

To a solution of (R)-phenyl-phenylamino-acetic acid (R)-(1-aza-bicyclo[2.2.2]oct-3-yl) ester (Diastereoisomer 1 of C2) (153 mg, 0.45 mmol), α-chloroacetophenone is added (107 mg, 0.54 mmol) and the mixture reacted in a closed vessel under MW irradiation for 1 hour at 100° C. (LC-MS monitoring: complete conversion). The resulting crude is purified by flash chromatography (DCM/MeOH=9/1) to obtain the title compound as a white solid (108.9 mg, 50% yield, chloride salt, single diastereoisomer).

$^1$H NMR (400 MHz, DMSO-d6) ppm: 7.96 (d, 2H) 7.70-7.81 (m, 1H) 7.58 (d, 2H) 7.62 (d, 2H)

7.29-7.47 (m, 3H) 7.09 (t, 2H) 6.74 (d, 2H) 6.59 (t, 1H) 6.41 (d, 1H) 5.39 (d, 1H) 5.16-5.26 (m, 1H) 5.13 (s, 2H) 4.08 (ddd, 1H) 3.47-3.71 (m, 4H) 3.35-3.47 (m, 1H) 2.36 (br. s., 1H) 1.84-2.13 (m, 4H);

LC-MS (ESI POS): 455.27 (MH$^+$).

The compounds listed in Table 17 are prepared as previously described for C33 by reaction of C12, diastereoisomer 1 of C2 or C24 with the commercially available alkylating agents

TABLE 17

| Compound | Structure | Yield and Appearance | Analytical |
|---|---|---|---|
| Diastereoisromer 1 of C142 | 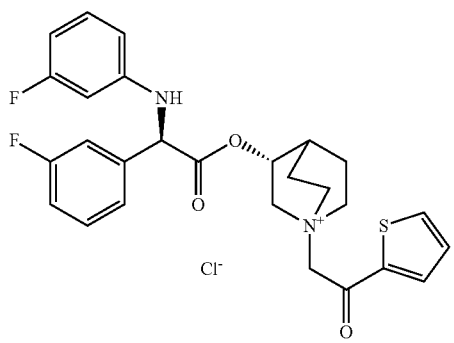<br>Single diastereoisomer | 25% yield Pale yellow solid | LC-MS (ESI POS): 497.1 (MH$^+$) $^1$H NMR (300 MHz, DMSO-d6) ppm: 8.15-8.27 (m, 1 H), 7.99-8.15 (m, 1 H), 7.29-7.53 (m, 4 H), 7.02-7.27 (m, 2 H), 6.81 (d, 1 H), 6.48-6.66 (m, 2 H), 6.25-6.48 (m, 1 H), 5.44-5.62 (m, 1 H), 5.14-5.31 (m, 1 H), 5.05 (s, 2 H), 3.96-4.23 (m, 1 H), 3.74-3.93 (m, 1 H), 3.66 (br. s., 2 H), 3.37-3.61 (m, 2 H), 1.37-2.42 (m, 5 H) [α]$_D$ = −37.51° (c = 0.225, MeOH) |

TABLE 17-continued

| Compound | Structure | Yield and Appearance | Analytical |
|---|---|---|---|
| Diastereoisomer 1 of C143 | Single diastereoisomer | 78% yield Yellow solid | LC-MS (ESI POS): 394.2 (MH+) $^1$H NMR (300 MHz, DMSO-d6) ppm: 7.88 (br. s., 1 H), 7.68 (br. s., 1 H), 7.48-7.61 (m, 2 H), 7.26-7.48 (m, 3 H), 6.98-7.20 (m, 2 H), 6.67-6.81 (m, 2 H), 6.52-6.67 (m, 1 H), 6.34 (d, 1 H), 5.35 (d, 1 H), 5.03-5.25 (m, 1 H), 4.02 (ddd, 1 H), 3.93 (d, 1 H), 3.87 (d, 1 H), 3.37-3.69 (m, 4 H), 3.13-3.27 (m, 1 H), 2.21-2.40 (m, 1 H), 1.76-2.05 (m, 4 H) $[\alpha]_D = -41.19°$ (c = 0.27, MeOH) |
| Diastereoisomer 1 of C144 | Single diastereoisomer | 86% yield Yellow solid | LC-MS (ESI POS): 470.3 (MH+) $^1$H NMR (300 MHz, DMSO-d6) ppm: 10.52 (s, 1 H), 7.47-7.70 (m, 4 H), 7.24-7.47 (m, 5 H), 6.98-7.24 (m, 3 H), 6.66-6.84 (m, 2 H), 6.51-6.66 (m, 1 H), 6.35 (d, 1 H), 5.37 (d, 1 H), 5.06-5.27 (m, 1 H), 4.17 (d, 1 H), 4.11 (d, 1 H), 3.99-4.09 (m, 1 H), 3.46-3.74 (m, 4 H), 3.20-3.36 (m, 1 H), 2.30-2.43 (m, 1 H), 1.80-2.13 (m, 4 H) $[\alpha]_D = -55.2°$ (c = 0.25, MeOH) |
| Diastereoisomer 1 of C145 | Single diastereoisomer | 50% yield White solid | LC-MS (ESI POS): 469.3 (MH+) $^1$H NMR (300 MHz, DMSO-d6) ppm: 7.86 (m, 2 H), 7.50-7.68 (m, 2 H), 7.23-7.50 (m, 5 H), 6.99-7.18 (m, 2 H), 6.74 (m, 2 H), 6.50-6.67 (m, 1 H), 6.36 (d, 1 H), 5.38 (d, 1 H), 5.11-5.30 (m, 1 H), 5.06 (s, 2 H), 3.97-4.21 (m, 1 H), 3.58-3.83 (m, 2 H), 3.33-3.58 (m, 3 H), 2.42 (s, 3 H), 2.31-2.39 (m, 1 H), 1.84-2.12 (m, 4 H) $[\alpha]_D = -57.92°$ (c = 0.5, MeOH) |
| C146 | Mixture of diastereoisomers | 28% yield Yellow solid | LC-MS (ESI POS): 475.2 (MH+) $^1$H NMR (300 MHz, DMSO-d6) ppm: 8.21 (td, 1 H), 7.99-8.14 (m, 1 H), 7.21-7.50 (m, 11 H), 5.10-5.26 (m, 1 H), 4.92-5.10 (m, 2 H), 4.36-4.50 (m, 1 H), 4.00-4.19 (m, 1 H), 3.64-3.81 (m, 4 H), 3.46-3.64 (m, 3 H), 3.06-3.24 (m, 1 H), 1.34-2.40 (m, 5 H) |

Example 41

Preparation of (R)-1-(2-oxo-2-phenyl-ethyl)-3-((R)-2-phenyl-2-phenylamino-acetoxy)-1-azonia-bicyclo[2.2.2]octane bromide (Diastereoisomer 1 of C147)

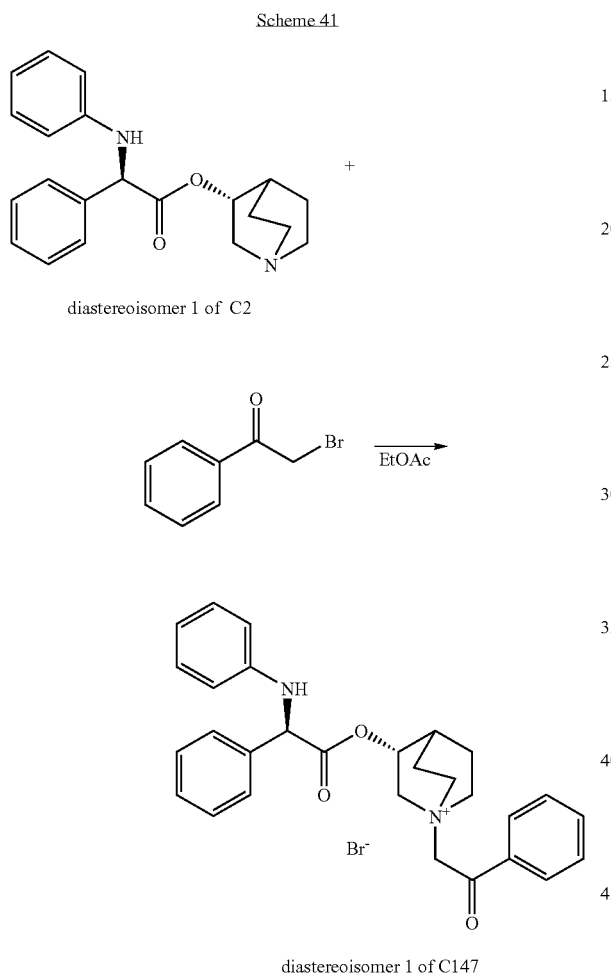

Scheme 41 diastereoisomer 1 of C2 diastereoisomer 1 of C147

(R)-quinuclidin-3-yl 2-phenyl-2-(phenylamino)acetate (Diastereoisomer 1 of C2) (20.3 mg, 0.06 mmol) is dissolved in EtOAc (0.60 mL) and 2-bromo-1-phenylethanone (12.0 mg, 0.06 mmol) is added. The reaction is stirred at room temperature for 2 hours (UPLC-MS: complete and clean conversion). $Et_2O$ (0.20 mL) were added and the product is triturated to obtain a white solid which is isolated by filtration and dried under vacuum overnight (31 mg, 96% yield, bromide salt, single diastereoisomer).

$^1$H NMR (300 MHz, DMSO-d6) ppm: 7.89-8.08 (m, 2H), 7.69-7.84 (m, 1H), 7.52-7.69 (m, 4H), 7.31-7.48 (m, 3H), 6.99-7.17 (m, 2H), 6.68-6.83 (m, 2H), 6.51-6.66 (m, 1H), 6.37 (d, 1H), 5.39 (d, 1H), 5.17-5.26 (m, 1H), 5.13 (s, 2H), 4.04-4.17 (m, 1H), 3.34-3.79 (m, 5H), 2.32-2.40 (m, 1H), 1.83-2.16 (m, 4H);

LC-MS (ESI POS): 455.3 (MH$^+$).

Example 42

Preparation of (R)-3-((S)-2-amino-phenylpropanoyloxy)-1-(2-phenoxyethyl)-1-azonia-bicyclo[2.2.2]octane trifluoroacetate trifluoroacetate anion (Diastereoisomer 1 of C149)

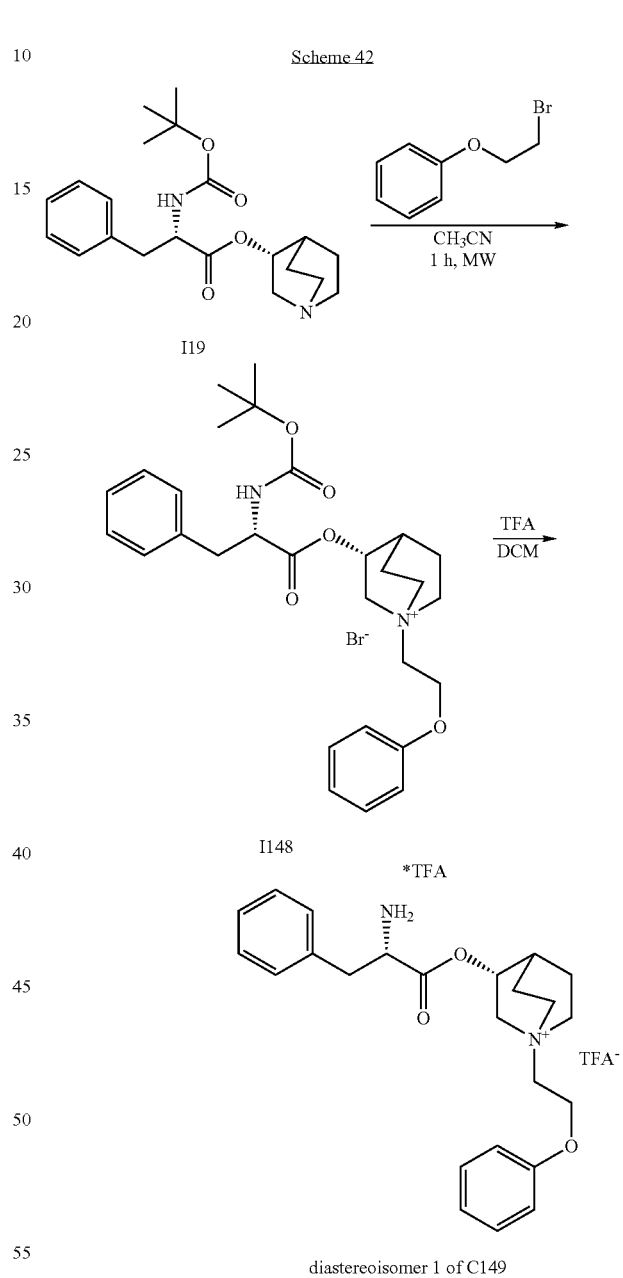

Scheme 42

I19

I148 diastereoisomer 1 of C149

Preparation of (R)-3-((S)-2-tertbutoxycarbonylamino-phenylpropanoyloxy)-1-(2-phenoxyethyl)-1-azonia-bicyclo[2.2.2]octane bromide (I148)

To a solution of (S)—((R)-quinuclidin-3-yl)-2-(tert-butoxycarbonylamino)-3-phenylpropanoate (I19) (200 mg, 0.53 mmol), α-bromophenethole is added (130 mg, 0.64 mmol) and the mixture reacted in a closed vessel under MW irradiation for 1 hour at 100° C. (LC-MS monitoring: complete conversion). The solvent is evaporated under reduced pressure and the resulting crude is used without any additional purification.

Preparation of (R)-3-((S)-2-amino-phenylpropanoyloxy)-1-(2-phenoxyethyl)-1-azonia-bicyclo[2.2.2]octane trifluoroacetate trifluoroacetate anion (Diastereoisomer 1 of C149)

To a solution of (R)-3-((S)-2-tertbutoxycarbonylaminophenylpropanoyloxy)-1-(2-phenoxyethyl)-1-azonia-bicyclo[2.2.2]octane bromide (I148) (0.53 mmol) in DCM (5 mL), is added trifluoroacetic acid (0.50 mL, 4.41 mmol) and the mixture stirred at RT overnight. The solvent is evaporated and the resulting crude is purified by preparative LC-MS in order to obtain the title compound as a brown gummy solid (112 mg, 43% overall yield, trifluoroacetate salt and trifluoroacetate anion, single diastereoisomer).

$^1$H NMR (300 MHz, DMSO-d6) ppm: 8.60 (br. s., 3H), 7.19-7.45 (m, 7H), 6.82-7.13 (m, 3H), 5.03-5.25 (m, 1H), 4.39-4.48 (m, 2H), 4.25-4.38 (m, 1H), 3.90-4.09 (m, 1H), 3.28-3.52 (m, 7H), 3.19 (dd, 1H), 3.10 (dd, 1H), 2.09 (br. s., 1H), 1.81-2.04 (m, 2H), 1.66-1.79 (m, 2H); LC-MS (ESI POS): 395.4 (MH$^+$).

The compounds listed in Table 18 are prepared as previously described for C149, by reaction of I19 with 2-chloroacetylthiophene, 3-phenoxypropyl bromide and α-bromoacetophenone.

TABLE 18

| Compound | Structure | Yield and Appearance | Analytical |
|---|---|---|---|
| Diastereoisomer 1 of C150 | Single diastereoisomer | 45% yield Pale yellow oil | LC-MS (ESI POS): 399.2 (MH$^+$) $^1$H NMR (300 MHz, DMSO-d6) ppm: 8.62 (br. s., 3H), 8.22 (dd, 1H), 8.08 (dd, 1H), 7.15-7.47 (m, 6H), 5.14-5.30 (m, 1H), 5.06 (d, 1H), 4.99 (d, 1H), 4.38 (t, 1 H), 4.11 (dd, 1H), 3.44-3.74 (m, 5H), 3.22 (dd, 1H), 3.10 (dd, 1H), 2.06-2.14 (m, 1H), 1.90-2.07 (m, 2H), 1.56-1.90 (m, 2H) |
| Diastereoisomer 1 of C151 | Single diastereoisomer | 41% yield Brown gummy solid | LC-MS (ESI POS): 409.3 (MH$^+$) $^1$H NMR (300 MHz, DMSO-d6) ppm: 8.62 (br. s., 3H), 7.22-7.41 (m, 7H), 6.90-7.01 (m, 3H), 4.99-5.29 (m, 1H), 4.22-4.49 (m, 1H), 4.04 (t, 2H), 3.78-3.94 (m, 1H), 3.25-3.50 (m, 7H), 3.20 (dd, 1H), 3.10 (dd, 1H), 2.02-2.15 (m, 3H), 1.80-2.02 (m, 2H), 1.65-1.78 (m, 2H) |
| Diastereoisomer 1 of C152 | Single diastereoisomer | 35% yield Pale yellow solid | LC-MS (ESI POS): 393.3 (MH$^+$) $^1$H NMR (300 MHz, DMSO-d6) ppm: 8.65 (br. s., 3H), 7.88-8.07 (m, 2H), 7.70-7.84 (m, 1H), 7.51-7.70 (m, 2H), 7.16-7.48 (m, 5H), 5.21-5.30 (m, 1H), 5.19 (d, 1H), 5.12 (d, 1H), 4.39 (dd, 1H), 4.11 (dd, H), 3.47-3.81 (m, 5H), 3.23 (dd, 1H), 3.10 (dd, 1H), 1.90-2.22 (m, 3H), 1.65-1.90 (m, 2H) |

Example 43

Preparation of (R)-1-(2-oxo-2-phenylethyl)-3-((R)-3-phenyl-2-(phenylamino)propanoyloxy)-1-azoniabicyclo[2.2.2]octane bromide (Diastereoisomer 1 of C153)

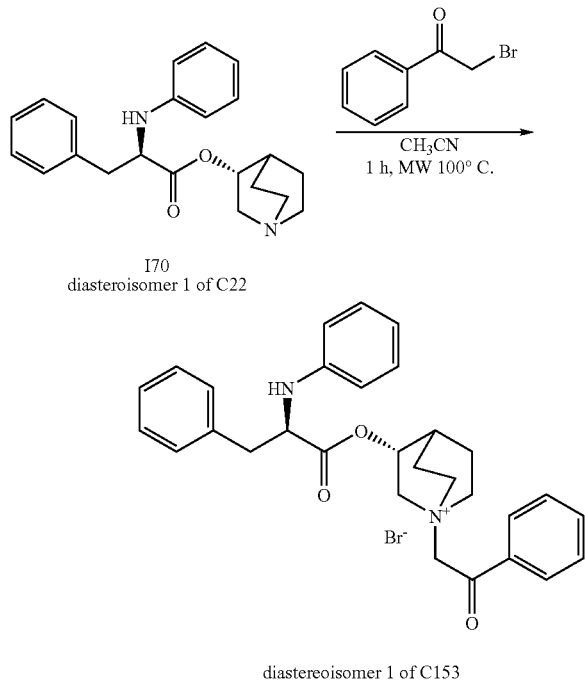

Scheme 43

I70 diastereoisomer 1 of C22 diastereoisomer 1 of C153

To a solution of (R)—((R)-quinuclidin-3-yl) 3-phenyl-2-(phenylamino)propanoate (Diastereoisomer 1 of C22) (50.0 mg, 0.14 mmol), is added 2-bromo-1-phenylethanone (28.4 mg, 0.14 mmol) and the mixture reacted in a closed vessel under MW irradiation for 1 hour at 100° C. (LC-MS monitoring: complete conversion). Solvent is removed under reduced pressure and residue is triturated with EtOAc to obtain the title compound as a white solid (75.5 mg, 98% yield, bromide salt, single diastereoisomer).

$^1$H NMR (300 MHz, DMSO-d6) ppm: 7.92-8.10 (m, 2H), 7.71-7.85 (m, 1H), 7.51-7.71 (m, 2H), 7.27-7.44 (m, 4H), 7.17-7.26 (m, 1H), 6.95-7.16 (m, 2H), 6.45-6.77 (m, 3H), 6.11 (d, 1H), 5.05-5.21 (m, 3H), 4.23-4.50 (m, 1H), 3.94-4.20 (m, 1H), 3.49-3.81 (m, 3H), 3.35-3.49 (m, 2H), 3.15 (dd, 1H), 3.08 (dd, 1H), 2.17-2.37 (m, 1H), 1.94-2.17 (m, 2H), 1.70-1.94 (m, 2H);

LC-MS (ESI POS): 469.3 (MH+);

$[\alpha]_D = -8.19°$ (c=0.53, MeOH).

Diastereoisomer 2 of C154 listed in Table 19 is prepared as previously described for C153, by reaction of I70 with 2-chloroacetylthiophene

TABLE 19

| Compound | Structure | Yield and Appearance | Analytical |
|---|---|---|---|
| Diastereoisomer 2 of C154 | Single diastereoisomer | 90% yield Yellow Solid | LC-MS (ESI POS): 475.2 (MH+) $^1$H NMR (300 MHz, DMSO-d6) ppm: 8.22 (dd, 1 H), 8.11 (dd, 1 H), 7.15-7.45 (m, 6 H), 6.92-7.15 (m, 2 H), 6.53-6.68 (m, 3 H), 6.12 (d, 1 H), 5.05-5.17 (m, 1 H), 5.02 (s, 2 H), 4.24-4.52 (m, 1 H), 4.06 (ddd, 1 H), 3.47-3.80 (m, 3 H), 3.33-3.47 (m, 2 H), 3.15 (dd, 1 H), 3.08 (dd, 1 H), 2.16-2.34 (m, 1 H), 1.77-2.10 (m, 4 H) $[\alpha]_D = -14.2°$ (c = 0.25, MeOH) |

Example 44

Preparation of (R)-1-[2-(4-methoxy-phenyl)-2-oxo-ethyl]-3-((R)-2-phenyl-2-phenyl amino-acetoxy)-1-azonia-bicyclo[2.2.2]octane trifluoroacetate (diastereoisomer 1 of C155)

Scheme 44

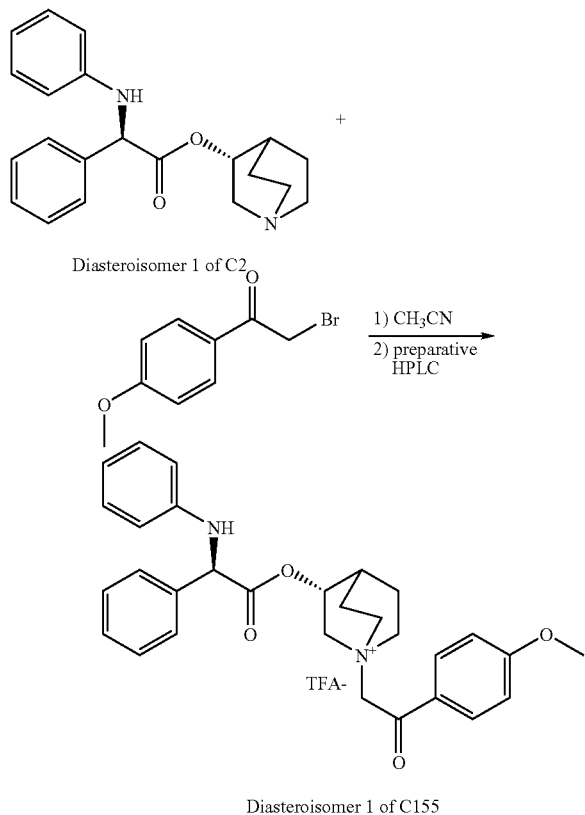

Diastereoisomer 1 of C155

To a solution of (R)-phenyl-phenylamino-acetic acid (R)-(1-aza-bicyclo[2.2.2]oct-3-yl) ester (Diastereoisomer 1 of C2) (120 mg, 0.35 mmol) in acetonitrile (5 mL), is added 2-bromo-1-(4-methoxy-phenyl)-ethanone (99 mg, 0.43 mmol) and the mixture is heated under MW irradiation for 1 hour at 100° C. (UPLC-MS monitoring: complete conversion). Solvent was evaporated and the resulting crude is first purified by flash chromatography (DCM/MeOH=99/1 to 9/1) and then purified by preparative LC-MS to obtain the title compound as a white solid (70.2 mg, 33% yield, trifluoroacetate salt, single disatereoisomer).

$^1$H NMR (300 MHz, DMSO-d6) ppm: 7.84-8.06 (m, 2H), 7.51-7.71 (m, 2H), 7.25-7.51 (m, 3H), 6.95-7.22 (m, 4H), 6.67-6.80 (m, 2H), 6.53-6.67 (m, 1H), 6.35 (br. s., 1H), 5.38 (s, 1H), 5.13-5.30 (m, 1H), 5.01 (s, 2H), 3.97-4.17 (m, 1H), 3.88 (s, 3H), 3.19-3.50 (m, 5H), 2.31-2.42 (m, 1H), 1.68-2.20 (m, 4H);

LC-MS (ESI POS): 485.2 (MH$^+$);

$[\alpha]_D = -48.32°$ (c=0.25, MeOH).

Final compounds listed in Table 20 are prepared as previously described for C155, by alkylation of suitable intermediate (Diastereoisomer 1 of C2, Diastereoisomer 2 of C2, Diastereoisomer 1 of C37, C29, C105, C13, C14) and the commercially available alkylating agents.

TABLE 20

| Compound | Structure | Yield and Appearance | Analytical |
|---|---|---|---|
| Diastereoisomer 1 of C156 | Single diastereoisomer | 10% yield colorless viscous oil | LC-MS (ESI POS): 483.1 (MH$^+$)<br>$^1$H NMR (300 MHz, DMSO-d6) ppm: 7.84-8.11 (m, 2 H), 7.64-7.71 (m, 1 H), 7.52-7.61 (m, 4 H), 7.20-7.50 (m, 3 H), 6.95-7.20 (m, 2 H), 6.67-6.84 (m, 2 H), 6.52-6.67 (m, 1 H), 5.36 (s, 1 H), 5.04-5.19 (m, 1 H), 3.68-3.98 (m, 1 H), 3.29-3.56 (m, 3 H), 3.01-3.27 (m, 4 H), 2.80-2.93 (m, 1 H), 2.65-2.77 (m, 1 H), 2.20-2.37 (m, 1 H), 1.99 (br. s., 2 H), 1.75-1.94 (m0.0., 4 H) |

TABLE 20-continued

| Compound | Structure | Yield and Appearance | Analytical |
|---|---|---|---|
| Diastereoisomer 1 of C157 | Single stereoisomer | 51% yield brown viscous oil | LC-MS (ESI POS): 427.2 (MH$^+$) $^1$H NMR (300 MHz, DMSO-d$_6$) ppm: 7.29-7.62 (m, 10 H), 6.95-7.16 (m, 2 H), 6.64-6.78 (m, 2 H), 6.52-6.64 (m, 1 H), 5.31 (s, 1 H), 4.99-5.19 (m, 1 H), 4.40 (d, 1 H), 4.33 (d, 1 H), 3.81 (ddd, 1 H), 3.27-3.47 (m, 3 H), 2.87-3.03 (m, 1 H), 2.69-2.87 (m, 1 H), 2.20-2.38 (m, 1 H), 1.72-2.04 (m, 4 H) |
| Diastereoisomer 2 of C113 | Single stereoisomer | 97% yield brown viscous oil | LC-MS (ESI POS): 455.1 (MH$^+$) $^1$H NMR (300 MHz, DMSO-d$_6$) ppm: 7.91-8.03 (m, 2 H), 7.71-7.81 (m, 1 H), 7.54-7.67 (m, 4 H), 7.27-7.47 (m, 3 H), 6.97-7.17 (m, 2 H), 6.74 (m, 2 H), 6.50-6.66 (m, 1 H), 5.35 (s, 1 H), 5.20-5.27 (m, 1 H), 5.17 (s, 2 H), 4.12 (dd, 1 H), 3.42-3.84 (m, 5 H), 2.09-2.20 (m, 1 H), 1.85-2.07 (m, 2 H), 1.65-1.84 (m, 1 H), 1.38-1.60 (m, 1 H) $[\alpha]_D = -14.60°$ (c = 0.2, MeOH |
| Diastereoisomer 2 of C109 | Single diastereoisomer | 81% yield brown viscous oil | LC-MS (ESI POS): 461.1 (MH$^+$) $^1$H NMR (300 MHz, DMSO-d$_6$) ppm: 8.21 (dd, 1 H), 8.07 (dd, 1 H), 7.51-7.69 (m, 2 H), 7.27-7.49 (m, 4 H), 6.99-7.21 (m, 2 H), 6.66-6.80 (m, 2 H), 6.50-6.66 (m, 1 H), 5.34 (s, 1 H), 5.15-5.27 (m, 1 H), 5.07 (d, 1 H), 5.01 (d, 1 H), 4.11 (dd, 1 H), 3.60-3.87 (m, 4 H), 3.40-3.60 (m, 1 H), 2.06-2.21 (m, 1 H), 1.83-2.06 (m, 2 H), 1.63-1.83 (m, 1 H), 1.38-1.63 (m, 1 H) $[\alpha]_D = -14.00°$ (c = 0.2, MeOH |
| Diastereoisomer 1 of C158 | Single diastereoisomer | 28% yield Yellow oil | LC-MS (ESI POS): 495.1 (MH$^+$) $^1$H NMR (300 MHz, DMSO-d6) ppm: 7.96 (d, 1 H), 7.50-7.68 (m, 2 H), 7.20-7.50 (m, 4 H), 6.93-7.20 (m, 2 H), 6.67-6.85 (m, 2 H), 6.50-6.67 (m, 1 H), 6.35 (br. s., 1 H), 5.37 (s, 1 H), 5.09-5.25 (m, 1 H), 4.91 (s, 2 H), 3.97-4.13 (m, 1 H), 3.50-3.70 (m, 2 H), 3.18-3.50 (m, 3 H), 2.31-2.42 (m, 1 H), 1.96-2.15 (m, 2 H), 1.74-1.96 (m, 2 H) $[\alpha]_D = -40.32°$ (c = 0.3, MeOH) |

TABLE 20-continued

| Compound | Structure | Yield and Appearance | Analytical |
|---|---|---|---|
| Diastereoisomer 2 of C159 | Single diastereoisomer | 57% yield brown viscous oil | LC-MS (ESI POS): 495.0 (MH$^+$) <br> $^1$H NMR (300 MHz, DMSO-d$_6$) ppm: 7.99 (d, 1 H), 7.52-7.64 (m, 2 H), 7.44 (d, 1 H), 7.30-7.42 (m, 3 H), 7.00-7.18 (m, 2 H), 6.69-6.76 (m, 2 H), 6.56-6.64 (m, 1 H), 5.33 (s, 1 H), 5.13-5.25 (m, 1 H), 5.02 (d, 1 H), 4.96 (d, 1 H), 4.08 (dd, 1 H), 3.67-3.83 (m, 1 H), 3.46-3.67 (m, 4 H), 2.06-2.19 (m, 1 H), 1.83-2.04 (m, 2 H), 1.63-1.82 (m, 1 H), 1.39-1.61 (m, 1 H) <br> $[\alpha]_D = -17.47°$ (c = 0.3, MeOH) |
| Diastereoisomer 1 of C160 | Single diastereoisomer | 47% yield brown viscous oil | LC-MS (ESI POS): 470.1 (MH$^+$) <br> $^1$H NMR (300 MHz, DMSO-d$_6$) ppm: 10.51 (s, 1 H), 7.49-7.67 (m, 4 H), 7.28-7.47 (m, 5 H), 7.12-7.23 (m, 1 H), 7.01-7.12 (m, 2 H), 6.72 (m, 2 H), 6.58 (m, 1 H), 6.35 (br. s., 1 H), 5.32 (br. s., 1 H), 5.10-5.24 (m, 1 H), 4.23 (d, 1 H), 4.17 (d, 1 H), 4.01-4.14 (m, 1 H), 3.75-3.85 (m, 1 H), 3.55-3.70 (m, 4 H), 2.06-2.20 (m, 1 H), 1.81-2.04 (m, 2 H), 1.62-1.79 (m, 1 H), 1.42-1.62 (m, 1 H) <br> $[\alpha]_D = -19.6°$ (c = 0.25, MeOH) |
| Diastereoisomer 2 of C115 | Single diastereoisomer | 58% yield brown viscous oil | LC-MS (ESI POS): 473.2 (MH$^+$) <br> $^1$H NMR (300 MHz, DMSO-d$_6$) ppm: 7.96-8.18 (m, 2 H), 7.54-7.63 (m, 2 H), 7.26-7.52 (m, 5 H), 6.98-7.16 (m, 2 H), 6.69-6.77 (m, 2 H), 6.55-6.67 (m, 1 H), 5.35 (s, 2 H), 5.18-5.28 (m, 1 H), 5.11-5.18 (m, 2H), 3.83-4.27 (m, 1H), 3.70-3.85 (m, 1H), 3.47-3.70 (m, 4 H), 2.08-2.17 (m, 1 H), 1.86-2.04 (m, 2 H), 1.64-1.82 (m, 1 H), 1.44-1.64 (m, 1 H) <br> $[\alpha]_D = -11.44°$ (c = 0.25, MeOH) |
| Diastereoisomer 2 of C161 | Single diastereoisomer | 65% yield brown viscous oil | LC-MS (ESI POS): 485.2 (MH$^+$) <br> $^1$H NMR (300 MHz, DMSO-d$_6$) ppm: 7.84-8.03 (m, 2 H), 7.53-7.65 (m, 2 H), 7.28-7.49 (m, 3 H), 7.01-7.24 (m, 4 H), 6.69-6.79 (m, 2 H), 6.53-6.65 (m, 1 H), 5.34 (s, 1 H), 5.18-5.28 (m, 1 H), 5.02-5.12 (m, 2 H), 4.05-4.16 (m, 1 H), 3.89 (s, 3 H), 3.51-3.83 (m, 5 H), 2.08-2.18 (m, 1 H), 1.85-2.05 (m, 2 H), 1.65-1.81 (m, 1 H), 1.41-1.63 (m, 1 H) <br> $[\alpha]_D = -13.13°$ (c = 0.3, MeOH) |

TABLE 20-continued

| Compound | Structure | Yield and Appearance | Analytical |
|---|---|---|---|
| Diastereoisomer 1 of C162 | Single diastereoisomer | 36% yield brown viscous oil | LC-MS (ESI POS): 533.1 (MH+)<br>¹H NMR (300 MHz, DMSO-d6) ppm: 7.88-8.31 (m, 4 H), 7.52-7.68 (m, 2 H), 7.30-7.49 (m, 3 H), 7.01-7.17 (m, 1 H), 6.67-6.82 (m, 2 H), 6.51-6.67 (m, 1 H), 5.39 (s, 1 H), 5.17-5.27 (m, 1 H), 5.13 (s, 2 H), 3.99-4.15 (m, 1 H), 3.34-3.73 (m, 5 H), 3.31 (s, 3 H), 2.30-2.45 (m, 1 H), 1.69-2.21 (m, 5 H)<br>$[\alpha]_D = -34.15°$ (c = 0.4, MeOH) |
| Diastereoisomer 1 of C163 | Single diastereoisomer | 44% yield brown viscous oil | LC-MS (ESI POS): 471.2 (MH+)<br>¹H NMR (300 MHz, DMSO-d6) ppm: 9.99 (br. s., 1 H), 7.52-7.63 (m, 2 H), 7.26-7.49 (m, 6 H), 6.99-7.22 (m, 3 H), 6.69-6.81 (m, 2 H), 6.55-6.66 (m, 1 H), 5.38 (s, 1 H), 5.14-5.28 (m, 1 H), 5.04 (s, 2 H), 3.89-4.20 (m, 1 H), 3.19-3.85 (m, 5 H), 2.29-2.42 (m, 1 H), 1.71-2.14 (m, 4 H)<br>$[\alpha]_D = -42.75°$ (c = 0.4, MeOH) |
| Diastereoisomer 1 of C164 | Single diastereoisomer | 38% yield brown viscous oil | LC-MS (ESI POS): 422.1 (MH+)<br>¹H NMR (300 MHz, DMSO-d₆) ppm: 7.48-7.66 (m, 2 H), 7.25-7.47 (m, 3 H), 6.99-7.18 (m, 2 H), 6.73 (m, 2 H), 6.55-6.65 (m, 1 H), 5.35 (s, 1 H), 5.06-5.23 (m, 1 H), 4.25 (s, 2 H), 4.03 (ddd, 1 H), 3.43-3.73 (m, 4 H), 3.22-3.42 (m, 1 H), 2.92 (s, 3 H), 2.87 (s, 3 H), 2.29-2.38 (m, 1 H), 1.64-2.10 (m, 4 H)<br>$[\alpha]_D = -40.0°$ (c = 0.1, MeOH) |
| Diastereoisomer 1 of C165 | single diastereoisomer | 24% yield brown oil | LC-MS (ESI POS): 393.3 (MH+)<br>¹H NMR (300 MHz, DMSO-d₆) ppm: 7.50-7.61 (m, 2 H), 7.26-7.47 (m, 3 H), 7.03-7.16 (m, 2 H), 6.68-6.78 (m, 2 H), 6.54-6.65 (m, 1 H), 5.36 (s, 1 H), 4.99-5.22 (m, 1 H), 4.37 (s, 2 H), 3.88-4.00 (m, 1 H), 3.36-3.57 (m, 3 H), 3.05-3.36 (m, 2 H), 2.28-2.38 (m, 1 H), 2.11 (s, 3 H), 1.70-2.07 (m, 4 H) |

TABLE 20-continued

| Compound | Structure | Yield and Appearance | Analytical |
|---|---|---|---|
| Diastereoisomer 1 of C166 | Single stereoisomer | 18% yield Pale yellow solid | LC-MS (ESI POS): 518.9 (MH+) $^1$H NMR (300 MHz, DMSO-d6) ppm: 7.90-8.07 (m, 2 H), 7.72-7.82 (m, 2 H), 7.57-7.68 (m, 3 H), 7.33-7.55 (m, 5 H), 6.60-6.84 (m, 1 H), 5.57-5.87 (m, 1 H), 5.21-5.39 (m, 1 H), 4.98-5.21 (m, 2 H), 4.00-4.23 (m, 1 H), 3.78 (s, 3 H), 3.26-3.51 (m, 5 H), 2.30-2.47 (m, 1 H), 1.43-2.23 (m, 4 H) |
| Diastereoisomer 1 of C167 | Single diastereoisomer | 27% yield Yellow solid | LC-MS (ESI POS): 525.0 (MH$^+$) $^1$H NMR (300 MHz, DMSO-d6) ppm: 8.13-8.28 (m, 1 H) 8.05 (m, 1 H) 7.72-7.86 (m, 1 H) 7.66 (d, 1 H) 7.27-7.56 (m, 4 H) 6.72 (d, 1 H) 5.68 (d, 1 H) 5.19-5.32 (m, 1 H) 5.02 (s, 2 H) 4.02-4.24 (m, 1 H) 3.78 (s, 3 H) 3.37-3.68 (m, 7 H) 2.32-2.43 (m, 1 H) 1.88-2.23 (m, 3 H) 1.36-1.64 (m, 1 H) |
| C168 | Mixture of diastereoisomers | 26% yield White solid | LC-MS (ESI POS): 485.0 (MH$^+$) $^1$H NMR (300 MHz, DMSO-d$_6$) ppm: 8.47 (s, 1 H, formiate ion), 7.83-8.06 (m, 2 H), 7.68-7.82 (m, 1 H), 7.55-7.68 (m, 2 H), 7.39-7.55 (m, 2 H), 7.02-7.17 (m, 2 H), 6.90-7.02 (m, 2 H), 6.66-6.80 (m, 2 H), 6.52-6.63 (m, 1 H), 6.31 (d, 1 H), 5.24-5.38 (m, 1 H), 4.99-5.22 (m, 3 H), 3.98-4.20 (m, 1 H), 3.76 (s, 3 H), 3.45-3.83 (m, 5 H), 2.11-2.40 (m, 1 H), 1.45-2.10 (m, 4 H) |
| C169 | Mixture of diastereoisomers | 58% yield Pale yellow solid | LC-MS (ESI POS): 489.1 (MH$^+$) $^1$H NMR (300 MHz, DMSO-d6) ppm: 7.88-8.09 (m, 2 H), 7.70-7.87 (m, 1 H), 7.50-7.70 (m, 4 H), 7.27-7.50 (m, 3 H), 7.12 (m, 2 H), 6.76 (m, 2 H), 6.60 (d, 1 H), 5.31-5.49 (m, 1 H), 5.19-5.31 (m, 1 H), 5.14 (s, 2 H), 3.91-4.21 (m, 1 H), 3.57-3.88 (m, 5 H), 1.35-2.44 (m, 5 H) |

TABLE 20-continued

| Compound | Structure | Yield and Appearance | Analytical |
|---|---|---|---|
| C170 | 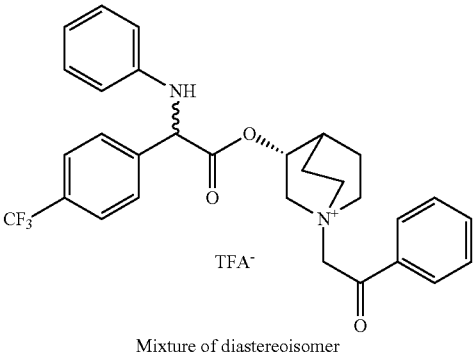 [SMILES: O=C(C[N+]12CCC(CC1)[C@@H](OC(=O)C(Nc1ccccc1)c1ccc(C(F)(F)F)cc1)C2)c1ccccc1 ; "TFA-"]<br>Mixture of diastereoisomer | 41% yield<br>White solid | LC-MS (ESI POS): 523.3 (MH+)<br>$^1$H NMR (300 MHz, DMSO-d$_6$) ppm: 8.45 (s, 1 H, formite ion), 7.91-8.04 (m, 2 H), 7.69-7.91 (m, 4 H), 7.48-7.69 (m, 3 H), 7.03-7.18 (m, 2 H), 6.70-6.80 (m, 2 H), 6.52-6.67 (m, 2 H), 5.50-5.64 (m, 1 H), 5.00-5.30 (m, 3 H), 3.51-4.32 (m, 6 H), 2.14-2.41 (m, 1 H), 1.54-2.14 (m, 4 H) |
| C171 | 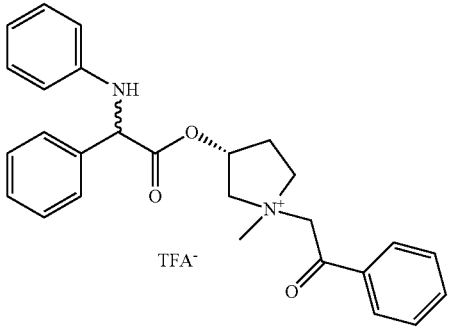<br>Mixture of diastereoisomers | 38% yield<br>yellow sticky oil | LC-MS (ESI POS): 429.1 (MH+)<br>$^1$H NMR (300 MHz, DMSO-d6) ppm: 7.90-8.09 (m, 2 H), 7.54-7.90 (m, 5 H), 6.90-7.52 (m, 5 H), 6.29-6.82 (m, 3 H), 5.43-5.57 (m, 1 H), 5.14-5.42 (m, 3 H), 3.72-4.19 (m, 4 H), 3.17 (s, 3 H), 2.55-2.73 (m, 1 H), 1.93-2.42 (m, 1 H) |
| C172 | 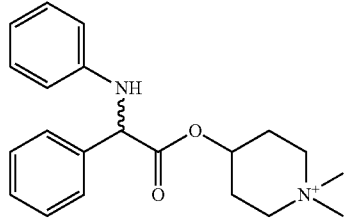<br>Mixture of stereoisomers | 43% yield<br>yellow sticky oil | LC-MS (ESI POS): 339.2 (MH+)<br>$^1$H NMR (300 MHz, DMSO-d6) ppm: 7.52-7.65 (m, 2 H), 7.29-7.49 (m, 3 H), 6.97-7.16 (m, 2 H), 6.66-6.79 (m, 2 H), 6.54-6.66 (m, 1 H), 6.32 (s, 1 H), 5.11-5.39 (m, 1 H), 4.81-5.01 (m, 1 H), 3.14-3.45 (m, 3 H), 3.04 (s, 6 H), 2.82-2.95 (m, 1 H), 1.35-2.25 (m, 4 H) |
| Diastereoisomer 1 of C173 | 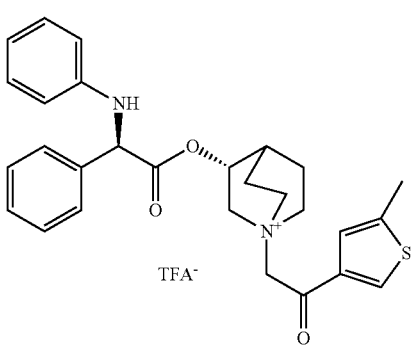<br>Single diastereoisomer | 84% yield<br>brown solid | LC-MS (ESI POS): 475.2 (MH+)<br>$^1$H NMR (300 MHz, DMSO-d6) ppm: 8.36 (d, 1 H), 7.54-7.60 (m, 2 H), 7.31-7.48 (m, 3 H), 7.24 (t, 1 H), 7.03-7.15 (m, 2 H), 6.68-6.80 (m, 2 H), 6.52-6.64 (m, 1 H), 5.37 (s, 1 H), 5.11-5.27 (m, 1 H), 4.89 (s, 2 H), 3.97-4.15 (m, 1 H), 3.20-3.51 (m, 5 H), 2.49 (s, 3 H), 2.32-2.40 (m, 1 H), 1.76-2.16 (m, 4 H)<br>$[\alpha]_D$ = −46.51° (c = 0.35, MeOH) |

Example 45

Preparation of (R)-1-[2-(2,4-difluoro-phenyl)-2-oxo-ethyl]-3-(2-phenyl-2-phenylamino-acetoxy)-1-azonia-bicyclo[2.2.2]octane bromide(diastereoisomer 1 of C174)

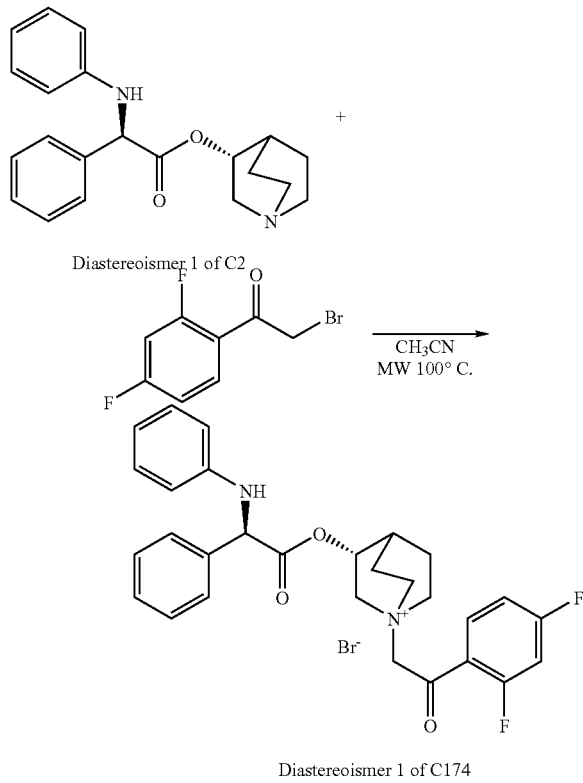

To a solution of (R)-phenyl-phenylamino-acetic acid (R)-(1-aza-bicyclo[2.2.2]oct-3-yl)ester (Diastereoisomer 1 of C2) (50 mg, 0.15 mmol) in acetonitrile (1 mL), is added 2-bromo-1-(2,4-difluoro-phenyl)-ethanone (35 mg, 0.15 mmol) and the mixture reacted in a closed vessel under MW irradiation for 1 hour at 100° C. (UPLC-MS monitoring: complete conversion). The solvent is evaporated and the resulting crude is purified by flash chromatography (DCM/MeOH=95/5) to obtain the title compound as a white solid (37.3 mg, 44% yield, bromide salt, single diastereoisomer).

$^1$NMR (300 MHz, DMSO-d6) ppm: 7.97-8.07 (m, 1H), 7.52-7.72 (m, 3H), 7.39-7.52 (m, 2H), 7.25-7.39 (m, 2H), 6.92-7.21 (m, 2H), 6.67-6.84 (m, 2H), 6.51-6.67 (m, 1H), 6.36 (d, 1H), 5.38 (d, 1H), 5.00-5.30 (m, 1H), 4.88 (br. s., 2H), 3.91-4.20 (m, 1H), 3.51-3.74 (m, 3H), 3.41-3.51 (m, 1H), 3.31-3.41 (m, 1H), 2.31-2.43 (m, 1H), 1.86-2.09 (m, 4H);

LC-MS (ESI POS): 491.1 (MH$^+$);

$[\alpha]_D$=−45.42° (c=0.24, MeOH).

Final compounds listed in Table 21 are prepared as previously described for C174, by alkylation of suitable intermediate (Diastereoisomer 1 of C2, C2, C80, C83, C85, C89, C87, C95, C101, C94, C95 C100, C132, C133, C143, C27, C138) and the commercially available alcylating agents.

TABLE 21

| Compound | Structure | Yield and Appearance | Analytical |
|---|---|---|---|
| Diastereoisomer 1 of C175 | Single diastereoisomer | 69% yield White solid | LC-MS (ESI POS): 491.1 (MH$^+$) $^1$H NMR (300 MHz, DMSO-d6) ppm: 7.95-8.15 (m, 1 H), 7.81-7.95 (m, 1 H), 7.70 (s, 1 H), 7.50-7.63 (m, 2 H), 7.22-7.50 (m, 3 H), 6.95-7.21 (m, 2 H), 6.67-6.82 (m, 2 H), 6.50-6.67 (m, 1 H), 6.36 (d, 1 H), 5.38 (d, 1 H), 5.13-5.29 (m, 1 H), 5.06 (s, 2 H), 3.92-4.17 (m, 1 H), 3.53-3.67 (m, 3 H), 3.32-3.50 (m, 2 H), 2.31-2.43 (m, 1 H), 1.73-2.19 (m, 4 H) $[\alpha]_D$ = −42.45° (c = 0.22, MeOH) |

TABLE 21-continued

| Compound | Structure | Yield and Appearance | Analytical |
|---|---|---|---|
| Diastereoisomer 1 of C176 | Single diastereoisomer | 25% yield Off-white solid | LC-MS (ESI POS): 473.0 (MH+)<br>1H NMR (300 MHz, DMSO-d6) ppm: 7.87-8.02 (m, 1 H), 7.72-7.87 (m, 1 H), 7.52-7.68 (m, 2 H), 7.28-7.52 (m, 5 H), 6.98-7.23 (m, 2 H), 6.67-6.84 (m, 2 H), 6.48-6.69 (m, 1 H), 6.36 (d, 1 H), 5.38 (d, 1 H), 5.08-5.30 (m, 1 H), 4.91 (br. s., 2 H), 3.91-4.23 (m, 1 H), 3.35-3.73 (m, 5 H), 2.30-2.46 (m, 1 H), 1.55-2.20 (m, 4 H) |
| Diastereoisomer 1 of C177 | Single diastereoisomer | 41% yield Yellow solid | LC-MS (ESI POS): 473.1 (MH+)<br>1H NMR (300 MHz, DMSO-d6) ppm: 7.75-7.86 (m, 2 H), 7.51-7.73 (m, 4 H), 7.26-7.51 (m, 3 H), 6.95-7.25 (m, 2 H), 6.68-6.85 (m, 2 H), 6.51-6.68 (m, 1 H), 6.36 (d, 1 H), 5.39 (d, 1 H), 5.15-5.30 (m, 1 H), 5.10 (s, 2 H), 4.00-4.15 (m, 1 H), 3.60-3.75 (m, 2 H), 3.34-3.60 (m, 3 H), 2.31-2.42 (m, 1 H), 1.84-2.14 (m, 4 H) |
| Diastereoisomer 1 of C178 | Single diastereoisomer | 47% yield White solid | LC-MS (ESI POS): 610.7 (MH+)<br>1H NMR (300 MHz, DMSO-$d_6$) ppm: 8.12 (d, 1 H), 7.86 (dd, 1 H), 7.79 (d, 1 H), 7.53-7.64 (m, 2 H), 7.29-7.47 (m, 3 H), 7.00-7.17 (m, 2 H), 6.75 (m, 2 H), 6.53-6.68 (m, 1 H), 6.39 (d, 1 H), 5.39 (d, 1 H), 5.17-5.28 (m, 1 H), 5.03 (s, 2 H), 3.94-4.17 (m, 1 H), 3.34-3.77 (m, 5 H), 2.31-2.41 (m, 1 H), 1.68 -2.19 (m, 4 H)<br>$[\alpha]_D = -50.30°$ (c = 0.6, MeOH) |
| Diastereoisomer 1 of C179 | Single diastereoisomer | 100% yield Orange solid | LC-MS (ESI POS): 500.1 (MH+)<br>1H NMR (300 MHz, DMSO-$d_6$) ppm: 8.36-8.53 (m, 2 H), 8.10-8.25 (m, 2 H), 7.53-7.65 (m, 2 H), 7.32-7.48 (m, 3 H), 7.01-7.20 (m, 2 H), 6.70-6.84 (m, 2 H), 6.55-6.65 (m, 1 H), 6.37 (d, 1 H), 5.39 (d, 1 H), 5.19-5.30 (m, 1 H), 5.16 (s, 2 H), 4.00-4.17 (m, 1 H), 3.34-3.78 (m, 5 H), 2.31-2.42 (m, 1 H), 1.67-2.12 (m, 4 H) |

TABLE 21-continued

| Compound | Structure | Yield and Appearance | Analytical |
|---|---|---|---|
| Diastereoisomer 1 of C180 Single diastereoisomer | | 64% yield light brown solid | LC-MS (ESI POS): 471.0 (MH$^+$) $^1$H NMR (300 MHz, DMSO-d$_6$) ppm: 7.69-7.89 (m, 2 H), 7.51-7.65 (m, 2 H), 7.30-7.49 (m, 3 H), 6.98-7.15 (m, 2 H), 6.83-6.96 (m, 2 H), 6.70-6.79 (m, 2 H), 6.60 (m, 1 H), 6.36 (d, 1 H), 5.38 (d, 1 H), 5.15-5.25 (m, 1 H), 4.96 (s, 2 H), 3.89-4.20 (m, 1 H), 3.34-3.77 (m, 5 H), 2.31-2.43 (m, 1 H), 1.70-2.16 (m, 4 H) $[\alpha]_D$ = −44.08° (c = 0.25, MeOH) |
| Diastereoisomer 1 of C181 Single diastereoisomer | | 81% yield Yellow solid | LC-MS (ESI POS): 510.0 (MH$^+$) $^1$H NMR (300 MHz, DMSO-d$_6$) ppm: 10.95 (s, 1 H), 7.87 (dd, 1 H), 7.82 (d, 1 H), 7.53-7.65 (m, 2 H), 7.26-7.48 (m, 3 H), 7.03-7.15 (m, 2 H), 6.98 (d, 1 H), 6.69-6.81 (m, 2 H), 6.52-6.63 (m, 1 H), 6.38 (d, 1 H), 5.38 (d, 1 H), 5.15-5.26 (m, 1 H), 5.05 (s, 2 H), 3.98-4.22 (m, 1 H), 3.63-3.80 (m, 2 H), 3.61 (s, 2 H), 3.48-3.59 (m, 2 H), 3.34-3.47 (m, 1 H), 2.31-2.42 (m, 1 H), 1.65-2.19 (m, 4 H) $[\alpha]_D$ = −47.07° (c = 0.28, MeOH) |
| Diastereoisomer 1 of C182 Single diastereoisomer | | 33% yield Yellow solid | LC-MS (ESI POS): 499.0 (MH$^+$) $^1$H NMR (300 MHz, DMSO-d$_6$) ppm: 7.53-7.64 (m, 3 H), 7.29-7.51 (m, 4 H), 7.14 (d, 1 H), 7.02-7.12 (m, 2 H), 6.69-6.82 (m, 2 H), 6.54-6.66 (m, 1 H), 6.36 (d, 1 H), 6.19 (s, 2 H), 5.38 (d, 1 H), 5.13-5.26 (m, 1 H), 4.98 (s, 2 H), 3.88-4.15 (m, 1 H), 3.35-3.75 (m, 5 H), 2.30-2.42 (m, 1 H), 1.70-2.12 (m, 4 H) $[\alpha]_D$ = −62.80° (c = 0.2, MeOH) |
| Diastereoisomer 1 of C183 Single diastereoisomer | | 73% yield yellow solid | LC-MS (ESI POS): 461.9 (MH$^+$) $^1$H NMR (300 MHz, DMSO-d$_6$) ppm: 8.39 (d, 1 H), 8.24 (d, 1 H), 7.51-7.65 (m, 2 H), 7.27-7.49 (m, 3 H), 6.98-7.18 (m, 2 H), 6.69-6.79 (m, 2 H), 6.60 (m, 1 H), 6.36 (d, 1 H), 5.38 (d, 1 H), 5.17-5.31 (m, 1 H), 5.12 (s, 2 H), 4.05-4.25 (m, 1 H), 3.58-3.77 (m, 3 H), 3.44-3.58 (m, 1 H), 3.33-3.41 (m, 1 H), 2.31-2.40 (m, 1 H), 1.76-2.16 (m, 4 H) $[\alpha]_D$ = −58.16° (c = 0.25, MeOH) |

TABLE 21-continued

| Compound | Structure | Yield and Appearance | Analytical |
|---|---|---|---|
| Diastereoisomer 1 of C184 | Single diastereoisomer | 27% yield yellow amorphous solid | LC-MS (ESI POS): 517.9 (MH$^+$) $^1$H NMR (300 MHz, DMSO-d$_6$) ppm: 7.86 (s, 1 H), 7.49-7.65 (m, 2 H), 7.29-7.49 (m, 3 H), 6.95-7.18 (m, 2 H), 6.68-6.82 (m, 2 H), 6.55-6.67 (m, 1 H), 6.36 (d, 1 H), 5.38 (d, 1 H), 5.14-5.25 (m, 1 H), 4.93 (s, 2 H), 4.43 (q, 2 H), 3.96-4.15 (m, 1 H), 3.34-3.71 (m, 5 H), 2.31-2.40 (m, 1 H), 1.85-2.09 (m, 4 H), 1.35 (t, 3 H) [α]$_D$ = −45.40° (c = 0.2, MeOH) |
| Diastereoisomer 1 of C185 | Single diastereoisomer | 6% yield White solid | LC-MS (ESI POS): 475.0 (MH$^+$) $^1$H NMR (300 MHz, DMSO-d$_6$) ppm: 7.89 (d, 1 H), 7.82 (s, 1 H), 7.51-7.62 (m, 2 H), 7.28-7.48 (m, 3 H), 7.01-7.18 (m, 2 H), 6.67-6.80 (m, 2 H), 6.52-6.65 (m, 1 H), 6.36 (d, 1 H), 5.37 (d, 1 H), 5.08-5.26 (m, 1 H), 4.92 (s, 2 H), 3.95-4.19 (m, 1 H), 3.41-3.75 (m, 5 H), 2.29-2.30 (m, 1 H), 2.29 (s, 3 H), 1.80-2.12 (m, 4 H) |
| Diastereoisomer 1 of C186 | Single diastereoisomer | 67% yield Off-white solid | LC-MS (ESI POS): 510.9 (MH$^+$) $^1$H NMR (300 MHz, DMSO-d$_6$) ppm: 8.56 (d, 1 H), 8.25 (d, 1 H), 7.97 (d, 1 H), 7.91 (dd, 1 H), 7.67 (d, 1 H), 7.52-7.62 (m, 2 H), 7.40-7.51 (m, 2 H), 7.28-7.40 (m, 1 H), 7.03-7.18 (m, 2 H), 6.69-6.84 (m, 2 H), 6.53-6.66 (m, 1 H), 6.38 (d, 1 H), 5.40 (d, 1 H), 5.20 (s, 2 H), 5.14-5.30 (m, 1 H), 4.06-4.23 (m, 1 H), 3.60-3.82 (m, 3 H), 3.50-3.60 (m, 1 H), 3.35-3.50 (m, 1 H), 2.34-2.42 (m, 1 H), 1.69-2.15 (m, 4 H) [α]$_D$ = −42.73° (c = 0.3, MeOH) |
| C187 | Mixture of diastereoisomers | 82% yield Off-white solid | LC-MS (ESI POS): 459.2 (MH$^+$) $^1$H NMR (300 MHz, DMSO-d$_6$) ppm: 7.50-7.61 (m, 4 H), 7.29-7.49 (m, 6 H), 7.08 (dd, 2 H), 6.65-6.79 (m, 2 H), 6.55-6.65 (m, 1 H), 6.40 (d, 1 H), 5.35 (d, 1 H), 5.04-5.15 (m, 1 H), 4.96 (s, 2 H), 3.76 (ddd, 1 H), 3.33-3.50 (m, 3 H), 2.85-3.06 (m, 2 H), 2.23-2.34 (m, 1 H), 1.67-2.04 (m, 4 H) [α]$_D$ = −55.41° (c = 1, MeOH) |

TABLE 21-continued

| Compound | Structure | Yield and Appearance | Analytical |
|---|---|---|---|
| Diastereoisomer 1 of C188 | Single diastereoisomer | 37% yield white solid | LC-MS (ESI POS): 462.2 (MH+)<br>¹H NMR (300 MHz, DMSO-d₆) ppm: 7.50-7.60 (m, 2 H) 7.29-7.46 (m, 3 H) 7.02-7.14 (m, 2 H) 6.67-6.79 (m, 2 H) 6.54-6.66 (m, 1 H) 6.37 (d, 1 H) 5.35 (d, 1 H) 5.06-5.22 (m, 1 H) 4.31 (s, 2 H) 3.97-4.15 (m, 1 H) 3.31-3.80 (m, 9 H) 2.23-2.39 (m, 1 H) 1.77-2.10 (m, 4 H) 1.38-1.69 (m, 6 H)<br>[α]$_D$ = −40.7° (c = 0.4, MeOH) |
| C189 | Mixture of diastereoisomers | 47% yield White solid | LC-MS (ESI POS): 476.9 (MH+)<br>¹H NMR (300 MHz, DMSO-d₆) ppm: 12.82 (br. s., 1 H), 7.55-7.60 (m, 2 H), 7.53 (d, 1 H), 7.33-7.47 (m, 3 H), 7.32 (d, 1 H), 7.00-7.15 (m, 2 H), 6.69-6.81 (m, 2 H), 6.53-6.66 (m, 1 H), 6.39 (d, 1 H), 5.37 (d, 1 H), 5.06-5.21 (m, 1 H), 4.30 (s, 2 H), 4.00-4.17 (m, 1 H), 3.46-3.75 (m, 5 H), 2.29-2.39 (m, 1 H), 1.41-2.13 (m, 4 H) |
| Diastereoisomer 1 of C190 | Single stereoisomer | 34% yield White solid | LC-MS (ESI POS): 461.0 (MH+)<br>¹H NMR (300 MHz, DMSO-d₆) ppm: 11.82 (br. s., 1 H), 8.89 (d, 1 H), 7.52-7.63 (m, 2 H), 7.26-7.50 (m, 3 H), 7.02-7.17 (m, 2 H), 6.90 (d, 1 H), 6.70-6.80 (m, 2 H), 6.53-6.64 (m, 1 H), 6.39 (d, 1 H), 5.36 (d, 1 H), 5.04-5.25 (m, 1 H), 4.28 (s, 2 H), 3.99-4.15 (m, 1 H), 3.44-3.75 (m, 5 H), 2.27-2.39 (m, 1 H), 1.71-2.13 (m, 4 H)<br>[α]$_D$ = −44.66° (c = 1, DCM) |
| C191 | Mixture of diastereoisomers | 36% yield White solid | LC-MS (ESI POS): 469.1 (MH+)<br>¹H NMR (300 MHz, DMSO-d₆) ppm: 7.88-8.07 (m, 2 H), 7.71-7.83 (m, 1 H), 7.51-7.68 (m, 4 H), 7.24-7.48 (m, 3 H), 6.91 (m, 2 H), 6.66 (m, 2 H), 6.16 (d, 1 H), 5.34 (d, 1 H), 5.15-5.27 (m, 1 H), 5.09 (s, 2 H), 3.92-4.19 (m, 1 H), 3.33-3.77 (m, 5 H), 2.31-2.41 (m, 1 H), 2.12 (s, 3 H), 1.77-2.08 (m, 4 H) |

TABLE 21-continued

| Compound | Structure | Yield and Appearance | Analytical |
|---|---|---|---|
| C192 | Mixture of diastereoisomers (Br⁻) | 32% yield Pale brown solid | LC-MS (ESI POS): 473.1 (MH$^+$) $^1$H NMR (300 MHz, DMSO-d$_6$) ppm: 7.90-8.05 (m, 2 H), 7.72-7.84 (m, 1 H), 7.52-7.70 (m, 4 H), 7.23-7.50 (m, 3 H), 6.86-7.01 (m, 2 H), 6.64-6.80 (m, 2 H), 6.35 (d, 1 H), 5.37 (d, 1 H), 5.16-5.26 (m, 1 H), 5.12 (s, 1 H), 3.99-4.13 (m, 1 H), 3.38-3.84 (m, 6 H), 2.30-2.41 (m, 1 H), 1.39-2.18 (m, 4 H) |
| C193 | Mixture of diastereoisomers (Cl⁻) | 6% yield White solid | LC-MS (ESI POS): 479.0 (MH$^+$) $^1$H NMR (300 MHz, DMSO-d$_6$) ppm: 8.14-8.29 (m, 1 H), 7.93-8.13 (m, 1 H), 7.51-7.63 (m, 2 H), 7.27-7.48 (m, 5 H), 6.86-7.04 (m, 2 H), 6.63-6.81 (m, 2 H), 6.11-6.43 (m, 1 H), 5.26-5.43 (m, 1 H), 5.13-5.26 (m, 1 H), 4.90-5.11 (m, 2 H), 3.92-4.25 (m, 1 H), 3.33-3.86 (m, 5 H), 2.30-2.42 (m, 0 H), 1.48-2.19 (m, 4 H) |
| C194 | Mixture of diastereoisomers (Br⁻) | 42% yield White powder | LC-MS (ESI POS): 513.0 (MH$^+$) $^1$H NMR (300 MHz, DMSO-d$_6$) ppm: 8.82 (t, 1 H), 7.93-8.09 (m, 2 H), 7.82-7.91 (m, 1 H), 7.70-7.81 (m, 1 H), 7.51-7.70 (m, 4 H), 7.21-7.51 (m, 4 H), 6.56-6.79 (m, 2 H), 5.61 and 5.67 (d, 1 H), 5.22-5.36 (m, 1 H), 5.14 and 5.20 (s, 2 H), 3.94-4.27 (m, 1 H), 3.86 (s, 3 H), 3.35-3.77 (m, 5 H), 2.15-2.24 and 2.37-2.46 (m, 1 H), 1.38-2.14 (m, 4 H) |
| C195 | Mixture of diastereoisomers (Br⁻) | 11% yield White powder | LC-MS (ESI POS): 485.1 (MH$^+$) $^1$H NMR (300 MHz, DMSO-d$_6$) ppm: 7.89-8.10 (m, 2 H), 7.71-7.82 (m, 1 H), 7.58-7.70 (m, 2 H), 7.50-7.58 (m, 2 H), 7.24-7.48 (m, 3 H), 6.88 (d, 1 H), 6.71 (td, 1 H), 6.63 (td, 1 H), 6.37-6.52 (m, 1 H), 5.44 (d, 1 H), 5.39 (d, 1 H), 5.21-5.29 (m, 1 H), 5.13 and 5.20 (s, 2 H), 4.00-4.21 (m, 1 H), 3.85 (s, 3 H), 3.35-3.76 (m, 5 H), 2.14-2.20 and 2.35-2.45 (m, 1 H), 1.33-2.11 (m, 4H) |

TABLE 21-continued

| Compound | Structure | Yield and Appearance | Analytical |
|---|---|---|---|
| C196 | 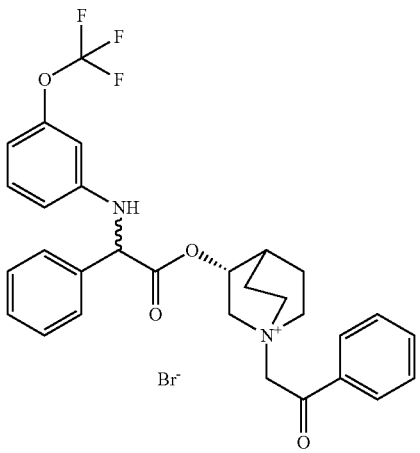<br>Mixture of diastereoisomers | 20% yield<br>White solid | LC-MS (ESI POS): 539.0 (MH$^+$)<br>$^1$H NMR (300 MHz, DMSO-d$_6$) ppm: 7.89-8.07 (m, 2 H), 7.70-7.82 (m, 1 H), 7.52-7.70 (m, 4 H), 7.30-7.52 (m, 3 H), 7.19 (t, 1 H), 6.80-6.97 (m, 1 H), 6.69-6.80 (m, 2 H), 6.46-6.57 (m, 1 H), 5.44 and 5.48 (d, 1 H), 5.21-5.29 (m, 1 H), 5.14 and 5.20 (s, 2 H), 3.99-4.24 (m, 1 H), 3.39-3.87 (m, 5 H), 2.09-2.18 and 2.33-2.43 (m, 1 H), 1.42-2.18 (m, 4 H) |
| C197 | 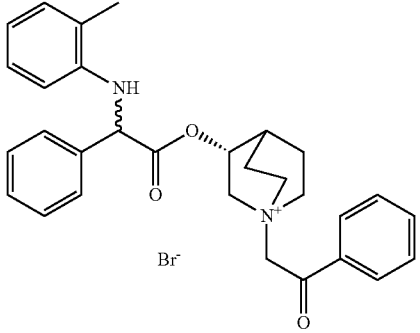<br>Mixture of diastereoisomers | 37% yield<br>White solid | LC-MS (ESI POS): 469.1 (MH$^+$)<br>$^1$H NMR (300 MHz, DMSO-d$_6$) ppm: 7.89-8.11 (m, 2 H), 7.69-7.85 (m, 1 H), 7.51-7.69 (m, 4 H), 7.27-7.49 (m, 3 H), 7.04 (d, 1 H), 6.87-7.01 (m, 1 H), 6.55-6.64 (m, 1 H), 6.46 (d, 1 H), 5.38-5.50 (m, 1 H), 5.09-5.31 (m, 4 H), 3.99-4.23 (m, 1 H), 3.45-3.89 (m, 5 H), 2.34-2.43 (m, 1 H), 2.25 (s, 3 H), 1.37-2.09 (m, 4 H) |
| C198 | 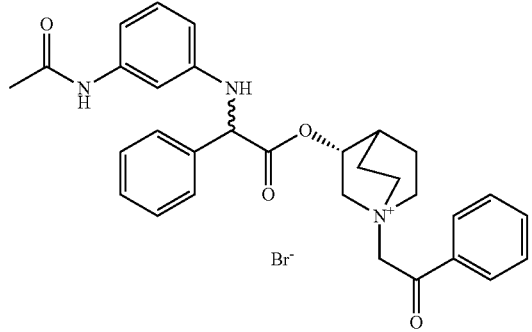<br>Mixture of diastereoisomers | 41% yield<br>Off-white solid | LC-MS (ESI POS): 512.1 (MH$^+$)<br>$^1$H NMR (300 MHz, DMSO-d$_6$) ppm: 9.69 and 9.71 (d, 1 H), 7.89-8.07 (m, 2 H), 7.69-7.83 (m, 1 H), 7.50-7.68 (m, 4 H), 7.30-7.49 (m, 3 H), 7.09-7.25 (m, 1 H), 7.00 (t, 1 H), 6.61-6.81 (m, 1 H), 6.27-6.56 (m, 2 H), 5.03-5.32 (m, 4 H), 4.05-4.27 (m, 1 H), 3.44-3.90 (m, 5 H), 2.11-2.21 and 2.32-2.42 (m, 1 H), 1.94 and 1.96 (s, 3 H), 1.59-2.10 (m, 4 H) |
| C199 | 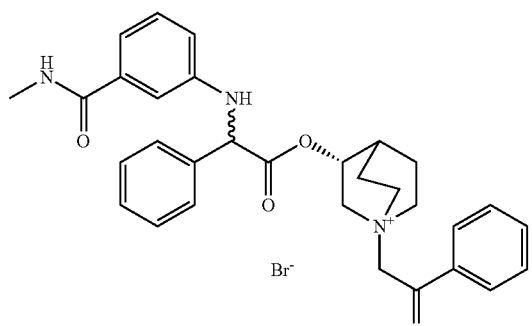<br>Mixture of diastereoisomers | 51% yield<br>Off-white solid | LC-MS (ESI POS): 512.1 (MH$^+$)<br>$^1$H NMR (300 MHz, DMSO-d$_6$) ppm: 8.14-8.30 (m, 1 H), 7.92-8.05 (m, 2 H), 7.55-7.86 (m, 5 H), 7.30-7.50 (m, 3 H), 7.11-7.23 (m, 1 H), 6.99-7.10 (m, 1 H), 6.91 (d, 1 H), 6.62 (d, 2 H), 5.45 (d, 1 H), 5.19-5.24 (m, 1 H), 5.14 (s, 2 H), 4.03-4.26 (m, 1 H), 3.35-3.86 (m, 5 H), 2.70 (d, 3 H), 2.10-2.40 (m, 1 H), 1.61-2.09 (m, 4 H) |

TABLE 21-continued

| Compound | Structure | Yield and Appearance | Analytical |
|---|---|---|---|
| C200 | 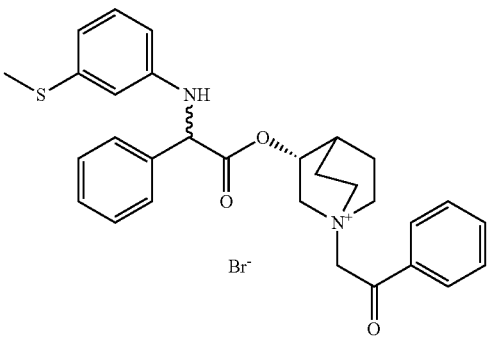<br>Mixture of diastereoisomers | 42% yield<br>Off-white solid | LC-MS (ESI POS): 501.3 (MH$^+$)<br>$^1$H NMR (300 MHz, DMSO-d$_6$) ppm: 7.90-8.09 (m, 2 H), 7.71-7.84 (m, 1 H), 7.52-7.70 (m, 4 H), 7.28-7.49 (m, 3 H), 7.01 and 7.04 (d, 1 H), 6.67 (s, 1 H), 6.37-6.59 (m, 3 H), 5.40 and 5.43 (d, 1 H), 5.19-5.30 (m, 1 H), 5.14 and 5.21 (s, 2 H), 4.01-4.25 (m, 1 H), 3.40-3.88 (m, 5 H), 2.37 (s, 3 H), 1.38-2.21 (m, 5 H) |
| C201 | 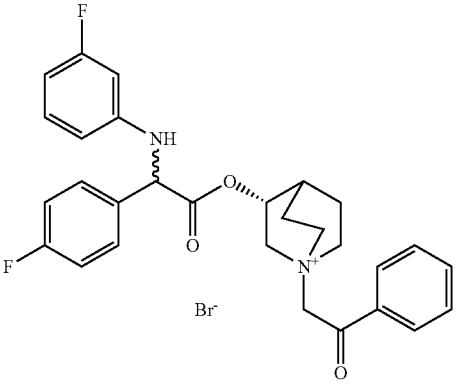<br>Mixture of diastereoisomers | 42% yield<br>pale pink solid | LC-MS (ESI POS): 491.2 (MH$^+$)<br>$^1$H NMR (300 MHz, DMSO-d$_6$):<br>Diastereisomer 1: 7.88-8.07 (m, 2 H), 7.70-7.81 (m, 1 H), 7.49-7.68 (m, 4 H), 7.19-7.33 (m, 2 H), 6.99-7.16 (m, 1 H), 6.69-6.85 (m, 1 H), 6.49-6.62 (m, 2 H), 6.22-6.44 (m, 1 H), 5.49 (d, 1 H), 5.21-5.28 (m, 1 H), 5.13 (s, 2 H), 3.96-4.10 (m, 1 H), 3.43-3.88 (m, 5 H), 2.32-2.43 (m, 1 H), 1.46-2.21 (m, 4 H)<br>Diastereisomer 2: 7.88-8.07 (m, 2 H), 7.70-7.81 (m, 1 H), 7.49-7.68 (m, 4 H), 7.19-7.33 (m, 2 H), 6.99-7.16 (m, 1 H), 6.69-6.85 (m, 1 H), 6.49-6.62 (m, 2 H), 6.22-6.44 (m, 1 H), 5.46 (d, 1 H), 5.21-5.28 (m, 1 H), 5.18 (s, 2 H), 4.10-4.20 (m, 1 H), 3.43-3.88 (m, 5 H), 2.13-2.21 (m, 1 H), 1.36-2.11 (m, 4 H) |
| C202 | 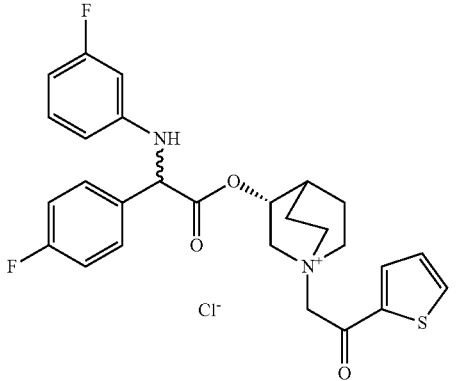<br>Mixture of diastereoisomers | 52% yield<br>beige solid | LC-MS (ESI POS): 497.1 (MH$^+$)<br>$^1$H NMR (300 MHz, DMSO-d$_6$):<br>Diastereisomer 1: 8.20 (dd, 1.03 Hz, 1 H), 8.06 (dd, 1 H), 7.51-7.72 (m, 2 H), 7.31-7.41 (m, 1 H), 7.19-7.29 (m, 2 H), 6.98-7.17 (m, 1 H), 6.69-6.88 (m, 1 H), 6.45-6.62 (m, 2 H), 6.24-6.45 (m, 1 H), 5.48 (d, 1 H), 5.14-5.31 (m, 1 H), 5.03 (s, 2 H), 3.96-4.21 (m, 1 H), 3.36-3.86 (m, 5 H), 2.28-2.43 (m, 1 H), 1.46-2.11 (m, 4 H)<br>Diastereisomer 2: 8.21 (dd, 1 H), 8.10 (dd, J = 3.96, 1.03 Hz, 1 H), 7.51-7.72 (m, 2 H), 7.31-7.41 (m, 1 H), 7.19-7.29 (m, 2 H), 6.98-7.17 (m, 1 H), 6.69-6.88 (m, 1 H), 6.45-6.62 (m, 2 H), 6.24-6.45 (m, 1 H), 5.44 (d, 1 H), 5.14-5.31 (m, 1 H), 5.09 (s, 2 H), 3.96-4.21 (m, 1 H), 3.36-3.86 (m, 5 H), 2.11-2.20 (m, 1 H), 1.46-2.11 (m, 4 H) |

TABLE 21-continued

| Compound | Structure | Yield and Appearance | Analytical |
|---|---|---|---|
| C203 | 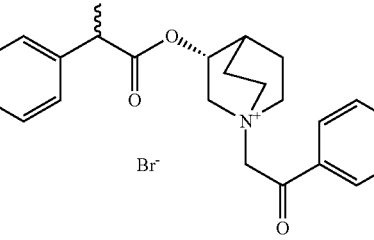 Mixture of diastereoisomers | 94% yield white solid | LC-MS (ESI POS): 491.2 (MH+) ¹H NMR (300 MHz, DMSO-d₆): Diastereisomer 1: 7.86-8.04 (m, 2 H), 7.70-7.83 (m, 1 H), 7.53-7.70 (m, 4 H), 7.19-7.33 (m, 2 H), 7.03-7.14 (m, 1 H), 6.89-7.00 (m, 1 H), 6.56-6.80 (m, 2 H), 5.73-5.89 (m, 1 H), 5.52 (d, 1 H), 5.20-5.29 (m, 1 H), 5.12 (s, 2 H), 3.95-4.29 (m, 1 H), 3.35-3.87 (m, 5 H), 2.32-2.42 (m, 1 H), 1.42-2.13 (m, 4 H) Diastereisomer 2: 7.86-8.04 (m, 2 H), 7.70-7.83 (m, 1 H), 7.53-7.70 (m, 4 H), 7.19-7.33 (m, 2 H), 7.03-7.14 (m, 1 H), 6.89-7.00 (m, 1 H), 6.56-6.80 (m, 2 H), 5.73-5.89 (m, 1 H), 5.50 (d, 1 H), 5.20-5.29 (m, 1 H), 5.17 (s, 2 H), 3.95-4.29 (m, 1 H), 3.35-3.87 (m, 5 H), 2.14-2.23 (m, 1 H), 1.42-2.13 (m, 4 H) |
| C204 | 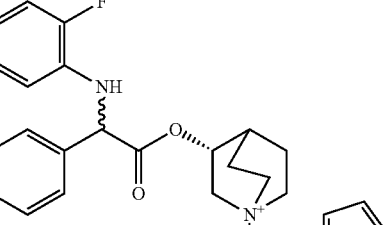 Mixture of diastereoisomers | 83% yield white solid | LC-MS (ESI POS): 497.1 (MH+) ¹H NMR (300 MHz, DMSO-d₆) ppm: 8.17-8.24 (m, H), 8.03 8.14 (m, 1 H), 7.51-7.74 (m, 2 H), 7.28-7.41 (m, 1 H), 7.17-7.27 (m, 2 H), 7.02-7.14 (m, 1 H), 6.87-6.99 (m, 1 H), 6.44-6.78 (m, 2 H), 5.72-5.91 (m, 1 H), 5.50 (m, 1 H), 5.22 (br. s., 1 H), 5.07 (s, 2 H), 3.99-4.29 (m, 1 H), 3.35-3.94 (m, 5 H), 2.13-2.42 (m, 1 H), 1.41-2.12 (m, 4 H) |
| C205 | 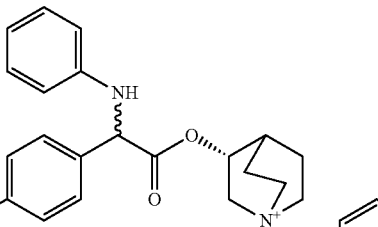 Mixture of diastereoisomers | 81% yield Off-white solid | LC-MS (ESI POS): 513.0 (MH+) ¹H NMR (300 MHz, DMSO-d₆) ppm: 7.89-8.07 (m, 4 H), 7.70-7.80 (m, 3 H), 7.47-7.67 (m, 2 H), 7.03-7.17 (m, 2 H), 6.70-6.82 (m, 2 H), 6.55-6.65 (m, 1 H), 6.49 (d, 1 H), 5.56 and 5.52 (d, 1 H), 5.21-5.33 (m, 1 H), 5.20 and 5.12 (s, 2 H), 3.97-4.23 (m, 1 H), 3.85 (s, 3 H), 3.41-3.82 (m, 5 H), 2.33-2.42 and 2.10-2.21 (m, 1 H), 1.49-2.11 (m, 4 H) |
| C206 | 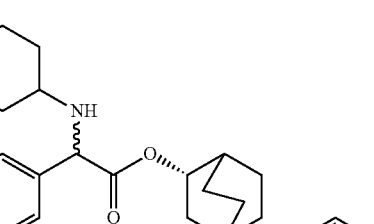 Mixture of diastereoisomers | 46% yield Colorless sticky oil | LC-MS (ESI POS): 461.1 (MH+) ¹H NMR (300 MHz, DMSO-d6) ppm: 9.77 (br. s., 1 H), 9.58 (br. s., 1 H), 7.87-8.05 (m, 2 H), 7.72-7.82 (m, 1 H), 7.40-7.71 (m, 7 H), 5.45-5.70 (m, 1 H), 5.28-5.45 (m, 1 H), 5.06-5.26 (m, 2 H), 3.97-4.21 (m, 1 H), 3.81 (d, 1 H), 3.23-3.76 (m, 4 H), 2.77-3.04 (m, 1 H), 1.88-2.46 (m, 6 H), 1.69-1.86 (m, 3 H), 1.26-1.69 (m, 3 H), 0.80-1.26 (m, 3 H) |

TABLE 21-continued

| Compound | Structure | Yield and Appearance | Analytical |
|---|---|---|---|
| C207 | Mixture of diastereoisomers | 41% yield White solid | LC-MS (ESI POS): 467.0 (MH$^+$) $^1$H NMR (300 MHz, DMSO-d6) ppm: 9.56 (br. s., 2 H), 8.17-8.28 (m, 1 H), 7.94-8.12 (m, 1 H), 7.44-7.77 (m, 5 H), 7.24-7.39 (m, 1 H), 5.44-5.68 (m, 1 H), 5.26-5.44 (m, 1 H), 4.84-5.14 (m, 2 H), 3.92-4.24 (m, 1 H), 3.43-3.91 (m, 6 H), 2.78-3.08 (m, 1 H), 2.32-2.45 (m, 1 H), 1.84-2.23 (m, 3 H), 1.47-1.84 (m, 2 H), 0.83-1.47 (m, 8 H) |
| C208 | Mixture of diastereoisomers | 41% yield Off-white solid | LC-MS (ESI POS): 460.9 (MH$^+$) $^1$H NMR (300 MHz, DMSO-d$_6$) ppm Diastereoisomer 1: 7.92-8.03 (m, 2 H), 7.71-7.82 (m, 1 H), 7.57-7.69 (m, 2 H), 7.50-7.57 (m, 1 H), 7.24-7.34 (m, 1 H), 7.01-7.17 (m, 3 H), 6.75-6.83 (m, 2 H), 6.58-6.67 (m, 1 H), 6.43 (d, 1 H), 5.69 (d, 1 H), 5.23-5.34 (m, 1 H), 5.17 (s, 2 H), 4.05-4.24 (m, 1 H), 3.44-3.86 (m, 5 H), 2.31-2.43 (m, 1 H), 1.64-2.14 (m, 4 H) Diastereoisomer 2: 7.92-8.03 (m, 2 H), 7.71-7.82 (m, 1 H), 7.57-7.69 (m, 2 H), 7.50-7.57 (m, 1 H), 7.24-7.34 (m, 1 H), 7.01-7.17 (m, 3 H), 6.75-6.83 (m, 2 H), 6.58-6.67 (m, 1 H), 6.42 (d, 1 H), 5.66 (d, 1 H), 5.23-5.34 (m, 1 H), 5.21 (s, 2 H), 4.05-4.24 (m, 1 H), 3.44-3.86 (m, 5 H), 2.18-2.24 (m, 1 H), 1.64-2.14 (m, 4 H) |

Example 46

Preparation of (R)-3-[2-(3-fluoro-4-methyl-phenylamino)-2-phenyl-acetoxy]-1-(2-oxo-2-phenyl-ethyl)-1-azonia-bicyclo[2.2.2]octane bromide (C209)

Scheme 46

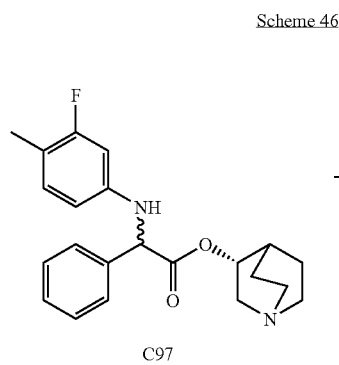

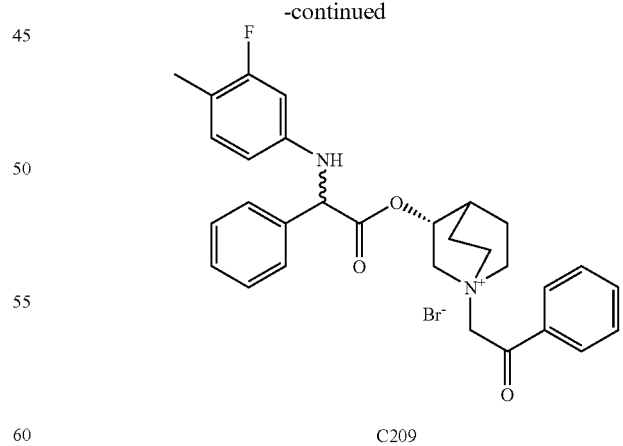

(R)-Quinuclidin-3-yl 2-(3-fluoro-4-methylphenylamino)-2-phenylacetate (C97) (80 mg, 0.22 mmol) and 2-bromo-1-phenylethanone (45.4 mg, 0.23 mmol) are dissolved in acetonitrile (3 mL) and stirred at RT overnight (Conversion complete by UPLC/MS). Acetonitrile is evaporated and the residue is purified by flash chromatography (DCM/MeOH=97/3) affording the title compound as a white solid (29 mg, 23% yield, bromide salt, mixture of diastereoisomers).

$^1$H NMR (300 MHz, DMSO-d6) ppm: 7.92-8.05 (m, 2H), 7.71-7.86 (m, 1H), 7.50-7.71 (m, 4H), 7.28-7.50 (m, 3H), 6.95 and 6.97 (d, 1H), 6.38-6.62 (m, 3H), 5.37 and 5.41 (d, 1H), 5.19-5.27 (m, 1H), 5.15 (s, 2H), 4.00-4.27 (m, 1H), 3.79 (d, 1H), 3.40-3.72 (m, 4H), 2.10-2.20 and 2.33-2.42 (m, 1H), 2.04 (s, 3H), 1.85-2.02 (m, 2H), 1.65-1.85 (m, 1H), 1.42-1.65 (m, 1H);

LC-MS (ESI POS): 487.1 (MH+).

Final compounds listed in Table 22 are prepared as previously described for C209, by alkylation of suitable intermediate (C103, C106, C107, C109, C112, C115, C117, C147, C148) and the commercially available alkylating agents.

TABLE 22

| Compound | Structure | Yield and Appearance | Analytical |
|---|---|---|---|
| C210 | 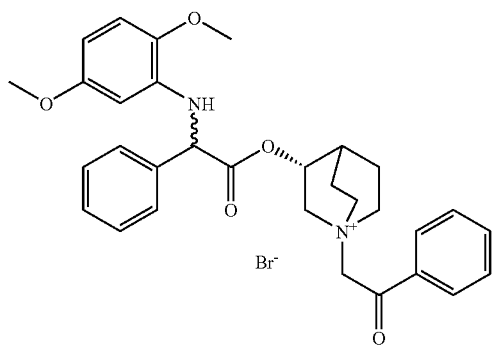 | 40% yield Yellow solid | LC-MS (ESI POS): 515.1 (MH$^+$) $^1$H NMR (300 MHz, DMSO-d$_6$) ppm: 7.89-8.04(m, 2 H), 7.70-7.83(m, 1 H), 7.49-7.69(m, 4 H), 7.27-7.49(m, 3 H), 6.77(d, 1 H), 6.15(dd, 1 H), 6.03 and 6.06(d, 1 H), 5.36-5.53(m, 2 H), 5.21-5.30(m, 1 H), 5.13 and 5.19(s, 2 H), 3.94-4.28(m, 1 H), 3.80(s, 3 H), 3.59-3.73(m, 3 H), 3.56 and 3.57 (s, 3 H), 3.34-3.54(m, 2 H), 2.12-222 and 2.35-2.45(m, 1 H), 1.29-2.12(m, 4 H) |
| | Mixture of diastereoisomers | | |
| C211 | 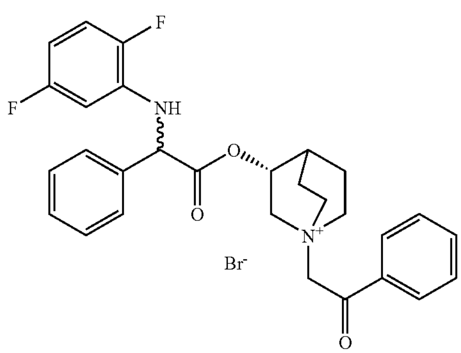 | 55% yield White solid | LC-MS (ESI POS): 491.3 (MH$^+$) $^1$H NMR (300 MHz, DMSO-d$_6$) ppm: 7.92-8.03(m, 2 H) 7.71-7.81(m, 1 H) 7.54-7.67(m, 4 H) 7.31-7.47(m, 3 H) 7.11(ddd, 1 H) 6.51-6.63(m, 1 H) 6.36-6.47(m, 1 H) 6.02-6.15(m, 1 H) 5.54 and 5.56(d, 1 H) 5.22-5.31(m, 1 H) 5.19(d, 1 H) 5.12(d, 1 H) 4.01-4.22(m, 1 H) 3.36-3.88(m, 5 H) 1.34-2.43(m, 5 H) |
| | Mixture of diastereoisomer | | |
| C212 | 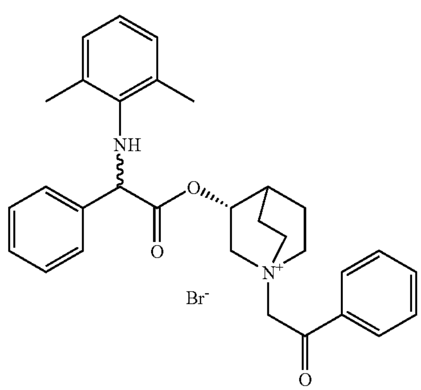 | 58% yield White solid | LC-MS (ESI POS): 483.1 (MH$^+$) $^1$H NMR (300 MHz, DMSO-d$_6$) ppm: 7.86-8.06(m, 2 H), 7.68-7.83(m, 1 H), 7.48-7.67(m, 4 H), 7.24-7.46(m, 3 H), 6.94(d, 2 H), 6.75(t, 1 H), 5.21-5.25(m, 1 H), 5.15 and 5.18(s, 2 H), 5.00 and 5.02(d, 1 H), 4.70 and 4.75(d, 1 H), 3.96-4.24(m, 1 H), 3.44-3.75(m, 5 H), 2.22(s, 6 H), 1.27-2.19(m, 5H) |
| | Mixture of diastereoisomer | | |

TABLE 22-continued

| Compound | Structure | Yield and Appearance | Analytical |
|---|---|---|---|
| C213 | 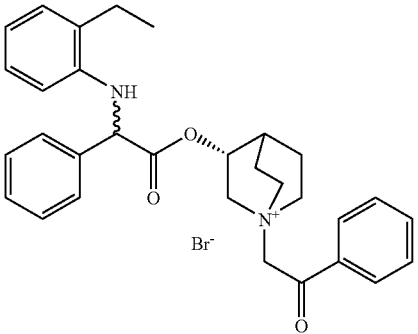 Mixture of diastereoisomer | 60% yield Yellow solid | LC-MS (ESI POS): 483.1 (MH$^+$) $^1$H NMR (300 MHz, DMSO-d$_6$) ppm: 7.88-8.12(m, 2 H), 7.71-7.84(m, 1 H), 7.53-7.70(m, 4 H), 7.26-7.49(m, 3 H), 7.04(d, 1 H), 6.90-7.01(m, 1 H), 6.57-6.70(m, 1 H), 6.47(d, 1 H), 5.42 and 5.45(d, 1 H), 5.19-5.30(m, 2 H), 5.14 and 5.20(s, 2 H), 4.01-4.24(m, 1 H), 3.33-3.89(m, 5 H), 2.64(q, 2 H), 2.12-2.20 and 2.32-2.43(m, 1 H), 1.37-2.13(m, 4 H), 1.24(t, 3 H) |
| C214 | 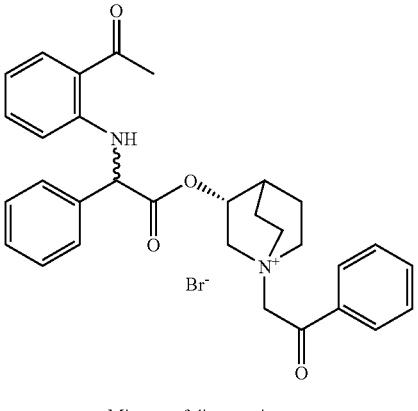 Mixture of diastereoisomer | 83% yield Off-white solid | LC-MS (ESI POS): 497.1 (MH$^+$) $^1$H NMR (300 MHz, DMSO-d$_6$) ppm: 9.84 and 9.86(d, 1 H), 7.86-8.09(m, 3 H), 7.69-7.84(m, 1 H), 7.56-7.69(m, 2 H), 7.49-7.56 (m, 2 H), 7.24-7.48(m, 4 H), 6.54-6.73(m, 2 H), 5.62 and 5.67 (d, 1 H), 5.23-5.31(m, 1 H), 5.15 and 5.22(s, 2 H), 4.00-4.27(m, 1 H), 3.35-3.87(m, 5 H), 2.60(s, 3 H), 2.17-2.24 and 2.36-2.47 (m, 1 H), 1.42-2.16(m, 4 H) |
| C215 | 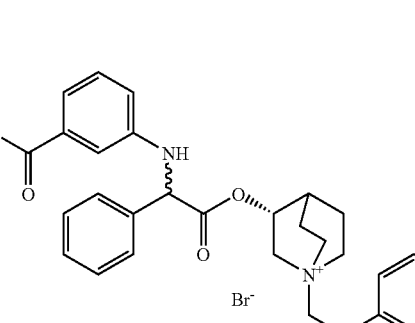 Mixture of diastereoisomer | 24% yield Off-white solid | LC-MS (ESI POS): 527.3 (MH$^+$) $^1$H NMR (300 MHz, DMSO-d$_6$) ppm: 7.90-8.04(m, 2 H) 7.71-7.82(m, 1 H) 7.55-7.68(m, 4 H), 7.30-7.49(m, 4 H) 7.15-7.28 (m, 2 H) 6.93-7.04(m, 1 H) 6.78(t, 1 H) 5.44(d, 1 H) 5.19-5.31 (m, 1 H) 5.14(s, 2 H) 4.25(q, 2 H) 3.97-4.19(m, 1 H) 3.42-3.80 (m, 5 H) 1.85-2.22(m, 4 H) 1.49-1.85(m, 1 H) 1.28(t, 3 H) |

TABLE 22-continued

| Compound | Structure | Yield and Appearance | Analytical |
|---|---|---|---|
| C216 | 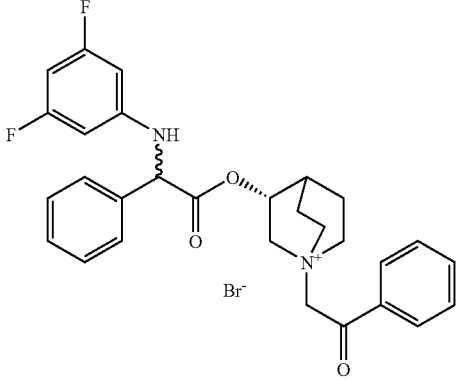<br>Mixture of diastereoisomer | 60% yield<br>White solid | LC-MS (ESI POS): 491.2 (MH$^+$)<br>$^1$H NMR (300 MHz, DMSO-d$_6$) ppm<br>Diastereoisomer 2: 7.90-1.06(m, 2 H), 7.70-7.82(m, 1 H), 7.51-7.68(m, 4 H), 7.30-7.51(m, 3 H), 7.09(d, 1 H), 6.36-6.53(m, 2 H), 6.20-6.36(m, 1 H), 5.52(d, 1 H), 5.22-5.29(m, 1 H), 5.15(s, 2 H), 3.95-4.27(m, 1 H), 3.42-3.87(m, 5 H), 2.31-2.44(m, 1 H), 1.85-2.12(m, 4 H)<br>Diastereoisomer 2: 7.90-8.06(m, 2 H), 7.70-7.82(m, 1 H), 7.51-7.68(m, 4 H), 7.30-7.51(m, 3 H), 7.12(d, 1 H), 6.36-6.53(m, 2 H), 6.20-6.36(m, 1 H), 5.48(d, 0 H), 5.22-5.30(m, 1 H), 5.20(s, 2 H), 3.95-4.27(m, 1 H), 3.42-3.87(m, 5 H), 2.11-2.20(m, 1 H), 1.87-2.10(m, 3 H), 1.65-1.85(m, 1 H), 1.38-1.62(m, 1 H) |
| C217 | 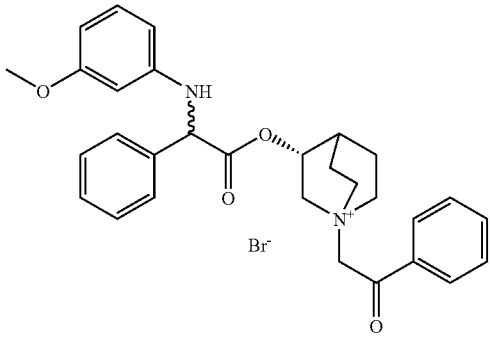<br>Mixture of diastereoisomer | 90% yield<br>Yellow solid | LC-MS (ESI POS): 485.1 (MH$^+$)<br>$^1$H NMR (300 MHz, DMSO-d$_6$) ppm<br>Diastereoisomer 1: 7.92-7.99(m, 2 H), 7.70-7.81(m, 1 H), 7.51-7.70(m, 4 H), 7.26-7.49(m, 3 H), 6.99(t, 1 H), 6.29-6.42(m, 3 H), 6.13-6.24(m, 1 H), 5.38(d, 1 H), 5.19-5.27(m, 1 H), 5.10(s, 2 H), 3.92-4.20(m, 1 H), 3.65(s, 3 H), 3.41-3.81(m, 5 H), 2.31-2.43(m, 1 H), 1.74-2.19(m, 4 H)<br>Diastereoisomer 2: 7.92-7.99(m, 2 H), 7.70-7.81(m, 1 H), 7.51-7.70(m, 4 H), 7.26-7.49(m, 3 H), 6.99(t, 1 H), 6.29-6.42(m, 3 H), 6.13-6.24(m, 1 H), 5.35(d, 1 H), 5.19-5.27(m, 1 H), 5.17(s, 2 H), 3.92-4.20(m, 1 H), 3.65(s, 3 H), 3.41-3.81(m, 5 H), 2.31-2.43(m, 1 H), 1.74-2.19(m, 4 H) |
| | 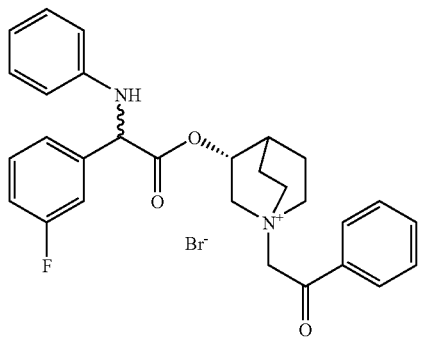<br>Mixture of diastereoisomer | 52% yield<br>White solid | LC-MS (ESI POS): 473.2 (MH$^+$)<br>$^1$H NMR (300 MHz, DMSO-d$_6$) ppm: 7.91-8.06(m, 2 H), 7.69-7.84(m, 1 H), 7.54-7.69(m, 2 H), 7.30-7.54(m, 3 H), 7.15-7.27 (m, 1 H), 7.00-7.15(m, 2 H), 6.71-6.78(m, 2 H), 6.54-6.66(m, 1 H), 6.45(d, 1 H), 5.45 and 5.49(d, 1 H), 5.23-5.29(m, 1 H), 5.14 and 5.20(s, 2 H), 3.97-4.21(m, 1 H), 3.37-3.90(m, 5 H), 2.13-2.23 and 2.33-2.41(m, 1 H), 1.46-2.10(m, 4 H) |

TABLE 22-continued

| Compound | Structure | Yield and Appearance | Analytical |
|---|---|---|---|
| | 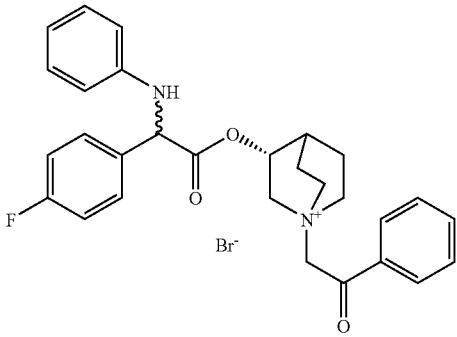Mixture of diastereoisomer | 61% yield White solid | LC-MS (ESI POS): 473.3 (MH+)<br>¹H NMR (300 MHz, DMSO-d₆) ppm: 7.91-8.05(m, 2 H), 7.71-7.83(m, 1 H), 7.55-7.71(m, 4 H), 7.19-7.32(m, 2 H), 7.04-7.16 (m, 2 H), 6.69-6.81(m, 2 H), 6.56-6.67(m, 1 H), 6.40(d, 1 H), 5.40 and 5.43(d, 1 H), 5.22-5.28(m, 1 H), 5.13 and 5.21(s, 2 H), 4.00-4.21(m, 1 H), 3.74-3.87(m, 1 H), 3.36-3.74(m, 4 H), 2.12-2.21 and 2.33-2.44(m, 1 H), 1.45-2.11(m, 4 H) |

Example 47

Preparation of (R)-1-(2-oxo-2-phenylethyl)-3-(R)-2-phenyl-2-(phenylamino)acetoxy)-1-azoniabicyclo[2.2.2]octane chloride (Diastereoisomer 1 of C113)

Scheme 47

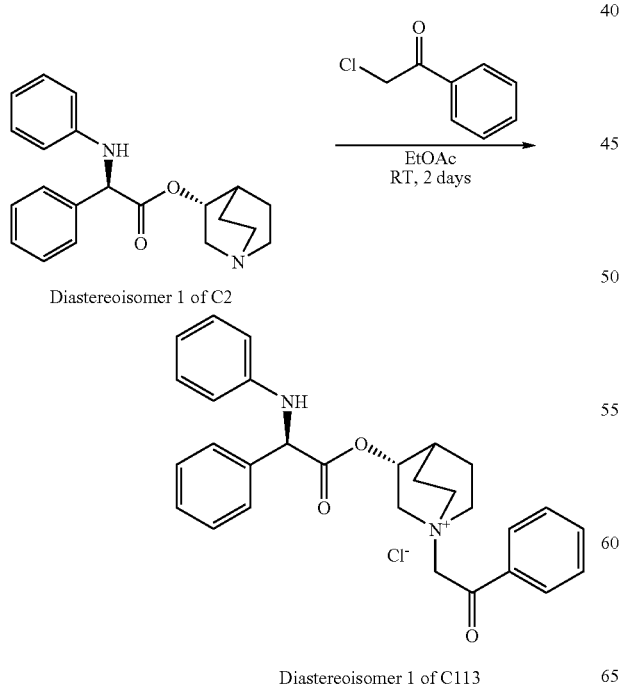

A mixture of 2-chloroacetophenone (6.20 g, 40.3 mmol) and (R)—((R)-quinuclidin-3-yl) 2-phenyl-2-(phenylamino) acetate) (Diastereoisomer 1 of C2) (12.3 g, 36.6 mmol) in EtOAc (100 ml) is stirred at RT for 2 days (UPLC-MS monitoring: complete conversion). The solvent is evaporated and the crude is purified by flash chromatography eluting with DCM/MeOH=95/5 to get 10.1 g of the title compound as a white solid (56% yield, chloride salt, single diastereoisomer).

¹H NMR (400 MHz, DMSO-d6): ppm 7.96 (d, 2H) 7.70-7.81 (m, 1H) 7.58 (d, 2H) 7.62 (d, 2H) 7.29-7.47 (m, 3H) 7.09 (t, 2H) 6.74 (d, 2H) 6.59 (t, 1H) 6.41 (d, 1H) 5.39 (d, 1H) 5.16-5.26 (m, 1H) 5.13 (s, 2H) 4.08 (ddd, 1H) 3.47-3.71 (m, 4H) 3.35-3.47 (m, 1H) 2.36 (br. s., 1H) 1.84-2.13 (m, 4H);

LC-MS (ESI POS): 455.3 (MH+).

Diastereoisomer 1 of C220 and C221 listed in Table 23 are obtained as previously described for diastereoisomer 1 of C113, using bromo-acetonitrile and bromo-acetic acid tert-butyl ester instead of 2-chloroacetophenone.

TABLE 23

| Compound | Structure | Yield and Appearance | Analytical |
|---|---|---|---|
| Diastereoisomer 1 of C220 | Single stereoisomer | 39% yield pale yellow solid | LC-MS (ESI POS): 467.0 (MH+) <br> $^1$H NMR (300 MHz, DMSO-$d_6$) ppm: 7.50-7.68 (m, 2 H), 7.28-7.46(m, 3 H), 6.96-7.17(m, 2 H), 6.69-6.80(m, 2 H), 6.54-6.65(m, 1 H), 6.36(d, 1 H), 5.37(d, 1 H), 4.99-5.28(m, 1 H), 4.77(s, 2 H), 3.99(ddd, 1 H), 3.35-3.69(m, 3 H), 3.05-3.24(m, 2 H), 2.29-2.42(m, 1 H), 1.64-2.14(m, 4 H) |
| Diastereoisomer 1 of C221 | Single stereoisomer | 33% yield yellow solid | LC-MS (ESI POS): 451.3 (MH+) <br> $^1$H NMR (300 MHz, DMSO-$d_6$) ppm: 7.49-7.60 (m, 2 H) 7.29-7.46(m, 3 H) 7.03-7.14(m, 2 H) 6.68-6.78(m, 2 H) 6.54-6.65(m, 1 H) 6.36(d, 1 H) 5.36(d, 1 H) 5.12-5.22(m, 1 H) 4.22(d, 1 H) 4.16(d, 1 H) 3.89-4.04(m, 1 H) 3.34-3.70(m, 4 H) 3.18-3.27(m, 1 H) 2.29-2.40(m, 1 H) 1.75-2.15(m, 4 H) 1.46(s, 9 H) |

Example 48

Preparation of (S)-1-(2-oxo-2-phenyl-ethyl)-3-(2-phenyl-2-phenylamino-acetoxy)-1-azonia-bicyclo[2.2.2]octane chloride (C222)

Scheme 48

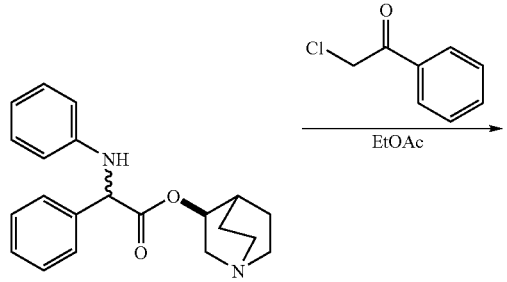

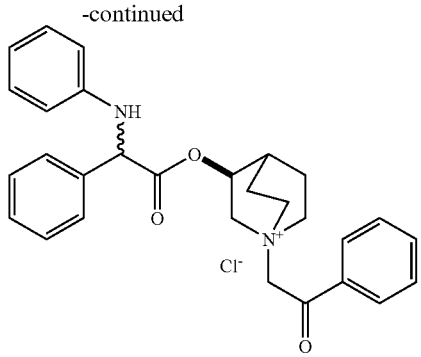

C222

To a solution of (S)-quinuclidin-3-yl 2-phenyl-2-(phenylamino)acetate (50.0 mg, 0.15 mmol) in EtOAc (2 mL), is added 2-chloro-1-phenylethanone (23.0 mg, 0.15 mmol) and the reaction is stirred first at RT for 15 hours, then at 70° C. for 7 hours and finally at RT for 3 days. The solvent is removed and the resulting crude is triturated with i-Pr$_2$O/Et$_2$O (3/1)

and then with i-Pr₂O to achieve the title compound as a beige solid (47.7 mg, 65% yield, chloride salt, mixture of diastereoisomers).

¹H NMR (300 MHz, DMSO-d$_6$) ppm: 7.92-8.03 (m, 2H) 7.71-7.81 (m, 1H) 7.52-7.67 (m, 4H) 7.30-7.47 (m, 3H) 7.04-7.15 (m, 2H) 6.69-6.79 (m, 2H) 6.55-6.64 (m, 1H) 6.38 (d, 1H) 5.39 (d, 1H) 5.18-5.28 (m, 1H) 5.13 (s, 2H) 4.00-4.19 (m, 1H) 3.48-3.78 (m, 4H) 3.34-3.48 (m, 1H) 2.31-2.42 (m, 1H) 1.84-2.16 (m, 4H);

LC-MS (ESI POS): 455.2 (MH+).

Example 49

Preparation of (R)-3-[2-(3-acetyl-phenylamino)-2-phenyl-acetoxy]-1-(2-oxo-2-phenyl-ethyl)-1-azonia-bicyclo[2.2.2]octane formate (C223)

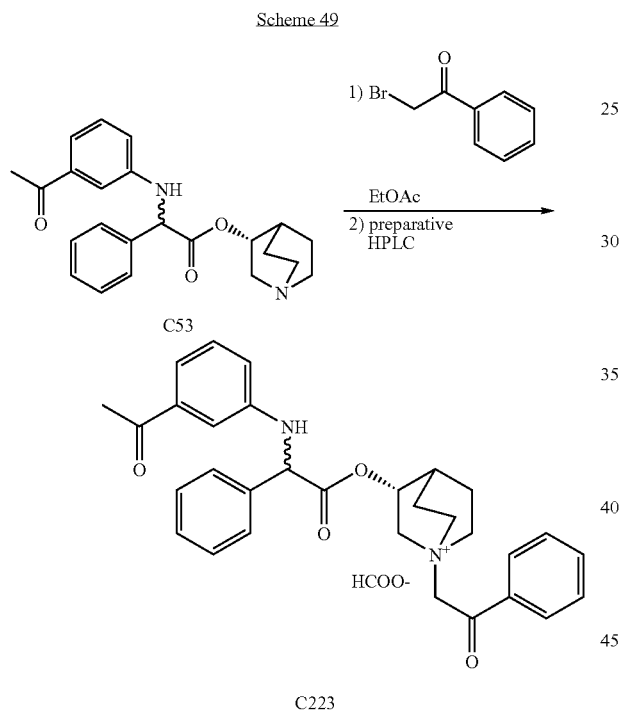

(R)-Quinuclidin-3-yl 2-(3-acetylphenylamino)-2-phenylacetate (C53) (134 mg, 0.35 mmol) and 2-bromo-1-phenylethanone (85.0 mg, 0.42 mmol) are dissolved in ethyl acetate (5 mL) and stirred at RT for 2 hours. EtOAc is evaporated and the resulting crude oil is first purified by flash chromatography (DCM/MeOH=95/5) and then by preparative HPLC. The fractions containing the product are combined and concentrated under vacuum to remove the organic solvent. The resulting aqueous solution is freeze-dried obtaining the title compound as a white-foam (77.7 mg, 40% yield, formate salt, mixture of diastereoisomers).

¹H NMR (300 MHz, DMSO-d$_6$) ppm: 8.44 (s, 1H, formiate), 7.92-8.05 (m, 2H), 7.69-7.80 (m, 1H), 7.51-7.66 (m, 4H), 7.15-7.49 (m, 6H), 6.97-7.07 (m, 1H), 6.76 and 6.78 (d, 1H), 5.46 and 5.49 (d, 1H), 5.23-5.28 (m, 1H), 5.17 and 5.22 (s, 2H), 4.01-4.26 (m, 1H), 3.36-3.87 (m, 5H), 2.48 (s, 3H), 2.12-2.20 and 2.33-2.40 (m, 1H), 1.48-2.11 (m, 4H);

LC-MS (ESI POS): 497.1 (MH⁺).

Example 50

Preparation of (R)-1-[2-(4-acetylamino-phenyl)-2-oxo-ethyl]-3-((R)-2-phenyl-2-phenylamino-acetoxy)-1-azonia-bicyclo[2.2.2]octane bromide (C224)

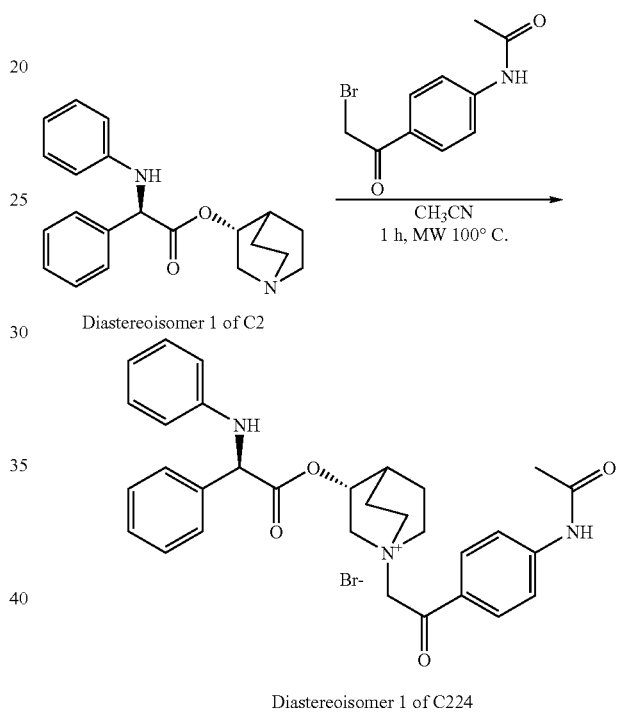

A mixture (R)—((R)-quinuclidin-3-yl) 2-phenyl-2-(phenylamino)acetate (Diastereoisomer 1 of C2) (80.0 mg, 0.24 mmol) and N-(4-(2-bromoacetyl)phenyl)acetamide (60.9 mg, 0.24 mmol) in acetonitrile (2 mL) is heated in a microwave oven at 100° C. for 1 hour (UPLC-MS monitoring: complete conversion). The title compound is isolated by suction filtration and washed with Et₂O (98.2 mg, 81% yield, off-white solid, bromide salt, single diastereoisomers).

¹H NMR (300 MHz, DMSO-d6) ppm: 10.44 (s, 1H), 7.85-7.97 (m, 2H), 7.69-7.84 (m, 2H), 7.52-7.63 (m, 2H), 7.25-7.49 (m, 3H), 6.97-7.19 (m, 2H), 6.70-6.79 (m, 2H), 6.52-6.64 (m, 1H), 6.37 (d, 1H), 5.38 (d, 1H), 5.14-5.27 (m, 1H), 5.04 (s, 2H), 3.88-4.20 (m, 1H), 3.33-3.78 (m, 5H), 2.31-2.43 (m, 1H), 2.11 (s, 3H), 1.84-2.05 (m, 4H);

LC-MS (ESI POS): 512.2 (MH⁺).

C225 listed in Table 24 is obtained as previously described for C224, using 4-(2-bromo-acetyl)-benzoic acid methyl ester instead of N-[4-(2-bromo-acetyl)-phenyl]-acetamide.

TABLE 24

| Compound | Structure | Yield and Appearance | Analytical |
|---|---|---|---|
| C225 | 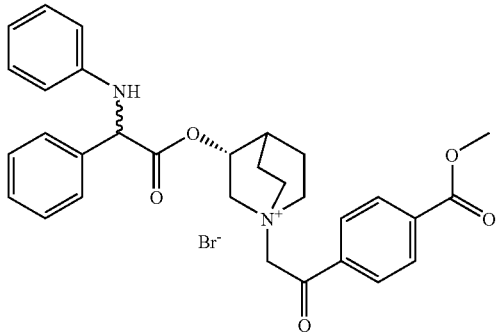<br>Mixture of diastereoisomers | 82% yield<br>pale yellow powder | LC-MS (ESI POS): 513.2 (MH+)<br>¹H NMR (300 MHz, DMSO-d₆) ppm: 8.13-8.25(m, 2 H), 8.03-8.13(m, 2 H), 7.54-7.66 (m, 2 H), 7.27-7.47(m, 3 H), 6.98-7.17(m, 2 H), 6.74(m, 2 H), 6.56-6.64(m, 1 H), 6.41(d, 1 H), 5.39(d, 1 H), 5.19-5.23(m, 1 H), 5.16(s, 2 H), 3.99-4.24(m, 1 H), 3.91(s, 3 H), 3.44-3.84(m, 5 H), 2.34-2.41(m, 1 H), 1.38-2.10 (m, 4 H) |

Example 51

Preparation of (R)-3-((R)-2-phenyl-2-phenylamino-acetoxy)-1-pyridin-2-ylmethyl-1-azonia-bicyclo[2.2.2]octane trifluoroacetate trifluoroacetate anion (Diastereoisomer 1 of C226)

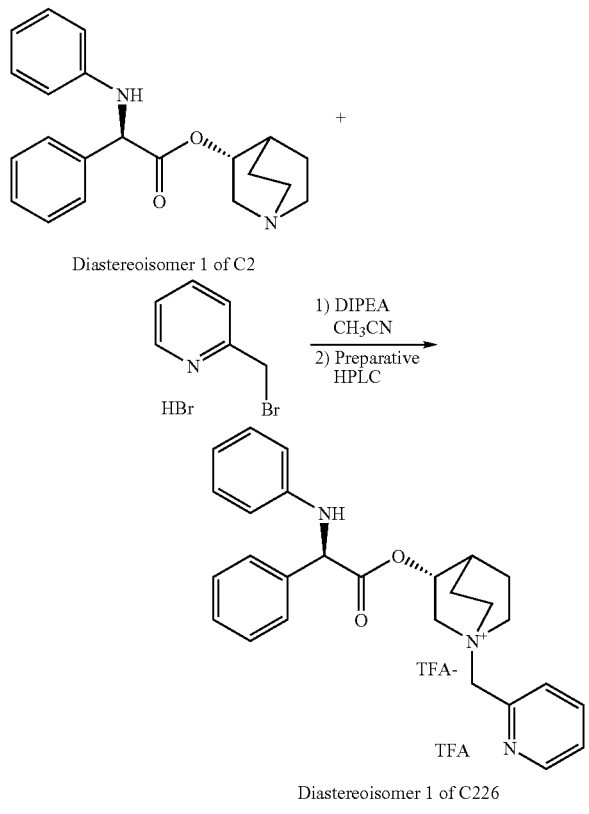

Scheme 51

To a solution of (R)-phenyl-phenylamino-acetic acid (R)-(1-aza-bicyclo[2.2.2]oct-3-yl) ester (Diastereoisomer 1 of C2) (100 mg, 0.30 mmol) and DIPEA (61 uL, 0.36 mmol) in acetonitrile (4 mL), is added 2-bromomethyl-pyridine hydrobromide (91.0 mg, 0.36 mmol) and the mixture is heated under MW irradiation for 1 hour at 100° C. (UPLC-MS monitoring: complete conversion). Solvent is evaporated and the resulting crude is first purified by flash chromatography (DCM/MeOH=98/2 to 9/1) and then by preparative LC-MS to obtain the title compound as a brown viscous oil (58 mg, 36% yield, trifluoroacetate trifluoroacetate anion, single diastereoisomer).

¹H NMR (300 MHz, DMSO-d6) ppm: 8.68 (ddd, 1H), 7.96 (td, 1H), 7.41-7.71 (m, 4H), 7.23-7.41 (m, 3H), 6.93-7.16 (m, 2H), 6.70 (m, 2H), 6.58 (m, 1H), 5.32 (s, 1H), 5.02-5.18 (m, 1H), 4.46 (d, 1H), 4.41 (d, 1H), 3.90 (ddd, 1H), 3.39-3.60 (m, 3H), 3.17 (d, 1H), 2.74-2.92 (m, 1H), 2.20-2.35 (m, 1H), 1.74-2.04 (m, 4H);

LC-MS (ESI POS): 428.2 (MH+);

[□]$_D$=−40.80° (c=0.25, MeOH).

Diastereoisomer 1 of C227 listed in Table 25 is obtained as previously described for diastereoisomer 1 of C226, using 2-bromo-1-pyridin-2-yl-ethanone hydrobromide instead of 2-bromomethyl-pyridine hydrobromide.

TABLE 25

| Compound | Structure | Yield and Appearance | Analytical |
|---|---|---|---|
| Diastereoisomer 1 of C227 | Single stereoisomer | 50% yield yellow solid | LC-MS (ESI POS): 456.0 (MH$^+$)<br>$^1$H NMR (300 MHz, DMSO-d$_6$) ppm: 8.76(ddd, 1 H), 8.37(s, 1 H, formiate ion), 8.11(ddd, 1 H), 8.05(dt, 1 H), 7.78(ddd, 1 H), 7.54-7.67(m, 2 H), 7.30-7.50(m, 3 H), 7.00-7.18(m, 2 H), 6.69-6.81(m, 2 H), 6.60(m, 1 H), 6.37(d, 1 H), 5.38(d, 1 H), 5.10-5.29(m, 3 H), 4.00-4.20(m, 1 H), 3.26-3.84(m, 5 H), 2.31-2.41(m, 1 H), 1.80-2.18(m, 4 H)<br>$[\alpha]_D = -51.68°$ (c = 0.25, MeOH) |

Example 52

Preparation of (R)-1-(2-(2-methylthiazol-4-yl)-2-oxoethyl)-3-((R)-2-phenyl-2-(phenylamino)acetoxy)-1-azoniabicyclo[2.2.2]octane bromide (C229)

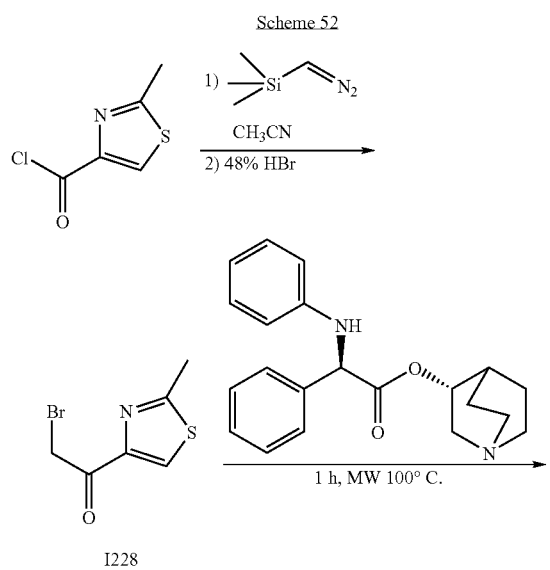

Preparation of 2-bromo-1-(2-methyl-thiazol-5-yl)-ethanone (I228)

To a solution of 2-methylthiazole-4-carbonyl chloride (0.34 g, 2.10 mmol) in dry MeCN (8 mL) cooled at 0° C., under nitrogen atmosphere, is slowly added (diazomethyl) trimethylsilane (3.14 ml, 6.29 mmol, 2.0M in hexane). The reaction is stirred at RT for 15 h (UPLC-MS monitoring: complete conversion). The reaction is cooled at 0° C. and 48% hydrobromic acid (1.23 mL, 7.34 mmol) is added dropwise. The reaction is stirred at RT for 3 hour. Then EtOAc and water are added, the organic layer is separated and the aqueous phase is neutralized with 1M NaOH and extracted with EtOAc. The combined organic layers are dried over Na$_2$SO$_4$, filtered and evaporated to dryness to obtain compound I228 as a dark brown gummy solid (400 mg, 87% yield).

Preparation of (R)-1-(2-(2-methylthiazol-4-yl)-2-oxoethyl)-3-((R)-2-phenyl-2-(phenylamino)acetoxy)-1-azoniabicyclo[2.2.2]octane bromide (C229)

(R)-Phenyl-phenylamino-acetic acid (R)-(1-aza-bicyclo[2.2.2]oct-3-yl)ester (Diastereoisomer 1 of C2) (75.0 mg, 0.22 mmol) and 2-bromo-1-(2-methylthiazol-4-yl)ethanone (I228) (49.1 mg, 0.22 mmol) in acetonitrile (5 mL) is heated at 100° C. for 75 minutes under microwave irradiation (UPLC-MS monitoring: complete conversion). The solvent is removed and the resulting brown solid is tritured with iPr$_{2O}$/Et$_2$O (1/1) and then with iPrOH to obtain the title compound as a grey powder (43.3 mg, 35% yield, bromide salt, single diastereoisomers).

$^1$H NMR (300 MHz, DMSO-d$_6$) ppm: 8.59 (s, 1H) 7.53-7.66 (m, 2H) 7.29-7.51 (m, 3H) 7.01-7.15 (m, 2H) 6.69-6.82 (m, 2H) 6.56-6.66 (m, 1H) 6.36 (d, 1H) 5.37 (d, 1H) 5.10-5.25 (m, 1H) 5.02 (s, 2H) 4.00-4.17 (m, 1H) 3.45-3.75 (m, 4H) 3.35-3.45 (m, 1H) 2.75 (s, 3H) 2.31-2.40 (m, 1H) 1.80-2.10 (m, 4H);

LC-MS (ESI POS): 476.2 (MH$^+$).

Example 53

Preparation of (R)-1-(6-amino-pyridin-2-ylmethyl)-3-((R)-2-phenyl-2-phenylamino-acetoxy)-1-azonia-bicyclo[2.2.2]octane trifluoroacetate trifluoroacetate anion (Diastereoisomers 1 of C233)

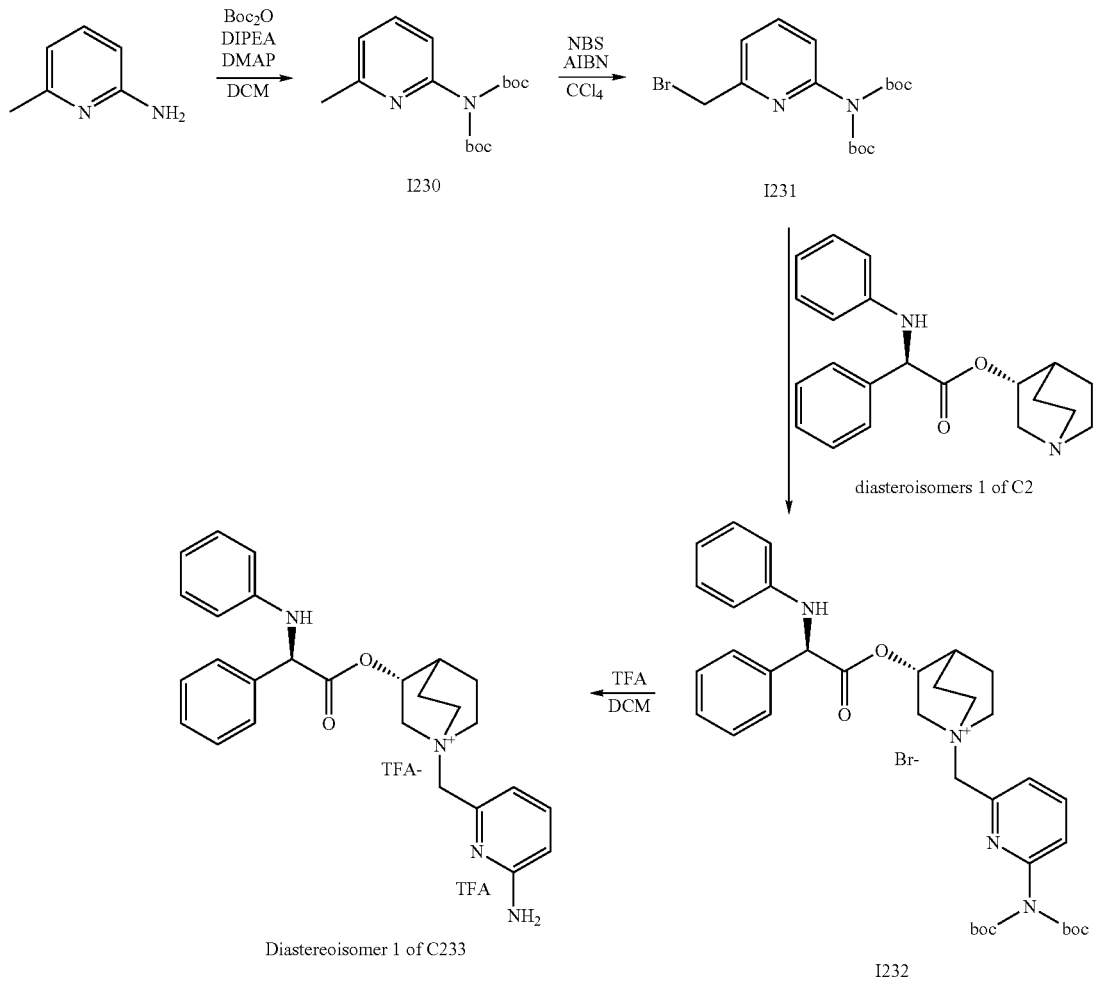

Scheme 53

Preparation of N,N-(bis-tert-butoxycarbonyl)-6-methylpyridin-2-amine (I230)

A mixture of 6-methylpyridin-2-amine (5.00 g, 46.3 mmol), di-tert-butyl dicarbonate (24.2 g, 111 mmol) and DIPEA (9.4 mL, 55.5 mmol) in DCM (40 mL) is stirred at RT for 3 days. The organic phase is washed with 5% citric acid and then with sat. NaHCO$_3$. The organic phase is dried over Na$_2$SO$_4$, filtered and evaporated to dryness. The crude is purified by flash chromatography (Petroleum ether/EtOAc=9/1) to obtain intermediate I230 as a white solid (3.0 g, 21% yield).

Preparation of N,N-(bis tert-butoxycarbonyl)-6-(bromomethyl)pyridin-2-amine (I231)

A catalytic amount of azobisisobutyronitrile (5% w/w) is added to a solution of N,N-(bis-tert-butoxycarbonyl)-6-methylpyridin-2-amine (I230) (308 mg, 1.00 mmol) and N-bromo-succinimide (284 mg; 1.6 mmol) in carbon tetrachloride (8 mL). The reaction is refluxed for two hours, diluted with DCM and washed with water. The organic phase is dried over Na$_2$SO$_4$, filtered and evaporated to dryness. The crude is purified by flash chromatography (DCM) to obtain intermediate I231 as a yellow solid (240 mg, 83% yield).

Preparation of (R)-1-(N,N-(bis tert-butoxycarbonyl)-6-amino-pyridin-2-ylmethyl)-3-(2-phenyl-2-phenylamino-acetoxy)-1-azonia-bicyclo[2.2.2]octane bromide (I232)

To a solution of (R)-phenyl-phenylamino-acetic acid (R)-(1-aza-bicyclo[2.2.2]oct-3-yl)ester (Diastereoisomer 1 of C2) (100 mg, 0.54 mmol) in acetonitrile (5 mL), is added N,N-(bis tert-butoxycarbonyl)-6-(bromomethyl)pyridin-2-amine (240 mg, 1.15 mmol) and the mixture is heated under MW irradiation for 30 minutes at 100° C. (UPLC-MS monitoring: complete conversion). The solvent is evaporated and the resulting crude is purified by flash chromatography (DCM to DCM/MeOH=9/1) to obtain intermediate I232 as a colorless oil (125 mg, 32% yield).

Preparation of (R)-1-(6-amino-pyridin-2-ylmethyl)-3-(2-phenyl-2-phenylamino-acetoxy)-1-azonia-bicyclo[2.2.2]octane trifluoracetate trifluoroacetate anion (diastereoisomers 1 of C233)

Trifluoroacetic acid (0.5 mL) is added to a solution of (R)-1-(N,N-(bis tert-butoxycarbonyl)-6-amino-pyridin-2-ylmethyl)-3-(2-phenyl-2-phenylamino-acetoxy)-1-azonia-bicyclo[2.2.2]octane bromide (I232) (125 mg, 0.19 mmol) in DCM (5 mL). The reaction is stirred at RT for 2 days. Solvent is removed under vacuum and the crude is purified by preparative LC-MS to obtain the title compound as a brown oil (21 mg, 16% yield, trifluoroacetate trifluoroacetate anion, single diastereoisomer).

$^1$H NMR (300 MHz, DMSO-d6) ppm: 7.42-7.59 (m, 3H), 7.22-7.42 (m, 3H), 6.97-7.17 (m, 2H), 6.66-6.82 (m, 2H), 6.44-6.66 (m, 3H), 5.33 (s, 1H), 5.03-5.21 (m, 1H), 4.13 (s, 2H), 3.75-3.95 (m, 1H), 3.29-3.61 (m, 3H), 3.14 (d, 1H), 2.75-2.96 (m, 1H), 2.18-2.35 (m, 1H), 1.54-2.14 (m, 4H);

LC-MS (ESI POS): 443.1 (MH+).

Example 54

Preparation of (R)-3-{2-[(4-fluoro-phenyl)-methyl-amino]-2-phenyl-acetoxy}-1-(2-oxo-2-thiophen-2-yl-ethyl)-1-azonia-bicyclo[2.2.2]octane chloride (C234)

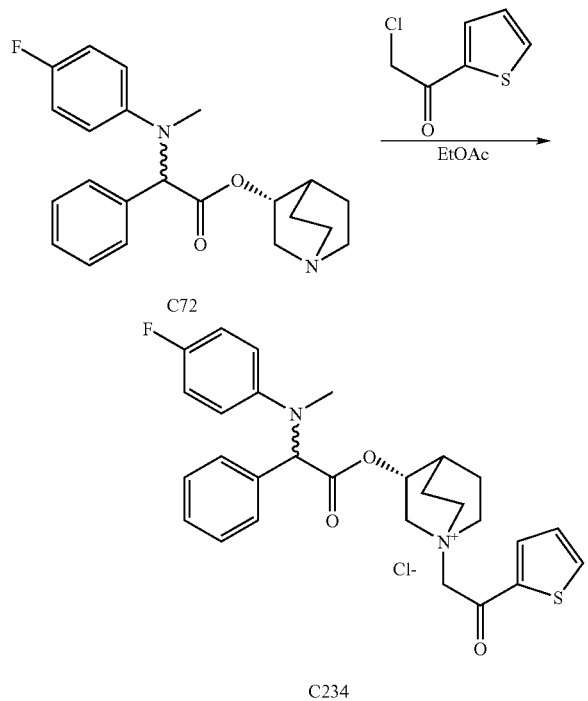

To a solution of [(4-fluoro-phenyl)-methyl-amino]-phenyl-acetic acid (R)-(1-aza-bicyclo[2.2.2]oct-3-yl)ester (C120) (100 mg, 0.27 mmol) in ethyl acetate (2.7 mL), is added 2-chloro-1-(thiophen-2-yl)ethanone (48.0 mg, 0.30 mmol). The reaction is stirred at RT for 3.5 days. The suspension is evaporated and the residue is triturated with Et2O (8 mL). The solid is filtered on a buckner funnel and the sticky solid is dissolved in DCM. The solution is evaporated giving the title compound as a pale yellow solid (120 mg, 84% yield, chloride salt, mixture of diastereoisomers).

$^1$H NMR (300 MHz, DMSO-$d_6$) ppm: 8.21 (dd, 1H), 8.11 (d, 1H), 7.26-7.52 (m, 6H), 7.02-7.15 (m, 2H), 6.88-7.02 (m, 2H), 5.91 and 5.92 (s, 1H), 5.23-5.44 (m, 1H), 5.19 (d, 1H), 5.11 (d, 1H), 4.07-4.34 (m, 1H), 3.36-3.92 (m, 5H), 2.73 (s, 3H), 2.20-2.33 (m, 1H), 1.47-2.12 (m, 4H);

LC-MS (ESI POS): 493.1 (MH$^+$).

Example 55

Preparation of (R)-3-[2-(methyl-phenyl-amino)-2-phenyl-acetoxy]-1-(2-oxo-2-thiazol-2-yl-ethyl)-1-azonia-bicyclo[2.2.2]octane bromide (C235)

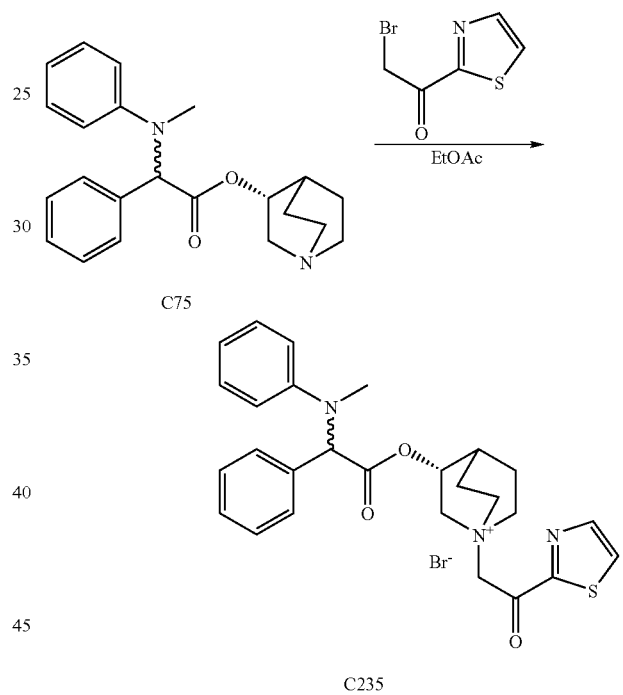

2-Bromo-1-(1,3-thiazol-2-yl)ethanone (54.2 mg, 0.26 mmol) is added to a solution of (R)-quinuclidin-3-yl 2-(methyl(phenyl)amino)-2-phenylacetate (C75) (92.2 mg, 0.26 mmol) in EtOAc (5 mL). The mixture is stirred at RT overnight. The solvent is evaporated to dryness and the crude is triturated with Et2O. The yellow solid is collected by filtration (120 mg, 82% yield, bromide salt, mixture of diastereoisomers).

$^1$H NMR (300 MHz, DMSO-$d_6$) ppm: 8.39 (d, 1H), 8.25 (d, 1H), 7.32-7.50 (m, 5H), 7.19-7.30 (m, 2H), 6.84-7.00 (m, 2H), 6.67-6.85 (m, 1H), 5.97 (s, 1H), 5.23-5.38 (m, 1H), 5.19 and 5.20 (s, 2H), 4.04-4.29 (m, 1H), 3.44-3.82 (m, 5H), 2.76 and 2.77 (s, 3H), 2.24-2.36 (m, 1H), 1.45-2.13 (m, 4H);

LC-MS (ESI POS): 476.0 (MH+).

C236 listed in Table 26 is obtained as previously described for C235, using 2-bromo-1-thiophen-3-yl-ethanone instead of 2-bromo-1-(1,3-thiazol-2-yl)ethanone.

TABLE 26

| Compound | Structure | Yield and Appearance | Analytical |
|---|---|---|---|
| C236 | 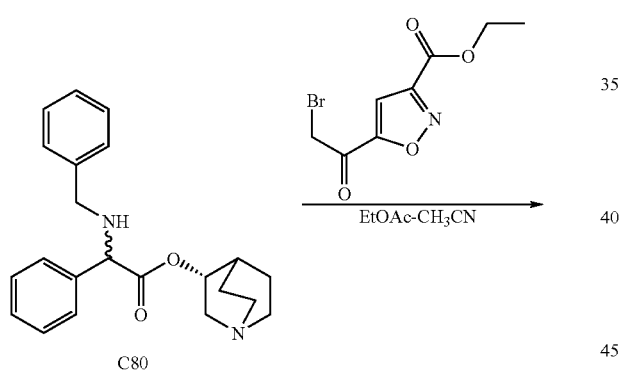Mixture of diastereoisomers | 41% overall yield Off-yellow solid | LC-MS (ESI POS): 475.3 (MH+)<br>$^1$H NMR (300 MHz, DMSO-$d_6$) ppm: 8.63(dd, 1 H), 7.75(dd, 1 H), 7.57(dd, 1 H), 7.33-7.50(m, 5 H), 7.17-7.31(m, 2 H), 6.88-7.02(m, 2 H), 6.68-6.80 (m, 1 H), 5.96 and 5.97(s, 1 H), 5.14-5.41(m, 1 H), 5.02 and 5.03(s, 2 H), 4.10-4.24(m, 1 H), 3.37-3.79(m, 5 H), 2.76 and 2.77(s, 3 H), 2.20-2.38(m, 1 H), 1.44-2.15(m, 4 H) |

Example 56

Preparation of (R)-3-(2-benzylamino-2-phenyl-acetoxy)-1-[2-(3-ethoxycarbonyl-isoxazol-5-yl)-2-oxo-ethyl]-1-azonia-bicyclo[2.2.2]octane bromide (C237)

Benzylamino-phenyl-acetic acid (R)-(1-aza-bicyclo[2.2.2]oct-3-yl)ester (C80) (100 mg, 0.28 mmol) is dissolved in ethyl acetate (1.90 mL) and acetonitrile (0.95 mL) and ethyl 5-(2-bromoacetyl)isoxazole-3-carboxylate (82.0 mg, 0.31 mmol) is added. The orange solution is stirred at RT overnight. The suspension is evaporated and the crude is purified by flash chromatography (DCM/EtOH=93/7) to obtain the title compound as a pale brown solid (61 mg, 35% yield, bromide salt, mixture of diastereoisomers).

$^1$H NMR (300 MHz, DMSO-d6) ppm: 7.86 and 7.89 (s, 1H), 6.97-7.60 (m, 10H), 5.10-5.24 (m, 1H), 5.00 and 5.04 (s, 2H), 4.33-4.53 (m, 3H), 4.10 (dd, 1H), 3.40-3.82 (m, 7H), 2.15-2.24 and 2.29-2.38 (m, 1H), 1.50-2.11 (m, 4H), 1.35 (t, 3H);

LC-MS (ESI POS): 532.3 (MH+).

Example 57

Preparation of (R)-3-(2-benzylamino-2-phenyl-acetoxy)-1-(2-oxo-2-thiazol-2-yl-ethyl)-1-azonia-bicyclo[2.2.2]octane trifluoroacetate trifluoroacetate anion (C238)

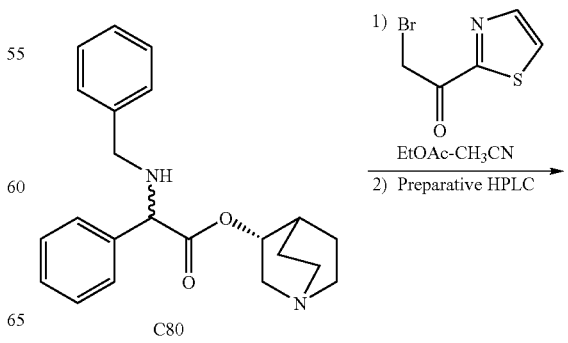

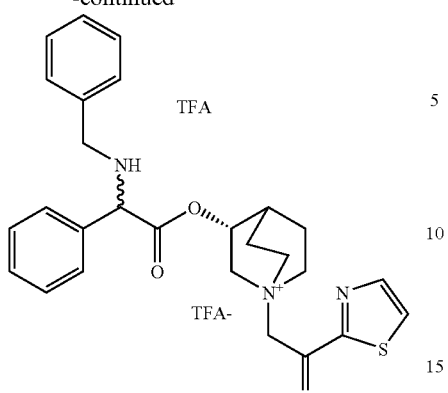

Benzylamino-phenyl-acetic acid (R)-(1-aza-bicyclo[2.2.2]oct-3-yl)ester (C80) (100 mg, 0.28 mmol) is dissolved in ethyl acetate (1.90 mL) and acetonitrile (0.95 mL) and 2-bromo-1-(thiazol-2-yl)ethanone (64.7 mg, 0.314 mmol) is added. The pale yellow solution is stirred at RT overnight. The suspension is evaporated and the crude is purified by flash chromatography (DCM/MeOH=93/7). The resulting compound is further purified by preparative LC/MS. The collected fractions are first concentrated with rotary evaporator to remove organic solvent and then with freeze-drier overnight to get the title compound as a pale yellow oil (31 mg, 15% yield, trifluoroacetate trifluoroacetate anion, mixture of diastereoisomers).

$^1$H NMR (300 MHz, DMSO-d6) ppm 8.40 (d, 1H), 8.24 (d, 1H), 7.36-7.71 (m, 10H), 5.25-5.40 (m, 2H), 5.17 and 5.21 (s, 2H), 3.99-4.24 (m, 3H), 3.46-3.84 (m, 5H), 2.15-2.25 and 2.32-2.44 (m, 1H), 1.35-2.14 (m, 4H);

LC-MS (ESI POS): 475.9 (MH+).

Example 58

Preparation of (R)-3-(2-benzylamino-2-phenyl-acetoxy)-1-(2-oxo-2-thiophen-3-yl-ethyl)-1-azonia-bicyclo[2.2.2]octane bromide (C239)

To a solution of (R)-quinuclidin-3-yl 2-(benzylamino)-2-phenylacetate (C80) (116 mg, 0.33 mmol) in ethyl acetate (3.31 mL) and acetonitrile (3.31 mL), is added 2-bromo-1-(thiophen-3-yl)ethanone (66.5 mg, 0.32 mmol). The mixture is stirred at RT overnight. The insoluble precipitate is filtered on a buckner funnel and washed with acetonitrile. The clear solution is evaporated and purified by flash chromatography (DCM/EtOH=9/1) to obtain the title compound as a white solid (26 mg, 14% yield, bromide salt, mixture of diastereoisomers).

$^1$H NMR (300 MHz, DMSO-d$_6$) ppm: 8.63 (br. s., 1H), 7.68-7.84 (m, 1H), 7.10-7.63 (m, 11H), 5.11-5.25 (m, 1H), 5.03 and 5.06 (s, 2H), 4.43 (br. s., 1H), 3.99-4.24 (m, 1H), 3.42-3.87 (m, 7H), 2.18 and 2.23 (br. s., 1H), 1.44-2.14 (m, 4H);

LC-MS (ESI POS): 475.3 (MH+).

Example 59

Preparation of (R)-3-[2-(4-methyl-benzylamino)-2-phenyl-acetoxy]-1-(2-oxo-2-thiophen-2-yl-ethyl)-1-azonia-bicyclo[2.2.2]octane formate formate anion (C240)

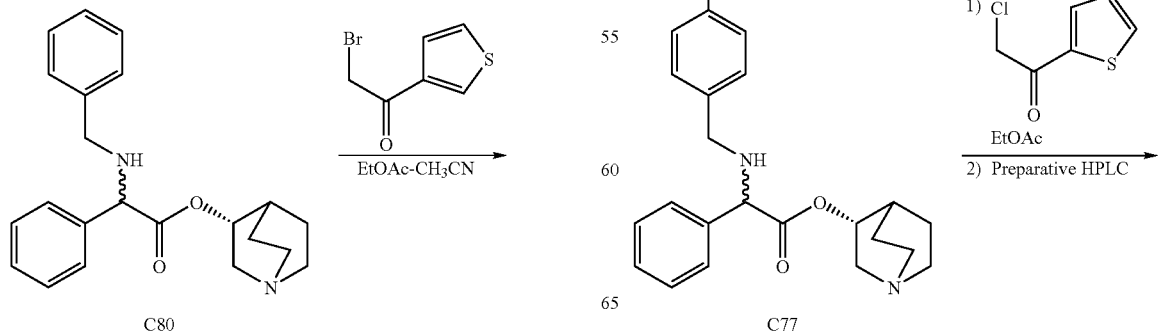

187

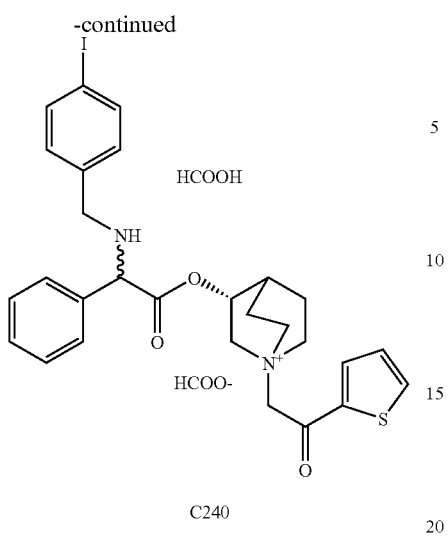

C240

188

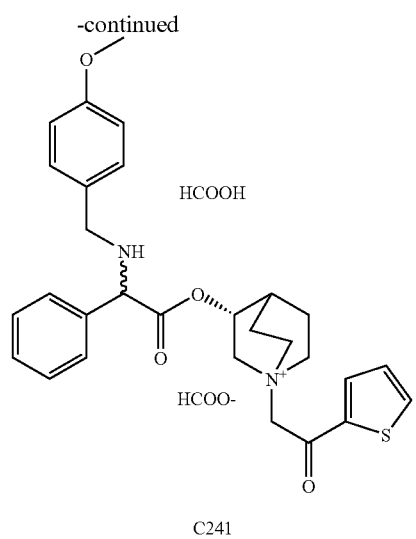

C241

(R)-Quinuclidin-3-yl 2-(4-methylbenzylamino)-2-phenylacetate (C77) (73 mg, 0.20 mmol) is dissolved in ethyl acetate (2.00 mL) and 2-chloro-1-(thiophen-2-yl)ethanone (35.4 mg, 0.22 mmol) is added. The colorless solution is stirred at RT overnight. Solvent is evaporated and the residue is first purified by flash chromatography (DCM/MeOH=9/1 to 85/15) and then by preparative LC/MS. Organic solvent is evaporated and then the aqueous solution is freeze-dried overnight to afford the title compound as a pale yellow oil (42 mg, 36% yield, formate formate anion, mixture of diastereoisomers).

$^1$H NMR (300 MHz, DMSO-d6) ppm: 8.43 (s, 2H) 8.16-8.24 (m, 1H) 8.03-8.12 (m, 1H) 7.28-7.51 (m, 6H) 7.04-7.25 (m, 4H) 4.94-5.26 (m, 3H) 4.40 (s, 1H) 4.00-4.18 (m, 1H) 3.48-3.76 (m, 7H) 2.29 (s, 3H) 2.11-2.22 (m, 1H) 1.39-2.12 (m, 5H);

LC-MS (ESI POS): 489.1 (MH+).

Example 60

Preparation of (R)-3-[2-(4-methoxy-benzylamino)-2-phenyl-acetoxy]-1-(2-oxo-2-thiophen-2-yl-ethyl)-1-azonia-bicyclo[2.2.2]octane formate formate anion (C241)

To a solution of (R)-quinuclidin-3-yl 2-(4-methoxybenzylamino)-2-phenylacetate (C79) (78 mg, 0.21 mmol) in ethyl acetate (2.05 mL), is added 2-chloro-1-(thiophen-2-yl)ethanone (36.2 mg, 0.23 mmol). The colorless solution is stirred at RT overnight. The residue is first purified by flash chromatography (DCM/MeOH=90/10 to 85/15) and then by preparative LC/MS. MeOH is evaporated from the fractions collected and then the aqueous solution is freeze-dried overnight to obtain the title compound as a pale pink oil (44 mg, 36% yield, formate formate anion, mixture of diastereoisomers).

$^1$H NMR (300 MHz, DMSO-d$_6$) ppm: 8.42 (s, 2H) 8.17-8.25 (m, 1H) 8.03-8.13 (m, 1H) 7.15-7.50 (m, 8H) 6.81-6.94 (m, 2H) 4.97-5.23 (m, 3H) 4.40 (s, 1H) 3.88-4.22 (m, 1H) 3.74 (s, 3H) 3.46-3.71 (m, 6H) 2.12-2.35 (m, 1H) 1.70-2.10 (m, 3H) 1.44-1.66 (m, 1H);

LC-MS (ESI POS): 505.1 (MH+).

Example 61

Preparation of (R)-3-[2-(4-fluoro-benzylamino)-2-phenyl-acetoxy]-1-(2-oxo-2-thiophen-2-yl-ethyl)-1-azonia-bicyclo[2.2.2]octane chloride (C242)

Scheme 60

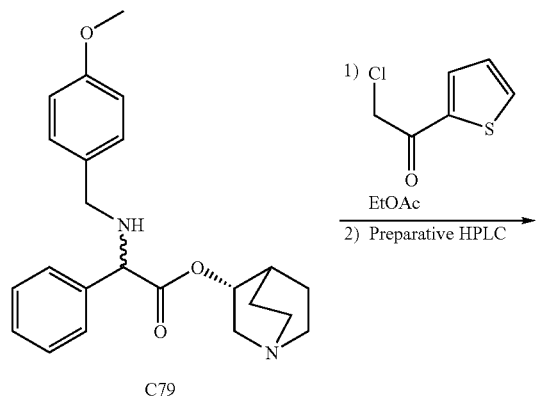

C79

Scheme 61

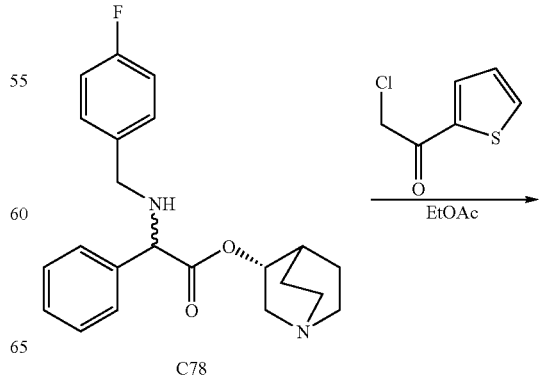

C78

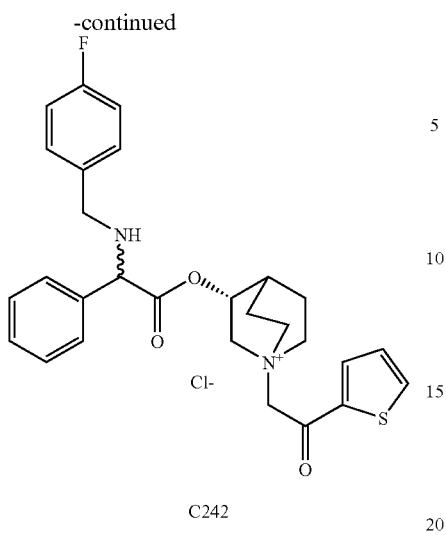

C242

(R)-Quinuclidin-3-yl 2-(4-fluorobenzylamino)-2-phenylacetate (C78) (85 mg, 0.23 mmol) is dissolved in ethyl acetate (2.31 mL) and 2-chloro-1-(thiophen-2-yl)ethanone (40.8 mg, 0.25 mmol) is added. The solution is stirred at RT overnight. The suspension is evaporated and the white residue is first purified by flash chromatography (DCM/MeOH=9/1 to 8/2) and then by trituration with Et2O to afford the title compound as an off-white powder (83 mg, 68% yield, chloride salt, mixture of diastereoisomers).

$^1$H NMR (300 MHz, DMSO-$d_6$) ppm: 8.18-8.25 (m, 1H), 8.04-8.18 (m, 1H), 7.43-7.52 (m, 2H), 7.26-7.43 (m, 6H), 7.09-7.21 (m, 2H), 5.16-5.24 (m, 1H), 5.12 and 5.15 (s, 2H), 4.42 (s, 1H), 4.01-4.22 (m, 1H), 3.67 (s, 2H), 3.54-3.85 (m, 5H), 2.13-2.23 and 2.29-2.33 (m, 1H), 1.48-2.10 (m, 4H);

LC-MS (ESI POS): 492.9 (MH+).

Example 62

Preparation of (R)-3-[2-(4-fluoro-benzylamino)-2-phenyl-acetoxy]-1-(2-oxo-2-phenyl-ethyl)-1-azoniabicyclo[2.2.2]octane bromide (C243)

Scheme 62

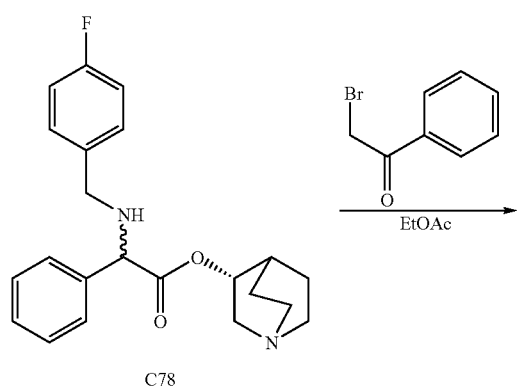

C78

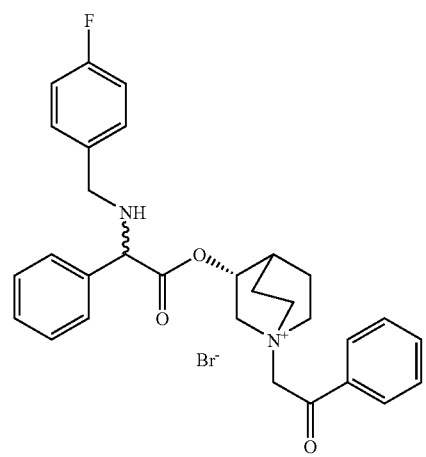

C243

A mixture of (R)-quinuclidin-3-yl 2-(4-fluorobenzylamino)-2-phenylacetate (C78) (61 mg, 0.17 mmol) and 2-bromo-1-phenylethanone (33.0 mg, 0.17 mmol) in ethyl acetate (3 mL) is stirred at RT overnight. The solid is collected by suction filtration and washed with Et$_2$O. The product is further purified by flash chromatography (DCM/MeOH=95/5 to 92/8) to obtain the title compound as a white solid (35 mg, 37% yield, bromide salt, mixture of diastereoisomers).

$^1$H NMR (300 MHz, METHANOL-$d_4$) ppm: 7.91-8.07 (m, 2H) 7.67-7.80 (m, 1H) 7.53-7.64 (m, 2H) 7.26-7.53 (m, 7H) 6.97-7.13 (m, 2H) 5.17-5.33 (m, 1H) 4.50 (s, 1H) 4.04-4.28 (m, 1H) 3.49-3.89 (m, 8H) 3.36 (s, 2H) 2.40-2.52 (m, 1H) 1.94-2.25 (m, 4H);

LC-MS (ESI POS): 487.1 (MH+).

Example 63

Preparation of (R)-1-(2-oxo-2-phenyl-ethyl)-3-(2-phenyl-2-p-methylphenyl-acetoxy)-1-azonia-bicyclo[2.2.2]octane bromide (C246)

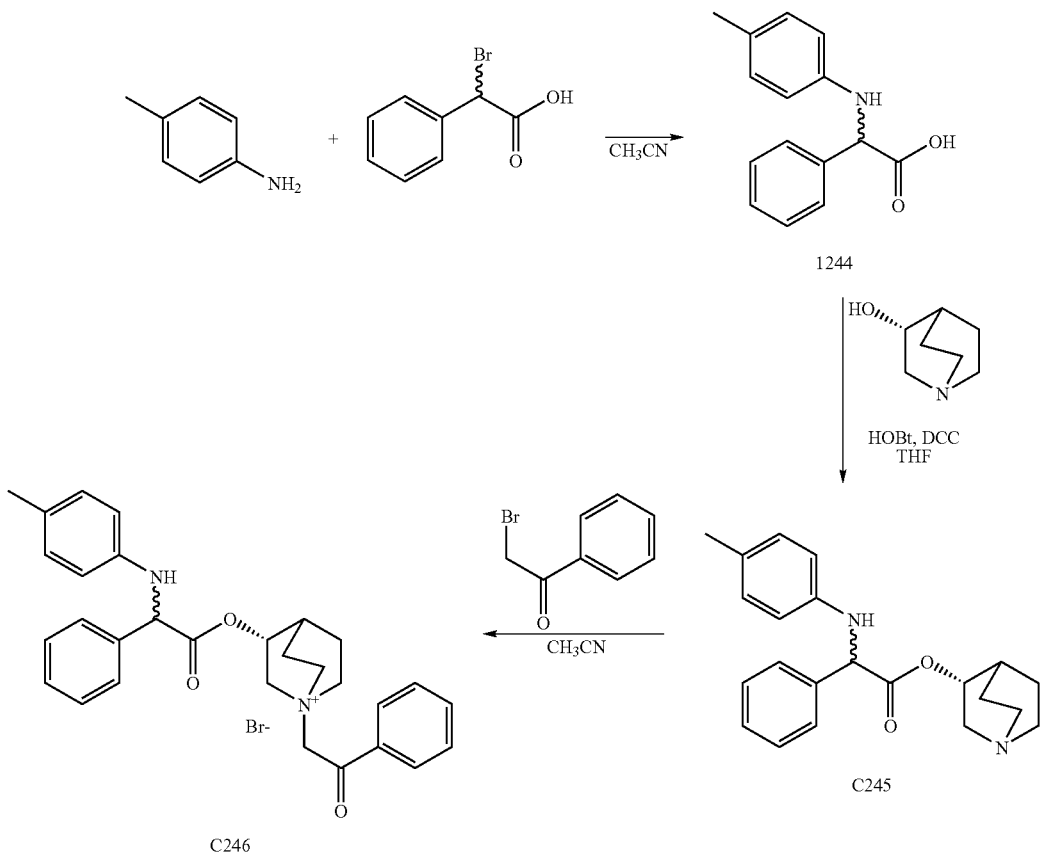

Scheme 63

Preparation of 4-methyl-phenyl-amino-phenyl-acetic acid (I244)

To a solution of α-bromophenylacetic acid (1.00 g, 4.65 mmol) in acetonitrile (20 mL), is added 4-methyl-phenylamine (0.96 g, 9.30 mmol) and the mixture reacted in a closed vessel under MW irradiation at 100° C. for 1 hour (UPLC-MS monitoring: complete conversion). Solvent is evaporated and residue is portioned between EtOAc and 2N HCl. The organic phase is dried over Na₂SO₄, filtered and evaporated to dryness to get desired compound as a yellow solid (0.88 g, 78% yield).

Preparation of 4-methyl-phenyl-amino-phenyl-acetic acid (R)-(1-aza-bicyclo[2.2.2]oct-3-yl)ester (C245)

To a solution of 4-methyl-phenyl-amino-phenyl-acetic acid (I244) (870 mg, 3.60 mmol) in dry THF (35 mL), are added DCC (891 mg, 4.32 mmol), HOBt (583 mg, 4.32 mmol) and 3(R)-quinuclidinol (915 mg, 7.20 mmol). The resulting mixture is stirred at RT for 48 hours (UPLC-MS monitoring: complete conversion). The solvent is evaporated and the residue is portioned between EtOAc and 1M K₂CO₃. The organic phase is dried over Na₂SO₄, filtered and evaporated to dryness. The resulting crude is dissolved in little DCM and filtered to remove the insoluble. The solution is concentrated under vacuum to obtain the title compound as a yellow solid, which is used in the next step without any further purification.

Preparation of (R)-1-(2-oxo-2-phenyl-ethyl)-3-(2-phenyl-4-methyl-phenyl-amino-acetoxy)-1-azonia-bicyclo[2.2.2]octane bromide (C246)

To a solution of 4-methyl-phenyl-amino-phenyl-acetic acid (R)-(1-aza-bicyclo[2.2.2]oct-3-yl)ester (C245) (63.5 mg, 0.18 mmol) in acetonitrile (5 mL), is added 2-bromo-1-phenyl-ethanone (36 mg, 0.18 mmol) and the mixture was heated at 100° C. for 1 hour in a MW oven (UPLC-MS monitoring: complete conversion). Solvent is evaporated and the resulting crude is purified by flash chromatography (DCM/MeOH=95/5) to obtain the title compound as a white solid (58 mg, 32% yield, bromide salt, mixture of diastereoisomers).

¹H NMR (300 MHz, DMSO-d₆) ppm: 7.88-8.07 (m, 2H), 7.71-7.83 (m, 1H), 7.51-7.68 (m, 4H), 7.24-7.48 (m, 3H), 6.91 (m, 2H), 6.66 (m, 2H), 6.16 (d, 1H), 5.34 (d, 1H), 5.15-5.27 (m, 1H), 5.09 (s, 2H), 3.92-4.19 (m, 1H), 3.33-3.77 (m, 5H), 2.31-2.41 (m, 1H), 2.12 (s, 3H), 1.77-2.08 (m, 4H);

LC-MS (ESI POS): 469.1 (MH⁺).

Example 64

Preparation of (R)-3-[2-(2-fluoro-phenylamino)-2-phenyl-acetoxy]-1-(2-oxo-2-phenyl-ethyl)-1-azonia-bicyclo[2.2.2]octane trifluoroacetate (C249)

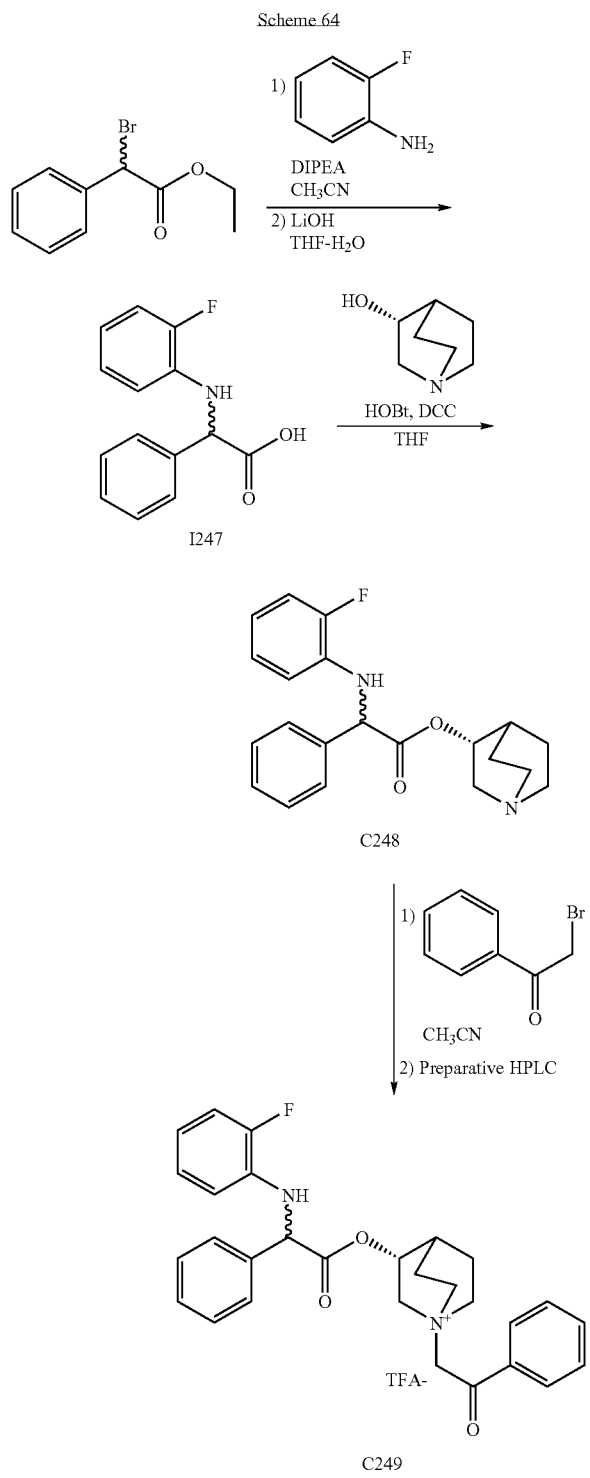

Scheme 64

C248

C249

Preparation of (2-fluoro-phenylamino)-phenyl-acetic acid hydrochloride (I247)

2-Fluoroaniline (347 ul, 3.60 mmol), ethyl 2-bromo-2-phenylacetate (420 ul, 2.40 mmol) and N-ethyl-N-isopropylpropan-2-amine (628 ul, 3.60 mmol) are dissolved in acetonotrile (5 mL) and stirred under MW irradiation at 100° C. for 1 hour and 30 minutes. Water (3.89 mL) and lithium hydroxide (230 mg, 9.59 mmol) are added to the reaction and the resulting mixture is stirred at RT overnight and then at 50° C. for 3 hours. Acetonitrile is removed and 1M HCl is added to the remaining aqueous solution until pH is about 1. The aqueous phase is extracted several time with DCM and the combined organic phases are washed with water and brine, dried ($Na_2SO_4$), filtered and evaporated to give intermediate I247 as a brown solid (464 mg, 69% yield).

Preparation of (2-fluoro-phenylamino)-phenyl-acetic acid (R)-(1-aza-bicyclo[2.2.2]oct-3-yl)ester (C248)

A solution of DCC (534 mg, 0.71 mmol), 1H-benzo[d][1,2,3]triazol-1-ol hydrate (217 mg, 1:42 mmol), (2-fluoro-phenylamino)-phenyl-acetic acid hydrochloride (I247) (200 mg, 0.71 mmol) and (R)-quinuclidin-3-ol (271 mg, 2.13 mmol) in THF (10 mL) is stirred at RT for 2 days. The solvent is evaporated and the residue is taken up with EtOAc, washed with sat $NaHCO_3$, water and brine. The organic layer is collected, dried over $Na_2SO_4$, filtered and evaporated to dryness. The residue is purified by preparative HPLC. The organic solvent is evaporated and the acid aqueous phase is basified with $Na_2CO_3$ and extracted with EtOAc. The organic layer is dried ($Na_2SO_4$), filtered and evaporated to afford the title compound as yellow oil (41 mg, 16% yield).

Preparation of (R)-3-[2-(2-fluoro-phenylamino)-2-phenyl-acetoxy]-1-(2-oxo-2-phenyl-ethyl)-1-azonia-bicyclo[2.2.2]octane trifluoroacetate (C249)

(2-Fluoro-phenylamino)-phenyl-acetic acid (R)-(1-aza-bicyclo[2.2.2]oct-3-yl) ester (C248) (267 mg, 0.75 mmol) and 2-bromo-1-phenylethanone (157 mg, 0.79 mmol) are dissolved in CH3CN (20 mL). The resulting reaction is stirred at RT for two days. The solvent is evaporated and the crude is purified with preparative HPLC to obtain the title compound as a yellow amorphous solid (178 mg, 40.3% yield, trifluoroacetate salt, mixture of diastereoisomers).

$^1$H NMR (300 MHz, DMSO-$d_6$) ppm: 7.87-8.14 (m, 2H), 7.67-7.81 (m, 1H), 7.50-7.68 (m, 4H), 7.26-7.50 (m, 3H), 7.01-7.16 (m, 1H), 6.85-7.00 (m, 1H), 6.56-6.77 (m, 2H), 5.75 (br. s., 1H), 5.46 and 5.49 (s, 1H), 5.24 (br. s., 1H), 5.12 and 5.17 (s, 2H), 4.00-4.20 (m, 1H), 3.29-3.83 (m, 5H), 2.12-2.23 and 2.31-2.42 (m, 1H), 1.37-2.11 (m, 4H);

LC-MS (ESI POS): 473.2 (MH+).

C250 and C251 listed in Table 27 are prepared as previously described for C249, using 3-fluoroaniline instead of 2-fluoroaniline and the suitable commercially available alkylating agents.

TABLE 27

| Compound | Structure | Yield and appearance | Analytical |
|---|---|---|---|
| C250 | (Mixture of diastereoisomer) | 14% overall yield White solid | LC-MS (ESI POS): 473.4 (MH+).<br>$^1$H NMR (300 MHz, DMSO-$d_6$) ppm: 7.89-8.05(m, 2 H), 7.69-7.83(m, 1 H), 7.53-7.67(m, 4 H), 7.30-7.49(m, 3 H), 7.09(td, 1 H), 6.74 and 6.76(d, 1 H), 6.48-6.64(m, 2 H), 6.37(td, 1 H), 5.41 and 5.45(d, 1 H), 5.23-5.30(m, 1 H), 5.15 and 5.21(s, 2 H), 3.96-4.29(m, 1 H), 3.37-3.95(m, 5 H), 2.11-2.19 and 2.36-2.42(m, 1 H), 1.37-2.10(m, 4 H) |
| C251 | (Mixture of diastereoisomer) | 7% overall yield White solid | LC-MS (ESI POS): 479.3 (MH+).<br>$^1$H NMR (300 MHz, DMSO-$d_6$) ppm: 8.20 and 8.22(dd, 1 H), 8.04 and 8.08(dd, 1 H), 7.50-7.63(m, 2 H), 7.29-7.48(m, 4 H), 7.09(td, 1 H), 6.74(br. s., 1 H), 6.47-6.63(m, 2 H), 6.36 (td, 1 H), 5.39 and 5.44(br. s., 1 H), 5.17-5.28(m, 1 H), 4.99 and 5.04(s, 2 H), 4.03-4.19(m, 1 H), 3.25-3.85(m, 5 H), 2.10-2.20 and 2.33-2.41(m, 1 H), 1.45-2.09(m, 4 H) |

Example 65

Preparation of (R)-3-[(R)-2-(4-fluoro-phenylamino)-2-phenyl-acetoxy]-1-(2-oxo-2-thiophen-2-yl-ethyl)-1-azonia-bicyclo[2.2.2]octane chloride (C255)

Scheme 65

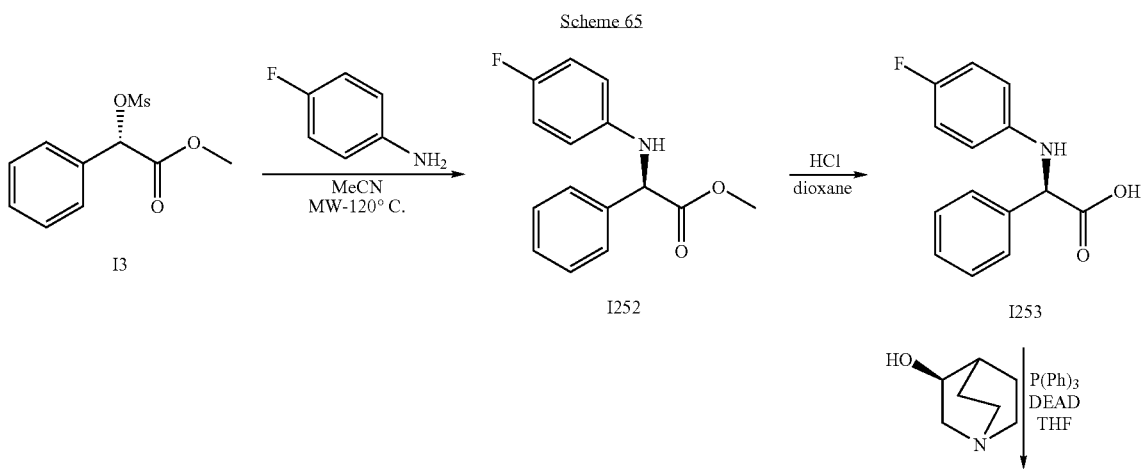

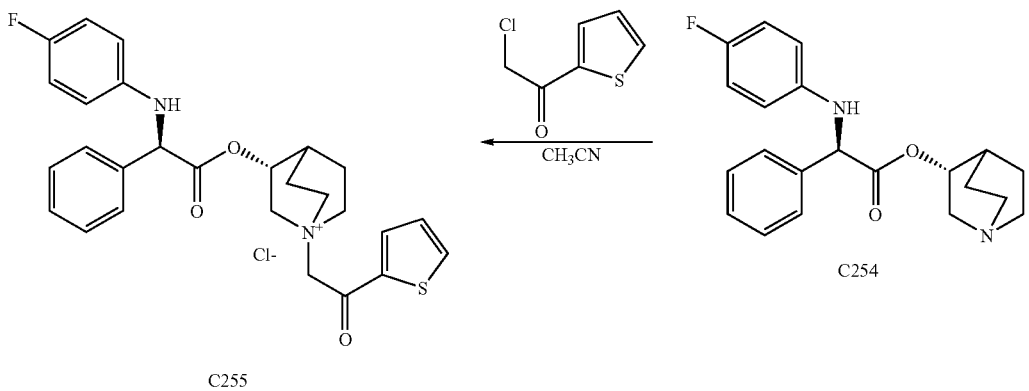

Preparation of (R)-(4-fluoro-phenylamino)-phenyl-acetic acid methyl ester (I252)

To a solution of (S)-methyl 2-(methylsulfonyloxy)-2-phenylacetate (I5) (520 mg, 2.13 mmol) in CH₃CN (10 mL), is added 4-fluoroaniline (473 mg, 4.26 mmol) and the mixture is heated at 120° C. for 5 minutes under MW irradiation (UPLC-MS: complete conversion). Acetonitrile was evaporated and the resulting crude is dissolved in 1N HCl and extracted several times with EtOAc. The combined organic phase is dried over Na₂SO₄, filtered and evaporated to dryness to obtain intermediate I254 as a pale yellow oil (520 mg, 94% yield).

Preparation of (R)-(4-fluoro-phenylamino)-phenyl-acetic acid (I253)

To a solution of (R)-(4-fluoro-phenylamino)-phenyl-acetic acid methyl ester (I252) (510 mg, 1.97 mmol) in dioxane (10 mL), is added 12N HCl (10 mL) and the mixture is heated at 70° C. for 12 hours. The organic solvent is evaporated, the mixture is cooled to 0° C. and the resulting solid is collected by filtration to obtain intermediate I255 as a brownish solid (420 mg, 87% yield).

Preparation of (R)-(4-fluoro-phenylamino)-phenyl-acetic acid (R)-(1-aza-bicyclo[2.2.2]oct-3-yl)ester (C254)

To a solution of (R)-(4-fluoro-phenylamino)-phenyl-acetic acid (I253) (420 mg, 1.71 mmol) in dry THF (40 mL), are sequentially added (S)-quinuclidin-3-ol (218 mg, 1.71 mmol), DEAD (407 ul, 2.57 mmol) and triphenylphosphine (674 mg, 2.57 mmol). The reaction is refluxed for 30 minutes under N₂ flowstream and then the solvent is evaporated. The residue is partitioned between water and EtOAc, the organic layer is separated, dried over Na₂SO₄, filtered and evaporated to dryness. The resulting crude is purified by flash chromatography (DCM/MeOH=95/5) to obtain the title compound as a pale yellow oil (480 mg, 79% yield).

Preparation of (R)-3-[(R)-2-(4-fluoro-phenylamino)-2-phenyl-acetoxyl-1-(2-oxo-2-thiophen-2-yl-ethyl)-1-azonia-bicyclo[2.2.2]octane chloride (C255)

To a solution of (R)-(4-fluoro-phenylamino)-phenyl-acetic acid (R)-(1-aza-bicyclo[2.2.2]oct-3-yl)ester (C254) (200 mg, 0.56 mmol) in CH₃CN (2 mL), is added 2-chloro-1-(thiophen-2-yl)ethanone (100 mg, 0.62 mmol). The reaction is heated at 100° C. for 1 hour under MW irradiation. The solvent is evaporated and the crude is purified by flash chromatography (DCM/MeOH=9/1) recovering the title compound as a white solid (104 mg, 36% yield, chloride salt, single diastereoisomer).

$^1$H NMR (300 MHz, DMSO-d₆) ppm: 8.21 (d, 1H), 8.08 (d, 1H), 7.50-7.65 (m, 2H), 7.23-7.48 (m, 4H), 6.84-6.99 (m, 2H), 6.61-6.84 (m, 2H), 6.39 (d, 1H), 5.36 (d, 1H), 5.15-5.26 (m, 1H), 5.06 (s, 2H), 3.99-4.21 (m, 1H), 3.38-3.85 (m, 5H), 2.30-2.40 (m, 1H), 1.70-2.17 (m, 4H);

LC-MS (ESI POS): 478.9 (MH⁺).

Example 66

Preparation of (R)-3-[2-(4-chloro-phenyl)-2-phenylamino-acetoxy]-1-(2-oxo-2-phenyl-ethyl)-1-azoniabicyclo[2.2.2]octane trifluoroacetate (C258)

Scheme 66

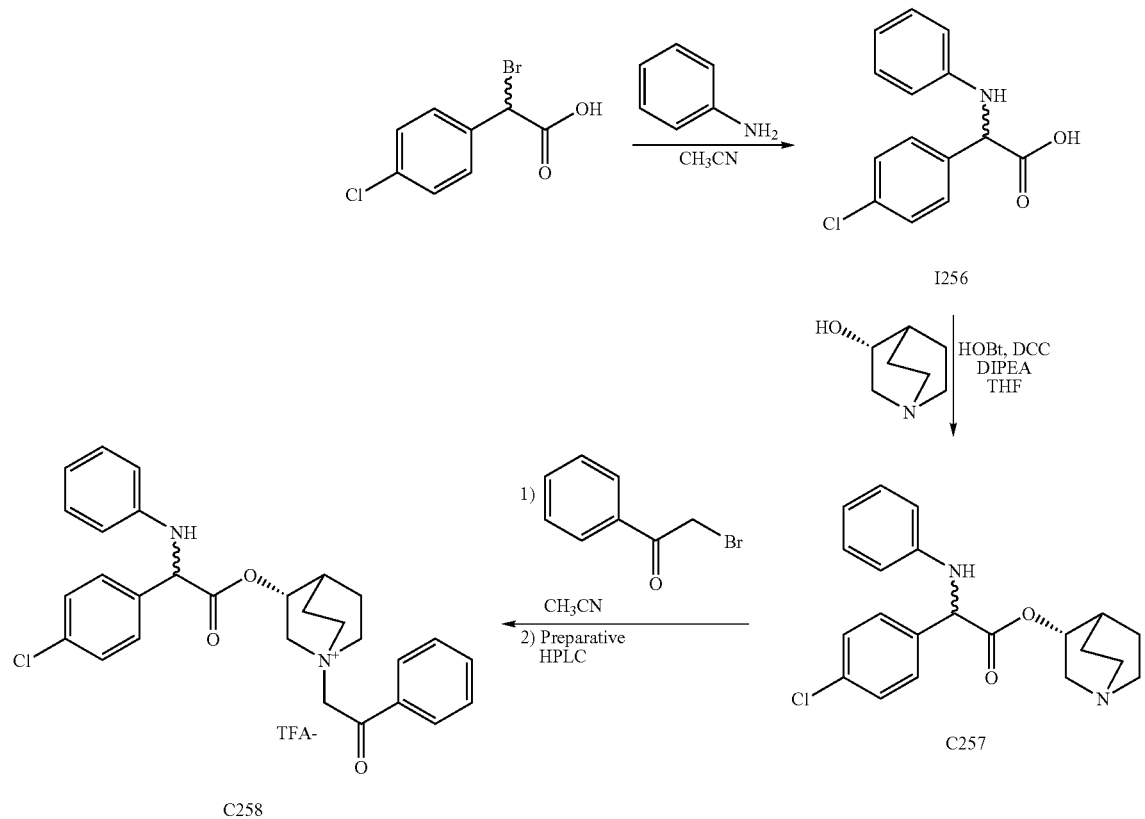

Preparation of (4-chloro-phenyl)-phenylamino-acetic acid (I256)

2-Bromo-2-(4-chlorophenyl)acetic acid (1.2 g, 4.67 mmol) and aniline (0.85 mL, 9.33 mmol) are dissolved in acetonitrile (29 mL). The reaction is heated under microwave irradiation at 100° C. for 5 minutes. The solvent is evaporated and the residue is dissolved in EtOAc and washed with 3M HCl and then brine. The organic layer is dried over $Na_2SO_4$, filtered and evaporated to dryness to give intermediate I258 as a white solid (1.22 g, quantitative yield).

Preparation of (4-chloro-phenyl)-phenylamino-acetic acid (R)-(1-aza-bicyclo[2.2.2]oct-3-yl)ester (C257)

(4-Chloro-phenyl)-phenylamino-acetic acid (I256) (1.22 g, 4.97 mmol), HOBT (0.99 g, 6.46 mmol) and DCC (1.33 g, 6.46 mmol) are dissolved in THF (250 mL). The reaction is stirred for 15 minutes and then (R)-quinuclidin-3-ol (1.26 g, 9.93 mmol) is added. The reaction is stirred at RT for 4 days. The solvent is evaporated and the residue is taken up with EtOAc. The insoluble is filtered off, the solution is washed with 1M $K_2CO_3$ and brine. The organic phase is dried ($Na_2SO_4$), filtered and evaporated to dryness. The crude is purified by flash chromatography (DCM/MeOH=98/2 to 90/10) to afford compound C259 as a yellow solid (462 mg, 25% yield).

Preparation of (R)-3-[2-(4-chloro-phenyl)-2-phenylamino-acetoxy]-1-(2-oxo-2-phenyl-ethyl)-1-azoniabicyclo[2.2.2]octane trifluoroacetate (C258)

2-Bromo-1-phenylethanone (54.8 mg, 0.27 mmol) is added to a solution of (4-chloro-phenyl)-phenylamino-acetic acid (R)-(1-aza-bicyclo[2.2.2]oct-3-yl)ester (C257) (100 mg, 0.27 mmol) in acetonitrile (4 mL). The reaction is heated in a microwave oven at 100° C. for 1 hour. The solvent is evaporated and the crude is first purified by flash chromatography (DCM/MeOH=98/2 to 85/15) and then by preparative HPLC to collect the title compound as a brown viscous oil (37 mg, 22.76% yield, trifluoroacetate salt, mixture of diastereoisomers).

$^1$H NMR (300 MHz, DMSO-$d_6$) ppm: 7.94-8.02 (m, 2H), 7.72-7.83 (m, 1H), 7.54-7.68 (m, 4H), 7.40-7.54 (m, 2H), 6.96-7.17 (m, 2H), 6.68-6.78 (m, 2H), 6.52-6.67 (m, 1H), 5.42 (s, 1H), 5.19-5.28 (m, 1H), 5.16 (s, 2H), 4.05-4.19 (m, 1H), 3.44-3.86 (m, 5H), 2.09-2.22 (m, 1H), 1.90-2.08 (m, 2H), 1.75-1.88 (m, 1H), 1.54-1.73 (m, 1H);

LC-MS (ESI POS): 488.9 (MH+).

Example 67

Preparation of (R)-3-[2-(2-fluoro-phenyl)-2-phenylamino-acetoxy]-1-(2-oxo-2-phenyl-ethyl)-1-azonia-bicyclo[2.2.2]octane trifluoroacetate (C263)

Scheme 67

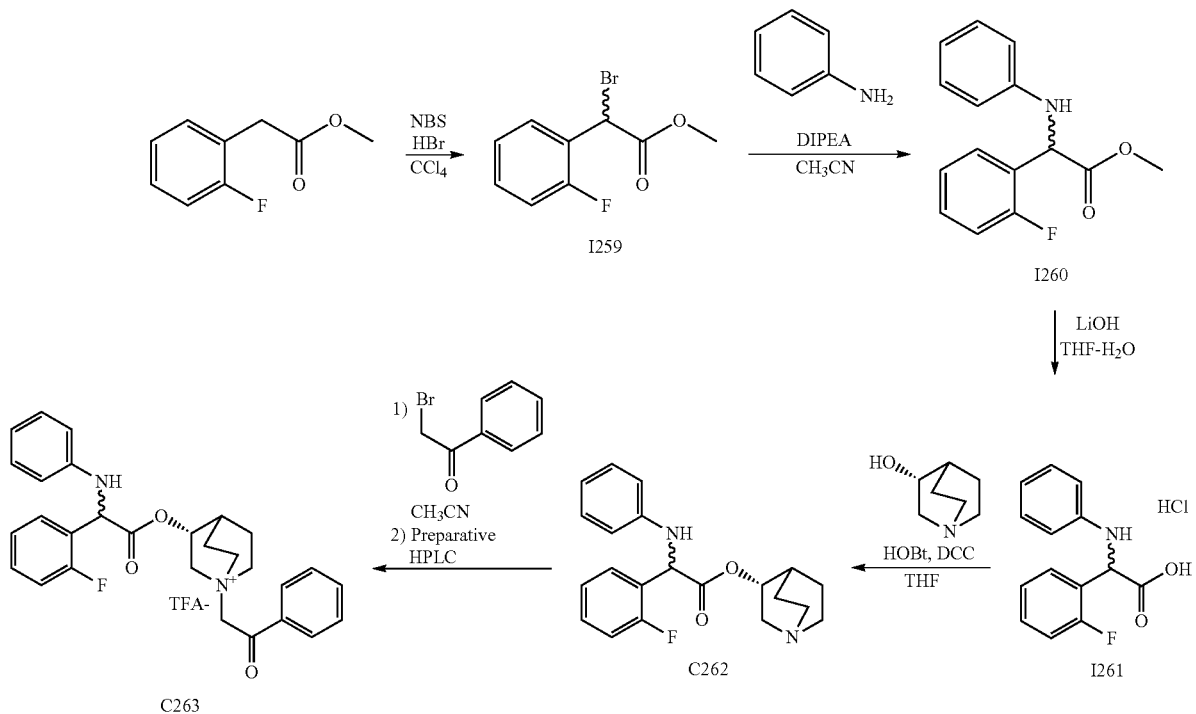

Preparation of bromo-(2-fluoro-phenyl)-acetic acid methyl ester (I259)

To a solution of methyl 2-(2-fluorophenyl)acetate (1.0 g, 5.95 mmol) in CCl4 (15 mL), are added N-bromo succinimide (1.06 g, 5.95 mmol) and 48% hydrogen bromide (33 uL, 0.30 mmol) and the reaction is refluxed for 15 hours. Reaction is diluted with DCM and washed with Na₂CO₃ and water. The organic phase is dried over Na₂SO₄, filtered and evaporated under vacuum to afford intermediate I261 as a dark brown oil (1.47 g, quantitative yield).

Preparation of (2-fluoro-phenyl)-phenylamino-acetic acid methyl ester (I260)

A solution of bromo-(2-fluoro-phenyl)-acetic acid methyl ester (I259) (1.47 g, 5.95 mmol), aniline (814 ul, 8.93 mmol) and N-ethyl-N-isopropylpropan-2-amine (1.53 mL, 8.93 mmol) in acetonitrile (10 mL) is heated under microwave irradiation at 100° C. for 1 hour. The solvent is evaporated, the residue is taken up with DCM and washed with water and brine, dried over Na₂SO₄ and evaporated to afford intermediate I262 as a dark brown oil (1.54 g, quantitative yield).

Preparation of (2-fluoro-phenyl)-phenylamino-acetic acid hydrochloride (I261)

To a solution of (2-fluoro-phenyl)-phenylamino-acetic acid methyl ester (I260) (1.54 g, 5.95 mmol) in THF (15 mL), cooled at 0° C., is added 2.0M lithium hydroxide (5.95 mL, 11.9 mmol) and the reaction is stirred at RT for 72 hours. The solvent is evaporated, 1M HCl is added to the reaction until pH 1. The product is extracted with EtOAc, and the organic phase is washed with water and brine, dried over Na₂SO₄ and evaporated to provide intermediate I263 as a dark brown gummy solid (1.34 g, 80% yield).

Preparation of (2-fluoro-phenyl)-phenylamino-acetic acid (R)-(1-aza-bicyclo[2.2.2]oct-3-yl)ester (C262)

To a solution of (2-fluoro-phenyl)-phenylamino-acetic acid hydrochloride (I261) (217 mg, 0.77 mmol), (R)-quinuclidin-3-ol (338 mg, 2.66 mmol) and 1H-benzo[d][1,2,3]triazol-1-ol (180 mg, 1.332 mmol) in dry THF (15 mL), is added PS-DCC (1.0 g, 1.33 mmol). The mixture is shaken at RT for 15 hours. Then (R)-quinuclidin-3-ol (49.0 mg, 0.38 mmol) and PS-DCC (290 mg, 0.38 mmol) are added again and the reaction is shaken for additional 3 hours at RT. The resin is removed by filtration and washed several time with EtOAc. The solvent is evaporated, the residue is taken up with EtOAc and washed with NaHCO₃, water and brine. The organic phase is dried (Na₂SO₄), filtered and evaporated to afford the title compound as a brown oil (225 mg, 82% yield).

Preparation of (R)-3-[2-(2-fluoro-phenyl)-2-phenylamino-acetoxy]-1-(2-oxo-2-phenyl-ethyl)-1-azonia-bicyclo[2.2.2]octane trifluoroacetate (C263)

To a solution of (2-fluoro-phenyl)-phenylamino-acetic acid (R)-(1-aza-bicyclo[2.2.2]oct-3-yl)ester (C262) (225 mg, 0.63 mmol) in acetonitrile (8 mL), is added 2-bromo-1-phe nylethanone (126 mg, 0.63 mmol) and the reaction is stirred at RT for 15 hours. The solvent is evaporated and the resulting crude is purified by preparative HPLC to obtain the title compound as a brown oil (130 mg, 35% yield, trifluoroacetate salt, mixture of diastereoisomers).

$^1$H NMR (300 MHz, DMSO-$d_6$) ppm: 7.92-8.07 (m, 2H), 7.69-7.82 (m, 1H), 7.52-7.68 (m, 3H), 7.35-7.49 (m, 1H), 7.19-7.35 (m, 2H), 7.05-7.15 (m, 2H), 6.68-6.81 (m, 2H), 6.56-6.67 (m, 1H), 6.42 (br. s., 1H), 5.57 and 5.59 (s, 1H), 5.21-5.34 (m, 1H), 5.12 and 5.17 (s, 2H), 4.02-4.24 (m, 1H), 3.27-3.83 (m, 5H), 2.13-2.22 and 2.32-2.43 (m, 1H), 1.34-2.13 (m, 4H);

LC-MS (ESI POS): 473.4 (MH+).

Example 68

Preparation of (R)-3-[2-(5-methyl-thiophen-2-yl)-2-phenylamino-acetoxy]-1-(2-oxo-2-phenyl-ethyl)-1-azonia-bicyclo[2.2.2]octane trifluoroacetate (C270)

Preparation of (5-methyl-thiophen-2-yl)-oxo-acetic acid methyl ester (I264)

To a suspension of aluminum trichloride (2.75 g, 20.6 mmol) and methyl 2-chloro-2-oxoacetate (1.90 mL, 20.7 mmol) in dry DCM (25 mL), cooled at 0° C. and under nitrogen atmosphere, is added 2-methylthiophene (1.00 mL, 10.33 mmol) dropwise. The reaction is stirred at RT for 15 hours. Then the mixture is cooled at 0° C. ice-water is slowly added and the organic phase is washed with aq. NaHCO$_3$ and brine, dried over Na$_2$SO$_4$ and evaporated to obtain intermediate I266 as a brown oil (1.9 g, quantitative yield).

Preparation of hydroxy-(5-methyl-thiophen-2-yl)-acetic acid methyl ester (I265)

To a solution of methyl (5-methyl-thiophen-2-yl)-oxo-acetic acid methyl ester (I264) (1.90 g, 10.3 mmol) in MeOH (25

Scheme 68

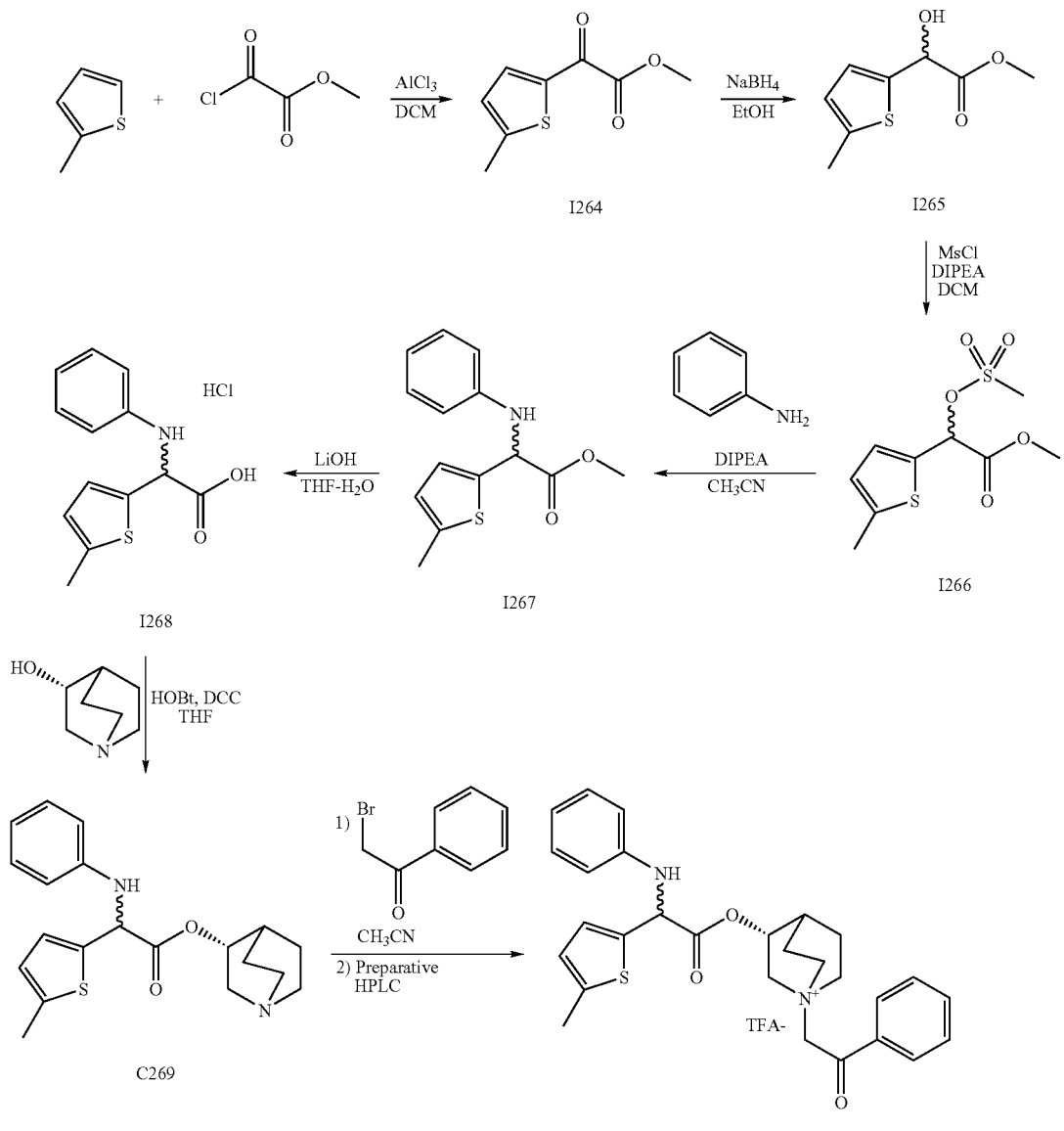

mL) cooled at 0° C., sodiumboron hydride (0.19 g, 5.17 mmol) is added portionwise. The reaction is stirred at 0° C. for 10 minutes then at RT for 1 hour. The solvent is evaporated, the residue is taken up with EtOAc and washed with ice-water and brine. The organic phase is dried over Na$_2$SO$_4$, filtered and evaporated to collect intermediate I267 as a brown oil (1.84 g, 96% yield).

Preparation of methanesulfonyloxy-(5-methyl-thiophen-2-yl)-acetic acid methyl ester (I266)

To a solution of hydroxy-(5-methyl-thiophen-2-yl)-acetic acid methyl ester (I265) (1.84 g, 9.89 mmol) in dry DCM, cooled at 0° C. under nitrogen atmosphere, N-ethyl-N-isopropylpropan-2-amine (2.54 mL, 14.8 mmol) and methanesulfonyl chloride (1.16 mL, 14.8 mmol) are added and the reaction is stirred at RT for 2 hours. DCM is added and the organic phase is washed with aq. NaHCO$_3$, water and brine, dried over Na$_2$SO$_4$ and evaporated to obtain intermediate I268 as a dark brown oil (2.1 g, 80% yield).

Preparation of (5-methyl-thiophen-2-yl)-phenylamino-acetic acid methyl ester (I267)

A solution of methanesulfonyloxy-(5-methyl-thiophen-2-yl)-acetic acid methyl ester (I266) (2.10 g, 7.94 mmol), aniline (1.09 mL, 11.9 mmol) and N-ethyl-N-isopropylpropan-2-amine (2.04 mL, 11.9 mmol) in MeCN (10 mL) is heated under microwave irradiation at 100° C. for 1 hour. The solvent is removed, DCM is added and the organic phase is washed with water and brine, dried over Na$_2$SO$_4$ and evaporated. The resulting brown oil is purified by silica gel flash chromatography (Hexane/EtOAc=9575 to 90/10) to obtain intermediate I269 as a yellow oil (500 mg, 24% yield).

Preparation of (5-methyl-thiophen-2-yl)-phenylamino-acetic acid hydrochloride (I268)

To a solution of (5-methyl-thiophen-2-yl)-phenylamino-acetic acid methyl ester (I267) (500 mg, 1.91 mmol) in THF (15 mL), cooled at 0° C., is added 2.0M lithium hydroxide (1.91 mL, 3.83 mmol) and the reaction is stirred at RT for 72 hours. Then the solvent is evaporated, 1M HCl is added to the reaction until pH 1 and the product is extracted with EtOAc. The organic phase is washed with water and brine, dried over Na$_2$SO$_4$, filtered and evaporated to obtain intermediate I270 as a light brown solid (410 mg, 76% yield).

Preparation of (5-methyl-thiophen-2-yl)-phenylamino-acetic acid (R)-(1-aza-bicyclo[2.2.2]oct-3-yl) ester (C269)

To a solution of (5-methyl-thiophen-2-yl)-phenylamino-acetic acid hydrochloride (I268) (220 mg, 0.77 mmol), (R)-quinuclidin-3-ol (338 mg, 2.66 mmol) and 1H-benzo[d][1,2,3]triazol-1-ol (180 mg, 1.33 mmol) in dry THF (15 mL), is added PS-DCC (1.0 g, 1.330 mmol) and the mixture is shaken at RT for 15 hours. Then (R)-quinuclidin-3-ol (49.3 mg, 0.39 mmol) and PS-DCC (291 mg, 0.39 mmol) are added again and the reaction is shaken at RT for other 3 hours. The resin is filtered off and washed several time with EtOAc. The solvent is concentrated and washed with aq. NaHCO$_3$, water and brine. The organic phase is dried over Na$_2$SO$_4$ and evaporated to obtain the title compound as a brown oil (175 mg, 63% yield).

Preparation of (R)-3-[2-(5-methyl-thiophen-2-yl)-2-phenylamino-acetoxy]-1-(2-oxo-2-phenyl-ethyl)-1-azonia-bicyclo[2.2.2]octane trifluoroacetate (C270)

To a solution of (5-methyl-thiophen-2-yl)-phenylamino-acetic acid (R)-(1-aza-bicyclo[2.2.2]oct-3-yl)ester (C269) (175 mg, 0.49 mmol) in acetonitrile (8 mL), is added 2-bromo-1-phenylethanone (98.0 mg, 0.49 mmol) and the reaction is stirred at RT for 15 hours. The solvent is evaporated and the resulting brown crude is purified by preparative HPLC to obtain the title compound as a brown oil (60 mg, 21% yield, trifluoroacetate salt, mixture of diastereoisomers).

$^1$H NMR (300 MHz, DMSO-d$_6$) ppm: 7.91-8.08 (m, 2H), 7.69-7.88 (m, 1H), 7.54-7.69 (m, 2H), 7.06-7.16 (m, 2H), 6.99-7.07 (m, 1H), 6.69-6.83 (m, 3H), 6.54-6.69 (m, 1H), 6.33 (br. s., 1H), 5.52 and 5.56 (d, 1H), 5.23-5.34 (m, 1H), 5.13 and 5.17 (s, 2H), 3.98-4.21 (m, 1H), 3.55-3.86 (m, 5H), 2.43 and 2.44 (d, 3H), 2.19-2.25 and 2.33-2.40 (m, 1H), 1.40-2.15 (m, 4H);

LC-MS (ESI POS): 475.3 (MH$^+$).

Example 69

Preparation of (R)-1-[2-(4-amino-phenyl)-2-oxo-ethyl]-3-((R)-2-phenyl-2-phenylamino-acetoxy)-1-azonia-bicyclo[2.2.2]octane formate (diastereoisomer 1 of C271)

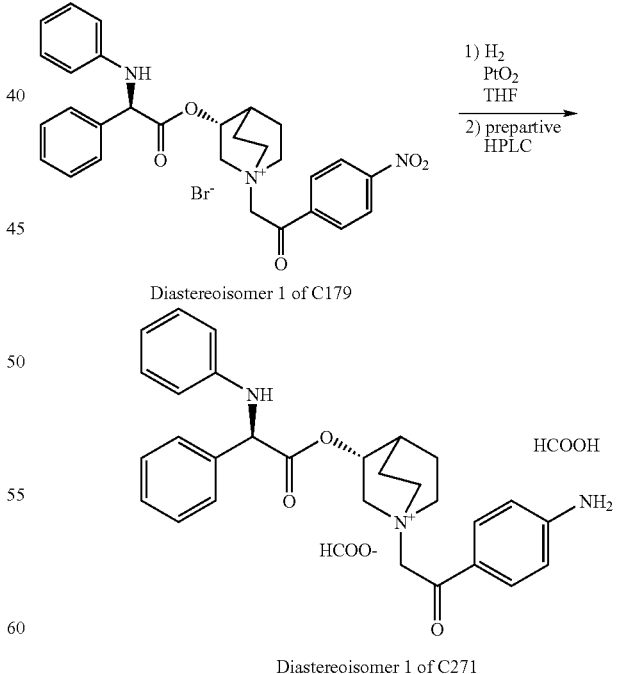

Scheme 69

Diastereoisomer 1 of C179

Diastereoisomer 1 of C271

A solution of (R)-1-[2-(4-nitro-phenyl)-2-oxo-ethyl]-3-((R)-2-phenyl-2-phenylamino-acetoxy)-1-azonia-bicyclo[2.2.2]octane bromide (Diastereoisomer 1 of C179) (88 mg, 0.152 mmol) in THF (30 mL) is hydrogenated in presence of a catalytic amount of Pt₂O at 15 psi for 2 hours and then at 20 psi for additional 2 hours (UPLC-MS monitoring: complete conversion). Catalyst is removed by filtration and the solution evaporated to dryness. The crude is purified by preparative HPLC to give the title compound as a pale yellow solid (31 mg, 37% yield, formate formate anion, single diastereoisomer).

¹H NMR (300 MHz, DMSO-$d_6$) ppm: 8.51 (s, 1H, formate), 7.63-7.77 (m, 2H), 7.47-7.61 (m, 2H), 7.30-7.46 (m, 3H), 7.02-7.18 (m, 3H), 6.68-6.81 (m, 2H), 6.54-6.66 (m, 2H), 6.41 (br. s., 2H), 6.36 (d, 1H), 5.37 (d, 1H), 4.99-5.25 (m, 1H), 4.82 (s, 2H), 3.91-4.18 (m, 1H), 3.41-3.74 (m, 5H), 2.30-2.43 (m, 1H), 1.56-2.09 (m, 4H);

LC-MS (ESI POS): 470.1 (MH⁺).

Example 70

Preparation of (R)-1-(2-hydroxy-2-phenyl-ethyl)-3-((R)-2-phenyl-2-phenylamino-acetoxy)-1-azonia-bicyclo[2.2.2]octane trifluoroacetate (C272)

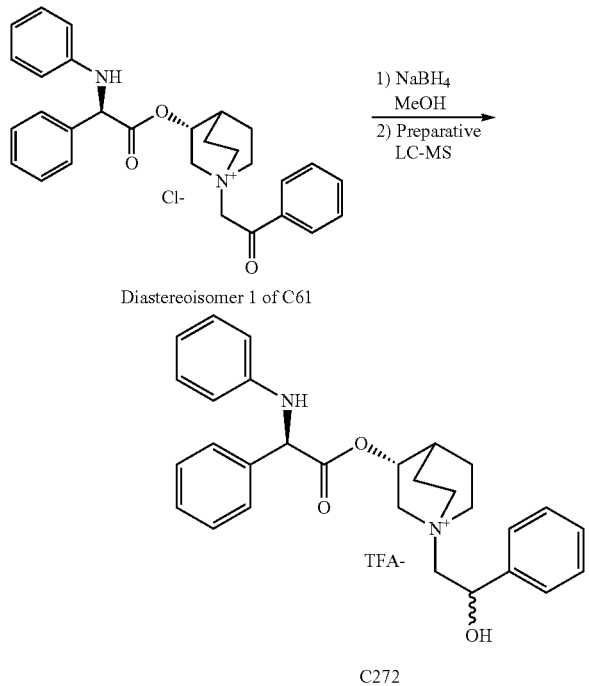

To a solution of (R)-1-(2-oxo-2-phenyl-ethyl)-3-((R)-2-phenyl-2-phenylamino-acetoxy)-1-azonia-bicyclo[2.2.2]octane chloride (Diastereoisomer 1 of C113) (80 mg, 0.163 mmol) in MeOH, is added NaBH₄ (6.16 mg, 0.163 mmol) and the mixture is stirred at RT for 1 hour (UPLC-MS: complete conversion). The solvent is evaporated and the resulting crude is first purified by flash chromatography (DCM/MeOH=9/1) and then by preparative LC-MS to obtain the title compound as of a brown oil (31.2 mg, 39% yield, trifluoroacetate, mixture of diastereoisomers).

¹H NMR (300 MHz, DMSO-$d_6$) ppm 7.51-7.64 (m, 2H), 7.28-7.50 (m, 8H), 6.99-7.17 (m, 1H), 6.66-6.86 (m, 2H), 6.51-6.66 (m, 1H), 5.01-5.54 (m, 3H), 3.02-4.07 (m, 9H), 2.29-2.42 (m, 1H), 1.71-2.17 (m, 4H);

LC-MS (ESI POS): 457.1 (MH⁺).

Biological Characterisation.

Example 71

Examples of Radioligand Binding Assay for Cloned Human Muscarinic Receptors and for Human beta Adrenergic Receptors CHO-K1 clone cells expressing the human M1-, M2-, M3-receptors (Euroscreen, Swissprot P11229, P08172, P20309, Genbank: J02960 respectively) were harvested in Ca⁺⁺/Mg⁺⁺ free phosphate-buffered saline and collected by centrifugation at 1500 rpm for 10 minutes, at 4° C. min. The pellets were resuspended in ice cold buffer A (15 mM Tris-HCl pH 7.4, 2 mM MgCl₂, 0.3 mM EDTA, 1 mM EGTA). Cloned cells expressing M1-, M2-, and M3-receptors were homogenized by a PBI politron (setting 5 for 15 s). The crude membrane fraction was collected by two consecutive centrifugation steps at 40000 g for 20 minutes at 4° C., separated by a washing step in buffer A.

The pellets obtained from the three cell lines were finally resuspended in buffer C (75 mM Tris HCl pH 7.4, 12.5 mM MgCl₂, 0.3 mM EDTA, 1 mM EGTA, 250 mM sucrose) and aliquots were stored at −80° C.

The day of experiment, M1-, M2-, and M3-receptor frozen membranes were resuspended in buffer D (50 mM Tris-HCl pH 7.4, 2.5 mM MgCl₂, 1 mM EDTA). The non-selective muscarinic radioligand [3H]-N-methyl scopolamine (Mol. Pharmacol. 45:899-907) was used to label the M1, M2, and M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 µM. Samples (final volume 0.75 mL) were incubated at RT for 120 minutes for M1, 60 minutes for M2 and 90 minutes for M3 binding assay.

The reaction was terminated by rapid filtration through GF/B Unifilter plates and two washes (0.75 mL) with cold buffer using a Packard Filtermate Harvester. Radioactivity on the filters was measured by a microplate scintillation counter TopCount NXT (Canberra Packard).

In the present assays, Ki values for the tested compounds were determined from the observed IC50 values according to known methods. A lower Ki value indicates that the tested compound has a higher binding affinity for the receptor.

The interaction with M3 muscarinic receptors can be estimated by the results of in vitro studies which evaluated the potency of the test compounds and the offset of the inhibitory activity produced after washout of the antagonists in isolated guinea pig trachea and by the in vivo duration of action against acetylcholine-induced bronchospasm in the guinea pig.

Example 72

In Vitro Interaction with Guinea Pigs M3 Receptors

The potency of the antagonist activity in isolated guinea pig trachea was investigated following a method previously described by Haddad E B et al. in Br. J. Pharmacol., 127, 413-420, 1999 (which is incorporated herein by reference in its entirety), with few modifications.

A cumulative concentration-response curve to test antagonists was constructed on preparations precontracted by carbachol, until a complete inhibition of smooth muscle tone was achieved. The concentration of antagonist producing a 50% reversal of carbachol-induced tonic contraction (IC₅₀) was taken as a measure of its potency in this bioassay.

In the experiments aiming at assessing the offset of the inhibitory effects produced by test compounds, the minimal concentration of the test compounds known to produce a maximal inhibitory effect was administered to carbachol-precontracted preparations. As soon as the tonic contraction was completely reversed, the organ bath solution was renewed and preparations were thoroughly washed with fresh Krebs solution. Carbachol (0.3 µM) was administered again (at 30 minute intervals between washout and next administration) during the next 4 hours.

After the administration of carbachol, the inhibitory effects of the compounds of the invention, administered at a concentration of 10 nM, were expressed as percentage of the recovery of the contracting response to carbachol. The percentage of recovery four hours after the washout was lower than 50%.

The compounds of the invention show a remarkable inhibitory M3 activity. In particular, the $IC_{50}$ values being tested for some representative compounds result to be comprised between 0.03 and 10 nM.

Example 73

In Vivo Studies

The in vivo tests on acetylcholine-induced bronchospasm in guinea pig were performed according to H. Konzett H and Rössler F., *Arch. Exp. Path. Pharmacol.*, 195, 71-74, 1940 (which is incorporated herein by reference in its entirety). Aqueous solutions of the test compounds were instilled intratracheally in anaesthetised mechanically ventilated guinea pigs. Bronchial response to intravenous acetylcholine challenge was determined before and after drug administration and changes in pulmonary resistance at several timepoints were expressed as percent of inhibition of bronchospasm. The bronchodilator activity of the tested compounds persisted unchanged up to 24 hours after the administration.

Example 74

Plasma Stability

In order to demonstrate that the compounds are degraded, stability in human plasma at 1 and 5 hours was tested for the compound of the invention. Briefly 10 µl of a stock solution 250 µM of the compound in acetonitrile were added to 1 ml of human plasma and samples were incubated at 37° C. Plasma (50 µL) was taken after 0, 1 and 5 hours of incubation and added to 140 µl of acetonitrile with addition of verapamil as internal standard (250 ng/ml). Samples were analysed by HPLC-MS/MS analysis.

Plasma stability is calculated as percentage remaining after 1 and 5 hours by dividing the peak area at 1 or 5 hours by the area of the peak at time 0. After 1 and 5 hours of incubation, plasma stability being tested for some representative compounds of the invention result to be comprised between 0 and 25%, indicating that the compounds of the invention are very unstable in human plasma.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

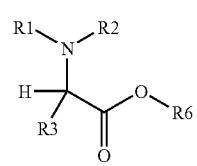

wherein:
R1 is H or a group selected from the group consisting of ($C_1$-$C_{10}$)-alkyl, aryl, ($C_3$-$C_8$)-cycloalkyl, arylalkyl, and heteroaryl, each of which may be optionally substituted by one or more substituents selected from the group consisting of halogen atoms, OH, oxo (=O), SH, $NO_2$, CN, CON(R5)$_2$, COOH, NHCOR5, COR5, $CO_2$R5, $CF_3$, ($C_1$-$C_{10}$)-alkoxycarbonyl, ($C_1$-$C_{10}$)-alkylsulfanyl, ($C_1$-$C_{10}$)-alkylsulfinyl, ($C_1$-$C_{10}$)-alkylsulfonyl, ($C_1$-$C_{10}$)-alkyl, and ($C_1$-$C_{10}$)-alkoxyl;

R2 is a group selected from the group consisting of ($C_1$-$C_{10}$)-alkyl, aryl, ($C_3$-$C_8$)-cycloalkyl, arylalkyl, and heteroaryl, each of which may be optionally substituted by one or more substituents selected from the group consisting of halogen atoms, OH, oxo (=O), SH, $NO_2$, CN, CON(R5)$_2$, COOH, NHCOR5, COR5, $CO_2$R5, $CF_3$, ($C_1$-$C_{10}$)-alkoxycarbonyl, ($C_1$-$C_{10}$)-alkylsulfanyl, ($C_1$-$C_{10}$)-alkylsulfinyl, ($C_1$-$C_{10}$)-alkylsulfonyl, ($C_1$-$C_{10}$)-alkyl, and ($C_1$-$C_{10}$)-alkoxyl;

R3 is aryl, ($C_3$-$C_8$)-cycloalkyl, heteroaryl, arylalkyl, or heteroarylalkyl, each of which may be optionally substituted by one or more substituents selected from the group consisting of halogen atoms, OH, oxo (=O), SH, $NO_2$, CN, CON(R5)$_2$, COOH, $CO_2$R5, $CF_3$, ($C_1$-$C_{10}$)-alkoxycarbonyl, ($C_1$-$C_{10}$)-alkylsulfinyl, ($C_1$-$C_{10}$)-alkylsulfonyl, ($C_1$-$C_{10}$)-alkyl, and ($C_1$-$C_{10}$)-alkoxyl;

R6 represents a group of formula (I) or (ii) or (iii) or (iv):

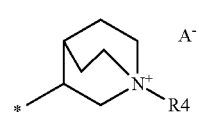

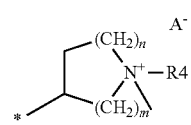

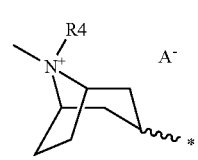

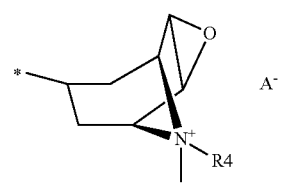

wherein
* indicates the position at which R6 is bonded to formula (I);
m=1, 2, or 3;

n=1, 2, or 3;
A⁻ is a physiologically acceptable anion;
R4 is a group of formula (Y)

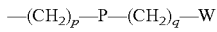  (Y)

wherein
p is 0 or an integer from 1 to 4;
q is 0 or an integer from 1 to 4;
P is absent or is selected from the group consisting of O, S, SO, SO₂, CO, NR5 CH=CH, N(R5)SO₂, N(R5)COO, N(R5)C(O), SO₂N(R5), CO(O)N(R5), and C(O)N(R5);
W is H or a group selected from the group consisting of $(C_1-C_6)$-alkyl, $(C_3-C_8)$-cycloalkyl, aryl, and heteroaryl, each of which may be optionally substituted by one or more substituents selected from the group consisting of halogen atoms, OH, oxo (=O), SH, $NO_2$, CN, CON$(R5)_2$, COOH, $NH_2$, NHCOR5, $CO_2R5$, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, and $(C_1-C_{10})$-alkoxyl;
R5 is H or a group selected from the group consisting of $(C_1-C_{10})$alkyl, $(C_1-C_6)$alkylhalo, $(C_2-C_6)$alkynyl, $(C_2-C_6)$alkenyl, $(C_3-C_7)$cycloalkyl, $(C_3-C_7)$cycloalkyl-$(C_1-C_6)$alkyl, heteroaryl, $(C_1-C_6)$alkyl-heteroaryl, and aryl, each of which may be optionally substituted by one or more substituents selected from the group consisting of halogen atoms, OH, oxo (=O), SH, $NO_2$, CN, $CONH_2$, COOH, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, and $(C_1-C_{10})$-alkoxyl;
or a pharmaceutically acceptable salt thereof.

2. A compound according to claim 1, wherein R1 is H, R2 is arylalkyl or $(C_1-C_{10})$-alkyl or aryl or $(C_3-C_8)$-cycloalkyl or heteroaryl, and R3 is aryl or $(C_3-C_8)$-cycloalkyl or heteroaryl, which may be substituted with one or more halogen atoms, and wherein R6 is a group of formula (I):

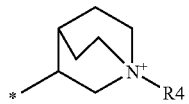  (i)

according to formula (XIII):

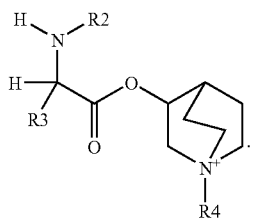  (XIII)

3. A compound according to claim 2, wherein R1 is H, and R2 and R3 are phenyl.

4. A compound according to claim 3, wherein R1 is H, R2 and R3 are phenyl, and R4 is a group of formula (Y):

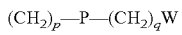  (Y)

wherein p is 1, P is CO, q is 0, and W is aryl.

5. A compound according to claim 4, wherein R4 is a group of formula (Y), wherein p is 1, P is CO, q is 0 and W is phenyl.

6. A compound according to claim 4, wherein R4 is a group of formula (Y), wherein p is 1, P is CO, q is 0 and W is thienyl.

7. A compound according to claim 4, wherein R4 is a group of formula (Y), wherein p is 2, P is O, q is 0 and W is phenyl.

8. A compound according to claim 4, wherein R4 is a group of formula (Y), wherein p is 3, P is O, q is 0 and W is phenyl.

9. A compound of formula (VI):

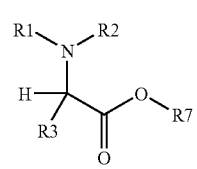  (VI)

wherein:
R1 is H or a group selected from the group consisting of $(C_1-C_{10})$-alkyl, aryl, $(C_3-C_8)$-cycloalkyl, arylalkyl, and heteroaryl, each of which may be optionally substituted by one or more substituents selected from the group consisting of halogen atoms, OH, oxo (=O), SH, $NO_2$, CN, CON$(R5)_2$, COOH, NHCOR5, COR5, $CO_2R5$, $CF_3$, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, and $(C_1-C_{10})$-alkoxyl;

R2 is a group selected from the group consisting of $(C_1-C_{10})$-alkyl, aryl, $(C_3-C_8)$-cycloalkyl, arylalkyl, and heteroaryl, each of which may be optionally substituted by one or more substituents selected from the group consisting of halogen atoms, OH, oxo (=O), SH, $NO_2$, CN, CON$(R5)_2$, COOH, NHCOR5, COR5, $CO_2R5$, $CF_3$, $(C_1-C_{10})$-alkoxycarbonyl, $(C_1-C_{10})$-alkylsulfanyl, $(C_1-C_{10})$-alkylsulfinyl, $(C_1-C_{10})$-alkylsulfonyl, $(C_1-C_{10})$-alkyl, and $(C_1-C_{10})$-alkoxyl;

R3 is aryl, $(C_3-C_8)$-cycloalkyl, heteroaryl, arylalkyl, or heteroarylalkyl, each of which may be optionally substituted by one or more substituents selected from the group consisting of halogen atoms, OH, oxo (=O), SH, $NO_2$, CN, CON$(R5)_2$, COOH, $CO_2R5$, $CF_3$, $(C_1-C_{10})$-alkoxycarbonyl, $(C_1-C_{10})$-alkylsulfinyl, $(C_1-C_{10})$-alkylsulfonyl, $(C_1-C_{10})$-alkyl, and $(C_1-C_{10})$-alkoxyl;

R7 represents a group of formula (vi) or (vii) or (viii) or (ix):

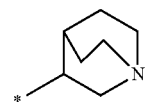  (vi)

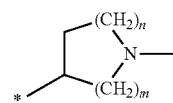  (vii)

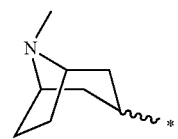  (viii)

-continued

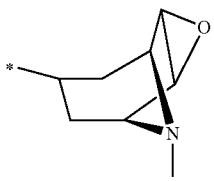

(ix)

wherein
* indicates the position at which R7 is bonded to formula (VI);
m=1, 2, or 3;
n=1, 2, or 3;
or a pharmaceutically acceptable salt thereof,
with the proviso that:
the compound of formula (VI) is not N-methyl-3-piperidyl-2'-N'-dimethylaminoacetate or N-methyl-4-piperidyl-2'-N'-dimethylaminoacetate.

10. A compound according to claim 9, wherein R1 is H, R2 is $(C_1-C_{10})$-alkyl or aryl or $(C_3-C_8)$-cycloalkyl or arylalkyl or heteroaryl, and R3 is aryl or $(C_3-C_8)$-cycloalkyl or arylalkyl or heteroaryl, optionally substituted with one or more halogen atoms and wherein R7 is a group of formula (vi):

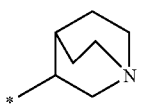

(vi)

according to formula (XII):

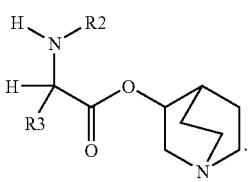

(XII)

11. A compound according to claim 10, wherein R1 is H, R2 is arylalkyl or $(C_1-C_{10})$-alkyl or aryl or $(C_3-C_8)$-cycloalkyl or heteroaryl, and R3 is aryl or $(C_3-C_8)$-cycloalkyl or arylalkyl or heteroaryl, optionally substituted with one or more halogen atoms and wherein R7 is a group of formula (vii):

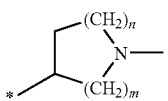

(vii)

according to formula (XIV):

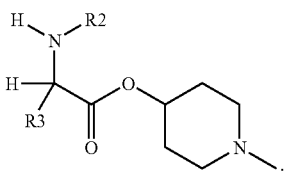

(XIV)

12. A compound according to claim 10, wherein R1 is H, R2 is arylalkyl or $(C_1-C_{10})$-alkyl or aryl or $(C_3-C_8)$-cycloalkyl or heteroaryl, and R3 is aryl or $(C_3-C_8)$-cycloalkyl or arylalkyl or heteroaryl, optionally substituted with one or more halogen atoms and wherein R7 is a group of formula (vii), according to formula (XV):

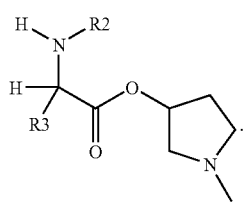

(XV)

13. A compound according to claim 10, wherein R1 is H, R2 is arylalkyl or $(C_1-C_{10})$-alkyl or aryl or $(C_3-C_8)$-cycloalkyl or heteroaryl, and R3 is aryl or $(C_3-C_8)$-cycloalkyl or arylalkyl or heteroaryl, optionally substituted with one or more halogen atoms and wherein R7 is a group of formula (vii), according to formula (XVI):

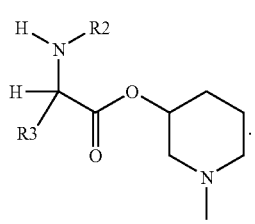

(XVI)

14. A compound according to claim 10, wherein R1 is H, R2 is arylalkyl or $(C_1-C_{10})$-alkyl or aryl or $(C_3-C_8)$-cycloalkyl or heteroaryl, and R3 is aryl or $(C_3-C_8)$-cycloalkyl or arylalkyl or heteroaryl, optionally substituted with one or more halogen atoms and wherein R7 is a group of formula (viii):

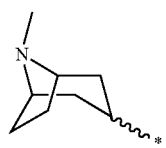

according to formula (XVII):

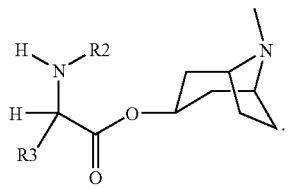

(XVII)

15. A compound according to claim 10, wherein R1 is H, R2 is arylalkyl or (C1-C10)-alkyl or aryl or $(C_3-C_8)$-cycloalkyl or heteroaryl, and R3 is aryl or $(C_3-C_8)$-cycloalkyl or arylalkyl or heteroaryl, optionally substituted with one or more halogen atoms and wherein R7 is a group of formula (ix):

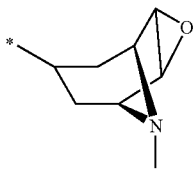

according to formula (XVIII):

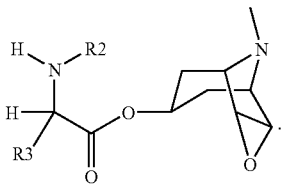

16. A compound or pharmaceutically acceptable salt thereof according to claim 1, which is selected from the group consisting of:

(R)-quinuclidin-3-yl 2-phenyl-2-(phenylamino)acetate;
(R)-quinuclidin-3-yl 2-(4-fluorophenyl)-2-(4-fluorophenylamino)acetate;
(R)-quinuclidin-3-yl 2-(methyl(phenyl)amino)-2-phenylacetate;
(R)-quinuclidin-3-yl 2-(3-fluorophenyl)-2-(3-fluorophenylamino)acetate;
(R)-1-methylpiperidin-4-yl-2-phenyl-2-(phenylamino)acetate;
(R)-1-methylpyrrolidin-4-yl-2-phenyl-2-(phenylamino)acetate;
(S)-1-methylpyrrolidin-4-yl-2-phenyl-2-(phenylamino)acetate;
(R)-1-methylpiperidin-3-yl 2-phenyl-2-(phenylamino)acetate;
8-methyl-8-azabicyclo[3.2.1]octan-3-yl 2-phenyl-2-(phenylamino)acetate;
phenyl-phenylamino-acetic acid 9-methyl-3-oxa-9-azatricyclo[3.3.1.0*2,4*]non-7-yl ester;
(R)-quinuclidin-3-yl) 2-amino-3-phenylpropanoate di-trifluoroacetate;
3-phenyl-2-phenylamino-propionic acid (R)-(1-aza-bicyclo[2.2.2]oct-3-yl)ester;
(R)-quinuclidin-3-yl 2-(benzylamino)-2-phenylacetate;
(R)-quinuclidin-3-yl 2-amino-2-phenylacetate di-hydrochloride;
(R)-quinuclidin-3-yl 2-(cyclopentylamino)-2-phenylacetate di-trifluoroacetate;
(R)-quinuclidin-3-yl 2-(cyclohexylamino)-2-phenylacetate;
(R)-1-(2-phenoxyethyl)-3-(2-phenyl-2-(phenylamino)acetoxy)-1-azonia-bicyclo[2.2.2]octane trifluoroacetate;
(R)-1-(2-oxo-2-(thiophen-2-yl)ethyl)-3-(2-phenyl-2-(phenylamino)acetoxy)-1-azonia-bicyclo[2.2.2]octane trifluoroacetate;
(R)-1-(3-phenoxypropyl)-3-(2-phenyl-2-(phenylamino)acetoxy)-1-azonia-bicyclo[2.2.2]octane trifluoroacetate;
(R)-1-methyl-3-(2-phenyl-2-(phenylamino)acetoxy)-1-azonia-bicyclo[2.2.2]octane trifluoroacetate;
(R)-1-(2-phenoxyethyl)-3-(2-phenyl-2-(phenylamino)acetoxy)-1-azonia-bicyclo[2.2.2]octane trifluoroacetate;
(R)-1-(2-oxo-2-phenylethyl)-3-(2-phenyl-2-(phenylamino)acetoxy)-1-azonia-bicyclo[2.2.2]octane trifluoroacetate;
1-(2-oxo-2-(thiophen-3-yl)ethyl)-3-(2-phenyl-2-(phenylamino)-acetoxy)-1-azonia-bicyclo[2.2.2]octane trifluoroacetate;
1-(2-(4-fluorophenyl)-2-oxoethyl)-3-(2-phenyl-2-(phenylamino)-acetoxy)-1-azonia-bicyclo[2.2.2]octane trifluoroacetate;
(R)-1-phenethyl-3-(2-phenyl-2-(phenylamino)acetoxy)-1-azonia-bicyclo[2.2.2]octane trifluoroacetate;
(R)-1-(2-(benzo[b]thiophen-2-yl)-2-oxoethyl)-3-(2-phenyl-2-(phenylamino)acetoxy)-1-azonia-bicyclo[2.2.2]octane trifluoroacetate;
3-(2-(4-fluorophenyl)-2-(4-fluorophenylamino)acetoxy)-1-(2-oxo-2-(thiophen-2-yl)ethyl)-1-azonia-bicyclo[2.2.2]octane trifluoroacetate;
(3R)-3-(2-(4-fluorophenyl)-2-(4-fluorophenylamino)acetoxy)-1-(2-oxo-2-phenylethyl)-1-azonia-bicyclo[2.2.2]octane trifluoroacetate;
3-(2-(4-fluorophenyl)-2-(4-fluorophenylamino)acetoxy)-1-methyl-1-azonia-bicyclo[2.2.2]octane trifluoroacetate;
3-(2-(3-fluorophenyl)-2-(3-fluorophenylamino)acetoxy)-1-(2-oxo-2-phenylethyl)-1-azonia-bicyclo[2.2.2]octane trifluoroacetate;
3-(2-(methyl(phenyl)amino)-2-phenylacetoxy)-1-(2-oxo-2-(thiophen-2-yl)ethyl)-1-azonia-bicyclo[2.2.2]octane trifluoroacetate;
3-(2-(methyl(phenyl)amino)-2-phenylacetoxy)-1-(2-oxo-2-phenylethyl)-1-azonia-bicyclo[2.2.2]octane trifluoroacetate;
(R)-1-(2-phenoxyethyl)-3-(3-phenyl-2-(phenylamino)propanoyloxy)-1-azonia-bicyclo[2.2.2]octane trifluoroacetate;
(R)-1-(2-oxo-2-(thiophen-2-yl)ethyl)-3-((S)-3-phenyl-2-(phenylamino)propanoyloxy)-1-azonia-bicyclo[2.2.2]octane trifluoroacetate;
(R)-1-methyl-3-(3-phenyl-2-(phenylamino)propanoyloxy)-1-azonia-bicyclo[2.2.2]octane trifluoroacetate;
(R)-1-(2-oxo-2-phenylethyl)-3-((S)-3-phenyl-2-(phenylamino)propanoyloxy)-1-azonia-bicyclo[2.2.2]octane trifluoroacetate;
3-(2-(benzylamino)-2-phenylacetoxy)-1-(2-oxo-2-phenylethyl)-1-azonia-bicyclo[2.2.2]octane trifluoroacetate;
(R)-1-(2-oxo-2-pyridin-4-yl-ethyl)-3-(2-phenyl-2-phenylamino-acetoxy)-1-azonia-bicyclo[2.2.2]octane trifluoroacetate;
(R)-1-[2-(3-chloro-thiophen-2-yl)-2-oxo-ethyl]-3-(2-phenyl-2-phenylamino-acetoxy)-1-azonia-bicyclo[2.2.2]octane trifluoroacetate;
(R)-1-[2-(5-methyl-thiophen-2-yl)-2-oxo-ethyl]-3-(2-phenyl-2-phenylamino-acetoxy)-1-azonia-bicyclo[2.2.2]octane trifluoroacetate;
(R)-1-[2-(1-methyl-1H-pyrrol-2-yl)-2-oxo-ethyl]-3-(2-phenyl-2-phenylamino-acetoxy)-1-azonia-bicyclo[2.2.2]octane trifluoroacetate;
(R)-1-[2-(2,4-dimethyl-oxazol-5-yl)-2-oxo-ethyl]-3-(2-phenyl-2-phenylamino-acetoxy)-1-azonia-bicyclo[2.2.2]octane trifluoroacetate;
(R)-3-(2-phenyl-2-phenylamino-acetoxy)-1-(3-phenylsulfanyl-propyl)-1-azonia-bicyclo[2.2.2]octane formate;
(R)-3-[2-(3-ethyl-phenylamino)-2-phenyl-acetoxy]-1-(2-oxo-2-phenyl-ethyl)-1-azonia-bicyclo[2.2.2]octane formate;

(R)-3-[2-(4-methoxycarbonyl-phenylamino)-2-phenyl-acetoxy]-1-(2-oxo-2-phenyl-ethyl)-1-azonia-bicyclo[2.2.2]octane trifluoroacetate;
(3R)-3-(2-phenyl-2-(phenylamino)acetoxy)-1-(2-(phenylthio)ethyl)-1-azonia-bicyclo[2.2.2]octane trifluoroacetate;
1-(cyclohexylmethyl)-3-(2-phenyl-2-(phenylamino)acetoxy)-1-azonia-bicyclo[2.2.2]octane trifluoroacetate;
1-(4-methylpent-3-enyl)-3-(2-phenyl-2-(phenylamino)acetoxy)-1-azonia-bicyclo[2.2.2]octane trifluoroacetate;
1-(2-(3,4-dichlorophenyl)-2-oxoethyl)-3-(2-phenyl-2-(phenylamino)acetoxy)-1-azonia-bicyclo[2.2.2]octane trifluoroacetate;
(R)-1-(2-oxo-2-phenylethyl)-3-(2-phenyl-2-(phenylamino)acetoxy)-1-azonia-bicyclo[2.2.2]octane chloride;
3-(3-(3-fluorophenyl)-3-(3-fluorophenylamino)-2-oxopropyl)-1-(2-oxo-2-(thiophen-2-yl)ethyl)-1-azonia-bicyclo[2.2.2]octane chloride;
(R)-1-(2-amino-2-oxoethyl)-3-(2-phenyl-2-(phenylamino)acetoxy)-1-azonia-bicyclo[2.2.2]octane;
(R)-1-(2-oxo-2-(phenylamino)ethyl)-3-(2-phenyl-2-(phenylamino)-acetoxy)-1-azonia-bicyclo[2.2.2]octane;
1-(2-oxo-2-phenylethyl)-3-(2-phenyl-2-(phenylamino)acetoxy)-1-azonia-bicyclo[2.2.2]octane;
3-(2-(benzylamino)-2-phenylacetoxy)-1-(2-oxo-2-(thiophen-2-yl)ethyl)-1-azonia-bicyclo[2.2.2]octane;
(R)-1-(2-oxo-2-phenylethyl)-3-(2-phenyl-2-(phenylamino)acetoxy)-1-azonia-bicyclo[2.2.2]octane bromide;
(R)-3-((S)-2-amino-phenylpropanoyloxy)-1-(2-phenoxyethyl)-1-azonia-bicyclo[2.2.2]octane;
(R)-3-((S)-2-amino-3-phenylpropanoyloxy)-1-(2-oxo-2-(thiophen-2-yl)ethyl)-1-azonia-bicyclo[2.2.2]octane trifluoroacetate;
(R)-3-((S)-2-amino-3-phenylpropanoyloxy)-1-(3-phenoxypropyl)-1-azonia-bicyclo[2.2.2]octane trifluoroacetate;
(R)-3-((S)-2-amino-3-phenylpropanoyloxy)-1-(2-oxo-2-phenylethyl)-1-azonia-bicyclo[2.2.2]octane trifluoroacetate;
(R)-1-(2-oxo-2-phenylethyl)-3-((R)-3-phenyl-2-(phenylamino)-propanoyloxy)-1-azoniabicyclo[2.2.2]octane bromide;
(R)-1-(2-oxo-2-(thiophen-2-yl)ethyl)-3-((R)-3-phenyl-2-(phenylamino)-propanoyloxy)-1-azonia-bicyclo[2.2.2]octane chloride;
((4-chloro-phenylamino)-phenyl-acetic acid (R)-(1-aza-bicyclo[2.2.2]oct-3-yl)ester;
4-({[(R)-(1-aza-bicyclo[2.2.2]oct-3-yl)oxycarbonyl]-phenyl-methyl}-amino)-benzoic acid methyl ester;
3-({[(R)-(1-aza-bicyclo[2.2.2]oct-3-yl)oxycarbonyl]-phenyl-methyl}-amino)-thiophene-2-carboxylic acid methyl ester;
(4-fluoro-phenylamino)-phenyl-acetic acid (R)-(1-aza-bicyclo[2.2.2]oct-3-yl)ester;
(4-fluoro-phenyl)-phenylamino-acetic acid (R)-(1-aza-bicyclo[2.2.2]oct-3-yl)ester;
2-({[(R)-(1-aza-bicyclo[2.2.2]oct-3-yl)oxycarbonyl]-phenyl-methyl}-amino)-benzoic acid methyl ester;
(2-methoxy-phenylamino)-phenyl-acetic acid (R)-(1-aza-bicyclo[2.2.2]oct-3-yl)ester;
phenyl-o-methyl phenylamino-acetic acid (R)-(1-aza-bicyclo[2.2.2]oct-3-yl)ester;
phenyl-(3-trifluoromethoxy-phenylamino)-acetic acid (R)-(1-aza-bicyclo[2.2.2]oct-3-yl) ester;
(3-ethyl-phenylamino)-phenyl-acetic acid (R)-(1-aza-bicyclo[2.2.2]oct-3-yl)ester;
(3-acetylamino-phenylamino)-phenyl-acetic acid (R)-(1-aza-bicyclo[2.2.2]oct-3-yl)ester;
(3-methylcarbamoyl-phenylamino)-phenyl-acetic acid (R)-(1-aza-bicyclo[2.2.2]oct-3-yl)ester;
(3-fluoro-4-methyl-phenylamino)-phenyl-acetic acid (R)-(1-aza-bicyclo[2.2.2]oct-3-yl)ester;
(3-methylsulfanyl-phenylamino)-phenyl-acetic acid (R)-(1-aza-bicyclo[2.2.2]oct-3-yl)ester;
(3-acetyl-phenylamino)-phenyl-acetic acid (R)-(1-aza-bicyclo[2.2.2]oct-3-yl)ester;
(2,5-dimethoxy-phenylamino)-phenyl-acetic acid (R)-(1-aza-bicyclo[2.2.2]oct-3-yl)ester;
(2,5-difluoro-phenylamino)-phenyl-acetic acid (R)-(1-aza-bicyclo[2.2.2]oct-3-yl)ester;
(2,6-dimethyl-phenylamino)-phenyl-acetic acid (R)-(1-aza-bicyclo[2.2.2]oct-3-yl)ester;
(2-ethyl-phenylamino)-phenyl-acetic acid (R)-(1-aza-bicyclo[2.2.2]oct-3-yl) ester;
(2-acetyl-phenylamino)-phenyl-acetic acid (R)-(1-aza-bicyclo[2.2.2]oct-3-yl)ester;
(3,5-difluoro-phenylamino)-phenyl-acetic acid (R)-(1-aza-bicyclo[2.2.2]oct-3-yl)ester;
3-({[(R)-(1-aza-bicyclo[2.2.2]oct-3-yl)oxycarbonyl]-phenyl-methyl}-amino)-benzoic acid ethyl ester;
(3-methoxy-phenylamino)-phenyl-acetic acid (R)-(1-aza-bicyclo[2.2.2]oct-3-yl)ester;
[(4-fluoro-phenyl)-methyl-amino]-phenyl-acetic acid (R)-(1-aza-bicyclo[2.2.2]oct-3-yl)ester;
(methyl-phenyl-amino)-phenyl-acetic acid (R)-(1-aza-bicyclo[2.2.2]oct-3-yl)ester;
(4-methyl-benzylamino)-phenyl-acetic acid (R)-(1-aza-bicyclo[2.2.2]oct-3-yl)ester;
(4-fluoro-benzylamino)-phenyl-acetic acid (R)-(1-aza-bicyclo[2.2.2]oct-3-yl)ester;
(4-methoxy-benzylamino)-phenyl-acetic acid (R)-(1-aza-bicyclo[2.2.2]oct-3-yl)ester;
benzylamino-phenyl-acetic acid (R)-(1-aza-bicyclo[2.2.2]oct-3-yl)ester;
(4-fluoro-benzylamino)-phenyl-acetic acid (R)-(1-aza-bicyclo[2.2.2]oct-3-yl)ester;
(4-fluoro-phenyl)-(3-fluoro-phenylamino)-acetic acid (R)-(1-aza-bicyclo[2.2.2]oct-3-yl)ester;
(4-fluoro-phenyl)-(2-fluoro-phenylamino)-acetic acid (R)-(1-aza-bicyclo[2.2.2]oct-3-yl)ester;
(R)-quinuclidin-3-yl 2-(phenylamino)-2-(thiophen-2-yl) acetate hydrochloride;
(4-methoxy-phenyl)-phenylamino-acetic acid (R)-(1-aza-bicyclo[2.2.2]oct-3-yl)ester;
4-{[(R)-(1-aza-bicyclo[2.2.2]oct-3-yl)oxycarbonyl]-phenylamino-methyl}-benzoic acid methyl ester;
(3-fluoro-phenyl)-phenylamino-acetic acid (R)-(1-aza-bicyclo[2.2.2]oct-3-yl)ester;
(4-fluoro-phenyl)-phenylamino-acetic acid (R)-(1-aza-bicyclo[2.2.2]oct-3-yl)ester;
phenylamino-(4-trifluoromethyl-phenyl)-acetic acid (R)-(1-aza-bicyclo[2.2.2]oct-3-yl)ester;
(S)-quinuclidin-3-yl 2-phenyl-2-(phenylamino)-acetate;
phenyl-phenylamino-acetic acid 1-methyl-azepan-4-yl ester;
(R)-1-[2-(4-methoxy-phenyl)-2-oxo-ethyl]-3-(2-phenyl-2-phenylamino-acetoxy)-1-azonia-bicyclo[2.2.2]octane trifluoroacetate;
(R)-1-(4-oxo-4-phenyl-butyl)-3-(2-phenyl-2-phenylamino-acetoxy)-1-azonia-bicyclo[2.2.2]octane trifluoroacetate;

(R)-1-benzyl-3-(2-phenyl-2-phenylamino-acetoxy)-1-azonia-bicyclo[2.2.2]octane trifluoroacetate;
(R)-1-[2-(5-chloro-thiophen-2-yl)-2-oxo-ethyl]-3-(2-phenyl-2-phenylamino-acetoxy)-1-azonia-bicyclo[2.2.2]octane trifluoroacetate;
(R)-1-benzyl-3-(2-phenyl-2-phenylamino-acetoxy)-1-azonia-bicyclo[2.2.2]octane trifluoroacetate;
(R)-1-[2-(4-methoxy-phenyl)-2-oxo-ethyl]-3-(2-phenyl-2-phenylamino-acetoxy)-1-azonia-bicyclo[2.2.2]octane trifluoroacetate;
(R)-1-[2-(3-hydroxy-phenyl)-2-oxo-ethyl]-3-(2-phenyl-2-phenylamino-acetoxy)-1-azonia-bicyclo[2.2.2]octane trifluoroacetate;
(R)-1-dimethylcarbamoylmethyl-3-(2-phenyl-2-phenylamino-acetoxy)-1-azonia-bicyclo[2.2.2]octane trifluoroacetate;
(R)-1-(2-oxo-propyl)-3-(2-phenyl-2-phenylamino-acetoxy)-1-azonia-bicyclo[2.2.2]octane trifluoroacetate;
(R)-1-(2-oxo-propyl)-3-(2-phenyl-2-phenylamino-acetoxy)-1-azonia-bicyclo[2.2.2]octane trifluoroacetate;
(R)-3-[2-(2-methoxycarbonyl-thiophen-3-yl)-2-phenylamino-acetoxy]-1-(2-oxo-2-phenyl-ethyl)-1-azonia-bicyclo[2.2.2]octane trifluoroacetate;
(R)-3-[2-(2-methoxycarbonyl-thiophen-3-yl)-2-phenylamino-acetoxy]-1-(2-oxo-2-thiophen-2-yl-ethyl)-1-azonia-bicyclo[2.2.2]octane trifluoroacetate;
(R)-3-[2-(4-methoxy-phenyl)-2-phenylamino-acetoxy]-1-(2-oxo-2-phenyl-ethyl)-1-azonia-bicyclo[2.2.2]octane formate;
(R)-3-[2-(4-chloro-phenylamino)-2-phenyl-acetoxy]-1-(2-oxo-2-phenyl-ethyl)-1-azonia-bicyclo[2.2.2]octane trifluoroacetate;
(R)-1-(2-oxo-2-phenyl-ethyl)-3-[2-phenylamino-2-(4-trifluoromethyl-phenyl)-acetoxy]-1-azonia-bicyclo[2.2.2]octane trifluoroacetate;
(R)-1-methyl-1-(2-oxo-2-phenyl-ethyl)-3-(2-phenyl-2-phenylamino-acetoxy)-pyrrolidinium trifluoroacetate;
1,1-dimethyl-4-(2-phenyl-2-phenylamino-acetoxy)-piperidinium trifluoroacetate;
(R)-1-[2-(5-methyl-thiophen-3-yl)-2-oxo-ethyl]-3-(2-phenyl-2-phenylamino-acetoxy)-1-azonia-bicyclo[2.2.2]octane trifluoroacetate;
(R)-1-[2-(2,4-difluoro-phenyl)-2-oxo-ethyl]-3-(2-phenyl-2-phenylamino-acetoxy)-1-azonia-bicyclo[2.2.2]octane bromide;
(R)-1-[2-(3,4-difluoro-phenyl)-2-oxo-ethyl]-3-(2-phenyl-2-phenylamino-acetoxy)-1-azonia-bicyclo[2.2.2]octane bromide;
(R)-1-[2-(2-fluoro-phenyl)-2-oxo-ethyl]-3-(2-phenyl-2-phenylamino-acetoxy)-1-azonia-bicyclo[2.2.2]octane bromide;
(R)-1-[2-(3-fluoro-phenyl)-2-oxo-ethyl]-3-(2-phenyl-2-phenylamino-acetoxy)-1-azonia-bicyclo[2.2.2]octane bromide;
(R)-1-[2-(2,4-dibromo-phenyl)-2-oxo-ethyl]-3-(2-phenyl-2-phenylamino-acetoxy)-1-azonia-bicyclo[2.2.2]octane chloride;
(R)-1-[2-(4-nitro-phenyl)-2-oxo-ethyl]-3-(2-phenyl-2-phenylamino-acetoxy)-1-azonia-bicyclo[2.2.2]octane bromide;
(R)-1-[2-(4-hydroxy-phenyl)-2-oxo-ethyl]-3-(2-phenyl-2-phenylamino-acetoxy)-1-azonia-bicyclo[2.2.2]octane bromide;
(R)-1-[2-oxo-2-(2-oxo-2,3-dihydro-1H-indol-5-yl)-ethyl]-3-(2-phenyl-2-phenylamino-acetoxy)-1-azonia-bicyclo[2.2.2]octane bromide;
(R)-1-(2-benzo[1,3]dioxol-5-yl-2-oxo-ethyl)-3-(2-phenyl-2-phenylamino-acetoxy)-1-azonia-bicyclo[2.2.2]octane bromide;
(R)-1-(2-oxo-2-thiazol-2-yl-ethyl)-3-(2-phenyl-2-phenylamino-acetoxy)-1-azonia-bicyclo[2.2.2]octane bromide;
(R)-1-[2-(3-ethoxycarbonyl-isoxazol-5-yl)-2-oxo-ethyl]-3-(2-phenyl-2-phenylamino-acetoxy)-1-azonia-bicyclo[2.2.2]octane bromide;
(R)-1-[2-(4-methyl-thiophen-2-yl)-2-oxo-ethyl]-3-(2-phenyl-2-phenylamino-acetoxy)-1-azonia-bicyclo[2.2.2]octane bromide;
(R)-1-(2-benzo[b]thiophen-5-yl-2-oxo-ethyl)-3-(2-phenyl-2-phenylamino-acetoxy)-1-azonia-bicyclo[2.2.2]octane bromide;
(R)-3-(2-phenyl-2-phenylamino-acetoxy)-1-phenylsulfanylmethyl-1-azonia-bicyclo[2.2.2]octane chloride;
(R)-1-(2-oxo-2-piperidin-1-yl-ethyl)-3-(2-phenyl-2-phenylamino-acetoxy)-1-azonia-bicyclo[2.2.2]octane chloride;
(R)-3-(2-phenyl-2-phenylamino-acetoxy)-1-(thiazol-2-ylcarbamoylmethyl)-1-azonia-bicyclo[2.2.2]octane chloride;
(R)-1-(isoxazol-3-ylcarbamoylmethyl)-3-(2-phenyl-2-phenylamino-acetoxy)-1-azonia-bicyclo[2.2.2]octane chloride;
(R)-1-(2-oxo-2-phenyl-ethyl)-3-(2-phenyl-2-p-methylphenylamino-acetoxy)-1-azonia-bicyclo[2.2.2]octane bromide;
(R)-3-[2-(4-fluoro-phenylamino)-2-phenyl-acetoxy]-1-(2-oxo-2-phenyl-ethyl)-1-azonia-bicyclo[2.2.2]octane bromide;
(R)-3-[2-(4-fluoro-phenylamino)-2-phenyl-acetoxy]-1-(2-oxo-2-thiophen-2-yl-ethyl)-1-azonia-bicyclo[2.2.2]octane chloride;
(R)-3-[2-(2-methoxycarbonyl-phenylamino)-2-phenyl-acetoxy]-1-(2-oxo-2-phenyl-ethyl)-1-azonia-bicyclo[2.2.2]octane bromide;
(R)-3-[2-(2-methoxy-phenylamino)-2-phenyl-acetoxy]-1-(2-oxo-2-phenyl-ethyl)-1-azonia-bicyclo[2.2.2]octane bromide;
(R)-1-(2-oxo-2-phenyl-ethyl)-3-[2-phenyl-2-(3-trifluoromethoxy-phenylamino)-acetoxy]-1-azonia-bicyclo[2.2.2]octane bromide;
(R)-1-(2-oxo-2-phenyl-ethyl)-3-(2-phenyl-2-(phenylamino-acetoxy)-1-azonia-bicyclo[2.2.2]octane bromide;
(R)-3-[2-(3-acetylamino-phenylamino)-2-phenyl-acetoxy]-1-(2-oxo-2-phenyl-ethyl)-1-azonia-bicyclo[2.2.2]octane bromide;
(R)-3-[2-(3-methylcarbamoyl-phenylamino)-2-phenyl-acetoxy]-1-(2-oxo-2-phenyl-ethyl)-1-azonia-bicyclo[2.2.2]octane bromide;
(R)-3-[2-(3-methylsulfanyl-phenylamino)-2-phenyl-acetoxy]-1-(2-oxo-2-phenyl-ethyl)-1-azonia-bicyclo[2.2.2]octane bromide;
(R)-3-[2-(4-fluoro-phenyl)-2-(3-fluoro-phenylamino)-acetoxy]-1-(2-oxo-2-phenyl-ethyl)-1-azonia-bicyclo[2.2.2]octane bromide;
(R)-3-[2-(4-fluoro-phenyl)-2-(3-fluoro-phenylamino)-acetoxy]-1-(2-oxo-2-thiophen-2-yl-ethyl)-1-azonia-bicyclo[2.2.2]octane chloride;
(R)-3-[2-(4-fluoro-phenyl)-2-(2-fluoro-phenylamino)-acetoxy]-1-(2-oxo-2-phenyl-ethyl)-1-azonia-bicyclo[2.2.2]octane bromide;

(R)-3-[2-(4-fluoro-phenyl)-2-(2-fluoro-phenylamino)-acetoxy]-1-(2-oxo-2-thiophen-2-yl-ethyl)-1-azonia-bicyclo[2.2.2]octane chloride;
(R)-3-[2-(4-methoxycarbonyl-phenyl)-2-phenylamino-acetoxy]-1-(2-oxo-2-phenyl-ethyl)-1-azonia-bicyclo[2.2.2]octane bromide;
(R)-3-(2-cyclohexylamino-2-phenyl-acetoxy)-1-(2-oxo-2-phenyl-ethyl)-1-azonia-bicyclo[2.2.2]octane bromide;
(R)-3-(2-cyclohexylamino-2-phenyl-acetoxy)-1-(2-oxo-2-thiophen-2-yl-ethyl)-1-azonia-bicyclo[2.2.2]octane chloride;
(R)-1-(2-oxo-2-phenyl-ethyl)-3-(2-phenylamino-2-thiophen-2-yl-acetoxy)-1-azonia-bicyclo[2.2.2]octane bromide;
(R)-3-[2-(3-fluoro-4-methyl-phenylamino)-2-phenyl-acetoxy]-1-(2-oxo-2-phenyl-ethyl)-1-azonia-bicyclo[2.2.2]octane bromide;
(R)-3-[2-(2,5-dimethoxy-phenylamino)-2-phenyl-acetoxy]-1-(2-oxo-2-phenyl-ethyl)-1-azonia-bicyclo[2.2.2]octane bromide;
(R)-3-[2-(2,5-difluoro-phenylamino)-2-phenyl-acetoxy]-1-(2-oxo-2-phenyl-ethyl)-1-azonia-bicyclo[2.2.2]octane bromide;
(R)-3-[2-(2,6-dimethyl-phenylamino)-2-phenyl-acetoxy]-1-(2-oxo-2-phenyl-ethyl)-1-azonia-bicyclo[2.2.2]octane bromide;
(R)-3-[2-(2-ethyl-phenylamino)-2-phenyl-acetoxy]-1-(2-oxo-2-phenyl-ethyl)-1-azonia-bicyclo[2.2.2]octane bromide;
(R)-3-[2-(2-acetyl-phenylamino)-2-phenyl-acetoxy]-1-(2-oxo-2-phenyl-ethyl)-1-azonia-bicyclo[2.2.2]octane bromide;
(R)-3-[2-(3-ethoxycarbonyl-phenylamino)-2-phenyl-acetoxy]-1-(2-oxo-2-phenyl-ethyl)-1-azonia-bicyclo[2.2.2]octane bromide;
(R)-3-[2-(3,5-difluoro-phenylamino)-2-phenyl-acetoxy]-1-(2-oxo-2-phenyl-ethyl)-1-azonia-bicyclo[2.2.2]octane bromide;
(R)-3-[2-(3-methoxy-phenylamino)-2-phenyl-acetoxy]-1-(2-oxo-2-phenyl-ethyl)-1-azonia-bicyclo[2.2.2]octane bromide;
(R)-3-[2-(3-fluoro-phenyl)-2-phenylamino-acetoxy]-1-(2-oxo-2-phenyl-ethyl)-1-azonia-bicyclo[2.2.2]octane bromide;
(R)-3-[2-(4-fluoro-phenyl)-2-phenylamino-acetoxy]-1-(2-oxo-2-phenyl-ethyl)-1-azonia-bicyclo[2.2.2]octane bromide;
(R)-1-cyanomethyl-3-(2-phenyl-2-phenylamino-acetoxy)-1-azonia-bicyclo[2.2.2]octane bromide;
(R)-1-tert-butoxycarbonylmethyl-3-(2-phenyl-2-phenylamino-acetoxy)-1-azonia-bicyclo[2.2.2]octane bromide;
(S)-1-(2-oxo-2-phenyl-ethyl)-3-(2-phenyl-2-phenylamino-acetoxy)-1-azonia-bicyclo[2.2.2]octane chloride;
(R)-3-[2-(3-acetyl-phenylamino)-2-phenyl-acetoxy]-1-(2-oxo-2-phenyl-ethyl)-1-azonia-bicyclo[2.2.2]octane formate;
(R)-1-[2-(4-acetylamino-phenyl)-2-oxo-ethyl]-3-(2-phenyl-2-phenylamino-acetoxy)-1-azonia-bicyclo[2.2.2]octane bromide;
(R)-1-[2-(4-methoxycarbonyl-phenyl)-2-oxo-ethyl]-3-(2-phenyl-2-phenylamino-acetoxy)-1-azonia-bicyclo[2.2.2]octane bromide;
(R)-3-(2-phenyl-2-phenylamino-acetoxy)-1-pyridin-2-yl-methyl-1-azonia-bicyclo[2.2.2]octane trifluoroacetate;
(R)-1-(2-oxo-2-pyridin-2-yl-ethyl)-3-(2-phenyl-2-phenylamino-acetoxy)-1-azonia-bicyclo[2.2.2]octane formate;
(R)-1-(2-(2-methylthiazol-4-yl)-2-oxoethyl)-3-((R)-2-phenyl-2-(phenylamino)acetoxy)-1-azoniabicyclo[2.2.2]octane bromide;
(R)-1-(6-amino-pyridin-2-ylmethyl)-3-(2-phenyl-2-phenylamino-acetoxy)-1-azonia-bicyclo[2.2.2]octane trifluoroacetate;
(R)-3-{2-[(4-fluoro-phenyl)-methyl-amino]-2-phenyl-acetoxy}-1-(2-oxo-2-thiophen-2-yl-ethyl)-1-azonia-bicyclo[2.2.2]octane chloride;
(R)-3-[2-(methyl-phenyl-amino)-2-phenyl-acetoxy]-1-(2-oxo-2-thiazol-2-yl-ethyl)-1-azonia-bicyclo[2.2.2]octane bromide;
(R)-3-[2-(methyl-phenyl-amino)-2-phenyl-acetoxy]-1-(2-oxo-2-thiophen-3-yl-ethyl)-1-azonia-bicyclo[2.2.2]octane;
(R)-3-(2-benzylamino-2-phenyl-acetoxy)-1-[2-(3-ethoxycarbonyl-isoxazol-5-yl)-2-oxo-ethyl]-1-azonia-bicyclo[2.2.2]octane bromide;
(R)-3-(2-benzylamino-2-phenyl-acetoxy)-1-(2-oxo-2-thiazol-2-yl-ethyl)-1-azonia-bicyclo[2.2.2]octane trifluoroacetate;
(R)-3-(2-benzylamino-2-phenyl-acetoxy)-1-(2-oxo-2-thiophen-3-yl-ethyl)-1-azonia-bicyclo[2.2.2]octane bromide;
(R)-3-[2-(4-methyl-benzylamino)-2-phenyl-acetoxy]-1-(2-oxo-2-thiophen-2-yl-ethyl)-1-azonia-bicyclo[2.2.2]octane formate;
(R)-3-[2-(4-methoxy-benzylamino)-2-phenyl-acetoxy]-1-(2-oxo-2-thiophen-2-yl-ethyl)-1-azonia-bicyclo[2.2.2]octane formate;
(R)-3-[2-(4-fluoro-benzylamino)-2-phenyl-acetoxy]-1-(2-oxo-2-thiophen-2-yl-ethyl)-1-azonia-bicyclo[2.2.2]octane chloride;
(R)-3-[2-(4-fluoro-benzylamino)-2-phenyl-acetoxy]-1-(2-oxo-2-phenyl-ethyl)-1-azonia-bicyclo[2.2.2]octane bromide;
4-methyl-phenyl-amino-phenyl-acetic acid (R)-(1-aza-bicyclo[2.2.2]oct-3-yl)ester;
(R)-1-(2-oxo-2-phenyl-ethyl)-3-(2-phenyl-4-methyl-phenyl-amino-acetoxy)-1-azonia-bicyclo[2.2.2]octane bromide;
(2-fluoro-phenylamino)-phenyl-acetic acid (R)-(1-aza-bicyclo[2.2.2]oct-3-yl)ester;
(R)-3-[2-(2-fluoro-phenylamino)-2-phenyl-acetoxy]-1-(2-oxo-2-phenyl-ethyl)-1-azonia-bicyclo[2.2.2]octane trifluoroacetate;
(R)-3-[2-(3-fluoro-phenylamino)-2-phenyl-acetoxy]-1-(2-oxo-2-phenyl-ethyl)-1-azonia-bicyclo[2.2.2]octane bromide;
(R)-3-[2-(3-fluoro-phenylamino)-2-phenyl-acetoxy]-1-(2-oxo-2-thiophen-2-yl-ethyl)-1-azonia-bicyclo[2.2.2]octane trifluoroacetate;
(R)-(4-fluoro-phenylamino)-phenyl-acetic acid (R)-(1-aza-bicyclo[2.2.2]oct-3-yl)ester;
(R)-3-[(R)-2-(4-fluoro-phenylamino)-2-phenyl-acetoxy]-1-(2-oxo-2-thiophen-2-yl-ethyl)-1-azonia-bicyclo[2.2.2]octane chloride;
(4-chloro-phenyl)-phenylamino-acetic acid (R)-(1-aza-bicyclo[2.2.2]oct-3-yl)ester;
(R)-3-[2-(4-chloro-phenyl)-2-phenylamino-acetoxy]-1-(2-oxo-2-phenyl-ethyl)-1-azonia-bicyclo[2.2.2]octane trifluoroacetate;
(2-fluoro-phenyl)-phenylamino-acetic acid (R)-(1-aza-bicyclo[2.2.2]oct-3-yl)ester;

(R)-3-[2-(2-fluoro-phenyl)-2-phenylamino-acetoxy]-1-(2-oxo-2-phenyl-ethyl)-1-azonia-bicyclo[2.2.2]octane trifluoroacetate;

(5-methyl-thiophen-2-yl)-phenylamino-acetic acid (R)-(1-aza-bicyclo[2.2.2]oct-3-yl)ester;

(R)-3-[2-(5-methyl-thiophen-2-yl)-2-phenylamino-acetoxy]-1-(2-oxo-2-phenyl-ethyl)-1-azonia-bicyclo[2.2.2]octane trifluoroacetate;

(R)-1-[2-(4-amino-phenyl)-2-oxo-ethyl]-3-(2-phenyl-2-phenylamino-acetoxy)-1-azonia-bicyclo[2.2.2]octane formate;

1-(2-hydroxy-2-phenylethyl)-3-(2-phenyl-2-(phenylamino)acetoxy)-1-azoniabicyclo[2.2.2]octane trifluoroacetate; and pharmaceutically acceptable salts thereof.

17. A pharmaceutical composition, comprising a compound of formula (I) or a pharmaceutically acceptable salt thereof according to claim 1 in admixture with one or more pharmaceutically acceptable carriers and/or excipients.

18. A pharmaceutical composition according to claim 17, which is in a form suitable for administration by inhalation.

19. A pharmaceutical composition according to claim 17, wherein said composition further comprises a second component selected from the group consisting of a beta2-agonist and a corticosteroid.

* * * * *